US012552837B2

(12) United States Patent
Bennett et al.

(10) Patent No.: US 12,552,837 B2
(45) Date of Patent: Feb. 17, 2026

(54) BICYCLIC PEPTIDE LIGANDS WITH DETECTABLE MOIETIES AND USES THEREOF

(71) Applicant: BicycleRD Limited, Cambridge (GB)

(72) Inventors: Gavin Bennett, Cambridge (GB); Daniel Paul Teufel, Cambridge (GB)

(73) Assignee: BicycleRD Limited, Cambridge (GB)

( * ) Notice: Subject to any disclaimer, the term of this patent is extended or adjusted under 35 U.S.C. 154(b) by 0 days.

(21) Appl. No.: 18/345,506

(22) Filed: Jun. 30, 2023

(65) Prior Publication Data

US 2024/0158444 A1 May 16, 2024

Related U.S. Application Data

(62) Division of application No. 17/060,409, filed on Oct. 1, 2020, now Pat. No. 11,746,126, which is a division of application No. 16/018,432, filed on Jun. 26, 2018, now Pat. No. 10,899,798.

(60) Provisional application No. 62/594,613, filed on Dec. 5, 2017, provisional application No. 62/524,721, filed on Jun. 26, 2017.

(51) Int. Cl.

| | |
|---|---|
| ***C07K 7/56*** | (2006.01) |
| ***A61K 49/00*** | (2006.01) |
| ***A61K 51/08*** | (2006.01) |
| ***C07K 7/08*** | (2006.01) |
| ***C07K 14/00*** | (2006.01) |

(52) U.S. Cl.

CPC ............ *C07K 7/56* (2013.01); *A61K 49/0032* (2013.01); *A61K 49/0043* (2013.01); *A61K 49/0056* (2013.01); *A61K 51/088* (2013.01); *C07K 7/08* (2013.01); *C07K 14/001* (2013.01)

(58) Field of Classification Search

CPC .......... C07K 7/56; C07K 7/08; C07K 14/001; A61K 49/0032; A61K 49/0043; A61K 49/0056; A61K 51/088

See application file for complete search history.

(56) References Cited

U.S. PATENT DOCUMENTS

| | | | |
|---|---|---|---|
| 2,642,514 | A | 6/1953 | Herkenhoff |
| 4,650,750 | A | 3/1987 | Giese |
| 4,709,016 | A | 11/1987 | Giese |
| 5,360,819 | A | 11/1994 | Giese |
| 5,516,931 | A | 5/1996 | Giese et al. |
| 5,595,756 | A | 1/1997 | Bally et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 6,326,144 | B1 | 12/2001 | Bawendi et al. |
| 6,468,808 | B1 | 10/2002 | Nie et al. |
| 6,552,065 | B2 | 4/2003 | Remiszewski et al. |
| 7,151,047 | B2 | 12/2006 | Chan et al. |
| 7,192,785 | B2 | 3/2007 | Nie et al. |
| 7,390,799 | B2 | 6/2008 | Bruncko et al. |
| 8,138,347 | B2 | 3/2012 | Knight et al. |
| 8,680,022 | B2 | 3/2014 | Gregory et al. |
| 8,685,890 | B2 | 4/2014 | Winter et al. |
| 8,778,844 | B2 | 7/2014 | Winter et al. |
| 8,906,682 | B2 | 12/2014 | June et al. |
| 8,986,655 | B2 | 3/2015 | Weiss et al. |
| 9,518,081 | B2 | 12/2016 | Winter et al. |
| 9,644,201 | B2 | 5/2017 | Winter et al. |
| 9,657,288 | B2 | 5/2017 | Winter et al. |
| 9,670,482 | B2 | 6/2017 | Winter et al. |
| 9,670,484 | B2 | 6/2017 | Winter et al. |
| 9,670,521 | B2 | 6/2017 | Grabstein et al. |
| 9,868,767 | B2 | 1/2018 | Pei et al. |
| 9,932,367 | B2 | 4/2018 | Stace et al. |
| 9,994,617 | B2 | 6/2018 | Tite et al. |
| 10,118,947 | B2 | 11/2018 | Teufel et al. |
| 10,294,274 | B2 | 5/2019 | Teufel et al. |
| 10,441,663 | B2 | 10/2019 | Bennett et al. |
| 10,532,106 | B2 | 1/2020 | Teufel et al. |
| 10,624,968 | B2 | 4/2020 | Bennett et al. |
| 10,626,147 | B2 | 4/2020 | Pei et al. |
| 10,792,368 | B1 | 10/2020 | Teufel et al. |
| 10,800,813 | B2 | 10/2020 | Tite et al. |
| 10,857,196 | B2 | 12/2020 | Beswick et al. |
| 10,870,679 | B2 | 12/2020 | Teufel et al. |
| 10,875,894 | B2 | 12/2020 | Chen et al. |
| 10,894,808 | B2 | 1/2021 | Teufel et al. |
| 10,899,798 | B2 | 1/2021 | Bennett et al. |
| 10,919,937 | B2 | 2/2021 | Beswick et al. |
| 10,994,019 | B2 | 5/2021 | Teufel et al. |
| 11,103,591 | B2 | 8/2021 | Teufel et al. |
| 11,180,531 | B2 | 11/2021 | Beswick et al. |
| 11,241,473 | B2 | 2/2022 | Beswick et al. |
| 11,261,214 | B2 | 3/2022 | Chen et al. |
| 11,306,123 | B2 | 4/2022 | Mudd et al. |

(Continued)

FOREIGN PATENT DOCUMENTS

| | | | |
|---|---|---|---|
| CN | 101497878 | A | 5/2009 |
| CN | 105307686 | A | 2/2016 |

(Continued)

OTHER PUBLICATIONS

Adams, "Molecular control of arterial-venous blood vessel identity," J Anat. Jan. 2003;202(1):105-12.

Annunziata et al., "Phase 1, open-label study of MEDI-547 in patients with relapsed or refractory solid tumors," Invest New Drugs. Feb. 2013;31(1):77-84.

(Continued)

*Primary Examiner* — Sudhakar Katakam

(74) *Attorney, Agent, or Firm* — Wolf, Greenfield & Sacks, P.C.

(57) ABSTRACT

The present invention provides compounds, compositions thereof, and methods of using the same.

3 Claims, 22 Drawing Sheets

Specification includes a Sequence Listing.

(56) References Cited

U.S. PATENT DOCUMENTS

| | | | |
|---|---|---|---|
| 11,312,749 | B2 | 4/2022 | Mudd et al. |
| 11,332,500 | B2 | 5/2022 | Mudd et al. |
| 11,396,530 | B2 | 7/2022 | Beswick et al. |
| 11,414,488 | B2 | 8/2022 | Bennett et al. |
| 11,433,137 | B2 | 9/2022 | Bennett et al. |
| 11,453,702 | B2 | 9/2022 | Beswick et al. |
| 11,453,703 | B2 | 9/2022 | Keen et al. |
| 11,484,602 | B2 | 11/2022 | Chen et al. |
| 11,542,304 | B2 | 1/2023 | Chen et al. |
| 11,613,560 | B2 | 3/2023 | Stephen et al. |
| 11,623,012 | B2 | 4/2023 | Chen et al. |
| 11,672,868 | B2 | 6/2023 | Teufel et al. |
| 11,696,956 | B2 | 7/2023 | Chen et al. |
| 11,730,819 | B2 | 8/2023 | Teufel et al. |
| 11,746,126 | B2 | 9/2023 | Bennett et al. |
| 11,814,447 | B2 | 11/2023 | Teufel et al. |
| 11,833,211 | B2 | 12/2023 | Chen et al. |
| 11,912,792 | B2 | 2/2024 | Beswick et al. |
| 11,946,041 | B2 | 4/2024 | Chen et al. |
| 11,970,553 | B2 | 4/2024 | Mudd et al. |
| 12,049,520 | B2 | 7/2024 | Chen et al. |
| 2002/0164788 | A1 | 11/2002 | Ellis et al. |
| 2005/0169931 | A1 | 8/2005 | Kinch et al. |
| 2009/0222937 | A1 | 9/2009 | Arnould et al. |
| 2009/0304721 | A1 | 12/2009 | Kinch et al. |
| 2012/0101253 | A1 | 4/2012 | Heinis et al. |
| 2012/0172235 | A1 | 7/2012 | Winter et al. |
| 2013/0064791 | A1 | 3/2013 | Poelstra et al. |
| 2013/0072598 | A1 | 3/2013 | Yang et al. |
| 2014/0163201 | A1 | 6/2014 | Winter et al. |
| 2014/0249292 | A1 | 9/2014 | Tite et al. |
| 2014/0256596 | A1 | 9/2014 | Tite et al. |
| 2014/0274759 | A1 | 9/2014 | Walker et al. |
| 2015/0038434 | A1 | 2/2015 | Yang et al. |
| 2015/0087810 | A1 | 3/2015 | Moore et al. |
| 2016/0031939 | A1 | 2/2016 | Stace et al. |
| 2016/0046721 | A1 | 2/2016 | Qian et al. |
| 2016/0122430 | A1 | 5/2016 | Gish et al. |
| 2016/0256579 | A1 | 9/2016 | Shalom |
| 2016/0326232 | A1 | 11/2016 | Rosa et al. |
| 2017/0067045 | A1 | 3/2017 | Winter et al. |
| 2017/0190743 | A1 | 7/2017 | Pei et al. |
| 2017/0204150 | A1 | 7/2017 | Liu et al. |
| 2017/0304342 | A1 | 10/2017 | Cox et al. |
| 2017/0306032 | A1 | 10/2017 | Gehlsen |
| 2017/0360952 | A1 | 12/2017 | Schwartz et al. |
| 2018/0169254 | A1 | 6/2018 | Bennett et al. |
| 2018/0200378 | A1 | 7/2018 | Bennett et al. |
| 2018/0280525 | A1 | 10/2018 | Teufel et al. |
| 2018/0311300 | A1 | 11/2018 | Beswick et al. |
| 2018/0318451 | A1 | 11/2018 | Skerra et al. |
| 2018/0362585 | A1 | 12/2018 | Teufel et al. |
| 2018/0371020 | A1 | 12/2018 | Bennett et al. |
| 2019/0134213 | A1 | 5/2019 | Teufel et al. |
| 2019/0184025 | A1 | 6/2019 | Chen et al. |
| 2019/0263866 | A1 | 8/2019 | Chen et al. |
| 2019/0307836 | A1 | 10/2019 | Keen et al. |
| 2019/0389906 | A1 | 12/2019 | Beswick et al. |
| 2019/0389907 | A1 | 12/2019 | Teufel et al. |
| 2020/0129630 | A1 | 4/2020 | Koehler et al. |
| 2020/0131228 | A1 | 4/2020 | Beswick et al. |
| 2020/0171161 | A1 | 6/2020 | Teufel et al. |
| 2020/0190213 | A1 | 6/2020 | Preyer et al. |
| 2020/0215199 | A1 | 7/2020 | Bennett et al. |
| 2020/0255477 | A1 | 8/2020 | Chen et al. |
| 2020/0283482 | A1 | 9/2020 | Keen et al. |
| 2020/0289657 | A1 | 9/2020 | Teufel et al. |
| 2020/0291096 | A1 | 9/2020 | Keen et al. |
| 2020/0316209 | A1 | 10/2020 | Teufel et al. |
| 2020/0338203 | A1 | 10/2020 | Chen et al. |
| 2020/0354406 | A1 | 11/2020 | Stephen et al. |
| 2020/0354456 | A1 | 11/2020 | Bennett et al. |
| 2020/0407709 | A1 | 12/2020 | Chen et al. |
| 2021/0040154 | A1 | 2/2021 | Mudd et al. |
| 2021/0046145 | A1 | 2/2021 | Beswick et al. |
| 2021/0069287 | A1 | 3/2021 | Mudd et al. |
| 2021/0079045 | A1 | 3/2021 | Bennett et al. |
| 2021/0101932 | A1 | 4/2021 | Chen et al. |
| 2021/0101933 | A1 | 4/2021 | Chen et al. |
| 2021/0101937 | A1 | 4/2021 | Mudd et al. |
| 2021/0122785 | A1 | 4/2021 | Teufel et al. |
| 2021/0122804 | A1 | 4/2021 | Teufel et al. |
| 2021/0147484 | A1 | 5/2021 | Beswick et al. |
| 2021/0147485 | A1 | 5/2021 | Teufel et al. |
| 2021/0261620 | A1 | 8/2021 | Teufel et al. |
| 2021/0269480 | A1 | 9/2021 | Beswick et al. |
| 2021/0299210 | A2 | 9/2021 | Keen et al. |
| 2022/0023432 | A1 | 1/2022 | Teufel et al. |
| 2022/0024982 | A1 | 1/2022 | Chen et al. |
| 2022/0031858 | A1 | 2/2022 | Mcdonnell et al. |
| 2022/0054646 | A1 | 2/2022 | Chen et al. |
| 2022/0064218 | A1 | 3/2022 | Baldassarre et al. |
| 2022/0064221 | A1 | 3/2022 | Lani et al. |
| 2022/0072140 | A1 | 3/2022 | Stace et al. |
| 2022/0088118 | A1 | 3/2022 | Baldassarre et al. |
| 2022/0088207 | A1 | 3/2022 | Chen et al. |
| 2022/0089643 | A1 | 3/2022 | Beswick et al. |
| 2022/0119488 | A1 | 4/2022 | Lani et al. |
| 2022/0133732 | A1 | 5/2022 | Baldassarre et al. |
| 2022/0133733 | A1 | 5/2022 | Baldassarre et al. |
| 2022/0135614 | A1 | 5/2022 | Teufel et al. |
| 2022/0184222 | A1 | 6/2022 | Bennett et al. |
| 2022/0194983 | A1 | 6/2022 | Teufel et al. |
| 2022/0213145 | A1 | 7/2022 | Chen et al. |
| 2022/0227811 | A1 | 7/2022 | Mudd et al. |
| 2022/0242911 | A1 | 8/2022 | Mudd et al. |
| 2022/0257784 | A1 | 8/2022 | Upadhyaya et al. |
| 2022/0275053 | A1 | 9/2022 | Upadhyaya et al. |
| 2022/0281918 | A1 | 9/2022 | Van Rietschoten et al. |
| 2022/0289792 | A1 | 9/2022 | Chen et al. |
| 2022/0306689 | A9 | 9/2022 | Chen et al. |
| 2022/0306694 | A1 | 9/2022 | Mudd et al. |
| 2022/0362390 | A1 | 11/2022 | Stace et al. |
| 2022/0387611 | A1 | 12/2022 | Bennett et al. |
| 2023/0002596 | A1 | 1/2023 | Zhang et al. |
| 2023/0008076 | A1 | 1/2023 | Keen et al. |
| 2023/0025916 | A1 | 1/2023 | Bennett et al. |
| 2023/0025971 | A1 | 1/2023 | Bennett et al. |
| 2023/0086865 | A1 | 3/2023 | Balmford et al. |
| 2023/0106511 | A1 | 4/2023 | Balmforth et al. |
| 2023/0129258 | A1 | 4/2023 | Upadhyaya et al. |
| 2023/0144799 | A1 | 5/2023 | Chen et al. |
| 2023/0165966 | A1 | 6/2023 | Koehler et al. |
| 2023/0181749 | A1 | 6/2023 | Dickson et al. |
| 2023/0220008 | A1 | 7/2023 | Chen et al. |
| 2023/0233698 | A1 | 7/2023 | Bennett et al. |
| 2023/0287047 | A1 | 9/2023 | Beswick et al. |
| 2023/0340020 | A1 | 10/2023 | Teufel et al. |
| 2024/0000957 | A1 | 1/2024 | Chen et al. |
| 2024/0082410 | A1 | 3/2024 | Teufel et al. |
| 2024/0108738 | A1 | 4/2024 | Keen et al. |
| 2024/0173422 | A1 | 5/2024 | Beswick et al. |
| 2024/0189436 | A1 | 6/2024 | Chen et al. |
| 2024/0197897 | A1 | 6/2024 | Keen et al. |
| 2024/0240255 | A1 | 7/2024 | Blakemore et al. |
| 2024/0325554 | A1 | 10/2024 | Keen et al. |
| 2024/0336656 | A1 | 10/2024 | Mudd et al. |

FOREIGN PATENT DOCUMENTS

| | | | |
|---|---|---|---|
| EP | 2393520 | A1 | 12/2011 |
| EP | 2970954 | A1 | 1/2016 |
| EP | 3192802 | A1 | 7/2017 |
| FR | 2932189 | A1 | 11/2009 |
| GB | 1239978 | A | 7/1971 |
| JP | 2006514104 | A | 4/2006 |
| JP | 2011513298 | A | 4/2011 |
| JP | 2011522794 | A | 4/2011 |
| WO | WO9708320 | A1 | 6/1997 |
| WO | WO9819705 | A1 | 5/1998 |
| WO | WO0128683 | A1 | 4/2001 |
| WO | WO-2001042246 | A2 | 6/2001 |
| WO | WO-2002088112 | A1 | 11/2002 |
| WO | WO-2003063794 | A2 | 8/2003 |

(56) References Cited

FOREIGN PATENT DOCUMENTS

| | | | |
|---|---|---|---|
| WO | WO-2004005348 | A1 | 1/2004 |
| WO | WO-2004019973 | A1 | 3/2004 |
| WO | WO-2004077062 | A2 | 9/2004 |
| WO | WO-2004089925 | A1 | 10/2004 |
| WO | WO2004106328 | A1 | 12/2004 |
| WO | WO-2005007623 | A2 | 1/2005 |
| WO | WO-2005103083 | A2 | 11/2005 |
| WO | WO-2005113554 | A2 | 12/2005 |
| WO | WO2006029879 | A2 | 3/2006 |
| WO | WO-2006078161 | A1 | 7/2006 |
| WO | WO-2006078846 | A1 | 7/2006 |
| WO | WO2006101187 | A1 | 9/2006 |
| WO | WO2006105021 | A2 | 10/2006 |
| WO | WO-2006122806 | A2 | 11/2006 |
| WO | WO-2007016176 | A2 | 2/2007 |
| WO | WO-2007044729 | A2 | 4/2007 |
| WO | WO-2007053452 | A1 | 5/2007 |
| WO | WO-2007070514 | A1 | 6/2007 |
| WO | WO2007005874 | A2 | 7/2007 |
| WO | WO-2007084786 | A1 | 7/2007 |
| WO | WO-2007129161 | A2 | 11/2007 |
| WO | WO-2008033561 | A2 | 3/2008 |
| WO | WO-2008039218 | A2 | 4/2008 |
| WO | WO2008134761 | A2 | 6/2008 |
| WO | WO2008089627 | A1 | 7/2008 |
| WO | WO-2008109943 | A1 | 9/2008 |
| WO | WO2008118802 | A1 | 10/2008 |
| WO | WO2008132601 | A1 | 11/2008 |
| WO | WO-2008157490 | A1 | 12/2008 |
| WO | WO2009009116 | A2 | 1/2009 |
| WO | WO2009044273 | A2 | 4/2009 |
| WO | WO2009073620 | A2 | 6/2009 |
| WO | WO-2009098450 | A2 | 8/2009 |
| WO | WO-2009114512 | A1 | 9/2009 |
| WO | WO2010019570 | A2 | 2/2010 |
| WO | WO2010077634 | A1 | 7/2010 |
| WO | WO2010089115 | A1 | 8/2010 |
| WO | WO2010089117 | A1 | 12/2010 |
| WO | WO-2011018227 | A2 | 2/2011 |
| WO | WO2011028683 | A1 | 3/2011 |
| WO | WO2011056652 | A1 | 5/2011 |
| WO | WO2011070024 | A1 | 6/2011 |
| WO | WO-2011079015 | A1 | 6/2011 |
| WO | WO-2011090760 | A1 | 7/2011 |
| WO | WO2011107553 | A1 | 9/2011 |
| WO | WO2011109400 | A2 | 9/2011 |
| WO | WO2011131407 | A1 | 10/2011 |
| WO | WO2011140249 | A2 | 11/2011 |
| WO | WO2012032433 | A1 | 3/2012 |
| WO | WO2012057624 | A1 | 5/2012 |
| WO | WO2012142237 | A1 | 10/2012 |
| WO | WO2012145493 | A1 | 10/2012 |
| WO | WO2013050615 | A1 | 4/2013 |
| WO | WO-2013050617 | A1 | 4/2013 |
| WO | WO2013079174 | A1 | 6/2013 |
| WO | WO2013087699 | A1 | 6/2013 |
| WO | WO2013119716 | A1 | 8/2013 |
| WO | WO2013132044 | A1 | 9/2013 |
| WO | WO2013050616 | A1 | 11/2013 |
| WO | WO2013169264 | A1 | 11/2013 |
| WO | WO2014008218 | A1 | 1/2014 |
| WO | WO2014036357 | A1 | 3/2014 |
| WO | WO2014044872 | A1 | 3/2014 |
| WO | WO2014063012 | A1 | 4/2014 |
| WO | WO2014142237 | A1 | 9/2014 |
| WO | WO-2014164693 | A2 | 10/2014 |
| WO | WO2014167122 | A1 | 10/2014 |
| WO | WO2014190257 | A2 | 11/2014 |
| WO | WO2015116904 | A1 | 6/2015 |
| WO | WO-2015171938 | A1 | 11/2015 |
| WO | WO-2015179691 | A2 | 11/2015 |
| WO | WO2016046574 | A1 | 3/2016 |
| WO | WO-2016067035 | A1 | 5/2016 |
| WO | WO2016050361 | A1 | 7/2016 |
| WO | WO-2016171242 | A1 | 10/2016 |
| WO | WO2016171272 | A1 | 10/2016 |
| WO | WO-2016174103 | A1 | 11/2016 |
| WO | WO2017046658 | A1 | 3/2017 |
| WO | WO2017102906 | A1 | 6/2017 |
| WO | WO-2017161069 | A1 | 9/2017 |
| WO | WO2017173408 | A1 | 10/2017 |
| WO | WO2017182672 | A1 | 10/2017 |
| WO | WO-2017191460 | A1 | 11/2017 |
| WO | WO2017205738 | A1 | 11/2017 |
| WO | WO2018096365 | A1 | 5/2018 |
| WO | WO-2018115203 | A1 | 6/2018 |
| WO | WO-2018115204 | A1 | 6/2018 |
| WO | WO2018222987 | A1 | 6/2018 |
| WO | WO-2018127699 | A1 | 7/2018 |
| WO | WO2018156740 | A1 | 8/2018 |
| WO | WO-2018197509 | A1 | 11/2018 |
| WO | WO2018197893 | A1 | 11/2018 |
| WO | WO-2019002842 | | 1/2019 |
| WO | WO2019025811 | A1 | 2/2019 |
| WO | WO2019034866 | A1 | 2/2019 |
| WO | WO2019034868 | A1 | 2/2019 |
| WO | WO2019084060 | A1 | 2/2019 |
| WO | WO2019094395 | A2 | 5/2019 |
| WO | WO-2019122860 | A1 | 6/2019 |
| WO | WO-2019122861 | A1 | 6/2019 |
| WO | WO-2019122863 | A1 | 6/2019 |
| WO | WO2019162682 | A1 | 8/2019 |
| WO | WO-2019193328 | A1 | 10/2019 |
| WO | WO2019136442 | A1 | 11/2019 |
| WO | WO2019226617 | A1 | 11/2019 |
| WO | WO-2019243313 | A1 | 12/2019 |
| WO | WO2019243329 | A1 | 12/2019 |
| WO | WO2019243353 | A1 | 12/2019 |
| WO | WO2019243455 | A1 | 12/2019 |
| WO | WO2019243832 | A1 | 12/2019 |
| WO | WO2019243833 | A1 | 12/2019 |
| WO | WO-2020084305 | A1 | 4/2020 |
| WO | WO2020089627 | A1 | 5/2020 |
| WO | WO2020120980 | A1 | 6/2020 |
| WO | WO2020120981 | A1 | 6/2020 |
| WO | WO2020120983 | A1 | 6/2020 |
| WO | WO2020120984 | A1 | 6/2020 |
| WO | WO2020128526 | A1 | 6/2020 |
| WO | WO2020128527 | A1 | 6/2020 |
| WO | WO2020148525 | A1 | 7/2020 |
| WO | WO2020148526 | A1 | 7/2020 |
| WO | WO2020148527 | A1 | 7/2020 |
| WO | WO2020148528 | A1 | 7/2020 |
| WO | WO2020148529 | A1 | 7/2020 |
| WO | WO2020148530 | A1 | 7/2020 |
| WO | WO2020165600 | A1 | 8/2020 |
| WO | WO2020178574 | A1 | 9/2020 |
| WO | WO-2020201753 | A1 | 10/2020 |
| WO | WO2020225577 | A1 | 11/2020 |
| WO | WO2020229803 | A1 | 11/2020 |
| WO | WO-2021019243 | A1 | 2/2021 |
| WO | WO2021019244 | A1 | 2/2021 |
| WO | WO-2021019245 | A1 | 2/2021 |
| WO | WO2021019246 | A1 | 2/2021 |
| WO | WO2021028686 | A1 | 2/2021 |
| WO | WO2021171028 | A1 | 2/2021 |
| WO | WO2021171029 | A1 | 2/2021 |
| WO | WO2021038232 | A1 | 4/2021 |
| WO | WO-2021064428 | A1 | 4/2021 |
| WO | WO2021074622 | A1 | 4/2021 |
| WO | WO2021074647 | A1 | 4/2021 |
| WO | WO-2021105694 | A1 | 6/2021 |
| WO | WO2021148974 | A1 | 7/2021 |
| WO | WO2021234391 | A1 | 11/2021 |
| WO | WO-2021250418 | A1 | 12/2021 |
| WO | WO2022038158 | A1 | 2/2022 |
| WO | WO2022148969 | A1 | 7/2022 |
| WO | WO2022148974 | A2 | 7/2022 |
| WO | WO2022148975 | A1 | 7/2022 |
| WO | WO2022148979 | A1 | 7/2022 |
| WO | WO2022029420 | A1 | 10/2022 |

(56) References Cited

FOREIGN PATENT DOCUMENTS

WO WO2023089308 A1 5/2023
WO WO2023031623 A2 9/2023

OTHER PUBLICATIONS

Ausiello et al., "Functional topography of discrete domains of human CD38," Tissue Antigens. Dec. 2000;56(6):539-47.
Berge et al., "Pharmaceutical salts," J Pharm Sci. 1977;66(1):1-19.
Binda et al., "The EphA2 receptor drives self-renewal and tumorigenicity in stem-like tumor-propagating cells from human glioblastomas," Cancer Cell. Dec. 12, 2012; 22(6); 765-80.
Booth et al., "Crowd control in the crypt," Nat Med. Dec. 2002;8(12):1360-1.
Brannan et al., "EphA2 in the early pathogenesis and progression of non-small cell lung cancer," Cancer Prev Res (Phila). Dec. 2009;2(12):1039-49.
Brantley-Sieders et al., "Eph receptor tyrosine kinases in tumor and tumor microenvironment," Curr Pharm Des. 2004; 10(27); 3431-42.
Brantley-Sieders et al., "Eph/ephrin profiling in human breast cancer reveals significant associations between expression level and clinical outcome," PLoS One. 2011; 6(9): e24426.
Brantley-Sieders et al., "Impaired tumor microenvironment in EphA2-deficient mice inhibits tumor angiogenesis and metastatic progression," FASEB J. Nov. 2005; 19(13): 1884-6.
Chan and Nie, "Quantum dot bioconjugates for ultrasensitive nonisotopic detection," Science. Sep. 25, 1998; 281 (5385): 2016-8.
Chang et al., "Five different anti-prostate-specific membrane antigen (PSMA) antibodies confirm PSMA expression in tumor-associated neovasculature," Cancer Res. Jul. 1, 1999; 59(13):3192-8.
Chen et al., "Structurally diverse cyclisation linkers impose different backbone conformations in bicyclic peptides," Chembiochem. May 7, 2012; 13(7): 1032-8.
Cheng et al., "Blockade of EphA receptor tyrosine kinase activation inhibits vascular endothelial cell growth factor-induced angiogenesis," Mol Cancer Res. Nov. 2002; 1(1): 2-11.
Cherney et al., "Macrocyclic amino carboxylates as selective MMP-8 inhibitors," J Med Chem. May 21, 1998;41(11):1749-51.
Chiche et al., "Hypoxia-inducible carbonic anhydrase IX and XII promote tumor cell growth by counteracting acidosis through the regulation of the intracellular pH," Cancer Res. Jan. 1, 2009;69(1):358-68.
Dagher et al., "c-Kit and CD38 are expressed by long-term reconstituting hematopoietic cells present in the murine yolk sac," Biol Blood Marrow Transplant. 1998;4(2):69-74.
Deaglio et al., "CD38 is a signaling molecule in B-cell chronic lymphocytic leukemia cells," Blood. Sep. 15, 2003;102(6):2146-55.
Di, "Strategic approaches to optimizing peptide ADME properties," AAPS J. Jan. 2015;17(1):134-43.
Driggers et al., "The exploration of macrocycles for drug discovery—an underexploited structural class," Nat Rev Drug Discov. Jul. 2008;7(7):608-24.
Duong and Rodan, "The role of integrins in osteoclast function," J Bone Miner Metab. 1999;17(1):1-6.
Funaro et al., "Human CD38 is associated to distinct molecules which mediate transmembrane signaling in different lineages," Eur J Immunol. Oct. 1993;23(10):2407-11.
Funaro et al., "Involvement of the multilineage CD38 molecule in a unique pathway of cell activation and proliferation," J Immunol. Oct. 15, 1990;145(8):2390-6.
Gandhi et al., "MP69-11 Carbonic Anhydrase IX Assay: A Paradigm Shift in Diagnosis of Malignant Cystic Renal Lesions," J Urol. May 18, 2015;193(4S):e870-e871.
Guo et al., "Prognostic significance of combinations of RNA-dependent protein kinase and EphA2 biomarkers for NSCLC," J Thorac Oncol. Mar. 2013;8(3):301-8.
Hess et al., "Molecular regulation of tumor cell vasculogenic mimicry by tyrosine phosphorylation: role of epithelial cell kinase (Eck/EphA2)," Cancer Res. Apr. 15, 2001;61(8):3250-5.
Hoshino et al., "Mapping of the catalytic and epitopic sites of human CD38/NAD+ glycohydrolase to a functional domain in the carboxyl terminus," J Immunol. Jan. 15, 1997;158(2):741-7.
PCT International Search Report and Written Opinion from PCT/GB2018/051779, dated Aug. 23, 2018.
Jin et al., "(alpha)V(beta)3 Integrin-Targeted Radionuclide Therapy with 64Cu-cyclam-RAFT-c(-RGDfK-)4," Mol Cancer Ther. Sep. 2016;15(9):2076-85.
Kemp and McNamara, "Conformationally restricted cyclic nonapeptides derived from L-cysteine and LL-3-amino-2-piperidone-6-carboxylic acid (LL-Acp), a potent .beta.-turn-inducing dipeptide analog," J Org Chem. 1985;50(26):5834-8.
Kinch et al., "Predictive value of the EphA2 receptor tyrosine kinase in lung cancer recurrence and survival," Clin Cancer Res. Feb. 2003;9(2):613-8.
Kitanaka et al., "CD38 ligation in human B cell progenitors triggers tyrosine phosphorylation of CD19 and association of CD19 with lyn and phosphatidylinositol 3-kinase," J Immunol. Jul. 1, 1997;159(1):184-92.
Kitanaka et al., "CD38-mediated signaling events in murine pro-B cells expressing human CD38 with or without its cytoplasmic domain," J Immunol. Feb. 15, 1999;162(4):1952-8.
Konopleva et al., "Ligation of cell surface CD38 protein with agonistic monoclonal antibody induces a cell growth signal in myeloid leukemia cells," J Immunol. Nov. 1, 1998;161(9):4702-8.
Kumagai et al., "Ligation of CD38 suppresses human B lymphopoiesis," J Exp Med. Mar. 1, 1995;181(3):1101-10.
Lee et al., "ADP-ribosyl cyclase and CD38. Multi-functional enzymes in Ca+2 signaling," Adv Exp Med Biol. 1997;419:411-9.
Lee and Aarhus, "ADP-ribosyl cyclase: an enzyme that cyclizes NAD+ into a calcium-mobilizing metabolite," Cell Regul. Mar. 1991;2(3):203-9.
Lee et al., "Structural determination of a cyclic metabolite of NAD+ with intracellular Ca2+-mobilizing activity," J Biol Chem. Jan. 25, 1989;264(3):1608-15.
Li et al., "Up-regulation of EphA2 and down-regulation of EphrinA1 are associated with the aggressive phenotype and poor prognosis of malignant glioma," Tumour Biol. Oct. 2010;31(5):477-88.
Lin et al., "EphA2 overexpression is associated with angiogenesis in ovarian cancer," Cancer. Jan. 15, 2007;109(2):332-40.
Lund et al., "CD38 signaling in B lymphocytes is controlled by its ectodomain but occurs independently of enzymatically generated ADP-ribose or cyclic ADP-ribose," J Immunol. Mar. 1, 1999;162(5):2693-702.
Mallone et al., "Signaling through CD38 induces NK cell activation," Int Immunol. Apr. 1, 2001;13(4):397-409.
Marme, "VEGFs, angiopoietins, Ephrins and their receptors: putative targets for tumor therapy?" Ann Hematol. 2002;81 Suppl 2:S66.
Morra et al., "CD38 is functionally dependent on the TCR/CD3 complex in human T cells," FASEB J. May 1998; 12(7):581-92.
Mudali et al., "Patterns of EphA2 protein expression in primary and metastatic pancreatic carcinoma and correlation with genetic status," Clin Exp Metastasis. 2006;23(7-8):357-65.
Nakamoto and Bergemann, "Diverse roles for the Eph family of receptor tyrosine kinases in carcinogenesis," Microsc Res Tech. Oct. 1, 2002;59(1):58-67.
Nakamura et al., "EPHA2/EFNA1 expression in human gastric cancer," Cancer Sci. Jan. 2005;96(1):42-7.
Nakamura et al., "Involvement of alpha(v)beta3 integrins in osteoclast function," J Bone Miner Metab. 2007;25(6):337-44.
Nan et al., "Dual function glutamate-related ligands: discovery of a novel, potent inhibitor of glutamate carboxypeptidase II possessing mGluR3 agonist activity," J Med Chem. Mar. 9, 2000;43(5):772-4.
Neri and Supuran, "Interfering with pH regulation in tumours as a therapeutic strategy," Nat Rev Drug Discov. Sep. 16, 2011;10(10):767-77.
Oliver et al., "Mouse CD38 is down-regulated on germinal center B cells and mature plasma cells," J Immunol. Feb. 1, 1997;158(3):1108-15.
Partida-Sánchez et al., "Cyclic ADP-ribose production by CD38 regulates intracellular calcium release, extracellular calcium influx and chemotaxis in neutrophils and is required for bacterial clearance in vivo," Nat Med. Nov. 2001;7(11):1209-16.

(56) References Cited

OTHER PUBLICATIONS

Partida-Sánchez et al., "Regulation of dendritic cell trafficking by the ADP-ribosyl cyclase CD38: impact on the development of humoral immunity," Immunity. Mar. 2004;20(3):279-91.
Pietraszek et al., "Lumican: a new inhibitor of matrix metalloproteinase-14 activity," FEBS Lett. Nov. 28, 2014;588(23):4319-24.
Poliakov et al., "Diverse roles of eph receptors and ephrins in the regulation of cell migration and tissue assembly," Dev Cell. Oct. 2004;7(4):465-80.
Ramirez et al., "Defining causative factors contributing in the activation of hedgehog signaling in diffuse large B-cell lymphoma," Leuk Res. Oct. 2012;36(10):1267-73.
Randall et al., "Expression of murine CD38 defines a population of long-term reconstituting hematopoietic stem cells," Blood. May 15, 1996;87(10):4057-67.
Remacle et al., "Novel MT1-MMP small-molecule inhibitors based on insights into hemopexin domain function in tumor growth," Cancer Res. May 1, 2012;72(9):2339-49.
Ridderstad and Tarlinton, "Kinetics of establishing the memory B cell population as revealed by CD38 expression," J Immunol. May 15, 1998;160(10):4688-95.
Rodan and Rodan, "Integrin function in osteoclasts," J Endocrinol. Sep. 1997; 154 Suppl:S47-56.
Ross and Christiano, "Nothing but skin and bone," J Clin Invest. May 2006;116(5):1140-9.
Rostovtsev et al., "A stepwise huisgen cycloaddition process: copper(I)-catalyzed regioselective "ligation" of azides and terminal alkynes," Angew Chem Int Ed Engl. Jul. 15, 2002;41(14):2596-9.
Schülke et al., "The homodimer of prostate-specific membrane antigen is a functional target for cancer therapy," Proc Natl Acad Sci U S A. Oct. 28, 2003;100(22):12590-5.
Sounni et al., "MT1-MMP expression promotes tumor growth and angiogenesis through an up-regulation of vascular endothelial growth factor expression," FASEB J. Apr. 2002;16(6):555-64.
Stein et al., "Eph receptors discriminate specific ligand oligomers to determine alternative signaling complexes, attachment, and assembly responses," Genes Dev. Mar. 1, 1998;12(5):667-678.
Stevenson et al., "Preliminary studies for an immunotherapeutic approach to the treatment of human myeloma using chimeric anti-CD38 antibody," Blood. Mar. 1, 1991;77(5):1071-9.
Sun et al., "Carbohydrate and protein immobilization onto solid surfaces by sequential Diels-Alder and azide-alkyne cycloadditions," Bioconjug Chem. Jan.-Feb. 2006;17(1):52-7.
Supuran, "Carbonic anhydrases: novel therapeutic applications for inhibitors and activators," Nat Rev Drug Discov. Feb. 2008;7(2):168-81.
Tasch et al., "A unique folate hydrolase, prostate-specific membrane antigen (PSMA): a target for immunotherapy?" Crit Rev Immunol. 2001;21(1-3):249-61.
Teitelbaum, "Osteoclasts, integrins, and osteoporosis," J Bone Miner Metab. Oct. 2000;18(6):344-9.
Teitelbaum, "Osteoporosis and Integrins," J Clin Endocrinol Metab. Apr. 2005;90(4):2466-8.
Teti et al., "The role of the alphaVbeta3 integrin in the development of osteolytic bone metastases: a pharmacological target for alternative therapy?" Calcif Tissue Int. Oct. 2002;71(4):293-9.
Teufel et al., "Backbone-driven collapse in unfolded protein chains," J Mol Biol. Jun. 3, 2011;409(2):250-62.
Timmerman et al., "Rapid and quantitative cyclization of multiple peptide loops onto synthetic scaffolds for structural mimicry of protein surfaces," Chembiochem. May 2005;6(5):821-4.
Todisco et al., "CD38 ligation inhibits normal and leukemic myelopoiesis," Blood. Jan. 15, 2000;95(2):535-42.
Uckun, "Regulation of human B-cell ontogeny," Blood. Nov. 15, 1990;76(10):1908-23.
Walker-Daniels et al., "Overexpression of the EphA2 tyrosine kinase in prostate cancer," Prostate. Dec. 1, 1999;41(4):275-80.
Wallbrecher et al., "Exploration of the design principles of a cell-penetrating bicylic peptide scaffold," Bioconjug Chem. May 21, 2014;25(5):955-64.
Wang et al., "Probing for integrin alpha v beta3 binding of RGD peptides using fluorescence polarization," Bioconjug Chem. May-Jun. 2005;16(3):729-34.
Wang, "An exact mathematical expression for describing competitive binding of two different ligands to a protein molecule," FEBS Lett. Feb. 27, 1995;360(2):111-4.
Wind et al., "Measuring carbonic anhydrase IX as a hypoxia biomarker: differences in concentrations in serum and plasma using a commercial enzyme-linked immunosorbent assay due to influences of metal ions," Ann Clin Biochem. Mar. 2011;48(Pt 2):112-20.
Wu et al., "Structures of the CXCR4 chemokine GPCR with small-molecule and cyclic peptide antagonists," Science. Nov. 19, 2010;330(6007):1066-71.
Wykosky et al., "EphA2 as a novel molecular marker and target in glioblastoma multiforme," Mol Cancer Res. Oct. 2005;3(10):541-51.
Xiong et al., "Crystal structure of the extracellular segment of integrin alpha Vbeta3 in complex with an Arg-Gly-Asp ligand," Science. Apr. 5, 2002;296(5565):151-5.
Yang et al., "Overexpression of EphA2, MMP-9, and MVD-CD34 in hepatocellular carcinoma: Implications for tumor progression and prognosis," Hepatol Res. Dec. 2009;39(12):1169-77.
Yuan et al., "Over-expression of EphA2 and EphrinA-1 in human gastric adenocarcinoma and its prognostic value for postoperative patients," Dig Dis Sci. Nov. 2009;54(11):2410-7.
Zelinski et al., "EphA2 overexpression causes tumorigenesis of mammary epithelial cells," Cancer Res. Mar. 1, 2001;61(5):2301-6.
Zhao et al., "Structural basis of specificity of a peptidyl urokinase inhibitor, upain-1," J Struct Biol. Oct. 2007;160(1):1-10.
Zhuang et al., "Elevation of receptor tyrosine kinase EphA2 mediates resistance to trastuzumab therapy," Cancer Res. Jan. 1, 2010;70(1):299-308.
Zilber et al., "CD38 expressed on human monocytes: a coaccessory molecule in the superantigen-induced proliferation," Proc Natl Acad Sci U S A. Mar. 14, 2000;97(6):2840-5.
Zubiaur et al., "CD38 ligation results in activation of the Raf-1/mitogen-activated protein kinase and the CD3-zeta/zeta-associated protein-70 signaling pathways in Jurkat T lymphocytes," J Immunol. Jul. 1, 1997;159(1):193-205.
Zupo et al., "CD38 signaling by agonistic monoclonal antibody prevents apoptosis of human germinal center B cells," Eur J Immunol. May 1994;24(5):1218-22.
Bennett et al., "Abstract 5855: Bicycle Drug Conjugates Targeting EphA2 for the Treatment of Solid Tumors: Discovery and Selection of BT5528," Cancer Res. 2018; 78 (13 suppl); 5855.
Bennett et al., "Development of BT1718, a Bicycle Drug Conjugate® (BDC) targeting MT1-MMP for treatment of solid tumours," Eur J Cancer. Dec. 2016;69(suppl 1):S21(42;P013).
Bennett, "BT1718, a Bicycle Drug Conjugate (BTC): Profound Efficacy Without Bleeding and Coagulation Abnormalities in Animal Models," AACR Annual Meeting 2019. 4481.
Chen et al., "Peptide ligands stabilized by small molecules," Angew Chem Int Ed Engl. Feb. 3, 2014;53(6):1602-6.
Deonarain et al., "Small-Format Drug Conjugates: A Viable Alternative to ADCs for Solid Tumours?" Antibodies (Basel). 2018;7(2):16.
Deyle et al., "Phage Selection of Cyclic Peptides for Application in Research and Drug Development." Acc Chem Res. 2017;50(8):1866-1874.
Harrison et al., "Abstract 5144: BT1718, a novel bicyclic peptide-maytansinoid conjugate targeting MT1-MMP for the treatment of solid tumors: Design of bicyclic peptide and linker selection," Cancer Res. 2017;77(13 suppl):5144.
Heinis et al., "Phage-encoded combinatorial chemical libraries based on bicyclic peptides," Nat. Chem. Biol. 2009;5(7):502-7.
Mitra et al., "Structure-Activity Relationship Analysis of Peptides Targeting the EphA2 Receptor," Biochemistry. 2010;49(31):6687-95.
Mudd et al., "Identification and Optimization of EphA2-Selective Bicycles for the Delivery of Cytotoxic Payloads," J Med Chem. 2020;63(8):4107-16.
PCT International Search Report and Written Opinion from PCT/GB2018/053678, dated Mar. 11, 2019.

(56) References Cited

OTHER PUBLICATIONS

PCT International Search Report and Written Opinion from PCT/EP2019/065993, dated Sep. 13, 2019.
PCT International Search Report and Written Opinion from PCT/GB2020/051829, dated Oct. 21, 2020.
Shi et al., "One-Bead-Two-Compound Thioether Bridged Macrocyclic (gamma)-AApeptide Screening Library Against EphA2," J Med Chem. Nov. 22, 2017;60(22):9290-9298.
U.S. Appl. No. 16/771,186, filed Jun. 9, 2020.
U.S. Appl. No. 17/590,875, filed Feb. 2, 2022.
U.S. Appl. No. 17/592,966, filed Feb. 4, 2022.
U.S. Appl. No. 17/630,314, filed Jan. 26, 2022.
U.S. Appl. No. 17/630,747, filed Jan. 27, 2022.
U.S. Appl. No. 17/655,822, filed Mar. 22, 2022.
U.S. Appl. No. 17/663,169, filed May 12, 2022.
U.S. Appl. No. 17/779,226, filed May 24, 2022.
Wu et al., "Design and Characterization of Novel EphA2 Agonists for Targeted Delivery of Chemotherapy to Cancer Cells," Chem. Biol. 2015;22(7):876-887.
PCT International Search Report and Written Opinion from PCT/GB2020/050874 dated Jun. 17, 2020.
PCT International Search Report and Written Opinion from PCT/GB2018/053676, dated Mar. 7, 2019.
PCT International Search Report and Written Opinion from PCT/GB2021/051451, dated Sep. 22, 2021.
Bicycle Therapeutics, "Bicycle Therapeutics to Present on BT5528, a Bicycle Toxin Conjugate Targeting EphA2 for the Treatment of Solid Tumours, at World ADC 2019," Business Wire Release. Mar. 5, 2019.
Bennett et al., "Abstract 5854: BT5528, a Bicycle Toxin Conjugate targeting EphA2 has potent anti-tumor activity without bleeding or coagulation abnormalities in preclinical models." Cancer Res. 2018;78(13 suppl):5854.
Jackson et al., "A human antibody-drug conjugate targeting EphA2 inhibits tumor growth in vivo," Cancer Res. Nov. 15, 2008;68(22):9367-74.
Bennett et al., "Abstract 4481: BT5528, an EphA2-targeting Bicycle Toxin Conjugate (BTC): Profound efficacy without bleeding and coagulation abnormalities in animal models," Cancer Res. 2019; 79 (13 suppl); 4481.
Merritt et al., "Analysis of EphA2 expression and mutant p53 in ovarian carcinoma," Cancer Biol Ther. Oct. 2006;5(10):1357-60.
Centers for Disease Control and Prevention, "What Can I Do to Reduce My Risk of Ovarian Cancer?" Division of Cancer Prevention and Control. Aug. 31, 2022.
Bennett et al., "MMAE Delivery Using the Bicycle Toxin Conjugate BT5528," Mol Cancer Ther. Jul. 2020; 19(7):1385-1394.
BicycleTx Limited, "Study BT5528-100 in Patients With Advanced Solid Tumors Associated With EphA2 Expression," ClinicalTrials.gov Identifier NCT04180371. First Posted Nov. 27, 2019; Accessed Dec. 30, 2022: https://clinicaltrials.gov/ct2/show/NCT04180371.
Tandon et al., "Emerging strategies for EphA2 receptor targeting for cancer therapeutics." Expert Opin Ther Targets. 2011;15(1):31-51.
Dunne et al., "EphA2 Expression Is a Key Driver of Migration and Invasion and a Poor Prognostic Marker in Colorectal Cancer," Clin Cancer Res. Jan. 1, 2016;22(1):230-242.
Bicycle Therapeutics, "Bicycle Therapeutics to Present New BT1718 Data in the 'New Drugs on the Horizon' Session at the 2018 American Association for Cancer Research Meeting," Press Release. Apr. 3, 2018: https://www.businesswire.com/news/home/20180403005152/en/Bicycle-Therapeutics-Present-New-BT1718-Data-New.
Chen et al., "The Bicycle platform: an efficient technology to generate high affinity, high selectivity molecules (Bicycles®) with unique drug like properties that are amenable to conjugation," URL:https://www.bicycletherapeutics.com/wp-content/uploads/16_PEGS-Bicycle_-30-40-2017-poster.pdf; Apr. 26, 2017.
EP Office Action issued for EP Application EP 18739911.8, dated Jan. 25, 2023.
Rhodes et al., "Bicyclic Peptides as Next-Generation Therapeutics," ChemPubSoc 2017;23:12690-12703.
Yuan et al., "Neuropilin-1 and the development progress of the same as a therapeutic target for malignant tumors," Tumor 2016;36:358-364.
Anonymous, "UPI000011DEEB," retrieved from the internet: URL:https://www.uniprot.org/uniparc/UPI000011DEEB, 2014, 2 pages.
Hacker et al., "Highly Constrained Bicyclic Scaffolds for the Discovery of Protease-Stable Peptides via mRNA Display", ACS Chem. Biol., 2017, 12(3):795-804.
Ho et al., "Expression of CD137 on Hodgkin and Reed-Sternberg cells inhibits T-cell activation by eliminating CD137 ligand expression," Cancer Res., Jan. 15, 2013, 73(2):652-661.
Lowe, Derek, "Not alphafold's fault," blog—In the pipeline, 2022, 6 pages.
Lowe, Derek, "The good sides and bad sides of polar compounds," blog—In the pipeline, 2017, 15 pages.
Micoine et al, "A general strategy for ligation of organic and biological molecules to dawson and keggin polyoxotungstates", Org Chem. Lett., 2007, 9(20):3981-3984.
Palma et al., "CD137 and CD137 ligand constitutively coexpressed on human T and B leukemia cells signal proliferation and survival," Int J Cancer, Jan. 20, 2004, 108(3):390-398.
Rajendran et al., "CD137 signaling in Hodgkin and Reed-Sternberg cell lines induces IL-13 secretion, immune deviation and enhanced growth," Oncoimmunology, 2016, 5(6):e1160188, 7 pages.
Remacle et al., "Membrane type I-matrix metalloproteinase (MT1-MMP) is internalised by two different pathways and is recycled to the cell surface," Journal of cell science, 2003, 116(19):3905-3916.
Solomons, "Organic Chemistry", 4th ed, 1988, p902 (3 pages).
Thornber, "Isosterism and molecular modification in drug design", Chem. Soc. Rev, 1979, 8(4):563-580.
Yampolsky et al., "The exchangeability of amino acids in proteins", Genetics, 2005, 170(4):1459-1472.
https://investors.bicycletherapeutics.com/static-files/f456c054-95c8-4e19-a62a-fcf5feb0650b, Aug. 2024, 61 pages.
Anonymous, "Bicycle Therapeutics 2023 R&D Day Deck", https://investors.bicycletherapeutics.com/static-files/46599fde-67dc-40a8-9dcb-10ed8444f31e, Dec. 14, 2023, 155 pages.
Anonymous, "Bicycle Therapeutics BT8009 Regulatory Update", https://investors.bicycletherapeutics.com/static-files/265210c3-233f-4dd8-af32-d34592398d85, Sep. 11, 2023, 23 pages.
Bader et al., "Abstract 3088: Breaking from the paradigm of antibody-drug conjugates: Evaluation of clinical pharmacokinetics and safety of Bicycle Toxin Conjugates® (BTCs)", American Society of Clinical Oncology Annual Meeting, May 31-Jun. 4, 2024, pp. 1-9.
Baldini et al., "Abstract 498: BT8009-100: A Phase I/II Study of Novel Bicyclic Peptide and MMAE Conjugate BT8009 in Patients (pts) with Advanced Malignancies Associated with Nectin-4 Expression, Including Urothelial Cancer (UC)", ASCO Genitourinary (GU) Cancers Symposium Conference, Feb. 17, 2023, pp. 1-6.
Banerji et al., "A Cancer Research UK phase I/IIa trial of BT1718 (a first in class Bicycle Toxin Conjugate) given intravenously in patients with advanced solid tumours", ASCO, Jun. 5, 2018, pp. 1-4.
Banerji et al., "A Cancer Research UK phase I/IIa trial of BT1718 (a first in class Bicycle Toxin Conjugate) given intravenously in patients with advanced solid tumours", NCRI, Oct. 1, 2018, 1 page.
Battula et al., "Abstract 4613: A novel fully synthetic dual targeted EphA2/CD137 Bicycle® peptide induces tumor localized CD137 agonism", American Association of Cancer Research, Jun. 22, 2020, pp. 1-4.
Battula et al., "Abstract P794: A novel fully synthetic dual targeted EphA2/4-1BB Bicycle® peptide induces tumor localized 4-1BB agonism", SITC, Nov. 9, 2019, pp. 1-4.
Bendell et al., "TPS3655: BT5528-100 Phase I/II Study; Safety, Pharmacokinetics & Preliminary Clinical Activity of BT5528 in Patients with Advanced Malignancies Associated with EphA2 Expression", ASCO, May 29, 2020, 1 page.
Bennett et al., "Abstract 1167/2: Development of BT1718, a novel Bicycle Drug Conjugate for the treatment of lung cancer", American Association of Cancer Research, Apr. 1, 2017, pp. 1-4.

(56) References Cited

OTHER PUBLICATIONS

Bennett et al., “Abstract 164: BT5528, an EphA2-targeting Bicycle Toxin Conjugate (BTC): profound efficacy without bleeding and coagulation abnormalities in animal models”, EORTC, Nov. 13, 2018, pp. 1-6.
Bennett et al., “Abstract 5854: BT5528, a Bicycle Toxin Conjugate (BTC) targeting EphA2 has potent antitumour activity without bleeding or coagulation abnormalities in animal models”, American Association of Cancer Research, Apr. 14, 2018, pp. 1-6.
Bennett et al., “Abstract 5855: Bicycle Toxin Conjugates (BTCs) targeting EphA2 for the treatment of solid tumours: Discovery and selection of BT5528”, American Association of Cancer Research, Apr. 14, 2018, pp. 1-8.
Bennett et al., “Abstract C066: BT5528, a Bicycle Toxin Conjugate targeting EphA2: mechanism of action and clinical translation”, AACR-NCI-EORTC, Oct. 29, 2019, pp. 1-6.
Bennett, “Abstract 4481: BT5528, an EphA2-targeting Bicycle® Toxin Conjugate (BTC): Profound efficacy without bleeding and coagulation abnormalities in animal models”, AACR Annual Meeting, Apr. 4, 2019, 11 pages.
Bennett, “Bicycle Conjugates to Target Solid Tumors”, Next Generation Conjugates Summit, Feb. 27, 2023, 23 pages.
Bennett, “BT5528: A Bicycle Toxin Conjugate Targeting EphA2 for the Treatment of Solid Tumours”, 9th Annual World ADC Conference, Mar. 6, 2019, 13 pages.
Bournakas et al., “PBP inhibitors discovered using a modified phage display platform (Bicycles)”, ESCMID, Oct. 11, 2022, 1 page.
Brandish, “Bicycle Therapeutics: Precision-guided immune agonism for the treatment of cancer”, Immuno UK meeting, Sep. 30, 2022, 25 pages.
Campbell et al., “Poster 1197: A multi tumor survey of Nectin-4 expression to guide BT8009 indication selection”, American Association of Cancer Research, Apr. 12, 2021, pp. 1-4.
Campbell et al., “Poster 5300: A survey of EphA2 expression by Immunohistochemistry (IHC) in tumor tissue microarrays (TMAs) to support BT5528 indication selection”, American Association of Cancer Research, Jun. 22, 2020, pp. 1-6.
Carabateas et al., “Strong Analgesics, Some 1-Substituted 4-Phenyl-4-Propionoxypiperidines”, Journal of Medicinal and Pharmaceutical Chemistry, Sep. 1962, 5:913-919.
CAS No. 18226-42-1, “1,3,5-Tris(bromomethyl)benzene”, Chemical Book, Retrieved from: https://www.chemicalbook.com/ProductChemicalPropertiesCB0500171_EN.htm, 2023, 2 pages.
Chen et al., “Abstract A8: Novel Multimers of Bicyclic Peptides Cluster and Activate CD137 (4-1BB): A Costimulatory T-Cell Checkpoint Receptor”, PEGS, Nov. 12, 2018, pp. 1-7.
Cohen et al., “Abstract 2: Quantitation of CD137 and Nectin-4 expression across Multiple tumor types to support indication selection for BT7480, a Bicycle tumor-targeted immune cell agonist™ (Bicycle TICA™)”, SITC, Nov. 12, 2021, pp. 1-7.
Cohen et al., “Abstract 5555: Development of a CD137 receptor occupancy assay to support the phase I/II study of BT7480, a Bicycle® tumor-targeted immune cell agonist (Bicycle TICA™)”, American Association of Cancer Research, Apr. 8, 2022, pp. 1-6.
Cohen et al., “Abstract A65: Development of a CD137 receptor occupancy assay to support the phase I/II study of BT7480, a Bicycle tumor-targeted immune cell agonist® (Bicycle TICA®)”, AACR-BC-EORTC, Oct. 26, 2022, pp. 1-7.
Cohen, “Translating preclinical findings into clinical biomarker assays to support the Phase I/II study of BT7480, a Bicycle tumor-targeted immune cell agonist®”, World Clinical Biomarkers & CDx Summit, Sep. 28, 2022, 21 pages.
Cohen, “Turning preclinical findings into clinic-ready biomarker assays to support BT7480 development”, Markets and Markets Biomarker and Companion Diagnostics Conference, Feb. 15, 2023, 21 pages.
Cook et al., “Abstract 5764: Pharmacokinetic (PK) assessment of BT1718 : A phase 1/2a study of BT1718, a first in class bicycle toxin conjugate (BTC), in patients with advanced solid tumours”, EMSO, Sep. 28, 2019, pp. 1-4.
Cooke, “Bicycles as precision guided therapeutics”, UK Symposium: Advancing Drug Discovery for Oncology, Mar. 13, 2023, 15 pages.
Drumm et al., “Genetic Variation and Clinical Heterogeneity in Cystic Fibrosis”, Annu. Rev. Pathol. Mech. Dis., 2012, 7:267-282.
Dufort et al., “Abstract 1340: Modulation of the natural killer cell immune response to tumor with a synthetic tumor-immune cell agonist, NK-TICA®”, American Association for Cancer Research Annual Meeting, Apr. 8, 2024, pp. 1-6.
Dufort et al., “Abstract 15699: Generation of a Bicycle NK-TICA™, a novel NK cell engaging molecule designed to induce targeted tumor cytotoxicity”, SITC, Nov. 12, 2022, pp. 1-5.
Dufort et al., Abstract 1806: Modulation of the natural killer (NK) cell immune response to tumor with novel synthetic tumor-immune cell agonist, NK-TICA™, American Association for Cancer Research Annual Meeting, Apr. 17, 2023, pp. 1-7.
Dufort et al., “Abstract 4233: Generation of a Bicycle NK-TICA™, a novel NK cell engaging molecule designed to induce targeted tumor cytotoxicity”, American Association for Cancer Research, Apr. 8, 2022, pp. 1-5.
Dufort, “Bicycles: Bispecific, Precision-guided NK Cell Activators for the Treatment of Solid Tumors”, Innate Killer Summit, Mar. 29, 2023, 23 pages.
Eder et al., “Bicyclic Peptides as a New Modality for Imaging and Targeting of Proteins Overexpressed by Tumors”, Cancer Res., Feb. 15, 2019, 79(4):841-852.
Evans et al., “Abstract CT253: Phase 1/2 study of the safety, pharmacokinetics, and preliminary clinical activity of BT7480 in patients with Nectin-4 associated advanced malignancies”, American Association for Cancer Research Annual Meeting, Apr. 18, 2023, pp. 1-5.
Frigerio, “Expanding the Potential of ADCs: Bicyclic Peptide (Bicycle®) Toxin Conjugates May Offer Advancements Over Traditional ADCs”, World ADC, Mar. 20, 2023, 28 pages.
Frigerio, “Targeting Tumors with Bicycle Conjugates”, PEGS Boston, May 17, 2023, 31 pages.
Gelb et al., “Abstract A047: MT1-MMP Immunohistochemistry (IHC) analysis of tumor microarrays (TMAs) using a novel scoring system guides patient selection for BT1718 expansion cohorts”, AACR-NCI-EORTC, Oct. 27, 2019, pp. 1-7.
GenBank Accession No. CZR33441.1, “uncharacterized protein FPRO_01747 [Fusariumn proliferatum ET1]”, National Center for Biotechnology Information, Retrieved from: https://www.ncbi.nlm.nih.gov/protein/1111492376, Dec. 6, 2016, 1 page.
Hadjicharalambous et al., “Investigating Penetration and Antimicrobial Activity of Vector Bicycle Conjugates”, ACS Infectious Diseases, Jun. 12, 2024, 10(7):2381-2389.
Harrison et al., “Abstract 5144: BT1718, a novel bicyclic peptide-maytansinoid conjugate targeting MT1-MMP for the treatment of solid tumours: Design of bicyclic peptide and linker selection”, AACR Annual meeting, Apr. 1, 2017, pp. 1-7.
Harrison et al., “Discovery and development of BT1718, a novel bicyclic peptidemaytansinoid conjugate targeting MT1-MMP for the treatment of solid tumours: In vitro and in vivo activities”, PEGS, Apr. 30, 2017, 1 page.
Hu et al., “Lessons Learned from Molecular Scaffold Analysis”, Journal of Chemical Information and Modeling, 2011, 51(8):1742-1753.
Hurov et al., “Abstract 1340: BT7455, a fully synthetic Bicycle tumor-targeted immune cell agonist®, leads to potent EphA2-dependent CD137 agonism and robust anti-tumor efficacy”, SITC, Nov. 10, 2022, pp. 1-6.
Hurov et al., “Abstract 3257: Activation of 4-1BB using multivalent and tumour targeted bicyclic peptides”, American Association of Cancer Research, Apr. 2, 2019, pp. 1-4.
Hurov et al., “Abstract 3257: Activation of CD137 using multivalent and tumor targeted Bicyclic peptides”, Cancer Res, Jul. 1, 2019, 79(13_Supplement):3257, 3 pages.
Hurov et al., “Abstract 700: EphA2/CD137 Bicycle® tumor-targeted immune cell agonists (TICAs™) induce tumor regressions, immunogenic memory, and reprogramming of the tumor immune microenvironment”, SITC, Nov. 9, 2020, pp. 1-4.

(56) References Cited

OTHER PUBLICATIONS

Hurov et al., "Abstract P398: Activation of the T cell costimulatory protein CD137 using multivalent bicyclic peptides", SITC, Nov. 6, 2018, pp. 1-5.
Hurov et al., "Abstract P782: A novel fully synthetic dual targeted Nectin-4/4-1BB Bicycle® peptide induces tumor localized 4-1BB agonism", SITC, Nov. 9, 2019, pp. 1-6.
Hurov et al., "BT7480, a novel fully synthetic Bicycle tumor-targeted immune cell agonist™ (Bicycle TICA™) induces tumor localized CD137 agonism", Journal for Immuno Therapy of Cancer, 2021, 9(11):e002883, pp. 1-13.
Hurov et al., "Poster 1728: Nectin-4-dependent immune cell stimulation and anti-tumor efficacy by BT7480, a Nectin-4/CD137 Bicycle® tumor-targeted immune cell agonist (TICA™)", American Association of Cancer Research, Apr. 12, 2021, pp. 1-6.
Hurov, "BT7480, a novel and fully synthetic Bicycle tumor-targeted immune cell agonist®", Festival of Biologics, Nov. 4, 2022, 23 pages.
Kanakia et al., "Development of CD137 (4-1BB) receptor occupancy assay using fluorescently labeled Bicycles®", AACR Tumor Immunology & Immunotherapy, Oct. 19, 2020, 5 pages.
Keen, "A novel fully synthetic dual targeted Nectin-4/4-1BB Bicycle® peptide induces tumor localized 4-1BB agonism", SITC, Nov. 6-10, 2019, 19 pages.
Keen, "BT5528, an EphA2-targeting Bicycle® Toxin Conjugate", World ADC congress, Oct. 11, 2019, 24 pages.
Keen, "BT7480, a novel Nectin-4 dependent agonist of the immune cell costimulatory receptor CD137", AACR Annual Meeting, Apr. 10-15 and May 17-21, 2021, 23 pages.
Kristensson et al., "Novel Bicyclic Peptide Multimers Activate T Cell Costimulatory Protein CD137", ELRIG Drug Discovery, Oct. 9, 2018, pp. 1-7.
Kristensson et al., "Novel Bicyclic Peptide Multimers Activate T Cell Costimulatory Protein CD137", Promega Biologics, Jul. 18, 2018, pp. 1-7.
Kumara et al., "Fusarium proliferatum, an endophytic fungus from Dysoxylum binectariferum Hook.f, produces rohitukine, a chromane alkaloid possessing anti-cancer activity", Antonie van Leeuwenhoek, 2012, 101(2):323-329.
Lahdenranta et al., "Abstract 1356: Transcriptional profiling of Bicycle® tumor-targeted CD137 agonist-treated mouse tumors revealed an early and rapid activation of myeloid cells followed by infiltration of cytotoxic T cells into the tumor", SITC, Nov. 10, 2022, pp. 1-9.
Lahdenranta et al., "Abstract 5301: Tumor-targeted activation of CD137 using Bicycle® molecules: New insights into mechanism of action and discovery of BT7455, a clinical candidate for the treatment of EphA2-expressing cancers", American Association for Cancer Research Annual Meeting, Apr. 9, 2024, pp. 1-5.
Lahdenranta et al., "Abstract A067: BT7480, a synthetic Bicycle tumor-targeted immune cell agonist® (Bicycle TICA®), induces reprogramming of the tumor immune microenvironment through tumor localized CD137 agonism", CICON, Sep. 29, 2022, pp. 1-9.
Lahdenranta et al., "Poster 1319: Rapid accumulation of cytotoxic payload in tumor tissue drives BT5528 activity in tumor models", American Association of Cancer Research, Apr. 12, 2021, pp. 1-4.
Lahdenranta et al., "Poster 1724: Microinjection of Nectin-4/CD137 tumor-targeted immune cell agonist (TICA™) activates the local tumor microenvironment", American Association of Cancer Research, Apr. 12, 2021, pp. 1-4.
Lahdenranta et al., "Poster 706: BT7480, a fully synthetic tumor-targeted immune cell agonist (TICA™) induces tumor localized CD137 agonism and modulation of tumor immune microenvironment", SITC, Nov. 9, 2020, pp. 1-6.
Loriot et al., "Abstract TPS4619: A phase 2/3 study of Bicycle® Toxin Conjugate zelenectide pevedotin (BT8009) targeting Nectin-4 in patients with locally advanced or metastatic urothelial cancer (la/mUC) (Duravelo-2)", American Society of Clinical Oncology Annual Meeting, May 31-Jun. 4, 2024, 1 page.
Ludbrook, "Bicycle Toxin Conjugates to Target Solid Tumors", 3rd ADC Target Selection Summit, Dec. 6, 2023, 20 pages.
Luus et al., "Abstract 1832: EphA2-dependent CD137 agonism and anti-tumor efficacy by BT7455, a Bicycle tumor-targeted immune cell agonist®", American Association for Cancer Research Annual Meeting, Apr. 17, 2023, pp. 1-7.
McDonnell, "Bicycles for precision guided delivery", Boulder Peptide Symposium, Nov. 9, 2022, 29 pages.
McKean et al., "A Combined Phase I/II Study of BT8009 a Novel Bicycle® Toxin Conjugate with MMAE in Patients with Advanced Malignancies with Nectin-4", ASCO, Jun. 4, 2021, 1 page.
McKean et al., "BT8009-100 Phase I/II Study of Novel Bicyclic Peptide and MMAE Conjugate BT8009 in Patients with Advanced Malignancies Associated with Nectin-4 Expression", American Association for Cancer Research, Apr. 8-13, 2022, 17 pages.
McKean et al., "BT8009-100 Phase I/II Study of the Safety, Pharmacokinetics, & Preliminary Clinical Activity of BT8009 in Patients with Nectin-4 Expressing Advanced Malignancies", ESMO, Sep. 17, 2020, 1 page.
McKean, "A first in class phase I/II study of the novel bicyclic peptide and MMAE conjugate, BT5528, in patients with advanced malignancies associated with EphA2 expression", AACR-NCI-EORTC, Oct. 7-10, 2021, 19 pages.
Mistry et al., "Abstract 15523: Establishing the preclinical/translational PK/PD relationship for BT7480, a Nectin4/CD137 Bicycle tumor-targeted immune cell agonist™ (Bicycle TICA™)", SITC, Nov. 12, 2021, pp. 1-5.
Mistry et al., "Synthesis of Bicycle® Peptides using Gold-mediated Cysteine Arylation", European Peptide Synthesis Conference, Mar. 7, 2023, 1 page.
Mudd et al., "Bicyclic Peptides for Positron Emission Tomography (PET) Imaging of MT1-MMP Expressing tumours", PEGS, Apr. 30, 2017, 1 page.
Mudd et al., "Discovery of BT8009: A Nectin-4 Targeting Bicycle Toxin Conjugate for the Treatment of Cancer", Journal of Medicinal Chemistry, 2022, 65(21): 14261-14970.
Mudd et al., "Gold-Mediated Multiple Cysteine Arylation for the Construction of Highly Constrained Bicycle Peptides", Bioconjugate Chemistry, 2022, 33(8):1441-1445.
Mudd et al., "Potent anti-tumor activity of a Lead-212 labelled MT1-MMP targeting Bicycle Radionuclide ConjugateTM ", TIDES USA—Oligonucleotide, May 8, 2023, pp. 1-7.
Newman et al., "Anti-Infectives Drug Discovery at Bicycle Therapeutics", ESCMID, Oct. 11, 2022, 1 page.
Newman, "Characterisation of novel, noncovalent cyclic peptide (Bicycles®) inhibitors of PBP3s from important Gram-negative pathogens", ESCMID, Oct. 11, 2022, 18 pages.
Ngo et al., "Abstract 333: Activity of the erythropoietin-producing hepatocellular A2 Receptor (EphA2) targeting Bicycle® Toxin Conjugate (BTC™) BCY6033 in EGFR inhibitor resistant non-small cell lung cancer (NSCLC) patient derived xenografts", American Association for Cancer Research, Apr. 8, 2022, pp. 1-6.
Nguyen, "Pancreatic Cancer", Merck Manual, Retrieved from: https://www.merckmanuals.com/home/digestive-disorders/tumors-of-the-digestive-system/pancreatic-cancer?query=pancreatic%20cancer, Mar. 2021, 4 pages.
Papadopoulos et al., "Abstract TPS2689: A Combined Phase I/II Study of a Novel Bicycle Tumor-targeted Immune Cell Agonist® BT7480 in Patients with Nectin-4 Associated Advanced Malignancies", ASCO, Jun. 6, 2022, 1 page.
Park et al., "Abstract 3756: Small Synthetic, Multivalent Bicyclic Peptides That Activate T Cell Costimulatory Protein CD137", American Association of Cancer Research, Apr. 14, 2018, pp. 1-9.
Park et al., "Abstract 3756: Small Synthetic, Multivalent Bicyclic Peptides That Activate T Cell Costimulatory Protein CD137", Cancer Res., Jul. 1, 2018, 78(13_Supplement):3756, 2 pages.
Park et al., "Abstract 3756: Small Synthetic, Multivalent Bicyclic Peptides That Activate T Cell Costimulatory Protein CD137", Elrig Drug Discovery, Oct. 9, 2018, pp. 1-9.
Repash et al., "BT7480, a novel fully synthetic tumor-targeted immune cell agonist (TICA™) induces tumor localized CD137 agonism", AACR Tumor Immunology & Immunotherapy, Oct. 19, 2020, 10 pages.

(56) References Cited

OTHER PUBLICATIONS

Rezvaya et al., "Abstract 1207: NKp46 engaging Bicycle NK-TICA® drives tumor targeted cytotoxicity", SITC, Nov. 10, 2022, 1 page.
Rhodes et al., "Bicyclic Peptides as Next-Generation Therapeutics", Chemistry—A European Journal, 2017, 23(52):12690-12703.
Rietschoten et al., "Abstract 268: Small Synthetic, Multivalent Bicyclic Peptides That Activate T Cell Costimulatory Protein CD137", 35th European Peptide Symposium, Aug. 1, 2018, 1 page.
Rigby et al., "Abstract 4479: BT8009: A bicyclic peptide toxin conjugate targeting Nectin-4 (PVRL4) displays efficacy in preclinical tumor models", Cancer Res, 2019, 79(13_Supplement):4479, 3 pages.
Rigby et al., "Abstract C061: BT8009, a Bicycle® Toxin Conjugate targeting Nectin-4, shows target selectivity, and efficacy in preclinical large and small tumor models", AACR-NCI-EORTC, Oct. 29, 2019, pp. 1-9.
Rigby et al., "BT8009; A Nectin-4 Targeting Bicycle® Toxin Conjugate for Treatment of Solid Tumors", Molecular Cancer Therapeutics, 2022, 21(12): 1-27.
Rigby, "Abstract 4479: BT8009: A bicyclic peptide toxin conjugate targeting Nectin-4 (PVRL4) displays efficacy in preclinical tumour models", AACR Annual Meeting, Apr. 2, 2019, 10 pages.
Santos et al., "Abstract 35472: Characterization of Nectin-4 protein expression in non-small cell lung cancer patients", AACR-BC-EORTC, Oct. 13, 2023, pp. 1-4.
Shah et al., "Abstract A28: Establishment of an ex vivo tissue culture platform as a preclinical model to assess the mechanism of action of Bicycle® tumor-targeted immune cell agonists in NSCLC", AACR-BC-EORTC, Oct. 26, 2022, pp. 1-8.
Singh et al., "Protein Engineering Approaches in the Post-Genomic Era", Current Protein and Peptide Science, 2017, 18(4):1-11.
Skynner et al., "BT1718, a novel Bicycle Drug Conjugate® shows potent anti-tumor activity in diverse cell-derived and patient-derived tumor xenograft models", PEGS, Apr. 30, 2017, 1 page.
Stanczuk et al., "Abstract 1388: Utility of humanized animal models for in vivo evaluation of NK-TICA®, novel Bicycle® tumor-targeted immune cell agonist® (Bicycle TICA®) designed to engage NK cells", SITC, Nov. 10, 2022, pp. 1-6.
Stanczuk et al., "Abstract 1826: Development of in vivo models for evaluation of NK-TICATM, novel Bicycle® tumortargeted immune cell agonist® designed to engage NK cells", American Association for Cancer Research Annual Meeting, Apr. 17, 2023, pp. 1-6.
Su, "Key DMPK Attributes of BT7480, a Bicycle Tumor-targeted Immune Cell AgonistTM Targeting Nectin-4 and Agonizing CD137", NEDMDG symposium, May 31, 2023, 20 pages.
Teufel et al., "Abstract 4920: Bicyclic Peptides for Positron Emission Tomography (PET) Imaging of MT1-MMP Expressing Tumors", American Association of Cancer Research, Apr. 1, 2017, pp. 1-8.
Tiberghien, "Highlighting the Potential of Bicycle Conjugates to Target Solid Tumours", World ADC, Mar. 20, 2023, 24 pages.
Uhlenbroich et al., "Abstract 0000: NKp46 engaging Bicycle NK-TICA™ drives tumor targeted cytotoxicity", PEGS Boston, May 17, 2023, 1 page.
Uhlenbroich, "Bicycles—a modality for Tumor-Targeted Immune Cell Agonism", Antibody Engineering & Therapeutics, Jun. 12, 2023, 23 pages.
Upadhyaya et al., "Abstract 888: An integrative approach to optimize a synthetic EphA2-dependent CD137 agonist: Balancing potency, physiochemical properties, and pharmacokinetics to achieve robust anti-tumor activity", SITC, Nov. 12, 2021, pp. 1-7.
Upadhyaya et al., "Anticancer immunity induced by a synthetic tumor-targeted CD137 agonist", Journal for Immunotherapy of Cancer, 2021, 9(1):e001762, pp. 1-10.
Upadhyaya et al., "Discovery and Optimization of a Synthetic Class of Nectin-4-Targeted CD137 Agonists for Immuno-oncology", Molecular Cancer Therapeutics, 2022, 65:9858-9872.
Upadhyaya, "Activation of CD137 using multivalent and tumour targeted bicyclic peptides", Peptide Congress, Retrieved from: https://www.bicycletherapeutics.com/wp-content/uploads/PU_2019-Peptide-Congress_publication.pdf, Apr. 2019, 25 pages.
Valko et al., "Application of biomimetic HPLC to estimate lipophilicity, protein and phospholipid binding of potential peptide therapeutics", ADMET and DMPK, 2018, 6(2):162-175.
Wagstaff et al., "An Assay for Periplasm Entry Advances the Development of Chimeric Peptide Antibiotics", ACS Infectious Diseases, 2020, 6(9):2355-2361.
Wallack et al., "Abstract P05: Investigating soluble Nectin-4 and EphA2 as cancer biomarkers in plasma", Bio-IT World, May 23, 2023, pp. 1-6.
Walsh et al., "Abstract 5807: Bicycle Toxin Conjugates® for the treatment of solid tumors", American Association for Cancer Research Annual Meeting, Apr. 9, 2024, pp. 1-7.
Wang et al., "Comprehensive Surfaceome Profiling to Identify and Validate Novel Cell-Surface Targets in Osteosarcoma", Molecular Cancer Therapeutics, Jun. 2022, 21(6):903-913.
Wang et al., "Integrative surfaceome profiling identifies immunotherapeutic targets in osteosarcoma and preclinical testing of BT1769, an MT1-MMP-targeted Bicycle® toxin conjugate, in osteosarcoma by the Pediatric Preclinical Testing Consortium (PPTC)", AACR Annual Meeting, April 10-15 and May 17-21, 2021, 15 pages.
Xu et al., "The application of PK/PD modelling in the clinical development of BT5528 a novel toxin delivery platform", ACoP, Oct. 30-Nov. 2, 2022, 21 pages.
Zhang et al., "Characterization and application of three novel monoclonal antibodies against human 4-1BB: distinct epitopes of human 4-1BB on lung tumor cells and immune cells", Tissue Antigens, 2007, 70(6):470-479.
Zhang et al., "Propagated Perturbations from a Peripheral Mutation Show Interactions Supporting WW Domain Thermostability", Structure, Nov. 6, 2018, 26(11):1474-1485.
U.S. Appl. No. 18/427,414, Beswick et al., filed Jan. 30, 2024.
U.S. Appl. No. 18/742,691, Chen, filed Jun. 13, 2024.
U.S. Appl. No. 18/906,616, Beswick et al., filed Oct. 4, 2024.
Adams et al., "Big Opportunities for Small Molecules in Immuno-oncology," Nature Reviews, 2015, 14:603-622.
Akanuma et al., "MicroRNA-133a regulates the mRNAs of two invadopodia-related proteins, FSCN1 and MMP14, in esophageal cancer," Br J Cancer., Jan. 7, 2014, 110(1):189-198.
Angelini et al., "Bicyclic peptide inhibitor reveals large contact interface with a protease target." ACS chemical biology 7, No. 5 (2012): 817-821.
Anonymous, "Bicycle Conjugates", URL:https://web.archive.org/web/20210104063050/https://www.bicycletherapeutics.com/programs, 2021, 4 pages.
Anonymous, "Bicycle Therapeutics to Present New Translational Research for BT5528 and Preclinical Data for Tumor-targeted Immune Cell Agonists at the AACR Virtual Annual Meeting II," May 15, 2020; 2 pages. URL:https://www.businesswire.com/news/home/20200515005111/en/Bicycle-Therapeutics- to-Present-New-Translational-Research-for-BT5528-and-Preelinical-Data-for-Tumor-targeted-Immune-Cell-Aaonists-at-the-AACR-Virtual-Annual-Meetina-II.
Anonymous, "Constrained Peptides Unconstrained Thinking Forward-Looking Statements", URL: https://investors.bicycletherapeutics.com/static-files/5f7f462f-2417-439d-b829-d723b3fd65f7, Aug. 2019, 26 pages.
Anthony et al., "Recapitulation of IVIG anti-inflammatory activity with a recombinant IgG Fc", Science Apr. 18, 2008;320(5874):373-376.
Arkadash et al., "Development of High Affinity and High Specificity Inhibitors of Matrix Metalloproteinase 14 through Computational Design and Directed Evolution" J. Biol. Chem. 2017, 292(8), 3481-3495.
Arnon et al., "The mechanisms controlling the recognition of tumor-and virus-infected cells by NKp46", Blood, Jan. 15, 2004;103(2):664-672.
Arnould et al., "Trastuzumab-based treatment of HER2-positive breast cancer: an antibody-dependent cellular cytotoxicity mechanism?", Br J Cancer, 2006, 94(2):259- 267.

(56) References Cited

OTHER PUBLICATIONS

Askoxylakis et al., "A New Peptide Ligand for Targeting Human Carbonic Anhydrase IX, Identified through the Phage Display Technology", PLoS One, Dec. 2010, 5(12):10 pages.
Augoff et al., "Upregulated expression and activation of membrane-associated proteases in esophageal squamous cell carcinoma." Oncology reports, 2014, 31(6):2820-2826.
Baek et al. "Effects of Histidine and Sucrose on the Biophysical Properties of a Monoclonal Antibody," Pharmaceutical Antibody, 2017, 34(3):629-639.
Banerji et al., "A Cancer research UK Phase I/IIA Trail of BT1718 (a first in class Bicycle Drug Conjugate) Given Intravenously in Patients with Advanced Solid Tumours," Journal of Clinical Oncology, Jan. 2018, 36(15):PS2610. (1 Page).
Banerji et al., "Preliminary pharmacokinetic assessment of BT1718: A phase I/IIa trial of BT1718 (a first in class Bicycle Toxin Conjugate) in patients with advanced solid tumours." In european journal of cancer, 2018, 103:E65-e65.
Barbas III et al., "Semisynthetic combinatorial antibody libraries: a chemical solution to the diversity problem," Proceedings of the National Academy of Sciences of the United States of America, May 1992, 89(10):4457-4461.
Barbolina et al., Microenvironmental regulation of membrane type 1 matrix metalloproteinase activity in ovarian carcinoma cells via collagen-induced EGR1 expression. Journal of Biological Chemistry, 2007, 282(7):4924-4931.
Bardia et al., "Efficacy and safety of anti-trop-2 antibody drug conjugate sacituzumab govitecan (IMMU-132) in heavily pre-treated patients with metastatic triple-negative breast cancer." Journal of Clinical Oncology, 2017, 35(19):2141.
Bech et al., "Chemical Strategies for Half-Life Extension of Biopharmaceuticals: Lipidation and Its Alternatives," ACS Medicinal Chemistry Letters, Jun. 2018, 9(7):577-580.
Bennett et al., "The Mechanism of Action of BT1718, a Novel Small-Molecule Drug Conjugate for the Treatment of Solid Tumors Expressing MT1-MMP," AACR-NCI- EOrTC International Conference: Molecular Taroets and Cancer Therapeutics, Jan. 2018, 26-30.
Ben-Shmuel et al., "Unleashing Natural Killer Cells in the Tumor Microenvironment—The Next Generation of Immunotherapy?", Front Immunol., 2020, 11:275.
Berenson, "Multiple Myeloma," Merck Manual, Retrieved from:https://www.merckmanuals.com/home/blood-disorders/plasma-cell-disorders/multiplemyeloma?query=multiple%20myeloma, Oct. 2022.
Berkel et al. "Binding of (5 S)-penicilloic acid to penicillin binding protein 3." ACS chemical biology 8, No. 10 (2013): 2112-2116.
Bernhagen et al., "Design, synthesis and characterization of different bicyclic peptides with enhanced binding and selectivity for various integrins", Retrieved form: https://ec.europa.eu/research/participants/documents/downloadPublic?documentIds=080166e5acfd6757&appId=PPGMS, Oct. 14, 2016, XP55622035:1-6.
Beswick, Paul, "Bicycles—An entirely new class of therapeutics," accessed on https://www.bicycletherapeutics.com/wp-content/uploads/RSC-02-May 2019.pdf, 2019, 21 pages.
Bicycle Therapeutics, "Bicycle Therapeutics and Cancer Research UK Announce Inititation of FirstClinical Study of a Bicyclic Peptide (Bicycle®)," Press Release, Feb. 13, 2018, https://investors.bicycletherapeutics.com/node/6651/pdf.
Bilsky, Mark H., "Gliomas", Merck Manual (https://www.merckmanuals.com/professional/neurologic-disorders/intracranial-and-spinal-tumors/gliomas), May 2023, 8 pages.
Biron et al., "Improving oral bioavailability of peptides by multiple N-methylation: somatostatin analoques," Angewandte Chemie International Edition, 2008, 47(14):2595-2599.
Blank et al., "Absence of Programmed Death Receptor 1 Alters Thymic Development and Enhances Generation of CD4/CD8 Double-Negative TCR-Transgenic T Cells " in Journal of Immunology, Nov. 2003, 171(19):4574-4581.
Bogaerts et al., "Individual patient data analysis to assess modifications to the RECIST criteria." European journal of cancer, 2009, 45(2):248-260.
Bolland et al., "Spontaneous autoimmune disease in Fc(gamma)RIIB-deficient mice results from strain-specific epistasis", Immunity, Aug. 2000, 13(2):277-285.
Borghaei et al., "Nivolumab versus docetaxel in advanced nonsquamous non—small-cell lung cancer." New England Journal of Medicine, 2015, 373(17):1627-1639.
Borrelli et al., "Cell Penetrating Peptides as Molecular Carriers for Anti-Cancer Agents," Molecules, Feb. 2018, 23(2):295. (28 pages).
Boruchov et al., "Activating and inhibitory IgG Fc receptors on human DCs mediate opposing functions", The Journal of Clinical Investigation, 2005, 115(10):2914-2923.
Bouchard et al., "Antibody—drug conjugates—a new wave of cancer drugs." Bioorganic & medicinal chemistry letters, 2014, 24(23):5357-5363.
Bristol-Myers Squibb, "An Investigational Immuno-Therapy Study to Investigate the Safety and Effectiveness of Nivolumab, and Nivolumab Combination Therapy in Virus-Associated Tumors—Full Text View—Clinicaltrials." Gov.[(accessed on Jan. 30, 2021)] (2018).
Brown et al., "Blockade of programmed death-1 ligands on dendritic cells enhances T cell activation and cytokine production", Journal of Immunolgy, Feb. 2003, 170(3):1257-1266.
Brahmer et al., "Nivolumab versus docetaxel in advanced squamous-cell non—small-cell lung cancer." New England Journal of Medicine 373, No. 2 (2015): 123-135.
Cabanillas et al., "Phase I study of maytansine using a 3-day schedule," Cancer Treat Rep., Mar. 1978, 62(3):425-428.
Cancer Research UK, "Soft tissue sarcomas," Retrieved from : http://aboutcancer.cancerresearchuk.org/about-cancer/soft-tissue-sarcoma, Sep. 2022.
Cancer Research UK, "Triple Negative Breast Cancer," Retrieved from: https://www.cancerresearchuk.org/about-cancer/breast-cancer/stages-types-grades/types/triplenegative-breast-cancer#, Sep. 2022, 6 pages.
Cancer Research UK, "Types of lung cancer," Retrieved form: https://www.cancerresearchuk.org/about-cancer/lung-cancer/stages-types-grades/types#, Sep. 2022.
Cancer Research UK, "Your mouth and cancer drugs," Retrieved form : https://www.cancerresearchuk.org/about-cancer/cancer-in-general/treatment/cancer-drugs/sideeffects/your-mouth, Sep. 2022, 5 pages.
Caratelli et al., "FCγ Chimeric Receptor-Engineered T Cells: Methodology, Advantages, Limitations, and Clinical Relevance", Frontiers in Immunology, Apr. 27, 2017, :8:457, 8 pages.
Center for Panceratic and Biliary Diseases, "Bile Duct Cancer," University of Southern California, Department of Surgery. Retrieved from https://web.archive.org/web/20171207023733/http://www.surgery.usc.edu:80/divisions/tumor/PancreasDiseases/web%20pages/BILIARY%20SYSTEM/cholangiocarcinoma.html.
Chabner et al., "Initial clinical trials of maytansine, an antitumor plant alkaloid." Cancer Treat Rep., 1978, 62(3):429-433.
Chahinian et al., "Phase I study of weekly maytansine given by iv bolus or 24-hour infusion," Cancer Treat Rep., Nov. 1979, 63(11-12), 1953-1960.
Challita-Eid et al., "Enfortumab Vedotin Antibody-Drug Conjugate Targeting Nectin-4 Is a Highly Potent Therapeutic Agent in Multiple Preclinical Cancer Models", Cancer Research, 2016, 76(10):3003-3013.
Chandrasekar, "Bladder Cancer," Merck Manual. ; Retrieve form: https://www.merckmanuals.com/professional/genitourinary-disorders/genitourinary-cancers/bladder-cancer, Sep. 2022.
Chandrasekar, "Prostate Cancer," Merck Manual. Retrieved from: https://www.merckmanuals.com/professional/genitourinary-disorders/genitourinary-cancers/prostate-cancer, Sep. 2022.
Chang et al., "Subtiligase: A Tool for Semisynthesis of Proteins", Proc Natl Acad Sci, 1994, 91(26):12544-12548.
Chemnitz et al., "RNA fingerprints provide direct evidence for the inhibitory role of TGFB and PD-1 on CD4+ T cells in Hodgkin lymphoma", Blood, 2007, 110(9):3226-3233.

(56) References Cited

OTHER PUBLICATIONS

Chen and Harrison, "Cell-Penetrating Peptides in Drug Development: Enabling Intracellular Targets," Biochemical Society Transactions, 2007, 35(4):821-825.
Chen et al., "Association of FCGR3A and FCGR3B copy number variations with systemic lupus erythematosus and rheumatoid arthritis in Taiwanese patients", Arthritis & Rheumatology, 2014, 66(11):3113-3121.
Cheng et al., "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology", J Molecular Diagnostics, 2015, 17(3):251-264.
Chinnery et al., "Viral antigen mediated NKp46 activation of NK cells results in tumor rejection via NK-DC crosstalk", Oncoimmunology, 2012, 1(6):874-883.
Christina Chun, "What are the most curable cancers?", Medical news Today (https://www.medicalnewstoday.com/articles/322700 Accessed May, 8, 2020), 2020, 8 pages.
Chung et al., "Bicycle synthesis through peptide macrocyclization using aziridine aldehydes followed by late stage disulfide bond installation." MedChemComm, 2023, 4(7):1124-1128.
Clarkson et al., "Treatment of refractory immune thrombocytopeniaurpura with an anti-Fc gamma-receptor antibody", The New England Journal of Medicine, 1986, 314(19):1236-1239.
Claus et al., "Tumor-targeted 4-1BB agonists for combination with T cell bispecific antibodies as off-the-shelf therapy", Sci Transl Med., Jun. 2019, 11(496):eaav5989. (12 Pages).
Clynes et al., "Inhibitory Fc receptors modulate in vivo cytotoxicity against tumor targets", Nature Medicine, Apr. 2000, 6(4):443-446.
Committee for Medicinal Products for Human Use (CHMP), "Assessment Report: Kadcyla; International non-proprietary name: Trastuzumab emtansine; Procedure No. EMEA/H/C/002389/0000," European Medicines Agency. Sep. 19, 2013; EMA/749228/2013.
Connolly et al., "Complexities of TGF-β Targeted Cancer Therapy", Int'l J. Biological Sciences, 2012, 8(7):964-978.
Cook et al., "Pharmacokinetic (PK) Assessment of BT1718: A Phase 1/2a Study of BT1718, a First in Class Bicycle Toxin Conjugate (BTC), in Patients (PTS) with Advanced Solid Tumours," Annals of Oncology 2019; vol. 30, Jan. 2019, Page v174.
Cortes et al., "Phase II study of the halichondrin B analog eribulin mesylate in patients with locally advanced or metastatic breast cancer previously treated with an anthracycline, a taxane, and capecitabine." Journal of Clinical Oncology, 2010, 28(25):3922-3928.
Costello et al., "Defective expression and function of natural killer cell-triggering receptors in patients with acute myeloid leukemia", Blood, 2002, 99(10):3661-3667.
Crameri et al., "Construction and evolution of antibody-phage libraries by DNA shuffling," Nature Medicine, Jan. 1996, 2(1):100-102.
Cui, J. Jean., "A New Challenging and Promising Era of Tyrosine Kinase Inhibitors", ACS Med Chem Lett., 2014, 5(4):272-274.
Curiel et al., "Blockade of B7-H1 improves myeloid dendritic cell-mediated antitumor immunity", In Nature medicine, 2003, 9(5):562-567.
Davies et al., "Antibody VH Domains as Small Recognition Units," Bio/Technology, May 13, 1995, 13(5):475-479.
Davis et al., "Natural killer cells unleashed: Checkpoint receptor blockade and BiKE/TriKE utilization in NK-mediated anti-tumor immunotherapy", Semin Immunol., 2017, 31:64-75.
Dawson et al., "Synthesis of proteins by native chemical ligation," Science, Nov. 1994, 266(5186):776-779.
De Kruif et al., "Selection and Application of Human Single Chain Fv Antibody Fragments from a Semi-synthetic Phage Antibody Display Library with Designed CDR3 Regions," Journal of Molecular Biology, Apr. 1995, 248(1):97-105.
De la Pena et al., "Expression of the matrix metalloproteases 2, 14, 24, and 25 and Tissue inhibitor 3 as potential molecular markers in advanced human gastric cancer." Disease markers 2014 (2014).
Debre et al., "Infusion of Fc gamma fragments for treatment of children with acute immune thrombocytopeniaurpura", Lancet, 1993, 342(8877):945-949.
Derossi et al., "The third helix of the Antennapedia homeodomain translocates through biological membranes," Journal if Biological Chemistry, Apr. 1994, 269(14):10444-10450.
Dharmadhikari, et al., "CD137 and CD137L signals are main drivers of type 1, cell-mediated immune responses." Oncoimmunology, 2016, 5(4):e1113367.
Diamantis and Banerji, "Antibody-drug conjugates—an emerging class of cancer treatment." British journal of cancer, 2016, 114(4):362-367.
Diaz-Perlas et al., "Branched BBB-shuttle peptides: chemoselective modification of proteins to enhance blood-brain barrier transport," Chemical Science, Sep. 2018, 9(44):8409-8415.
Dong, et al. "Tumor-associated B7-H1 promotes T-cell apoptosis: a potential mechanism of immune evasion", Nature Medicine, 2002, 8(8):793-800.
Dorfman et al., "Programmed death-1 (PD-1) is a marker of germinal center-associated T cells and angioimmunoblastic T-cell lymphoma." The American journal of surgical pathology, Jul. 2006, 30(7):802-810.
Dubois et al., "New ways to image and target tumour hypoxia and its molecular responses," Radiotherapy and Oncology, Sep. 2015, 116(3):352-357.
Dufort et al., "789: Generation of a Bicycle NK-TICA(TM), a novel NK cell engaging molecule to enhance targeted tumor cytotoxicity", Nov. 10, 2021, 9(Suppl 2):A824-A824. URL:https://jitc.bmj.com/contenl/jitc/9/SuppI_2/A824.full.pdf.
Eagan et al., "Early clinical study of an intermittent schedule for maytansine (NSC-153858): brief communication." Journal of the National Cancer Institute, 1978, 60(1):93-96.
Eisenhauer et al.,"New response evaluation criteria in solid tumours: revised RECIST guideline (version 1.1)." European journal of cancer, 2009, 45(2):228-247.
Ellenrieder et al., "Role of MT-MMPs and MMP-2 in pancreatic cancer progression." International Journal of Cancer, 2000, 85(1):14-20.
Elson-Schwab et al., "Guanidinylated neomycin delivers large, bioactive cargo into cells through a heparan sulfate-dependent pathway." Journal of Biological Chemistry, 2007, 282(18):13585-13591.
Fauriat et al., "Deficient expression of NCR in NK cells from acute myeloid leukemia: Evolution during leukemia treatment and impact of leukemia cells in NCRdull phenotype induction", Blood, 2007, 109(1):323-330.
Fehrenbacher et al., "Atezolizumab versus docetaxel for patients with previously treated non-small-cell lung cancer (POPLAR): a multicentre, open-label, phase 2 randomised controlled trial." The Lancet, 2016, 387(10030):1837-1846.
Felices et al., "Generation of BiKEs and TriKEs to Improve NK Cell-Mediated Targeting of Tumor Cells", Methods Mol Biol., 2016, 1441:333-346.
Felices et al., "Novel CD19-targeted TriKE restores NK cell function and proliferative capacity in CLL", Blood Adv., 2019, 3(6):897-907.
Fiacco et al., "N-Methyl Scanning Mutagenesis Generates Protease-Resistant G Protein Ligands with Improved Affinity and Selectivity," ChemBioChem, Sep. 2008, 9(14):2200-2203.
Figure 3.8 of "Immunobiology: The Immune System in Health and Disease," Garland Science, 2001.
Flaherty et al., "Nonclinical evaluation of GMA161—an antihuman CD 16 (FcγRIII) monoclonal antibody for treatment of autoimmune disorders in CD16 transgenic mice", Toxicological Sciences, 2012, 125(1):299-309.
Forsberg, et al., "CD137 plays both pathogenic and protective roles in type 1 diabetes development in NOD mice." The Journal of Immunology, 2017, 198(10):3857-3868.

(56) References Cited

OTHER PUBLICATIONS

Francis et al., "Bone and Soft Tissue Sarcomas: UK Incidence and Survival: 1996-2010," National Cancer Intelligence Network, Nov. 2013, v2.0.
Fumet et al. "Phase Ib/II trial evaluating the safety, tolerability and immunological activity of durvalumab (MEDI4736)(anti-PD-L1) plus tremelimumab (anti-CTLA-4) combined with FOLFOX in patients with metastatic colorectal cancer." ESMO open, 2018, 3(4):e000375.
Galsky et al., "Phase I trial of the prostate-specific membrane antigen-directed immunoconjugate MLN2704 in patients with progressive metastatic castration-resistant prostate cancer." Journal of clinical oncology, 2008, 26(13):2147-2154.
Garcia-Iglesias et al., "Low NKp30, NKp46 and NKG2D expression and reduced cytotoxic activity on NK cells in cervical cancer and precursor lesions", BMC Cancer, Jun. 16, 2009, 9:186, 8 pages.
Gauthier et al., "Multifunctional Natural Killer Cell Engagers Targeting NKp46 Trigger Protective Tumor Immunity", Cell, 2019, 177(7):1701-1713.
Gelb et al., "Abstract 391: Molecular-based enrichment strategy for Nectin-4 targeted Bicycle toxin conjugate BT8009," Cancer Res., Jul. 1, 2021, 81(13 suppl):391 (poster).
Gelb et al., "Abstract A047: MT1-MMP Immunohistochemistry (IHC) analysis of tumor microarrays(TMAs) using a novel scoring system guides patient selection for BT1718 expansion cohorts," In Molecular Cancer Therapeutics, 2019, 18(12_Suppl):A047.
Gen path diagnostics, "Solid Tumors", Accessed on |https://genpathdiagnostics.com/patients/oncology/solid-tumors/, Jun. 30, 2023, 4 pages.
Gentilucci et al., "Chemical Modifications Designed to Improve Peptide Stability: Incorporation of Non-Natural Amino Acids, Pseudo-Peptide Bonds, and Cyclization," Current Pharmacetical Design, 2010, 16(28):3185-3203.
Gfeller et al., "Current tools for predicting cancer-specific T cell immunity," Oncoimmunology, 2016, 5(7):e1177691.
Gleason et al., "CD16xCD33 bispecific killer cell engager (BiKE) activates NK cells against primary MDS and Mdsc CD33+ targets", Blood, 2014, 123(19):3016-3026.
Gokel et al., "Crown Ethers: Sensors for Ions and Molecular Scaffolds for Materials and Biological Models," Chem. Rev., 2004, 104(5):2723-2750.
Gradishar et al., "Significantly longer progression-free survival with nab-paclitaxel compared with docetaxel as first-line therapy for metastatic breast cancer." J Clin Oncol., 2009, 27(22):3611-3619.
Gresh, "Neuroblastoma," Merck Manual., Retrieved form: https://www.msdmanuals.com/en-in/professional/pediatrics/pediatric-cancers/neuroblastoma, Sep. 2022, 4 pages.
Griffiths et al., "Isolation of high affinity human antibodies directly from large synthetic repertoires," EMBO Journal, Jul. 1994, 13(14):3245-3260.
Grisold et al., "Peripheral neuropathies from chemotherapeutics and targeted agents: diagnosis, treatment, and prevention." Neuro-oncology, 2012, 14(suppl_4):iv45-iv54.
Gu et al., "The influence of the penetrating peptide iRGD on the effect of paclitaxel-loaded MT1-AF7p-conjugated nanoparticles on glioma cells." Biomaterials, 2013, 34(21):5138-5148.
Gupta et al, "Intracellular delivery of large molecules and small particles by cell-penetrating proteins and peptides," Advanced Drug Delivery Reviews, Feb. 2005, 57(4):637-651.
Hamanishi et al. "Programmed cell death 1 ligand 1 and tumor-infiltrating CD8+ T lymphocytes are prognostic factors of human ovarian cancer", Proc. Natl. Acad. Sci. USA, 2007, 104(9):3360-3365.
Han et al., "Altered NKp30, NKp46, NKG2D, and DNAM-1 Expression on Circulating NK Cells Is Associated with Tumor Progression in Human Gastric Cancer", Journal of Immunology Research, Sep. 3, 2018, 2018:6248590, 10 pages.
Hanna et al., "Randomized phase III trial of pemetrexed versus docetaxel in patients with non-small-cell lung cancer previously treated with chemotherapy." Journal of clinical oncology, 2004, 22(9):1589-1597.
Hart, et al., "De novo identification of lipid II binding lipopeptides with antibacterial activity against vancomycin-resistant bacteria." Chemical Science, 2017, 8(12):7991-7997.
Hart, et al., "Cell binding and internalization by filamentous phage displaying a cyclic Arg-Gly-Aspcontaining peptide", J. Biol. Chem., 1994, 269:12468-12474.
Hasmim et al., "Critical Role of Tumor Microenvironment in Shaping NK Cell Functions: Implication of Hypoxic Stress", Frontiers in Immunology, Sep. 23, 2015, 6:482, 9 pages.
He et al., "Matrix metalloproteinase-14 is a negative prognostic marker for patients with gastric cancer." Digestive diseases and sciences, 2013, 58:1264-1270.
Helft et al., "A phase I study of cantuzumab mertansine administered as a single intravenous infusion once weekly in patients with advanced solid tumors." Clinical cancer research, 2004, 10(13):4363-4368.
Henriques et al., "Functional characterization of peripheral blood dendritic cells and monocytes in systemic lupus erythematosus", Rheumatology International, Apr. 2012, 32(4):863-869.
Herbst et al., "Pembrolizumab versus docetaxel for previously treated, PD-L 1-positive, advanced non-small-cell lung cancer (KEYNOTE-010): a randomised controlled tria", Lancet, Apr. 2016, 387(10027):1540-1550.
Hershman, "Thyroid Cancers," Merck Manual, Retrieved from: https://www.merckmanuals.com/professional/endocrine-and-metabolic-disorders/thyroid-disorders/thyroid-cancers, Sep. 2020.
Hess et al., "Backbone Cyclic Peptidomimetic Melanocortin-4 Receptor Agonist as a Novel Orally Administrated Drug Lead for Treating Obesity," Journal of Medicinal Chemistry, Jan. 26, 2008, 51(4):1026-1034.
Hikari et al., "Tags for labeling protein N-termini with subtiligase for proteomics", Bioorganic & Medicinal Chemistry Letters, Nov. 2008, 18 (22):6000-6003.
Hill et al: "Constraining Cyclic Peptides to Mimic Protein Structure Motifs", Angewandte Chemie International Edition, Nov. 24, 2014, 53(48):13020-13041.
Hinner et al., "Tumor-Localized Costimulatory T-Cell Engagement by the 4-1BB/HER2 Bispecific Antibody-Anticalin Fusion PRS-343", Clinical Cancer Research Oct. 2019, 23(19):5878-5889.
Hirano et al. "Blockade of B7-H1 and PD-1 by monoclonal antibodies potentiates cancer therapeutic immunity," Cancer Research, 2005, 65(3):1089-1096.
Hoogenboom et al., "By-passing immunisation. Human antibodies from synthetic repertoires of germline VH gene segments rearranged in vitro," Journal of Molecular Biology, Sep. 1992, 227(2):381-388.
Hsu et al., "Efficacy of plasmin-treated intravenous gamma-globulin for therapy of Kawasaki syndrome", The Pediatric Infectious Disease Journal, Jun. 1993, 12(6):509-512.
Hu-Lieskovan and Ribas, "New Combination Strategies Using Programmed Cell Death 1/Programmed Cell Death Ligand 1 Checkpoint Inhibitors as a Backbone," Cancer J., Jan./Feb. 2017, 23(1):10-22.
Hurov et al., "BT7480, a novel fully synthetic tumor-targeted immune cell agonist (TICA™) induces tumor localized CD137 agonism", Retrieved from the Internet: URL: https://www.bicycletherapeutics.com/wp-content/uploads/2020-06-16-BT7480-AACR-2020-poster-P5552_Final_CD137-in-title-002.pdf, Jun. 20, 2020, 1 page.
Ide et al., "A novel method for artificial lipid-bilayer formation," Biosensors and Bioelectronics, 2005, 21(4):672-677.
Inman et al., "PD-L1 (B7-H1) expression by urothelial carcinoma of the bladder and BCG-induced granulomata: associations with localized stage progression", Cancer, 2007, 109(8):1499-1505.
Ip et al., "Atypical localization of membrane type 1-matrix metalloproteinase in the nucleus is associated with aggressive features of hepatocellular carcinoma." Molecular Carcinogenesis: Published in cooperation with the University of Texas MD Anderson Cancer Center, 2007, 46(3):225-230.

(56) References Cited

OTHER PUBLICATIONS

Izawa et al., "$H_2O_2$ production within tumor microenvironment inversely correlated with infiltration of CD56(dim) NK cells in gastric and esophageal cancer: possible mechanisms of NK cell dysfunction", Cancer Immunology, Immunotherapy, 2011, 60(12):1801-1810.
Jackson and Stover, "Using the lessons learned from the clinic to improve the preclinical development of antibody drug conjugates." Pharmaceutical research, 2015, 32(11):3458-3469.
Jespers et al., "Selection of optical biosensors from chemisynthetic antibody libraries," Protein Engineering, Design and Selection, Oct. 2004, 17(10):709-713.
Johnson et al., "Melanoma-specific MHC-II expression represents a tumour-autonomous phenotype and predicts response to anti-PD-1/PD-L1 therapy", Nature Communications, Jan. 29, 2016, 7:10582(10 pages).
Johnson et al., "Relationships between drug activity in NCI preclinical in vitro and in vivo models and early clinical trials," British Journal of Cancer, 2001, 84(10):1424-1431.
Jones et al., "Randomized phase III study of docetaxel compared with paclitaxel in metastatic breast cancer." Journal of Clinical Oncology, 2005, 23(24):5542-5551.
Jones et al., "Targeting membrane proteins for antibody discovery using phage display," Scientific Reports, May 18, 2016, 6(1):1-11.
Kamat et al., "The clinical relevance of stromal matrix metalloproteinase expression in ovarian cancer." Clinical Cancer Research, 2006, 12(6):1707-1714.
Kamijo et al., "Aberrant CD137 ligand expression induced by GATA6 overexpression promotes tumor progression in cutaneous T-cell lymphoma." Blood, The Journal of the American Society of Hematology, 2018, 132(18):1922-1935.
Kanazawa et al., "Non-obese-diabetic mice: immune mechanisms of pancreatic β-cell destruction," Diabetologia, 1984, 27:113-115.
Kang et al., "A randomized, open-label, multicenter, adaptive phase 2/3 study of trastuzumab emtansine (T-DM1) versus a taxane (TAX) in patients (pts) with previously treated HER2-positive locally advanced or metastatic gastric/gastroesophageal junction adenocarcinoma (LA/MGC/GEJC)." (2016): 5-5.
Kang, et al., "Anti-CD137 suppresses tumor growth by blocking reverse signaling by CD 137 ligand." Cancer research, 2017, 77(21):5989-6000.
Keith, "Lung Carcinoma," Merck Manual, Retrieved on: https://www.merckmanuals.com/professional/pulmonary-disorders/tumors-of-the-lungs/lung-carcinoma, Sep. 2021, 18 pages.
Kell, Douglas B., "The Transporter-Mediated Cellular Uptake and Efflux of Pharmaceutical Drugs and Biotechnology Projects: How and Why Phospholipid Bilayer Transport is Negligible in Real Biomembranes," Molecules, 2021, 26(5629):40 pages.
Kellog et al., "Disulfide-linked antibody—maytansinoid conjugates: Optimization of in vivo activity by varying the steric hindrance at carbon atoms adjacent to the disulfide linkage." Bioconjugate chemistry, 2011, 22(4):717-727.
Kerkela et al., "Differential patterns of stromelysin-2 (MMP-10) and MT1-MMP (MMP-14) expression in epithelial skin cancers." British journal of cancer, 2001, 84(5):659-669.
Kessenbrock et al., "Matrix metalloproteinases: regulators of the tumor microenvironment." Cell, 2010, 141(1):52-67.
Khan et al., "Engineering Lipid Bilayer Membranes for Protein Studies," International Journal of Molecular Sciences, Nov. 2013, 14(11):21561-21597.
Kikuchi et al., "Immunohistochemical detection of membrane-type-1-matrix metalloproteinase in colorectal carcinoma." British journal of cancer, 2000, 83(2):215-218.
Kim et al., "Synergistic signals for natural cytotoxicity are required to overcome inhibition by c-Cbl ubiquitin ligase", Immunity, Feb. 26, 2010, 32(2):175-186.
Kim, et al., "Reverse signaling through the costimulatory ligand CD137L in epithelial cells is essential for natural killer cell-mediated acute tissue inflammation." Proceedings of the National Academy of Sciences, 2012, 109(1): E13-E22.
Kleinau et al., "Induction and suppression of collagen-induced arthritis is dependent on distinct fcgamma receptors", J Exp Med., May 2000, 191(9):1611-1616.
Knight et al., "Three genes for lupus nephritis in NZB x NZW mice," Journal of Experimental Medicine, Jun. 1978, 147(6):1653-1660.
Konishi et al., "B7-H1 Expression on Non-Small Cell Lung Cancer Cells and Its Relationship with Tumor-Infiltrating Lymphocytes and Their PD-1 Expression", Clin Cancer Res., 2004, 10(15):5094-5100.
Koo et al., "Reduction of the CD16-CD56bright NK Cell Subset Precedes NK Cell Dysfunction in Prostate Cancer", PLoS One, 2013, 8(11):e78049, 8 pages.
Kreidieh et al., "Overview, prevention and management of chemotherapy extravasation." World journal of clinical oncology, 2016, 7(1):87.
Krishnamoorthy et al., "Breaking the Permeability Barrier of *Escherichia coli* by Controlled Hyperporination of the Outer Membrane." Antimicrob Agents Chemother, 2016, 60(12):7372-7381.
Krop et al., "Trastuzumab emtansine versus treatment of physician's choice for pretreated HER2-positive advanced breast cancer (TH3RESA): a randomised, open-label, phase 3 trial." The Lancet Oncology, 2014, 15(7):689-699.
Kylväjä, et al., "Penicillin binding protein 3 of *Staphylococcus aureus* NCTC 8325-4 binds and activates human plasminogen." BMC research notes, 2016, 9:1-10.
Landolt et al., "Clear cell renal cell carcinoma is linked to epithelial-to-mesenchymal transition and to fibrosis." Physiological reports, 2017, 5(11):e13305.
Lani et al., "Identification of high affinity, highly selective bicyclic peptides (Bicycles®) to transmembrane proteins using phage display screening on whole cells," Abstract, PEGS Summit, Boston, Massachusetts, May 2017, 1 page.
Lanman et al., "Analytical and Clinical Validation of a Digital Sequencing Panel for Quantitative, Highly Accurate Evaluation of Cell-Free Circulating Tumor DNA", PLoS One, 2015, 10(10):e0140712.
Laudanski et al., "Increased serum level of membrane type 1-matrix metalloproteinase (MT1-MMP/MMP-14) in patients with breast cancer." Folia histochemica et cytobiologica, 2010, 48(1):101-103.
Lea and Simeonov, "Fluorescence polarization assays in small molecule screening," Expert Opinion in Drug Discovery, Jan. 2011, 6(1):17-32.
Leighton, "Pharmacology Review: Kadcyla (ado-trastuzumab emtansine)," In Center for Drug Evaluation and Research Application No. 1254270riol sOOO., Feb. 2020.
Levi et al., "Characterization of tumor infiltrating Natural Killer cell subset", Oncotarget, May 30, 2015, 6(15):13835-13843.
Levine et al. "Methionine residues as endogenous antioxidants in proteins", PNAS, 1996, 93(26):15036-15040.
Li et al., "Fluorescent Mu selective opioid ligands from a mixture based cyclic peptide library." ACS combinatorial science, 2012, 14(12):673-679.
Li et al., "Targeting the Fc receptor in autoimmune disease", Expert Opinion on Therapeutic Targets, 2014, 18(3):335-350.
Li et al., "The overexpression membrane type 1 matrix metalloproteinase is associated with the progression and prognosis in breast cancer." American Journal of Translational Research, 2015, 7(1):120.
Li, et al., "A novel strategy for in vitro selection of peptide-drug conjugates." Chemistry & biology, 2003, 10(3):233-239.
Li, et al., "Increasing the Antimicrobial Activity of Nisin-Based Lantibiotics against Gram-Negative Pathogens." Applied and environmental microbiology, 2018, 84(12):e00052-18.
Lian at al, Screening Bicyclic Peptide Libraries for Protein-Protein Interaction Inhibitors: Discovery of Journal of the American Chemical Society, Aug. 14, 2013, 135(32):11990-11995.
Lian et al., "Cell-Permeable Bicyclic Peptide Inhibitors against Intracellular Proteins", Journal of the American Chemical Society, Jul. 2014, 136(28):9830-9833.
Linch et al., "OX40 Agonists and Combination Immunotherapy: Putting the Pedal to the Metal," Frontiers in Oncology, Feb. 16, 2015, 5(34):1-14.

(56) References Cited

OTHER PUBLICATIONS

Linde et al., "Structure-Activity Relationship and Metabolic Stability Studies of Backbone Cyclization and N-Methylation of Melanocortin Peptides," Biopolymers, 2008, 90(5):671-682.
Lindstrom et al., "Myasthenia gravis," Advances in Immunology, Dec. 1988, 42:233-284.
Liu et al., "Abstract 3642: Tumor-antigen expression-dependent activation of the CD137 costimulatory pathway by bispecific DART proteins," American Association for Cancer Research, Jul. 2017, 77(supp 13):1-4.
Liu et al., "Plasma cells from multiple myeloma patients express B7-H1 (PD-L1) and increase expression after stimulation with IFN-{gamma} and TLR ligands via a MyD88-, TRAF6-, and MEK-dependent pathway", Blood, 2007, 110(1):296-304.
Loktev et al., "Multicyclic Peptides as Scaffolds for the Development of Tumor Targeting Agents," Current Medicinal Chemistry, 2017, 24(999):2141-2155.
Lopus, Manu. "Antibody-DM1 conjugates as cancer therapeutics." Cancer letters, 2011, 307(2):113-118.
Lovering et al. "Escape from flatland: increasing saturation as an approach to improving clinical success." Journal of medicinal chemistry, 2009, 52(21):6752-6756.
Lovering, "Escape from Flatland 2: complexity and promiscuity," Meducinal Chemistry Communication, Dec. 2012, 4(3):515-519.
M.D. Anderson Cancer Center, "Nivolumab and HPV-16 Vaccination in Patients With HPV-16 Positive Incurable Solid Tumors," In ClinicalTrials.gov Identifier NCT02426892. Retrieved form https://clinicaltrials.gov/ct2/show/study/NCT02426892, 2015.
MacFarlane 4th et al., "NK cell dysfunction in chronic lymphocytic leukemia is associated with loss of the mature cells expressing inhibitory killer cell Ig-like receptors", Oncoimmunology, May 19, 2017, 6(7):e1330235.
Macheboeuf et al., "Penicillin binding proteins: key players in bacterial cell cycle and drug resistance processes", FEMS Microbiol Rev., 2006, 30(5):673-691.
Mamessier et al., "Human breast tumor cells induce self-tolerance mechanisms to avoid NKG2D-mediated and DNAM-mediated NK cell recognition", Cancer Res., 2011, 71(21):6621-6632.
Manches et al., "In vitro mechanisms of action of rituximab on primary non-Hodgkin lymphomas", Blood, 2003, 101(3):949-954.
Mark, "Renal Cell Carcinoma," Merck Manual, Retrieved form : https://www.merckmanuals.com/home/kidney-and-urinary-tract-disorders/cancers-of-the-kidney-and-genitourinary-tract/kidney-cahcer, Sep. 2021.
Marks et al., "By-passing immunization. Human antibodies from V-gene libraries displayed on phage," Journal of Molecular Biology, Dec. 1991, 222(3):581-597.
Maron et al., "H-2K mutation controls immune response phenotype of autoimmune thyroiditis. Critical expression of mutant gene product in both thymus and thyroid glands," Journal of Experimental Medicine, Oct. 1980, 152(4):1115-1120.
McFarlin et al., "Experimental Allergic Encephalomyelitis in the Rat: Response to Encephalitogenic Proteins and Peptides," Science, Feb. 1973, 179(4072):478-480.
Merck Manual (https://www.merckanuals.com/home/blood-disorders/plasma-celldisorders/multiple-myeloma?query=pancreaticmultiple%20myeloma accessed Apr. 9, 21).
Michel, et al., "Expression of soluble CD137 correlates with activation-induced cell death of lymphocytes." Cytokine, 2000, 12(6):742-746.
Milowsky et al., Phase 1/2 multiple ascending dose trial of the prostate-specific membrane antigen-targeted antibody drug conjugate MLN2704 in metastatic castration-resistant prostate cancer. In Urologic Oncology: Seminars and Original Investigations, 2016, 34(12):530-e15.
Mittler, el al., "Anti-CD137 antibodies in the treatment of autoimmune disease and cancer." Immunologic research, 2004, 29:197-208.
Miyoshi and Takai, "Nectin and nectin-like molecules: biology and pathology," Am J Nephrol., 2007, 27(6):590-604.
Mohammad et al., Prognostic value of membrane type 1 and 2 matrix metalloproteinase expression and gelatinase A activity in bladder cancer. The International journal of biological markers, 2010, 25(2):69-74.
Moore et al., "A novel bispecific antibody format enables simultaneous bivalent and monovalent co-engagement of distinct target antigens", Mabs, 2011, 3(6):546-557.
Moraes et al., "Immune checkpoint inhibitors (anti PD-1 or anti PD-L1) versus chemotherapy for second- or third-line treatment of metastatic non-small cell lung cancer," Cochrane Database Syst Rev., 2017, 2017(4):CD012644.
Moretta et al., "Surface NK receptors and their ligands on tumor cells", Seminars in Immunology, 2006, 18(3):151-158.
Morgan et al., "FcgammaRIIIA-158V and rheumatoid arthritis: a confirmation study", Rheumatology (Oxford), 2003, 42(4):528-533.
Morrison, "Chemical Strategies for Bicyclic Peptide Formation," Univ. of Leeds, Sep. 2015, pp. 1-60.
Mugera and Ward, "Acute toxicity of maytansine in F344 rats." Cancer Treatment Reports, 1977, 61(7):1333-1338.
Mulder et al., "Scaffold Optimization in Discontinuous Epitope Containing Protein Mimics of gp120 Using Smart Libraries," Org. Biomol. Chem., 2013, 11:2676-2684.
Mullis et al., "Specific synthesis of DNA in vitro via a polymerase-catalyzed chain reaction," Methods in Enzymology, Jan. 1987, 155:335-350.
Muta et al., "A 13-amino-acid motif in the cytoplasmic domain of Fc gamma RIIB modulates B-cell receptor signalling", Nature, Mar. 3, 1994, 368(6466):70-73.
Nabbe et al., "Coordinate expression of activating Fc gamma receptors I and III and inhibiting Fc gamma receptor type II in the determination of joint inflammation and cartilage destruction during immune complex-mediated arthritis", Arthritis & Rheumatology, Jan. 2003, 48(1):255-265.
Nair et al., "Mimicry of Native Peptide Antigens by the Corresponding Retro-Inverso Analogs is Dependent on Their Intrinsic Structure and Interaction Propensities," The Journal of Immunology, 2003, 170(3):1362-1373.
Nakanishi et al., "Overexpression of B7-H1 (PD-L1) significantly associates with tumor grade and postoperative prognosis in human urothelial cancers" Cancer Immunology, Immunotherapy, 2007, 56:1173-1182.
Nam et. al., "The therapeutic potential of 4-1BB (CD137) in cancer", Current cancer drug targets, 2005, 5(5):357-363.
National cancer institute, "Cancer prevention overview", (https://www.cancer.gov/about-cancer/causes-prevention/patient-prevention-overview-pdq accessed May 8, 2020), 2020, 12 pages.
National Cancer Institute, "What is Cancer", (https://www.cancer.gov/about-cancer/understanding/what-is-cancer, accessed Apr. 9, 2021), 10 pages.
National Cancer Institute, Understanding Cancer and Related Topics, (https://www.cancer.gov/about-cancer/understanding/what-is-cancer, accessed Apr. 9, 2021).
Nayyar et al., "Overcoming Resistance to Natural Killer Cell Based Immunotherapies for Solid Tumors", Feb. 11, 2019 ;9:51, 28 pages.
Nestor et al., "The Medicinal Chemistry of Peptides," Curr. Medicinal Chem, 2009, 16(33):4399-4418.
Nguyen, "Colorectal Cancer," Merck Manual, Retrieved from https://www.merckmanuals.com/professional/gastrointestinal-disorders/tumors-of-the-gastrointestinal-tract/colorectal-cancer, 2021.
Nguyen, "Pancreatic Cancer", Merck Manual (https://merckmanuals.com/professional/gastrointestinal-disorders/tumors-of-the-gastrointestinal-tract/pancreatic-cancer?query=adenocarcinomas), Sep. 2022, 4 pages.
NIH National Human Genome Research Institute, "Animal Model," Genome.gov., Jan. 4, 2022.
Nishiwada et al., "Nectin-4 expression contributes to tumor proliferation, angiogenesis and patient prognosis in human pancreatic cancer," Journal of Experimental & Clinical Cancer Research, 2015, 34(1):30. (9 pages.).
Nissim et al., "Antibody fragments from a 'single pot' phage display library as immunochemical reagents," EMBO Journal, Feb. 1994, 13(3):692-698.

(56) References Cited

OTHER PUBLICATIONS

Nomi et al., "Clinical Significance and Therapeutic Potential of the Programmed Death-1 Ligand/Programmed Death-1 Pathway in Human Pancreatic Cancer", Clin Cancer Res., 2007, 13(7): 2151-2157.
Oehlke et al., "Cellular uptake of an alpha-helical amphipathic model peptide with the potential to deliver polar compounds into the cell interior non-endocytically," Biochimica et Biophysica Acta, Nov. 1998, 1414(1-2):127-139.
Okazaki et al., "A Rheostat for Immune Responses: the Unique Properties of PD-1 and Their Advantages for Clinical Application," Nat. Immunol., 2013, 14(12):1212-1218.
Okuyama et al., "Small-molecule mimics of an a-helix for efficient transport of proteins into cells," Nature Methods, Feb. 2007, 4(2):153-159.
Ortiz et al., "Elucidating the interplay between IgG-Fc valency and FcγR activation for the design of immune complex inhibitors", Science Translational Medicine, Nov. 2016, 8(365):365ra158.
Pahwa et al., "Monitoring and inhibiting MT1-MMP during cancer initiation and progression." Cancers, 2014, 6(1):416-435.
Pasero et al., "Highly effective NK cells are associated with good prognosis in patients with metastatic prostate cancer", Oncotarget 6(16), Jun. 10, 2015, 14360-14373.
Pavlidou et al., "Nanodiscs Allow Phage Display Selection for Ligands to Non-Linear Epitopes on Membrane Proteins," PLoS One, Article No. e72272, Sep. 2013, 8(9):8 pages.
Pavlova et al., "A role for PVRL4-driven cell-cell interactions in tumorigenesis," Elife., Apr. 30, 2013, 2:e00358, 24 pages.
Pearson et al., "High-Level Clonal FGFR Amplification and Response to FGFR Inhibition in a Translational Clinical Trial", Cancer Discovery, 2016, 6(8):838-851.
Peng et al., Combined features based on MT1-MMP expression, CD11b+ immunocytes density and LNR predict clinical outcomes of gastric cancer. Journal of translational medicine, 2013, 11(1):1-11.
Phichith, et al., "Novel peptide inhibiting both TEM-1 β-lactamase and penicillin-binding proteins." The FEBS Journal, 2010, 277(23):4965-4972.
Pickens et al., "Practical Considerations, Challenges and Limitations of Bioconjugation via Azide—Alkyne Cycloaddition," Bioconjugate Chem., 2018, 29:686-701.
Pivot et al., "Pooled analyses of eribulin in metastatic breast cancer patients with at least one prior chemotherapy." Annals of Oncology, 2016, 27(8):1525-1531.
Platonova et al., "Profound coordinated alterations of intratumoral NK cell phenotype and function in lung carcinoma", Cancer Res., 2011, 71(16):5412-5422.
Polakis, "Antibody Drug Conjugates for Cancer Therapy," Pharmacol Rev., Jan. 2016, 68(1):3-19.
Poon et al., Preclinical safety profile of trastuzumab emtansine (T-DM1): mechanism of action of its cytotoxic component retained with improved tolerability. Toxicology and applied pharmacology, 2013, 273(2):298-313.
Poreba, "Protease-activated prodrugs: strategies, challenges, and future directions." The FEBS Journal, 2020, 287(10):1936-1969.
Pricop et al., "Differential modulation of stimulatory and inhibitory Fc gamma receptors on human monocytes by Th1 and Th2 cytokines", Journal of Immunology, 2001, 166(1):531-537.
Purdie and Benoiton, "Piperazinedione formation from esters of dipeptides containing glycine, alanine, and sarcosine: the kinetics in aqueous solution." Journal of the Chemical Society, Perkin Transactions 2, 1973, 14: 1845-1852.
Qi et al., "Serial determination of glomerular filtration rate in conscious mice using C252|FITC-inulin clearance," American Journal of Physiology—Renal Physiology, Mar. 2004, 286(3):F590-F596.
Rataj et al., "High-affinity CD16-polymorphism and Fc-engineered antibodies enable activity of CD16-chimeric antigen receptor-modified T cells for cancer therapy", British Journal of Cancer, 2019, 120(1):79-87.
Ravetch et al., "IgG Fc receptors", Annual Review of Immunology, 2001:19:275-290.
Reagan-Shaw et al., "Dose translation from animal to human studies revisited," Faseb J., Mar. 2008, 22(3):659-661.
Reinertsen et al., "B-Lymphocyte Alloantigens Associated with Systemic Lupus Erythematosus," The New England Journal of Medicine, Sep. 7, 1978, 299(10):515-518.
Remacle et al., "Novel MT1-MMP small-molecule inhibitors based on insights into hemopexin domain function in tumor growth," Cancer Res., May 1, 2012, 72(9):2339-2349.
Riddle et al., "Tumor cell surface display of immunoglobulin heavy chain Fc by gene transfer as a means to mimic antibody therapy", Human Gene Therapy, 2005, 16(7):830-844.
Robert Gale, "Cancer treatment principles", Merck Manual consumer version (https://www.merckmanuals.com/home/cancer/prevention-and-treatment-of-cancer/cancer-treatment-principles?query=Cancer%20treatment Accessed May 8, 2020), Jul. 2018, 2 pages.
Robert Gale, "Overview of Cancer therapy", Merck Manual consumer version (https://www.merckmanuals.com/professional/hematology-and-oncology/principles-of-cancer-therapy/overview-of-cancer-therapy?query=Cancer Accessed May 8, 2020), Jul. 2018, 3 pages.
Robinson et al., "Integrative Clinical Genomics of Advanced Prostate Cancer", Cell, 2015, 161(5):1215-1228.
Rocca et al., "Phenotypic and Functional Dysregulated Blood NK Cells in Colorectal Cancer Patients Can Be Activated by Cetuximab Plus IL-2 or IL-15", Frontiers in Immunology, 2016, 7:413.
Rodon et al., "Cantuzumab mertansine in a three-times a week schedule: a phase I and pharmacokinetic study." Cancer chemotherapy and pharmacology, 2008, 62(5):911-919.
Ross et al., "Bispecific T Cell Enager (BiTE) Antibody Constructs Can Mediate Bystander Tumor Cell Killing", PLoS One, Aug. 24, 2017, 12(8):1-24.
Roth et al., "Docetaxel, cisplatin, and fluorouracil; docetaxel and cisplatin; and epirubicin, cisplatin, and fluorouracil as systemic treatment for advanced gastric carcinoma: a randomized phase II trial of the Swiss Group for Clinical Cancer Research", J Clin Oncol. Aug. 1, 2007, 25(22):3217-3023.
Rothwell et al., "Utility of ctDNA to support patient selection for early phase clinical trials: the TARGET study", Nature Medicine, 2019, 25(5):738-743.
Rudgers et al., "Binding properties of a peptide derived from beta-lactamase inhibitory protein." Antimicrob Agents Chemother., 2001, 45(12):3279-3286.
Salmon et al., "Human receptors for immunoglobulin G: key elements in the pathogenesis of rheumatic disease", Arthritis & Rheumatology, 2001, 44(4):739-750.
Satoh et al., "Experimental allergic encephalomyelitis mediated by murine encephalitogenic T cell lines specific for myelin proteolipid apoprotein," Journal of Immunology, Jan. 1987, 138(1):179-184.
Sausville and Burger, "Contributions of Human Tumor Xenografts to Anticancer Drug Development," Cancer Res., 2006, 66(7):3351-3354.
Scagliotti et al., "Phase III study comparing cisplatin plus gemcitabine with cisplatin plus pemetrexed in chemotherapy-naive patients with advanced-stage non-small-cell lung cancer." Journal of clinical oncology, 2008, 26(21):3543-3551.
Schiller et al., "Comparison of four chemotherapy regimens for advanced non-small-cell lung cancer." New England Journal of Medicine, 2002, 346(2):92-98.
Schreiber et al., "Rapid, electrostatically assisted association of proteins," Nature Structural & Molecular Biology, May 1996, 3:427-431.
Seely and Frazier, "Regulatory Forum Opinion Piece*: Dispelling Confusing Pathology Terminology: Recognition and Interpretation of Selected Rodent Renal Tubule Lesions," Toxicol Pathol., 2015, 43(4):457-463.
Segal et al., "Results from an Integrated Safety Analysis of Urelumab, an Agonist Anti-CD 137 Monoclonal Antibody", clinical Cancer research, 2017, 23(8):1929-1936.
Seiki et al., "Membrane-type 1 matrix metalloproteinase: a key enzyme for tumor invasion." Cancer letters, 2003, 194(1):1-11.

(56) References Cited

OTHER PUBLICATIONS

Sepiashvili et al., "Potentially novel candidate biomarkers for head and neck squamous cell carcinoma identified using an integrated cell line-based discovery strategy." Molecular & Cellular Proteomics, 2012, 11(11):1404-1415.
Shaabani et al., "A patent review on PD-1/PD-L 1 antagonists: small molecules, peptides, and macrocycles (2015-2018)," Expert Opinion on Therapeutic Patents, 2018, 28(9):665-678.
Shah et al., "Phase I study of IMGN901, a CD56-targeting antibody-drug conjugate, in patients with CD56-positive solid tumors." Investigational new drugs, 2016, 34:290-299.
Shah, "Update on metastatic gastric and esophageal cancers." Journal of clinical oncology 33, No. 16 (2015): 1760-1769.
Shao et al., "CD137 ligand, a member of the tumor necrosis factor family, regulates immune responses via reverse signal transduction." Journal of leukocyte biology, 2011, 89(1):21-29.
Shao et al., "Copy number variation is highly correlated with differential gene expression: a pan-cancer study," BMC Medical Genetics, Nov. 9, 2019, 20(1):175.
Sharma et al., "Plasmacytoid dendritic cells from mouse tumor-draining lymph nodes directly activate mature Tregs via indoleamine 2, 3-dioxygenase", The Journal of clinical investigation, 2007, 117(9):2570-2582.
Shen et al., "Non-clinical disposition and metabolism of DM1, a Component of Trastuzumab Emtansine (T-DM1), in Sprague Dawley Rats." Drug Metabolism Letters, 2015, 9(2):119-131.
Shen, et.al., "Evaluation of phage display discovered peptides as ligands for prostate-specific membrane antigen (PSMA)." PLoS One, 2013, 8(7):e68339.
Shimauchi et al., "Augmented expression of programmed death-1 in both neoplastic and non-neoplastic CD4+ T-cells in adult T-cell leukemia/lymphoma", International journal of cancer, 2007, 121(12):2585-2590.
Sibaud et al., "Pigmentary disorders induced by anticancer agents. Part I: chemotherapy." In Annales de dermatologie et de venereologie, 2013, 140(3):183-196.
Siddharth et al., "Nectin-4 is a breast cancer stem cell marker that induces WNT/β-Catenin signaling via Pi3k/Akt axis," International Journal of Biochemistry and Cell Biology, 2017, 89:85-94.
Silver, "Multi-targeting by monotherapeutic antibacterials." Nat Rev Drug Discov., 2007, 6(1):41-55.
Smeenk et al., "Reconstructing the Discontinuous and Conformational β1/β3-Loop Site on hFSH/hCG by Using Highly Constrained Multicyclic Peptides." ChemBioChem, 2015, 16(1):91-99.
Soderstrom, et al., "CD137: A checkpoint regulator involved in atherosclerosis." Atherosclerosis, 2018, 272:66-72.
Sordo-Bahamonde et al., "Mechanisms of Resistance to NK Cell Immunotherapy", Cancers (Basel). Apr. 7, 2020, 12(4):893.
Sporn et at, "Chemoprevention of cancer." Carcinogenesis, 2000, 21(3):525-530.
Stathis et al., "A Phase I Study of IMGN529, an Antibody-Drug Conjugate (ADC) Targeting CD37, in Adult Patients with Relapsed or Refractory B-Cell Non-Hodgkin's Lymphoma (NHL)," Blood, 2014, 124(21):1760.
Steck et al., "Inside-out red cell membrane vesicles: preparation and purification," Science, Apr. 10, 1970, 168(3928):255-257.
Stojanovic et al., "Natural killer cells and solid tumors", Journal of Innate Immunity, 2011, 3(4):355-364.
Stringaris et al., "Leukemia-induced phenotypic and functional defects in natural killer predict failure to achieve remission in acute myeloid leukemia", Haematologica, May 2014, 99(5):836-847.
Strome et al., "B7-H1 blockade augments adoptive T-cell immunotherapy for squamous cell carcinoma", Cancer Res., 2003, 63(19):6501-6505.
Stuart et al., "Collagen Autoimmune Arthritis," Annual Review of Immunology, 1984, 2:199-218.
Sun et al., "NK cell receptor imbalance and NK cell dysfunction in HBV infection and hepatocellular carcinoma", Cellular & Molecular Immunology, May 2015, 12(3):292-302.
Suojanen et al., "A novel and selective membrane type-1 matrix metalloproteinase (MT1-MMP) inhibitor reduces cancer cell motility and tumor growth," Cancer Biology & Therapy, Dec. 2009, 8(24):2362-2370.
Tarazona et al., "Current progress in NK cell biology and NK cell-based cancer immunotherapy", Cancer Immunol Immunother, 2020, 69(5):879-899.
Tetu et al., "The influence of MMP-14, TIMP-2 and MMP-2 expression on breast cancer prognosis." Breast Cancer Research, 2006, 8(3):1-9.
Thake et al., "Toxicity of Maytansine (NSC 153858) in dogs and monkeys." PB-US National Technical Information Service (1975), Feb. 1975, 244628.
Thevenard et al., "The YSNSG cyclopeptide derived from tumstatin inhibits tumor angiogenesis by down-regulating endothelial cell migration." International journal of cancer, 2010, 126(5):1055-1066.
Thompson et al., "Costimulatory B7-H1 in renal cell carcinoma patients: Indicator of tumor aggressiveness and potential therapeutic target", Proceedings of the National Academy of Sciences, 2004, 101(49):17174-17179.
Tolcher et al., "Cantuzumab mertansine, a maytansinoid immunoconjugate directed to the CanAg antigen: a phase I, pharmacokinetic, and biologic correlative study." Journal of clinical oncology, 2003, 21(2):211-222.
Toogood, "Small Molecule Immuno-oncology Therapeutic Agents," Bioorganic & Medicinal Chemistry Letters, 2018, 28(3):319-329.
Touati et al., "Phage Selection of Bicyclic Peptide Ligands and Development of a New Peptide Cyclisation Method", These No. 5536, Oct. 2012, 117 pages.
Trouche et al., "Small multivalent architectures mimicking homotrimers of the TNF superfamily member CD40L: delineating the relationship between structure and effector function." Journal of the American Chemical Society, 2007, 129(44):13480-13492.
Trudel et al., "Membrane-type-1 matrix metalloproteinase, matrix metalloproteinase 2, and tissue inhibitor of matrix proteinase 2 in prostate cancer: identification of patients with poor prognosis by immunohistochemistry." Human pathology, 2008, 39(5):731-739.
Tugyi et al, "Partial D-amino acid substitution: Improved enzymatic stability and preserved Ab recognition of a MUC2 epitope peptide," Proceedings of the National Academy of Sciences U.S.A., Jan. 2005, 102(2):413-418.
Tutt et al., "Abstract S3-01: the TNT trial: a randomized phase III trial of carboplatin (C) compared with docetaxel (D) for patients with metastatic or recurrent locally advanced triple negative or BRCA1/2 breast cancer (CRUK/07/012)." Cancer Research, May 2015, 75(9_Suppl):S3-01.
Ulasov et al., "Inhibition of MMP 14 potentiates the therapeutic effect of temozolomide and radiation in gliomas." Cancer medicine, 2013, 2(4):457-467.
Ün, Sanya. Charakterisierung von Peptiden für die Bindung essentieller Penicillin-bindender Proteine und die Variationen der Linkerlänge einzelkettiger TetR Varianten. Friedrich-Alexander-Universitaet Erlangen-Nuernberg (Germany), 2010. 139 pages.
Upadhyaya, "Activation of CD137 using multivalent and tumor targeted Bicyclic peptides." Cancer Research, Jul. 2019, 79(13 Suppl):3257-3257.
Van Eden et al., "Cloning of the mycobacterial epitope recognized by T lymphocytes in adjuvant arthritis," Nature, Jan. 14, 1988, 331(6152):171-173.
Van Glabbeke et al., "Progression-free rate as the principal end-point for phase II trials in soft-tissue sarcomas." European Journal of Cancer, 2002, 38(4):543-549.
Vandenbroucke and Libert, "Is there new hope for therapeutic matrix metalloproteinase inhibition?." Nature reviews Drug discovery, 2014, 13(12):904-927.
Wang et al., "Co-expression of MMP-14 and MMP-19 predicts poor survival in human glioma." Clinical and Translational Oncology, 2013, 15:139-145.
Wang et al., "MMP-14 overexpression correlates with poor prognosis in non-small cell lung cancer." Tumor Biology, 2014, 35:9815-9821.

(56) References Cited

OTHER PUBLICATIONS

Watanabe et al., "NK cell dysfunction with down-regulated CD16 and up-regulated CD56 molecules in patients with esophageal squamous cell carcinoma", Diseases of the Esophagus, 2010, 23(8):675-681.
Waterhouse et al., "Safety profile of nivolumab administered as 30-min infusion: analysis of data from CheckMate 153," Cancer Chemother Pharmacol., Apr. 2018, 81(4):679-686.
Watts, "TNF/TNFR family members in costimulation of T cell responses", Annu. Rev, Immunol., Apr. 2005, 23:23-68.
Weber, J. "Immune Checkpoint Proteins: A New Therapeutic Paradigm for Cancer—Preclinical Background: CTLA-4 and PD-1 Blockade", Seminars in Oncology, Oct. 2010, 37(5):430-439.
Wei et al., "Discovery of Peptidomimetic Antibody-Drug Conjugate Linkers with Enhanced Protease Specificity," J. Med. Chem., 2018, 61(3):989-1000.
Winter et al., "Making antibodies by phage display technology," Annual Review of Immunology, 1994, 12:433-455.
Wu et al., "A novel polymorphism of FcgammaRIIIa (CD16) alters receptor function and predisposes to autoimmune disease", The Journal of Clinical Investigation, 1997, 100(5):1059-1070.
Wu et al., "Immunohistochemical localization of programmed death-1 ligand-1 (PD-L1) in gastric carcinoma and its clinical significance" Acta histochemica, 2006, 108(1):19-24.
Wu et al., "Natural killer cells in cancer biology and therapy", Molecular Cancer, Aug. 6, 2020, 19(1):120, 26 pages.
Yardley et al., "EMERGE: a randomized phase II study of the antibody-drug conjugate glembatumumab vedotin in advanced glycoprotein NMB-expressing breast cancer." Journal of clinical oncology: official journal of the American Society of Clinical Oncology, 2015, 33(14):1609.
Yoon et al., "An efficient strategy for cell-based antibody library selection using an integrated vector system," BMC Biotechnology, 2012, 12(62):10 pages.
Yoshihara et al., "Tags for labeling protein N-termini with subtiligase for proteomics," Bioorganic & Medicinal Chemistry Letters, Nov. 2008, 18(22):6000-6003.
Yu and Taylor, "A new strategy applied to the synthesis of an α-helical bicyclic peptide constrained by two overlapping i, i+ 7 side-chain bridges of novel design." Tetrahedron letters, 1996, 37(11):1731-1734.
Zarrabi et al., "Inhibition of matrix metalloproteinase 14 (MMP-14)-mediated cancer cell migration." Journal of Biological Chemistry, 2011, 286(38):33167-33177.
Zervosen et al., "Development of New Drugs for an Old Target—The Penicillin Binding Proteins." Molecules. 2012:17 (11);12478-12505.
Zhang et al., "A new anti-HER2 antibody that enhances the anti-tumor efficacy of trastuzumab and pertuzumab with a distinct mechanism of action", Mol Immunol., 2020, 119:48-58.
Zhang et al., "FCGR2A and FCGR3A Polymorphisms Associated with Clinical Outcome of Epidermal Growth Factor Receptor-Expressing Metastatic Colorectal Cancer Patients Treated With Single-Agent Cetuximab", Journal of Clinical Oncology, 2007, 25(24):3712-3718.
Zhou et al., "Significance of semaphorin-3A and MMP-14 protein expression in non-small cell lung cancer", Oncology letters, 2014, 7(5):1395-1400.
Zhu et al., "High-affinity peptide against MT1-MMP for in vivo tumor imaging." Journal of controlled release, 2011, 150(3):248-255.
Zou et al., "PD-L1 (B7-H1) and PD-1 Pathway Blockade for Cancer Therapy: Mechanisms, Response Biomarkers and Combinations," Sci. Transl. Med., 2016, 8(328):328rv4., 1-14.
Zugazagoitia et al., "Current Challenges in Cancer Treatment," Clinical Therapies, 2016, 38(7):1551-1566.
PCT International Preliminary Report on Patentability received for PCT/EP2017/083953, dated Jul. 4, 2019, 7 pages.
PCT International Preliminary Report on Patentability received for PCT/EP2017/083954, dated Jul. 4, 2019, 7 pages.
PCT International Preliminary Report on Patentability received for PCT/EP2018/060498, dated Nov. 7, 2019. 8 pages.
PCT International Preliminary Report on Patentability received for PCT/EP2019/065993, dated Dec. 30, 2020, 7 pages.
PCT International Preliminary Report on Patentability received for PCT/EP2019/066010, dated Dec. 30, 2020, 9 pages.
PCT International Preliminary Report on Patentability received for PCT/EP2019/066066, dated Dec. 30, 2020, 8 pages.
PCT International Preliminary Report on Patentability received for PCT/EP2019/066273, dated Dec. 30, 2020, 8 pages.
PCT International Preliminary Report on Patentability received for PCT/EP2021/072866, dated Mar. 2, 2023, 13 pages.
PCT International Preliminary Report on Patentability received for PCT/GB2015/053247, dated May 11, 2017, 8 pages.
PCT International Preliminary Report on Patentability received for PCT/GB2017/051250, dated Nov. 15, 2018, 7 pages.
PCT International Preliminary Report on Patentability received for PCT/GB2017/053560, dated Jun. 6, 2019, 7 pages.
PCT International Preliminary Report on Patentability received for PCT/GB2018/050017, dated Jul. 18, 2019, 8 pages.
PCT International Preliminary Report on Patentability received for PCT/GB2018/051118, dated Nov. 7, 2019, 11 pages.
PCT International Preliminary Report on Patentability received for PCT/GB2018/051779, dated Jan. 9, 2020, 6 pages.
PCT International Preliminary Report on Patentability received for PCT/GB2018/052222, dated Feb. 13, 2020, 7 pages.
PCT International Preliminary Report on Patentability received for PCT/GB2018/053676, dated Jul. 2, 2020, 7 pages.
PCT International Preliminary Report on Patentability received for PCT/GB2018/053678, dated Jul. 2, 2020, 9 pages.
PCT International Preliminary Report on Patentability received for PCT/GB2019/050485, dated Sep. 3, 2020, 8 pages.
PCT International Preliminary Report on Patentability received for PCT/GB2019/051740, dated Dec. 30, 2020, 8 pages.
PCT International Preliminary Report on Patentability received for PCT/GB2019/051741, dated Dec. 30, 2020, 7 pages.
PCT International Preliminary Report on Patentability received for PCT/GB2019/053020, dated May 6, 2021, 12 pages.
PCT International Preliminary Report on Patentability received for PCT/GB2019/053080, dated May 14, 2021, 16 pages.
PCT International Preliminary Report on Patentability received for PCT/GB2019/053536, dated Jun. 24, 2021, 07 pages.
PCT International Preliminary Report on Patentability received for PCT/GB2019/053537, dated Jun. 24, 2021, 7 pages.
PCT International Preliminary Report on Patentability received for PCT/GB2019/053539, dated Jun. 24, 2021, 7 pages.
PCT International Preliminary Report on Patentability received for PCT/GB2019/053540, dated Jun. 24, 2021, 8 pages.
PCT International Preliminary Report on Patentability received for PCT/GB2019/053679, dated Jul. 1, 2021, 7 pages.
PCT International Preliminary Report on Patentability received for PCT/GB2019/053680, dated Jul. 1, 2021, 7 pages.
PCT International Preliminary Report on Patentability received for PCT/GB2020/050069, dated Jul. 29, 2021, 8 pages.
PCT International Preliminary Report on Patentability received for PCT/GB2020/050070, dated Jul. 29, 2021, 11 pages.
PCT International Preliminary Report on Patentability received for PCT/GB2020/050071, dated Jul. 29, 2021, 7 pages.
PCT International Preliminary Report on Patentability received for PCT/GB2020/050072, dated Jul. 29, 2021, 11 pages.
PCT International Preliminary Report on Patentability received for PCT/GB2020/050073, dated Jul. 29, 2021, 8 pages.
PCT International Preliminary Report on Patentability received for PCT/GB2020/050074, dated Jul. 29, 2021, 14 pages.
PCT International Preliminary Report on Patentability received for PCT/GB2020/050505, dated Sep. 16, 2021, 7 pages.
PCT International Preliminary Report on Patentability received for PCT/GB2020/050874, dated Oct. 14, 2021, 11 pages.
PCT International Preliminary Report on Patentability received for PCT/GB2020/051140, dated Nov. 25, 2021, 8 pages.
PCT International Preliminary Report on Patentability received for PCT/GB2020/051144, dated Nov. 18, 2021, 9 pages.

(56) References Cited

OTHER PUBLICATIONS

PCT International Preliminary Report on Patentability received for PCT/GB2020/051827, dated Feb. 10, 2022, 8 pages.
PCT International Preliminary Report on Patentability received for PCT/GB2020/051829, dated Feb. 10, 2022, 8 pages.
PCT International Preliminary Report on Patentability received for PCT/GB2020/051831, dated Feb. 10, 2022, 10 pages.
PCT International Preliminary Report on Patentability received for PCT/GB2020/051923, dated Feb. 24, 2022, 9 pages.
PCT International Preliminary Report on Patentability received for PCT/GB2020/052058, dated Mar. 10, 2022, 8 pages.
PCT International Preliminary Report on Patentability received for PCT/GB2020/052445, dated Apr. 14, 2022, 26 pages.
PCT International Preliminary Report on Patentability received for PCT/GB2020/052590, dated Apr. 28, 2022, 7 pages.
PCT International Preliminary Report on Patentability received for PCT/GB2020/052619, dated Apr. 28, 2022, 9 pages.
PCT International Preliminary Report on Patentability received for PCT/GB2020/053026, dated Jun. 9, 2022, 8 pages.
PCT International Preliminary Report on Patentability received for PCT/GB2021/050490, dated Sep. 9, 2022, 9 pages.
PCT International Preliminary Report on Patentability received for PCT/GB2021/050491, dated Sep. 9, 2022, 10 pages.
PCT International Preliminary Report on Patentability received for PCT/GB2021/051220, dated Dec. 1, 2022, 7 pages.
PCT International Preliminary Report on Patentability received for PCT/GB2021/051451, dated Dec. 22, 2022, 09 pages.
PCT International Preliminary Report on Patentability received for PCT/GB2021/052001, dated Feb. 16, 2023, 13 pages.
PCT International Preliminary Report on Patentability received for PCT/GB2022/050043, dated Jul. 20, 2023, 13 pages.
PCT International Preliminary Report on Patentability received for PCT/GB2022/050044, dated Jul. 20, 2023, 13 pages.
PCT International Preliminary Report on Patentability received for PCT/GB2022/050055, dated Jul. 20, 2023, 17 pages.
PCT International Search Report and Written Opinion received for PCT/EP2017/083953, dated May 9, 2018, 9 pages.
PCT International Search Report and Written Opinion received for PCT/EP2017/083954, dated May 4, 2018, 9 pages.
PCT International Search Report and Written Opinion received for PCT/EP2018/060498, dated Jul. 5, 2018, 13 pages.
PCT International Search Report and Written Opinion received for PCT/EP2019/066010, dated Sep. 30, 2019, 12 pages.
PCT International Search Report and Written Opinion received for PCT/EP2019/066066, dated Oct. 1, 2019, 11 pages.
PCT International Search Report and Written Opinion received for PCT/EP2019/066273, dated Sep. 27, 2019, 11 pages.
PCT International Search Report and Written Opinion received for PCT/EP2021/072866, dated Dec. 21, 2021, 21 pages.
PCT International Search Report and Written Opinion received for PCT/GB2015/053247, dated Jan. 27, 2016, 12 pages.
PCT International Search Report and Written Opinion received for PCT/GB2017/051250, dated Aug. 4, 2017, 10 pages.
PCT International Search Report and Written Opinion received for PCT/GB2017/053560, dated Jul. 2, 2018, 9 pages.
PCT International Search Report and Written Opinion received for PCT/GB2018/050017, dated Mar. 23, 2018, 12 pages.
PCT International Search Report and Written Opinion received for PCT/GB2018/051118, dated Aug. 3, 2018, 20 pages.
PCT International Search Report and Written Opinion received for PCT/GB2019/050485, dated Jun. 4, 2019, 12 Pages.
PCT International Search Report and Written Opinion received for PCT/GB2019/050951, dated Jul. 4, 2019, 11 pages.
PCT International Search Report and Written Opinion received for PCT/GB2019/051740, dated Aug. 29, 2019, 11 pages.
PCT International Search Report and Written Opinion received for PCT/GB2019/051741, dated Aug. 5, 2019, 10 pages.
PCT International Search Report and Written Opinion received for PCT/GB2019/053020, dated Jun. 23, 2020, 19 pages.
PCT International Search Report and Written Opinion received for PCT/GB2019/053080, dated Feb. 7, 2020, 19 pages.
PCT International Search Report and Written Opinion received for PCT/GB2019/053536, dated Mar. 11, 2020, 11 pages.
PCT International Search Report and Written Opinion received for PCT/GB2019/053537, dated Mar. 11, 2020, 10 pages.
PCT International Search Report and Written Opinion received for PCT/GB2019/053539, dated Mar. 11, 2020, 8 pages.
PCT International Search Report and Written Opinion received for PCT/GB2019/053540, dated Mar. 11, 2020, 10 pages.
PCT International Search Report and Written Opinion received for PCT/GB2019/053679, dated Mar. 11, 2020, 12 pages.
PCT International Search Report and Written Opinion received for PCT/GB2019/053680, dated Mar. 11, 2020, 11 pages.
PCT International Search Report and Written Opinion received for PCT/GB2020/050069, dated Apr. 15, 2020, 10 pages.
PCT International Search Report and Written Opinion received for PCT/GB2020/050070, dated Jun. 23, 2020, 16 pages.
PCT International Search Report and Written Opinion received for PCT/GB2020/050071, dated May 12, 2020, 10 pages.
PCT International Search Report and Written Opinion received for PCT/GB2020/050072, dated Jun. 30, 2020, 16 pages.
PCT International Search Report and Written Opinion received for PCT/GB2020/050073, dated Apr. 7, 2020, 11 pages.
PCT International Search Report and Written Opinion received for PCT/GB2020/050074, dated Jun. 23, 2020, 21 pages.
PCT International Search Report and Written Opinion received for PCT/GB2020/050505, dated Apr. 28, 2020, 9 pages.
PCT International Search Report and Written Opinion received for PCT/GB2020/051140, dated Aug. 20, 2020, 10 pages.
PCT International Search Report and Written Opinion received for PCT/GB2020/051144, dated Aug. 18, 2020, 12 pages.
PCT International Search Report and Written Opinion received for PCT/GB2020/051827, dated Nov. 3, 2020, 11 pages.
PCT International Search Report and Written Opinion received for PCT/GB2020/051831, dated Nov. 4, 2020, 13 pages.
PCT International Search Report and Written Opinion received for PCT/GB2020/051923, dated Nov. 17, 2020, 12 pages.
PCT International Search Report and Written Opinion received for PCT/GB2020/052058, dated Nov. 12, 2020, 11 pages.
PCT International Search Report and Written Opinion received for PCT/GB2020/052445, dated Mar. 4, 2021, 34 pages.
PCT International Search Report and Written Opinion received for PCT/GB2020/052590, dated Jan. 28, 2021, 9 pages.
PCT International Search Report and Written Opinion received for PCT/GB2020/052619, dated Jan. 28, 2021, 12 pages.
PCT International Search Report and Written Opinion received for PCT/GB2020/053026, dated Mar. 23, 2021, 11 pages.
PCT International Search Report and Written Opinion received for PCT/GB2021/050490, dated May 19, 2021, 12 pages.
PCT International Search Report and Written Opinion received for PCT/GB2021/050491, dated May 14, 2021, 14 pages.
PCT International Search Report and Written Opinion received for PCT/GB2021/051220, dated Aug. 27, 2021, 12 pages.
PCT International Search Report and Written Opinion received for PCT/GB2021/052001, dated Nov. 12, 2021, 11 pages.
PCT International Search Report and Written Opinion received for PCT/GB2022/050043, dated Nov. 17, 2022, 18 pages.
PCT International Search Report and Written Opinion received for PCT/GB2022/050044, dated Jun. 28, 2022, 19 pages.
PCT International Search Report and Written Opinion received for PCT/GB2022/050055, dated Apr. 19, 2022, 21 pages.
PCT International Search Report and Written Opinion received for PCT/GB2022/052249, dated Mar. 28, 2023, 14 pages.
PCT International Search Report and Written Opinion received for PCT/GB2022/052903, dated Mar. 13, 2023, 12 pages.
PCT International Search Report and Written Opinion received for PCT/GB2018/052222, dated Oct. 11, 2018, 9 pages.
U.S. Appl. No. 17/769,668, filed Apr. 15, 2022.
U.S. Appl. No. 18/021,748, filed Feb. 16, 2023.
U.S. Appl. No. 18/271,360, filed Jul. 7, 2023.
U.S. Appl. No. 18/271,593, filed Jul. 10, 2023.

(56) References Cited

OTHER PUBLICATIONS

U.S. Appl. No. 18/313,983, filed May 8, 2023.
U.S. Appl. No. 18/345,506, filed Jun. 30, 2023.

Organ distribution [177Lu]I-23

(A) (B)

(A) (B) (C)

SEQUENCE LISTING

```
Sequence total quantity: 78
SEQ ID NO: 1            moltype = AA  length = 26
FEATURE                 Location/Qualifiers
REGION                  1..26
                        note = Description of Artificial Sequence: Synthetic peptide
SITE                    1
                        note = MOD_RES - Beta-Alanine (Beta-Ala)
SITE                    2..11
                        note = MOD_RES - Sarcosine
SITE                    14
                        note = MOD_RES - D-Ala
SITE                    17
                        note = MOD_RES - Naphthylalanine (1Nal)
SITE                    18
                        note = MOD_RES - D-Ala
SITE                    25
                        note = MOD_RES - tert-butyl-Glycine (tBuGly)
source                  1..26
                        mol_type = protein
```

-continued

```
                        organism = synthetic construct
SEQUENCE: 1
XXXXXXXXXX XACANEXACE DFYDXC                                      26

SEQ ID NO: 2            moltype = AA  length = 14
FEATURE                 Location/Qualifiers
REGION                  1..14
                        note = Description of Artificial Sequence: Synthetic peptide
SITE                    2
                        note = MOD_RES - D-Ala
SITE                    5
                        note = MOD_RES - Naphthylalanine (1Nal)
SITE                    6
                        note = MOD_RES - D-Ala
SITE                    13
                        note = MOD_RES - tert-butyl-Glycine (tBuGly)
source                  1..14
                        mol_type = protein
                        organism = synthetic construct
SEQUENCE: 2
CANEXACEDF YDXC                                                   14

SEQ ID NO: 3            moltype = AA  length = 24
FEATURE                 Location/Qualifiers
REGION                  1..24
                        note = Description of Artificial Sequence: Synthetic peptide
SITE                    1
                        note = MOD_RES - Beta-Alanine (Beta-Ala)
SITE                    2..11
                        note = MOD_RES - Sarcosine
source                  1..24
                        mol_type = protein
                        organism = synthetic construct
SEQUENCE: 3
XXXXXXXXXX XACTECWVDG WVPC                                        24

SEQ ID NO: 4            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 4
CTECWVDGWV PC                                                     12

SEQ ID NO: 5            moltype = AA  length = 22
FEATURE                 Location/Qualifiers
REGION                  1..22
                        note = Description of Artificial Sequence: Synthetic peptide
SITE                    1
                        note = N-term Acetylated residue
SITE                    4
                        note = MOD_RES - Homoarginine (HArg)
SITE                    15..20
                        note = MOD_RES - Sarcosine
source                  1..22
                        mol_type = protein
                        organism = synthetic construct
SEQUENCE: 5
CILXPNCDLD GRCAXXXXXX DK                                          22

SEQ ID NO: 6            moltype = AA  length = 14
FEATURE                 Location/Qualifiers
REGION                  1..14
                        note = Description of Artificial Sequence: Synthetic peptide
SITE                    1
                        note = N-term Acetylated residue
SITE                    4
                        note = MOD_RES - Homoarginine (HArg)
source                  1..14
                        mol_type = protein
                        organism = synthetic construct
SEQUENCE: 6
CILXPNCDLD GRCA                                                   14

SEQ ID NO: 7            moltype = AA  length = 21
FEATURE                 Location/Qualifiers
REGION                  1..21
```

```
                          note = Description of Artificial Sequence: Synthetic peptide
SITE                      15..20
                          note = MOD_RES - Sarcosine
SITE                      21
                          note = MOD_RES - Fluoresceinated Lysine
source                    1..21
                          mol_type = protein
                          organism = synthetic construct
SEQUENCE: 7
ACAECWIDGW VPCAXXXXXX K                                                 21

SEQ ID NO: 8              moltype = AA  length = 6
FEATURE                   Location/Qualifiers
REGION                    1..6
                          note = Description of Artificial Sequence: Synthetic peptide
SITE                      1
                          note = N-term Long Chain Fluorescein isocyanate (FITC-LC)
source                    1..6
                          mol_type = protein
                          organism = synthetic construct
SEQUENCE: 8
GRGDSP                                                                  6

SEQ ID NO: 9              moltype = AA  length = 5
FEATURE                   Location/Qualifiers
source                    1..5
                          mol_type = protein
                          organism = synthetic construct
SITE                      1
                          note = D-Ala
SITE                      4
                          note = Naphthylalanine
SITE                      5
                          note = D-Ala
SEQUENCE: 9
ANEXA                                                                   5

SEQ ID NO: 10             moltype = AA  length = 5
FEATURE                   Location/Qualifiers
source                    1..5
                          mol_type = protein
                          organism = synthetic construct
SITE                      3
                          note = Homoarginine
SEQUENCE: 10
ILXPN                                                                   5

SEQ ID NO: 11             moltype = AA  length = 6
FEATURE                   Location/Qualifiers
source                    1..6
                          mol_type = protein
                          organism = synthetic construct
SEQUENCE: 11
PWGPFW                                                                  6

SEQ ID NO: 12             moltype = AA  length = 6
FEATURE                   Location/Qualifiers
source                    1..6
                          mol_type = protein
                          organism = synthetic construct
SEQUENCE: 12
FWLGDE                                                                  6

SEQ ID NO: 13             moltype = AA  length = 5
FEATURE                   Location/Qualifiers
source                    1..5
                          mol_type = protein
                          organism = synthetic construct
SITE                      1
                          note = D-Ala
SITE                      4
                          note = Naphthylalanine
SEQUENCE: 13
ANEXA                                                                   5

SEQ ID NO: 14             moltype = AA  length = 6
FEATURE                   Location/Qualifiers
source                    1..6
                          mol_type = protein
```

-continued

```
                        organism = synthetic construct
SITE                    6
                        note = tert-butyl-Glycine
SEQUENCE: 14
EDFYDX                                                              6

SEQ ID NO: 15           moltype = AA  length = 7
FEATURE                 Location/Qualifiers
source                  1..7
                        mol_type = protein
                        organism = synthetic construct
SEQUENCE: 15
WVDGWVP                                                             7

SEQ ID NO: 16           moltype = AA  length = 5
FEATURE                 Location/Qualifiers
source                  1..5
                        mol_type = protein
                        organism = synthetic construct
SEQUENCE: 16
DLDGR                                                               5

SEQ ID NO: 17           moltype = AA  length = 7
FEATURE                 Location/Qualifiers
source                  1..7
                        mol_type = protein
                        organism = synthetic construct
SITE                    2
                        note = Norleucine
SITE                    3
                        note = Norleucine
SEQUENCE: 17
FXXEDGT                                                             7

SEQ ID NO: 18           moltype = AA  length = 6
FEATURE                 Location/Qualifiers
source                  1..6
                        mol_type = protein
                        organism = synthetic construct
SITE                    2
                        note = tert-butyl-Glycine
SITE                    5
                        note = 2-Aminoisobutyric acid
SEQUENCE: 18
PXNRXG                                                              6

SEQ ID NO: 19           moltype = AA  length = 6
FEATURE                 Location/Qualifiers
source                  1..6
                        mol_type = protein
                        organism = synthetic construct
SITE                    2
                        note = tert-butyl-Glycine
SITE                    4
                        note = Homoarginine
SITE                    6
                        note = D-Asp
SEQUENCE: 19
PXNXPD                                                              6

SEQ ID NO: 20           moltype = AA  length = 6
FEATURE                 Location/Qualifiers
source                  1..6
                        mol_type = protein
                        organism = synthetic construct
SITE                    2
                        note = tert-butyl-Glycine
SITE                    5
                        note = 2-Aminoisobutyric acid
SITE                    6
                        note = D-Asp
SEQUENCE: 20
PXNRXD                                                              6

SEQ ID NO: 21           moltype = AA  length = 7
FEATURE                 Location/Qualifiers
source                  1..7
                        mol_type = protein
                        organism = synthetic construct
```

```
SEQUENCE: 21
ADFPIWY                                                           7

SEQ ID NO: 22           moltype = AA  length = 6
FEATURE                 Location/Qualifiers
source                  1..6
                        mol_type = protein
                        organism = synthetic construct
SEQUENCE: 22
PVNRPG                                                            6

SEQ ID NO: 23           moltype = AA  length = 6
FEATURE                 Location/Qualifiers
source                  1..6
                        mol_type = protein
                        organism = synthetic construct
SEQUENCE: 23
FDWNHE                                                            6

SEQ ID NO: 24           moltype = AA  length = 6
FEATURE                 Location/Qualifiers
source                  1..6
                        mol_type = protein
                        organism = synthetic construct
SITE                    6
                        note = tert-butyl-Glycine
SEQUENCE: 24
ADFYDX                                                            6

SEQ ID NO: 25           moltype = AA  length = 6
FEATURE                 Location/Qualifiers
source                  1..6
                        mol_type = protein
                        organism = synthetic construct
SITE                    2
                        note = tert-butyl-Glycine
SITE                    5
                        note = 2-Aminoisobutyric acid
SEQUENCE: 25
AXNRXD                                                            6

SEQ ID NO: 26           moltype = AA  length = 15
FEATURE                 Location/Qualifiers
source                  1..15
                        mol_type = protein
                        organism = synthetic construct
SITE                    1
                        note = Beta-Alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = Sarcosine
SITE                    8
                        note = Sarcosine
SITE                    9
                        note = Sarcosine
SITE                    10
                        note = Sarcosine
SITE                    11
                        note = Sarcosine
SITE                    13
                        note = D-Asp
SEQUENCE: 26
XXXXXXXXXX XHDVP                                                  15

SEQ ID NO: 27           moltype = AA  length = 30
FEATURE                 Location/Qualifiers
source                  1..30
                        mol_type = protein
                        organism = synthetic construct
SITE                    1
```

```
                         note = 1,4,7,10-tetraazacyclododecane-1,4,7,10-tetraacetic
                          acid modified Beta-Alanine
SITE                     2
                         note = Sarcosine
SITE                     3
                         note = Sarcosine
SITE                     4
                         note = Sarcosine
SITE                     5
                         note = Sarcosine
SITE                     6
                         note = Sarcosine
SITE                     7
                         note = Sarcosine
SITE                     8
                         note = Sarcosine
SITE                     9
                         note = Sarcosine
SITE                     10
                         note = Sarcosine
SITE                     11
                         note = Sarcosine
SITE                     13
                         note = D-Asp
SITE                     18
                         note = Naphthylalanine
SITE                     20
                         note = 2-Aminoisobutyric acid
SITE                     22
                         note = Naphthylalanine
SITE                     25
                         note = tert-butyl-Glycine
SITE                     28
                         note = 2-Aminoisobutyric acid
SITE                     29
                         note = D-Asp
SITE                     30
                         note = Amidated residue
SITE                     16..23
                         note = Intrachain thioether bond via mesitylene
                          (tris-(bromomethyl)benzene)
SITE                     16..30
                         note = Intrachain thioether bond via mesitylene
                          (tris-(bromomethyl)benzene)
SITE                     23..30
                         note = Intrachain thioether bond via mesitylene
                          (tris-(bromomethyl)benzene)
SEQUENCE: 27
XXXXXXXXXX XHDVPCPXAX FXCAXNRXDC                                      30

SEQ ID NO: 28            moltype = AA  length = 14
FEATURE                  Location/Qualifiers
source                   1..14
                         mol_type = protein
                         organism = synthetic construct
SITE                     1
                         note = 1,4,7,10-tetraazacyclododecane-1,4,7,10-tetraacetic
                          acid modified residue
SITE                     2
                         note = D-Ala
SITE                     5
                         note = Naphthylalanine
SITE                     6
                         note = D-Ala
SITE                     13
                         note = tert-butyl-Glycine
SITE                     14
                         note = Amidated residue
SITE                     1..7
                         note = Intrachain thioether bond via mesitylene
                          (tris-(bromomethyl)benzene)
SITE                     1..14
                         note = Intrachain thioether bond via mesitylene
                          (tris-(bromomethyl)benzene)
SITE                     7..14
                         note = Intrachain thioether bond via mesitylene
                          (tris-(bromomethyl)benzene)
SEQUENCE: 28
CANEXACEDF YDXC                                                       14
```

```
SEQ ID NO: 29            moltype = AA  length = 15
FEATURE                  Location/Qualifiers
source                   1..15
                         mol_type = protein
                         organism = synthetic construct
SITE                     1
                         note = 1,4,7,10-tetraazacyclododecane-1,4,7,10-tetraacetic
                          acid modified residue
SITE                     3
                         note = D-Ala
SITE                     6
                         note = Naphthylalanine
SITE                     7
                         note = D-Ala
SITE                     14
                         note = tert-butyl-Glycine
SITE                     15
                         note = Amidated residue
SITE                     2..8
                         note = Intrachain thioether bond via mesitylene
                          (tris-(bromomethyl)benzene)
SITE                     2..15
                         note = Intrachain thioether bond via mesitylene
                          (tris-(bromomethyl)benzene)
SITE                     8..15
                         note = Intrachain thioether bond via mesitylene
                          (tris-(bromomethyl)benzene)
SEQUENCE: 29
ACANEXACED FYDXC                                                     15

SEQ ID NO: 30            moltype = AA  length = 26
FEATURE                  Location/Qualifiers
source                   1..26
                         mol_type = protein
                         organism = synthetic construct
SITE                     1
                         note = 1,4,7,10-tetraazacyclododecane-1,4,7,10-tetraacetic
                          acid modified Beta-Alanine
SITE                     2
                         note = Sarcosine
SITE                     3
                         note = Sarcosine
SITE                     4
                         note = Sarcosine
SITE                     5
                         note = Sarcosine
SITE                     6
                         note = Sarcosine
SITE                     7
                         note = Sarcosine
SITE                     8
                         note = Sarcosine
SITE                     9
                         note = Sarcosine
SITE                     10
                         note = Sarcosine
SITE                     11
                         note = Sarcosine
SITE                     14
                         note = D-Ala
SITE                     17
                         note = Naphthylalanine
SITE                     18
                         note = D-Ala
SITE                     25
                         note = tert-butyl-Glycine
SITE                     26
                         note = Amidated residue
SITE                     13..19
                         note = Intrachain thioether bond via mesitylene
                          (tris-(bromomethyl)benzene)
SITE                     13..26
                         note = Intrachain thioether bond via mesitylene
                          (tris-(bromomethyl)benzene)
SITE                     19..26
                         note = Intrachain thioether bond via mesitylene
                          (tris-(bromomethyl)benzene)
SEQUENCE: 30
```

```
XXXXXXXXXX XACANEXACE DFYDXC                                        26

SEQ ID NO: 31           moltype = AA  length = 26
FEATURE                 Location/Qualifiers
source                  1..26
                        mol_type = protein
                        organism = synthetic construct
SITE                    1
                        note = Alexafluor488 modified Beta-Alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = Sarcosine
SITE                    8
                        note = Sarcosine
SITE                    9
                        note = Sarcosine
SITE                    10
                        note = Sarcosine
SITE                    11
                        note = Sarcosine
SITE                    14
                        note = D-Ala
SITE                    17
                        note = Naphthylalanine
SITE                    18
                        note = D-Ala
SITE                    25
                        note = tert-butyl-Glycine
SITE                    26
                        note = Amidated residue
SITE                    13..19
                        note = Intrachain thioether bond via mesitylene
                         (tris-(bromomethyl)benzene)
SITE                    13..26
                        note = Intrachain thioether bond via mesitylene
                         (tris-(bromomethyl)benzene)
SITE                    19..26
                        note = Intrachain thioether bond via mesitylene
                         (tris-(bromomethyl)benzene)
SEQUENCE: 31
XXXXXXXXXX XACANEXACE DFYDXC                                        26

SEQ ID NO: 32           moltype = AA  length = 26
FEATURE                 Location/Qualifiers
source                  1..26
                        mol_type = protein
                        organism = synthetic construct
SITE                    1
                        note = Fluorescein modified Beta-Alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = Sarcosine
SITE                    8
                        note = Sarcosine
SITE                    9
                        note = Sarcosine
SITE                    10
                        note = Sarcosine
SITE                    11
                        note = Sarcosine
SITE                    14
```

```
                        note = D-Ala
SITE                    17
                        note = Naphthylalanine
SITE                    18
                        note = D-Ala
SITE                    25
                        note = tert-butyl-Glycine
SITE                    26
                        note = Amidated residue
SITE                    13..19
                        note = Intrachain thioether bond via mesitylene
                         (tris-(bromomethyl)benzene)
SITE                    13..26
                        note = Intrachain thioether bond via mesitylene
                         (tris-(bromomethyl)benzene)
SITE                    19..26
                        note = Intrachain thioether bond via mesitylene
                         (tris-(bromomethyl)benzene)
SEQUENCE: 32
XXXXXXXXXX XACANEXACE DFYDXC                                        26

SEQ ID NO: 33           moltype = AA  length = 12
FEATURE                 Location/Qualifiers
source                  1..12
                        mol_type = protein
                        organism = synthetic construct
SITE                    1
                        note = 1,4,7,10-tetraazacyclododecane-1,4,7,10-tetraacetic
                         acid modified residue
SITE                    12
                        note = Amidated residue
SITE                    1..4
                        note = Intrachain thioether bond via mesitylene
                         (tris-(bromomethyl)benzene)
SITE                    1..12
                        note = Intrachain thioether bond via mesitylene
                         (tris-(bromomethyl)benzene)
SITE                    4..12
                        note = Intrachain thioether bond via mesitylene
                         (tris-(bromomethyl)benzene)
SEQUENCE: 33
CTECWVDGWV PC                                                       12

SEQ ID NO: 34           moltype = AA  length = 13
FEATURE                 Location/Qualifiers
source                  1..13
                        mol_type = protein
                        organism = synthetic construct
SITE                    1
                        note = 1,4,7,10-tetraazacyclododecane-1,4,7,10-tetraacetic
                         acid modified residue
SITE                    13
                        note = Amidated residue
SITE                    2..5
                        note = Intrachain thioether bond via mesitylene
                         (tris-(bromomethyl)benzene)
SITE                    2..13
                        note = Intrachain thioether bond via mesitylene
                         (tris-(bromomethyl)benzene)
SITE                    5..13
                        note = Intrachain thioether bond via mesitylene
                         (tris-(bromomethyl)benzene)
SEQUENCE: 34
ACTECWVDGW VPC                                                      13

SEQ ID NO: 35           moltype = AA  length = 24
FEATURE                 Location/Qualifiers
source                  1..24
                        mol_type = protein
                        organism = synthetic construct
SITE                    1
                        note = 1,4,7,10-tetraazacyclododecane-1,4,7,10-tetraacetic
                         acid modified Beta-Alanine
SITE                    2
                        note = Sarcosine
SITE                    3
                        note = Sarcosine
SITE                    4
                        note = Sarcosine
```

-continued

```
SITE                  5
                      note = Sarcosine
SITE                  6
                      note = Sarcosine
SITE                  7
                      note = Sarcosine
SITE                  8
                      note = Sarcosine
SITE                  9
                      note = Sarcosine
SITE                  10
                      note = Sarcosine
SITE                  11
                      note = Sarcosine
SITE                  24
                      note = Amidated residue
SITE                  13..16
                      note = Intrachain thioether bond via mesitylene
                       (tris-(bromomethyl)benzene)
SITE                  13..24
                      note = Intrachain thioether bond via mesitylene
                       (tris-(bromomethyl)benzene)
SITE                  16..24
                      note = Intrachain thioether bond via mesitylene
                       (tris-(bromomethyl)benzene)
SEQUENCE: 35
XXXXXXXXXX XACTECWVDG WVPC                                        24

SEQ ID NO: 36         moltype = AA  length = 21
FEATURE               Location/Qualifiers
source                1..21
                      mol_type = protein
                      organism = synthetic construct
SITE                  1
                      note = Acetylated residue
SITE                  4
                      note = Homoarginine
SITE                  15
                      note = Sarcosine
SITE                  16
                      note = Sarcosine
SITE                  17
                      note = Sarcosine
SITE                  18
                      note = Sarcosine
SITE                  19
                      note = Sarcosine
SITE                  20
                      note = Sarcosine
SITE                  21
                      note = Amidated
                       1,4,7,10-tetraazacyclododecane-1,4,7,10-tetraacetic acid
                       modified residue
SITE                  1..7
                      note = Intrachain thioether bond via mesitylene
                       (tris-(bromomethyl)benzene)
SITE                  1..13
                      note = Intrachain thioether bond via mesitylene
                       (tris-(bromomethyl)benzene)
SITE                  7..13
                      note = Intrachain thioether bond via mesitylene
                       (tris-(bromomethyl)benzene)
SEQUENCE: 36
CILXPNCDLD GRCAXXXXXX K                                           21

SEQ ID NO: 37         moltype = AA  length = 21
FEATURE               Location/Qualifiers
source                1..21
                      mol_type = protein
                      organism = synthetic construct
SITE                  1
                      note = Acetylated residue
SITE                  4
                      note = Homoarginine
SITE                  15
                      note = Sarcosine
SITE                  16
                      note = Sarcosine
SITE                  17
```

-continued

```
                          note = Sarcosine
SITE                      18
                          note = Sarcosine
SITE                      19
                          note = Sarcosine
SITE                      20
                          note = Sarcosine
SITE                      21
                          note = Amidated
                           1,4,7,10-tetraazacyclododecane-1,4,7,10-tetraacetic acid
                           modified residue
SITE                      1..7
                          note = Intrachain thioether bond via mesitylene
                           (tris-(bromomethyl)benzene)
SITE                      1..13
                          note = Intrachain thioether bond via mesitylene
                           (tris-(bromomethyl)benzene)
SITE                      7..13
                          note = Intrachain thioether bond via mesitylene
                           (tris-(bromomethyl)benzene)
SEQUENCE: 37
CILXPNCDLD GRCAXXXXXX K                                              21

SEQ ID NO: 38             moltype = AA  length = 22
FEATURE                   Location/Qualifiers
source                    1..22
                          mol_type = protein
                          organism = synthetic construct
SITE                      1
                          note = Acetylated residue
SITE                      4
                          note = Homoarginine
SITE                      15
                          note = Sarcosine
SITE                      16
                          note = Sarcosine
SITE                      17
                          note = Sarcosine
SITE                      18
                          note = Sarcosine
SITE                      19
                          note = Sarcosine
SITE                      20
                          note = Sarcosine
SITE                      22
                          note = Amidated
                           1,4,7,10-tetraazacyclododecane-1,4,7,10-tetraacetic acid
                           modified residue
SITE                      1..7
                          note = Intrachain thioether bond via mesitylene
                           (tris-(bromomethyl)benzene)
SITE                      1..13
                          note = Intrachain thioether bond via mesitylene
                           (tris-(bromomethyl)benzene)
SITE                      7..13
                          note = Intrachain thioether bond via mesitylene
                           (tris-(bromomethyl)benzene)
SEQUENCE: 38
CILXPNCDLD GRCAXXXXXX DK                                             22

SEQ ID NO: 39             moltype = AA  length = 22
FEATURE                   Location/Qualifiers
source                    1..22
                          mol_type = protein
                          organism = synthetic construct
SITE                      1
                          note = Acetylated D-Glu
SITE                      5
                          note = D-Asp
SITE                      8
                          note = Norleucine
SITE                      9
                          note = Norleucine
SITE                      16
                          note = Sarcosine
SITE                      17
                          note = Sarcosine
SITE                      18
                          note = Sarcosine
```

-continued

```
SITE                     19
                         note = Sarcosine
SITE                     20
                         note = Sarcosine
SITE                     21
                         note = Sarcosine
SITE                     22
                         note = Amidated
                          1,4,7,10-tetraazacyclododecane-1,4,7,10-tetraacetic acid
                          modified residue
SITE                     3..6
                         note = Intrachain thioether bond via mesitylene
                          (tris-(bromomethyl)benzene)
SITE                     3..14
                         note = Intrachain thioether bond via mesitylene
                          (tris-(bromomethyl)benzene)
SITE                     6..14
                         note = Intrachain thioether bond via mesitylene
                          (tris-(bromomethyl)benzene)
SEQUENCE: 39
EVCWDCFXXE DGTCAXXXXX XK                                            22

SEQ ID NO: 40            moltype = AA  length = 30
FEATURE                  Location/Qualifiers
source                   1..30
                         mol_type = protein
                         organism = synthetic construct
SITE                     1
                         note = 1,4,7,10-tetraazacyclododecane-1,4,7,10-tetraacetic
                          acid modified Beta-Alanine
SITE                     2
                         note = Sarcosine
SITE                     3
                         note = Sarcosine
SITE                     4
                         note = Sarcosine
SITE                     5
                         note = Sarcosine
SITE                     6
                         note = Sarcosine
SITE                     7
                         note = Sarcosine
SITE                     8
                         note = Sarcosine
SITE                     9
                         note = Sarcosine
SITE                     10
                         note = Sarcosine
SITE                     11
                         note = Sarcosine
SITE                     13
                         note = D-Asp
SITE                     18
                         note = Naphthylalanine
SITE                     20
                         note = 2-Aminoisobutyric acid
SITE                     22
                         note = Naphthylalanine
SITE                     25
                         note = tert-butyl-Glycine
SITE                     28
                         note = 2-Aminoisobutyric acid
SITE                     30
                         note = Amidated residue
SITE                     16..23
                         note = Intrachain thioether bond via mesitylene
                          (tris-(bromomethyl)benzene)
SITE                     16..30
                         note = Intrachain thioether bond via mesitylene
                          (tris-(bromomethyl)benzene)
SITE                     23..30
                         note = Intrachain thioether bond via mesitylene
                          (tris-(bromomethyl)benzene)
SEQUENCE: 40
XXXXXXXXXX XHDVPCPXGX FXCPXNRXGC                                    30

SEQ ID NO: 41            moltype = AA  length = 30
FEATURE                  Location/Qualifiers
source                   1..30
```

-continued

```
                       mol_type = protein
                       organism = synthetic construct
SITE                   1
                       note = 1,4,7,10-tetraazacyclododecane-1,4,7,10-tetraacetic
                        acid modified Beta-Alanine
SITE                   2
                       note = Sarcosine
SITE                   3
                       note = Sarcosine
SITE                   4
                       note = Sarcosine
SITE                   5
                       note = Sarcosine
SITE                   6
                       note = Sarcosine
SITE                   7
                       note = Sarcosine
SITE                   8
                       note = Sarcosine
SITE                   9
                       note = Sarcosine
SITE                   10
                       note = Sarcosine
SITE                   11
                       note = Sarcosine
SITE                   13
                       note = D-Asp
SITE                   18
                       note = Naphthylalanine
SITE                   20
                       note = 2-Aminoisobutyric acid
SITE                   22
                       note = Naphthylalanine
SITE                   25
                       note = tert-butyl-Glycine
SITE                   27
                       note = Homoarginine
SITE                   29
                       note = D-Asp
SITE                   30
                       note = Amidated residue
SITE                   16..23
                       note = Intrachain thioether bond via mesitylene
                        (tris-(bromomethyl)benzene)
SITE                   16..30
                       note = Intrachain thioether bond via mesitylene
                        (tris-(bromomethyl)benzene)
SITE                   23..30
                       note = Intrachain thioether bond via mesitylene
                        (tris-(bromomethyl)benzene)
SEQUENCE: 41
XXXXXXXXXX XHDVPCPXGX FXCPXNXPDC                                    30

SEQ ID NO: 42          moltype = AA  length = 30
FEATURE                Location/Qualifiers
source                 1..30
                       mol_type = protein
                       organism = synthetic construct
SITE                   1
                       note = 1,4,7,10-tetraazacyclododecane-1,4,7,10-tetraacetic
                        acid modified Beta-Alanine
SITE                   2
                       note = Sarcosine
SITE                   3
                       note = Sarcosine
SITE                   4
                       note = Sarcosine
SITE                   5
                       note = Sarcosine
SITE                   6
                       note = Sarcosine
SITE                   7
                       note = Sarcosine
SITE                   8
                       note = Sarcosine
SITE                   9
                       note = Sarcosine
SITE                   10
                       note = Sarcosine
```

-continued

```
SITE                    11
                        note = Sarcosine
SITE                    13
                        note = D-Asp
SITE                    17
                        note = 2-Aminoisobutyric acid
SITE                    18
                        note = Naphthylalanine
SITE                    20
                        note = 2-Aminoisobutyric acid
SITE                    22
                        note = Naphthylalanine
SITE                    25
                        note = tert-butyl-Glycine
SITE                    27
                        note = Homoarginine
SITE                    29
                        note = D-Asp
SITE                    30
                        note = Amidated residue
SITE                    16..23
                        note = Intrachain thioether bond via mesitylene
                         (tris-(bromomethyl)benzene)
SITE                    16..30
                        note = Intrachain thioether bond via mesitylene
                         (tris-(bromomethyl)benzene)
SITE                    23..30
                        note = Intrachain thioether bond via mesitylene
                         (tris-(bromomethyl)benzene)
SEQUENCE: 42
XXXXXXXXXX XHDVPCXXGX FXCPXNXPDC                                   30

SEQ ID NO: 43           moltype = AA  length = 30
FEATURE                 Location/Qualifiers
source                  1..30
                        mol_type = protein
                        organism = synthetic construct
SITE                    1
                        note = 1,4,7,10-tetraazacyclododecane-1,4,7,10-tetraacetic
                         acid modified Beta-Alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = Sarcosine
SITE                    8
                        note = Sarcosine
SITE                    9
                        note = Sarcosine
SITE                    10
                        note = Sarcosine
SITE                    11
                        note = Sarcosine
SITE                    13
                        note = D-Asp
SITE                    14
                        note = (2S)-2-amino-2-cyclopentylacetic acid
SITE                    18
                        note = Naphthylalanine
SITE                    20
                        note = 2-Aminoisobutyric acid
SITE                    22
                        note = Naphthylalanine
SITE                    25
                        note = tert-butyl-Glycine
SITE                    27
                        note = Homoarginine
SITE                    29
                        note = D-Asp
SITE                    30
                        note = Amidated residue
SITE                    16..23
```

```
                        note = Intrachain thioether bond via mesitylene
                         (tris-(bromomethyl)benzene)
SITE                    16..30
                        note = Intrachain thioether bond via mesitylene
                         (tris-(bromomethyl)benzene)
SITE                    23..30
                        note = Intrachain thioether bond via mesitylene
                         (tris-(bromomethyl)benzene)
SEQUENCE: 43
XXXXXXXXXX XHDXPCPXGX FXCPXNXPDC                                  30

SEQ ID NO: 44           moltype = AA  length = 30
FEATURE                 Location/Qualifiers
source                  1..30
                        mol_type = protein
                        organism = synthetic construct
SITE                    1
                        note = 1,4,7,10-tetraazacyclododecane-1,4,7,10-tetraacetic
                         acid modified Beta-Alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = Sarcosine
SITE                    8
                        note = Sarcosine
SITE                    9
                        note = Sarcosine
SITE                    10
                        note = Sarcosine
SITE                    11
                        note = Sarcosine
SITE                    13
                        note = D-Asp
SITE                    18
                        note = Naphthylalanine
SITE                    20
                        note = 2-Aminoisobutyric acid
SITE                    22
                        note = Naphthylalanine
SITE                    25
                        note = tert-butyl-Glycine
SITE                    28
                        note = 2-Aminoisobutyric acid
SITE                    29
                        note = D-Asp
SITE                    30
                        note = Amidated residue
SITE                    16..23
                        note = Intrachain thioether bond via mesitylene
                         (tris-(bromomethyl)benzene)
SITE                    16..30
                        note = Intrachain thioether bond via mesitylene
                         (tris-(bromomethyl)benzene)
SITE                    23..30
                        note = Intrachain thioether bond via mesitylene
                         (tris-(bromomethyl)benzene)
SEQUENCE: 44
XXXXXXXXXX XHDVPCPXGX FXCPXNRXDC                                  30

SEQ ID NO: 45           moltype = AA  length = 30
FEATURE                 Location/Qualifiers
source                  1..30
                        mol_type = protein
                        organism = synthetic construct
SITE                    1
                        note = 1,4,7,10-tetraazacyclododecane-1,4,7,10-tetraacetic
                         acid modified Beta-Alanine
SITE                    2
                        note = Sarcosine
SITE                    3
                        note = Sarcosine
```

-continued

```
SITE                    4
                        note = Sarcosine
SITE                    5
                        note = Sarcosine
SITE                    6
                        note = Sarcosine
SITE                    7
                        note = Sarcosine
SITE                    8
                        note = Sarcosine
SITE                    9
                        note = Sarcosine
SITE                    10
                        note = Sarcosine
SITE                    11
                        note = Sarcosine
SITE                    13
                        note = D-Asp
SITE                    14
                        note = (2S)-2-amino-2-cyclopentylacetic acid
SITE                    17
                        note = 2-Aminoisobutyric acid
SITE                    18
                        note = Naphthylalanine
SITE                    20
                        note = 2-Aminoisobutyric acid
SITE                    22
                        note = Naphthylalanine
SITE                    25
                        note = tert-butyl-Glycine
SITE                    28
                        note = 2-Aminoisobutyric acid
SITE                    29
                        note = D-Asp
SITE                    30
                        note = Amidated residue
SITE                    16..23
                        note = Intrachain thioether bond via mesitylene
                         (tris-(bromomethyl)benzene)
SITE                    16..30
                        note = Intrachain thioether bond via mesitylene
                         (tris-(bromomethyl)benzene)
SITE                    23..30
                        note = Intrachain thioether bond via mesitylene
                         (tris-(bromomethyl)benzene)
SEQUENCE: 45
XXXXXXXXXX XHDXPCXXGX FXCPXNRXDC                                     30

SEQ ID NO: 46           moltype = AA  length = 27
FEATURE                 Location/Qualifiers
source                  1..27
                        mol_type = protein
                        organism = synthetic construct
SITE                    1
                        note = 1,4,7,10-tetraazacyclododecane-1,4,7,10-tetraacetic
                         acid modified Beta-Alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = Sarcosine
SITE                    8
                        note = Sarcosine
SITE                    9
                        note = Sarcosine
SITE                    10
                        note = Sarcosine
SITE                    11
                        note = Sarcosine
SITE                    27
                        note = Amidated residue
SITE                    13..20
```

-continued

```
                        note = Intrachain thioether bond via mesitylene
                         (tris-(bromomethyl)benzene)
SITE                    13..27
                        note = Intrachain thioether bond via mesitylene
                         (tris-(bromomethyl)benzene)
SITE                    20..27
                        note = Intrachain thioether bond via mesitylene
                         (tris-(bromomethyl)benzene)
SEQUENCE: 46
XXXXXXXXXX XACPWGPFWC PVNRPGC                                      27

SEQ ID NO: 47           moltype = AA  length = 30
FEATURE                 Location/Qualifiers
source                  1..30
                        mol_type = protein
                        organism = synthetic construct
SITE                    1
                        note = 1,4,7,10-tetraazacyclododecane-1,4,7,10-tetraacetic
                         acid modified Beta-Alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = Sarcosine
SITE                    8
                        note = Sarcosine
SITE                    9
                        note = Sarcosine
SITE                    10
                        note = Sarcosine
SITE                    11
                        note = Sarcosine
SITE                    13
                        note = D-Asp
SITE                    30
                        note = Amidated residue
SITE                    16..23
                        note = Intrachain thioether bond via mesitylene
                         (tris-(bromomethyl)benzene)
SITE                    16..30
                        note = Intrachain thioether bond via mesitylene
                         (tris-(bromomethyl)benzene)
SITE                    23..30
                        note = Intrachain thioether bond via mesitylene
                         (tris-(bromomethyl)benzene)
SEQUENCE: 47
XXXXXXXXXX XHDVPCPWGP FWCPVNRPGC                                   30

SEQ ID NO: 48           moltype = AA  length = 24
FEATURE                 Location/Qualifiers
source                  1..24
                        mol_type = protein
                        organism = synthetic construct
SITE                    1
                        note = 1,4,7,10-tetraazacyclododecane-1,4,7,10-tetraacetic
                         acid modified Beta-Alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = Sarcosine
SITE                    8
                        note = Sarcosine
SITE                    9
                        note = Sarcosine
```

-continued

```
SITE                  10
                      note = Sarcosine
SITE                  11
                      note = Sarcosine
SITE                  24
                      note = Amidated residue
SITE                  13..16
                      note = Intrachain thioether bond via mesitylene
                       (tris-(bromomethyl)benzene)
SITE                  13..24
                      note = Intrachain thioether bond via mesitylene
                       (tris-(bromomethyl)benzene)
SITE                  16..24
                      note = Intrachain thioether bond via mesitylene
                       (tris-(bromomethyl)benzene)
SEQUENCE: 48
XXXXXXXXXX XACVPCADFP IWYC                                          24

SEQ ID NO: 49         moltype = AA  length = 23
FEATURE               Location/Qualifiers
source                1..23
                      mol_type = protein
                      organism = synthetic construct
SITE                  1
                      note = Acetylated residue
SITE                  17
                      note = Sarcosine
SITE                  18
                      note = Sarcosine
SITE                  19
                      note = Sarcosine
SITE                  20
                      note = Sarcosine
SITE                  21
                      note = Sarcosine
SITE                  22
                      note = Sarcosine
SITE                  23
                      note = Amidated
                       1,4,7,10-tetraazacyclododecane-1,4,7,10-tetraacetic acid
                       modified residue
SITE                  1..8
                      note = Intrachain thioether bond via mesitylene
                       (tris-(bromomethyl)benzene)
SITE                  1..15
                      note = Intrachain thioether bond via mesitylene
                       (tris-(bromomethyl)benzene)
SITE                  8..15
                      note = Intrachain thioether bond via mesitylene
                       (tris-(bromomethyl)benzene)
SEQUENCE: 49
CFWLGDECFD WNHECAXXXX XXK                                           23

SEQ ID NO: 50         moltype = AA  length = 15
FEATURE               Location/Qualifiers
source                1..15
                      mol_type = protein
                      organism = synthetic construct
SITE                  1
                      note = 1,4,7,10-tetraazacyclododecane-1,4,7,10-tetraacetic
                       acid modified residue
SITE                  3
                      note = D-Ala
SITE                  6
                      note = Naphthylalanine
SITE                  7
                      note = D-Ala
SITE                  14
                      note = tert-butyl-Glycine
SITE                  15
                      note = Amidated residue
SITE                  2..8
                      note = Intrachain thioether bond via mesitylene
                       (tris-(bromomethyl)benzene)
SITE                  2..15
                      note = Intrachain thioether bond via mesitylene
                       (tris-(bromomethyl)benzene)
SITE                  8..15
                      note = Intrachain thioether bond via mesitylene
```

-continued

```
                        (tris-(bromomethyl)benzene)
SEQUENCE: 50
ACANEXACED FYDXC                                                   15

SEQ ID NO: 51           moltype = AA  length = 26
FEATURE                 Location/Qualifiers
source                  1..26
                        mol_type = protein
                        organism = synthetic construct
SITE                    1
                        note = 1,4,7,10-tetraazacyclododecane-1,4,7,10-tetraacetic
                         acid modified Beta-Alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = Sarcosine
SITE                    8
                        note = Sarcosine
SITE                    9
                        note = Sarcosine
SITE                    10
                        note = Sarcosine
SITE                    11
                        note = Sarcosine
SITE                    14
                        note = D-Ala
SITE                    17
                        note = Naphthylalanine
SITE                    18
                        note = D-Ala
SITE                    25
                        note = tert-butyl-Glycine
SITE                    26
                        note = Amidated residue
SITE                    13..19
                        note = Intrachain thioether bond via mesitylene
                         (tris-(bromomethyl)benzene)
SITE                    13..26
                        note = Intrachain thioether bond via mesitylene
                         (tris-(bromomethyl)benzene)
SITE                    19..26
                        note = Intrachain thioether bond via mesitylene
                         (tris-(bromomethyl)benzene)
SEQUENCE: 51
XXXXXXXXXX XACANEXACE DFYDXC                                       26

SEQ ID NO: 52           moltype = AA  length = 32
FEATURE                 Location/Qualifiers
source                  1..32
                        mol_type = protein
                        organism = synthetic construct
SITE                    1
                        note = Palmitoyl modified Beta-Alanine
SITE                    2
                        note = Sarcosine
SITE                    3
                        note = Sarcosine
SITE                    4
                        note = Sarcosine
SITE                    5
                        note = Sarcosine
SITE                    6
                        note = Sarcosine
SITE                    7
                        note = 1,4,7,10-tetraazacyclododecane-1,4,7,10-tetraacetic
                         acid modified residue
SITE                    8
                        note = Sarcosine
SITE                    9
                        note = Sarcosine
SITE                    10
```

-continued

```
                        note = Sarcosine
SITE                    11
                        note = Sarcosine
SITE                    12
                        note = Sarcosine
SITE                    13
                        note = Sarcosine
SITE                    14
                        note = Sarcosine
SITE                    15
                        note = Sarcosine
SITE                    16
                        note = Sarcosine
SITE                    17
                        note = Sarcosine
SITE                    20
                        note = D-Ala
SITE                    23
                        note = Naphthylalanine
SITE                    24
                        note = D-Ala
SITE                    31
                        note = tert-butyl-Glycine
SITE                    32
                        note = Amidated residue
SITE                    19..25
                        note = Intrachain thioether bond via mesitylene
                         (tris-(bromomethyl)benzene)
SITE                    19..32
                        note = Intrachain thioether bond via mesitylene
                         (tris-(bromomethyl)benzene)
SITE                    25..32
                        note = Intrachain thioether bond via mesitylene
                         (tris-(bromomethyl)benzene)
SEQUENCE: 52
XXXXXXKXXX XXXXXXXACA NEXACEDFYD XC                                   32

SEQ ID NO: 53           moltype = AA  length = 15
FEATURE                 Location/Qualifiers
source                  1..15
                        mol_type = protein
                        organism = synthetic construct
SITE                    1
                        note = 1,4,7,10-tetraazacyclododecane-1,4,7,10-tetraacetic
                         acid modified residue
SITE                    3
                        note = D-Ala
SITE                    6
                        note = Naphthylalanine
SITE                    14
                        note = tert-butyl-Glycine
SITE                    15
                        note = Amidated residue
SITE                    2..8
                        note = Intrachain thioether bond via mesitylene
                         (tris-(bromomethyl)benzene)
SITE                    2..15
                        note = Intrachain thioether bond via mesitylene
                         (tris-(bromomethyl)benzene)
SITE                    8..15
                        note = Intrachain thioether bond via mesitylene
                         (tris-(bromomethyl)benzene)
SEQUENCE: 53
ACANEXACAD FYDXC                                                      15

SEQ ID NO: 54           moltype = AA  length = 26
FEATURE                 Location/Qualifiers
source                  1..26
                        mol_type = protein
                        organism = synthetic construct
SITE                    1
                        note = 1,4,7,10-tetraazacyclododecane-1,4,7,10-tetraacetic
                         acid modified Beta-Alanine
SITE                    2
                        note = Sarcosine
SITE                    3
                        note = Sarcosine
SITE                    4
                        note = Sarcosine
```

```
SITE                  5
                      note = Sarcosine
SITE                  6
                      note = Sarcosine
SITE                  7
                      note = Sarcosine
SITE                  8
                      note = Sarcosine
SITE                  9
                      note = Sarcosine
SITE                  10
                      note = Sarcosine
SITE                  11
                      note = Sarcosine
SITE                  14
                      note = D-Ala
SITE                  17
                      note = Naphthylalanine
SITE                  25
                      note = tert-butyl-Glycine
SITE                  26
                      note = Amidated residue
SITE                  13..19
                      note = Intrachain thioether bond via mesitylene
                       (tris-(bromomethyl)benzene)
SITE                  13..26
                      note = Intrachain thioether bond via mesitylene
                       (tris-(bromomethyl)benzene)
SITE                  19..26
                      note = Intrachain thioether bond via mesitylene
                       (tris-(bromomethyl)benzene)
SEQUENCE: 54
XXXXXXXXXX XACANEXACA DFYDXC                                       26

SEQ ID NO: 55         moltype = AA  length = 6
FEATURE               Location/Qualifiers
source                1..6
                      mol_type = protein
                      organism = synthetic construct
SITE                  4
                      note = Aib
SITE                  2
                      note = Naphthylalanine
SITE                  6
                      note = Naphthylalanine
SEQUENCE: 55
PAGXFA                                                             6

SEQ ID NO: 56         moltype = AA  length = 6
FEATURE               Location/Qualifiers
source                1..6
                      mol_type = protein
                      organism = synthetic construct
SITE                  1
                      note = Aib
SITE                  4
                      note = Aib
SITE                  2
                      note = Naphthylalanine
SITE                  6
                      note = Naphthylalanine
SEQUENCE: 56
XAGXFA                                                             6

SEQ ID NO: 57         moltype = AA  length = 6
FEATURE               Location/Qualifiers
source                1..6
                      mol_type = protein
                      organism = synthetic construct
SITE                  4
                      note = Aib
SITE                  2
                      note = Naphthylalanine
SITE                  6
                      note = Naphthylalanine
SEQUENCE: 57
PAAXFA                                                             6

SEQ ID NO: 58         moltype = AA  length = 18
```

-continued

```
FEATURE                 Location/Qualifiers
source                  1..18
                        mol_type = protein
                        organism = synthetic construct
SITE                    2..6
                        note = sarcosine
SITE                    8..17
                        note = sarcosine
SITE                    1
                        note = Beta-Alanine (Beta-Ala)
SITE
                        note = linked to palmitoyl
SITE                    2..6
                        note = may be absent
SITE                    8..17
                        note = may be absent
SEQUENCE: 58
AGGGGGKGGG GGGGGGGA                                                  18

SEQ ID NO: 59           moltype = AA  length = 15
FEATURE                 Location/Qualifiers
source                  1..15
                        mol_type = protein
                        organism = synthetic construct
SITE                    2..11
                        note = sarcosine
SITE                    1
                        note = Beta-Alanine (Beta-Ala)
SITE                    13
                        note = D-aspartic acid
SITE                    14
                        note = (2S)-2-amino-2-cyclopentylacetic acid
SEQUENCE: 59
AGGGGGGGGG GHDXP                                                     15

SEQ ID NO: 60           moltype = AA  length = 18
FEATURE                 Location/Qualifiers
source                  1..18
                        mol_type = protein
                        organism = synthetic construct
SITE                    2..6
                        note = sarcosine
SITE                    8..17
                        note = sarcosine
SITE                    1
                        note = Beta-Alanine (Beta-Ala)
SITE
                        note = linked to palmitoyl
SEQUENCE: 60
AGGGGGKGGG GGGGGGGA                                                  18

SEQ ID NO: 61           moltype = AA  length = 9
FEATURE                 Location/Qualifiers
source                  1..9
                        mol_type = protein
                        organism = synthetic construct
SITE                    2..7
                        note = sarcosine
SEQUENCE: 61
AGGGGGGDK                                                            9

SEQ ID NO: 62           moltype = AA  length = 9
FEATURE                 Location/Qualifiers
source                  1..9
                        mol_type = protein
                        organism = synthetic construct
SITE                    2..7
                        note = sarcosine
MOD_RES                 9
                        note = epsilon-succinyllysine
SEQUENCE: 62
AGGGGGGDK                                                            9

SEQ ID NO: 63           moltype = AA  length = 13
FEATURE                 Location/Qualifiers
source                  1..13
                        mol_type = protein
                        organism = synthetic construct
SITE                    2..11
```

```
                        note = sarcosine
SEQUENCE: 63
AGGGGGGGGG GDK                                                      13

SEQ ID NO: 64           moltype = AA  length = 13
FEATURE                 Location/Qualifiers
source                  1..13
                        mol_type = protein
                        organism = synthetic construct
SITE                    2..11
                        note = sarcosine
MOD_RES                 13
                        note = epsilon-succinyllysine
SEQUENCE: 64
AGGGGGGGGG GDK                                                      13

SEQ ID NO: 65           moltype = AA  length = 12
FEATURE                 Location/Qualifiers
source                  1..12
                        mol_type = protein
                        organism = synthetic construct
SITE                    2..11
                        note = sarcosine
SEQUENCE: 65
AGGGGGGGGG GK                                                       12

SEQ ID NO: 66           moltype = AA  length = 12
FEATURE                 Location/Qualifiers
source                  1..12
                        mol_type = protein
                        organism = synthetic construct
SITE                    2..11
                        note = sarcosine
MOD_RES                 12
                        note = epsilon-succinyllysine
SEQUENCE: 66
AGGGGGGGGG GK                                                       12

SEQ ID NO: 67           moltype = AA  length = 8
FEATURE                 Location/Qualifiers
source                  1..8
                        mol_type = protein
                        organism = synthetic construct
SITE                    2..7
                        note = sarcosine
SEQUENCE: 67
AGGGGGGK                                                            8

SEQ ID NO: 68           moltype = AA  length = 7
FEATURE                 Location/Qualifiers
source                  1..7
                        mol_type = protein
                        organism = synthetic construct
SITE                    2..7
                        note = sarcosine
SEQUENCE: 68
GGGGGGG                                                             7

SEQ ID NO: 69           moltype = AA  length = 6
FEATURE                 Location/Qualifiers
source                  1..6
                        mol_type = protein
                        organism = synthetic construct
SITE                    1..6
                        note = sarcosine
SEQUENCE: 69
GGGGGG                                                              6

SEQ ID NO: 70           moltype = AA  length = 6
FEATURE                 Location/Qualifiers
source                  1..6
                        mol_type = protein
                        organism = synthetic construct
MOD_RES                 1..6
                        note = hydroxyproline
SEQUENCE: 70
PPPPPP                                                              6

SEQ ID NO: 71           moltype = AA  length = 12
```

-continued

```
FEATURE               Location/Qualifiers
source                1..12
                      mol_type = protein
                      organism = synthetic construct
MOD_RES               1..12
                      note = hydroxyproline
SEQUENCE: 71
PPPPPPPPPP PP                                                              12

SEQ ID NO: 72         moltype = AA  length = 12
FEATURE               Location/Qualifiers
source                1..12
                      mol_type = protein
                      organism = synthetic construct
SITE                  2..11
                      note = sarcosine
SEQUENCE: 72
AGGGGGGGGG GA                                                              12

SEQ ID NO: 73         moltype = AA  length = 10
FEATURE               Location/Qualifiers
source                1..10
                      mol_type = protein
                      organism = synthetic construct
SITE                  1..10
                      note = sarcosine
SEQUENCE: 73
GGGGGGGGGG                                                                 10

SEQ ID NO: 74         moltype = AA  length = 20
FEATURE               Location/Qualifiers
source                1..20
                      mol_type = protein
                      organism = synthetic construct
SITE                  2..7
                      note = sarcosine
SITE
                      note = linked to
                       1,4,7,10-tetraazacyclododecane-1,4,7,10-tetraacetate
SEQUENCE: 74
GGGGGGGCSW PARCLHQDLC                                                      20

SEQ ID NO: 75         moltype = AA  length = 15
FEATURE               Location/Qualifiers
source                1..15
                      mol_type = protein
                      organism = synthetic construct
SITE
                      note = linked to
                       1,4,7,10-tetraazacyclododecane-1,4,7,10-tetraacetate
SEQUENCE: 75
ACYNEFGCED FYDIC                                                           15

SEQ ID NO: 76         moltype = AA  length = 15
FEATURE               Location/Qualifiers
source                1..15
                      mol_type = protein
                      organism = synthetic construct
SITE
                      note = linked to
                       Lutetium-1,4,7,10-tetraazacyclododecane-1,4,7,10-tetraaceta
                       te complex
SEQUENCE: 76
ACYNEFGCED FYDIC                                                           15

SEQ ID NO: 77         moltype = AA  length = 16
FEATURE               Location/Qualifiers
source                1..16
                      mol_type = protein
                      organism = synthetic construct
SITE
                      note = linked to
                       1,4,7,10-tetraazacyclododecane-1,4,7,10-tetraacetate
SITE                  1..16
                      note = D amino acids
SEQUENCE: 77
AACYNEFGCE DFYDIC                                                          16

SEQ ID NO: 78         moltype = AA  length = 16
```

-continued

```
FEATURE                 Location/Qualifiers
source                  1..16
                        mol_type = protein
                        organism = synthetic construct
SITE
                        note = linked to
                         1,4,7,10-tetraazacyclododecane-1,4,7,10-tetraacetate
SITE                    4
                        note = D-alanine
SITE                    7
                        note = naphthylalanine
SITE                    8
                        note = D-alanine
MOD_RES                 13
                        note = 4-bromophenylalanine
SITE                    15
                        note = tert-butylglycine
SEQUENCE: 78
AACANEAACE DFFDGC                                            16
```

BICYCLIC PEPTIDE LIGANDS WITH DETECTABLE MOIETIES AND USES THEREOF

CROSS REFERENCE TO RELATED APPLICATIONS

This application is a divisional application of U.S. application Ser. No. 17/060,409, filed Oct. 1, 2020, which is a divisional of U.S. application Ser. No. 16/018,432, filed Jun. 26, 2018, which claims the benefit of U.S. Provisional Application No. 62/524,721, filed Jun. 26, 2017 and U.S. Provisional Application No. 62/594,613, filed Dec. 5, 2017, the entire contents of each of which are incorporated herein by reference.

SEQUENCE LISTING

The instant application contains a Sequence Listing which has been submitted electronically in XML file format and is hereby incorporated by reference in its entirety. Said XML copy, created on Aug. 27, 2025, is named B170170041US04-SUBSEQ-PJH.xml and is 279,910 bytes in size.

TECHNICAL FIELD OF THE INVENTION

The present invention relates to polypeptides which are covalently bound to molecular scaffolds such that two or more peptide loops are subtended between attachment points to the scaffold and further linked to a detectable moiety. In particular, the invention describes bicyclic peptide ligands useful for selectively delivering the linked detectable moiety to cancer cells. The invention also describes peptides which are high affinity binders of carbonic anhydrase IX (CAIX), membrane type 1 metalloprotease (MT1-MMP), prostate-specific membrane antigen (PSMA), cluster of differentiation 38 (CD38), Eph receptor tyrosine kinase A2 (EphA2), or integrin αvβ3 (αvβ3). The invention also includes pharmaceutical compositions comprising said peptide ligands and to the use of said peptide ligands in diagnosing, imaging, preventing, suppressing or treating a disease or disorder mediated by CAIX, MT1-MMP, PSMA, CD38, EphA2, or αvβ3.

BACKGROUND OF THE INVENTION

Transmembrane proteins which are overexpressed in cancer cells provide a potential means for selectively targeting and imaging cancer cells. Imaging of cancer cells plays an important role in the diagnosis and treatment of cancer. Six such transmembrane proteins are: carbonic anhydrase IX (CAIX), membrane type 1-matrix metalloproteinase (MT1-MMP), prostate-specific membrane antigen (PSMA), cluster of differentiation 38 (CD38), Eph receptor tyrosine kinase A2 (EphA2), and the integrin αvβ3 (αvβ3).

Human carbonic anhydrase IX (hCA IX) is an isoform bound to the outer cell membrane (its catalytic domain is located in the extracellular space). At physiological conditions, hCAIX is expressed only in specific tissues of gastrointestinal tract. Its overexpression was shown during hypoxia in cancer cells both in vitro and in vivo. Expression of hCAIX was detected in carcinomas of cervix, ovaries, kidneys, esophagus, lungs, breasts and brain. In tumors, hCAIX is a molecule crucial for the maintenance of intracellular pH on normal level and its expression provides the hypoxic tumor cells with an advantage in growth at acidic conditions (Chiche et al. (2009) Cancer Res 69, 358).

MT1-MMP is a transmembrane metalloprotease that plays a major role in the extracellular matrix remodelling, directly by degrading several of its components and indirectly by activating pro-MMP2. MT1-MMP is crucial for tumor angiogenesis (Sounni et al (2002) FASEB J. 16 (6), 555-564) and is over-expressed on a variety of solid tumors.

Prostate-specific membrane antigen (PSMA) (also known as Glutamate carboxypeptidase II (GCPII), N-acetyl-L-aspartyl-L-glutamate peptidase I (NAALADase I) and NAAG peptidase) is an enzyme that in humans is encoded by the FOLH1 (folate hydrolase 1) gene. Human GCPII contains 750 amino acids and weighs approximately 84 kDa. Human PSMA is highly expressed in the prostate, roughly a hundred times greater than in most other tissues. In some prostate cancers, PSMA is the second-most upregulated gene product, with an 8- to 12-fold increase over levels in noncancerous prostate cells. Because of this high expression, PSMA is being developed as potential biomarker for therapy and imaging of some cancers. In human prostate cancer, the higher expressing tumors are associated with quicker time to progression and a greater percentage of patients suffering relapse.

CD38 is a 45 kD type II transmembrane glycoprotein with a long C-terminal extracellular domain and a short N-terminal cytoplasmic domain. CD38 is upregulated in many hematopoeitic malignancies and in cell lines derived from various hematopoietic malignancies, including non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML).

EphA2 is a 130 kDa receptor tyrosine kinase that is expressed on adult epithelia. A member of the Eph family of tyrosine kinases known as Ephrins, EphA2 is a transmembrane receptor tyrosine kinase with a cell-bound ligand. EphA2 expression has been found to be altered in many metastatic cells, including lung, breast, colon, and prostate tumors. Additionally, the distribution and/or phosphorylation of EphA2 is altered in metastatic cells. Moreover, cells that have been transformed to overexpress EphA2 demonstrate malignant growth, and stimulation of EphA2 is sufficient to reverse malignant growth and invasiveness. EphA2 is a powerful oncoprotein.

Integrin αvβ3 is a transmembrane glycoprotein receptor that plays a major role in tumor growth, invasion, metastasis, and angiogenesis. It is over-expressed in various types of tumor cells (Jin et al (2016) Mol Cancer Ther; 15 (9). 2076-2085).

Accordingly, there remains a high unmet need in developing agents that selectively bind transmembrane proteins such as CAIX, MT1-MMP, PSMA, CD38, EphA2, or αvβ3 for the diagnosis, imaging, and treatment of cancer

SUMMARY OF THE INVENTION

It has now been found that compounds of this invention, and pharmaceutically acceptable compositions thereof, are effective as inhibitors of CAIX, MT1-MMP, PSMA, CD38, EphA2, or αvβ3. Such compounds have the general formula I:

I

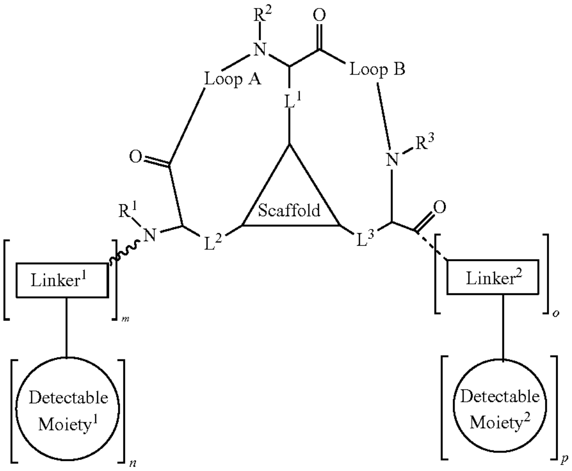

or a pharmaceutically acceptable salt thereof, wherein each variable is as defined and described herein.

Compounds of the present invention, and pharmaceutically acceptable compositions thereof, are useful for treating a variety of diseases, disorders or conditions, associated with CAIX, MT1-MMP, PSMA, CD38, EphA2, or αvβ3. Such diseases, disorders, or conditions include those described herein.

Compounds provided by this invention are also useful for the study of CAIX, MT1-MMP, PSMA, CD38, EphA2, or αvβ3 enzymes in biological and pathological phenomena; the study of these enzymes occurring in bodily tissues; and the comparative evaluation of new CAIX, MT1-MMP, PSMA, CD38, EphA2, or αvβ3 inhibitors in vitro or in vivo.

DETAILED DESCRIPTION OF CERTAIN EMBODIMENTS

Figure 1:
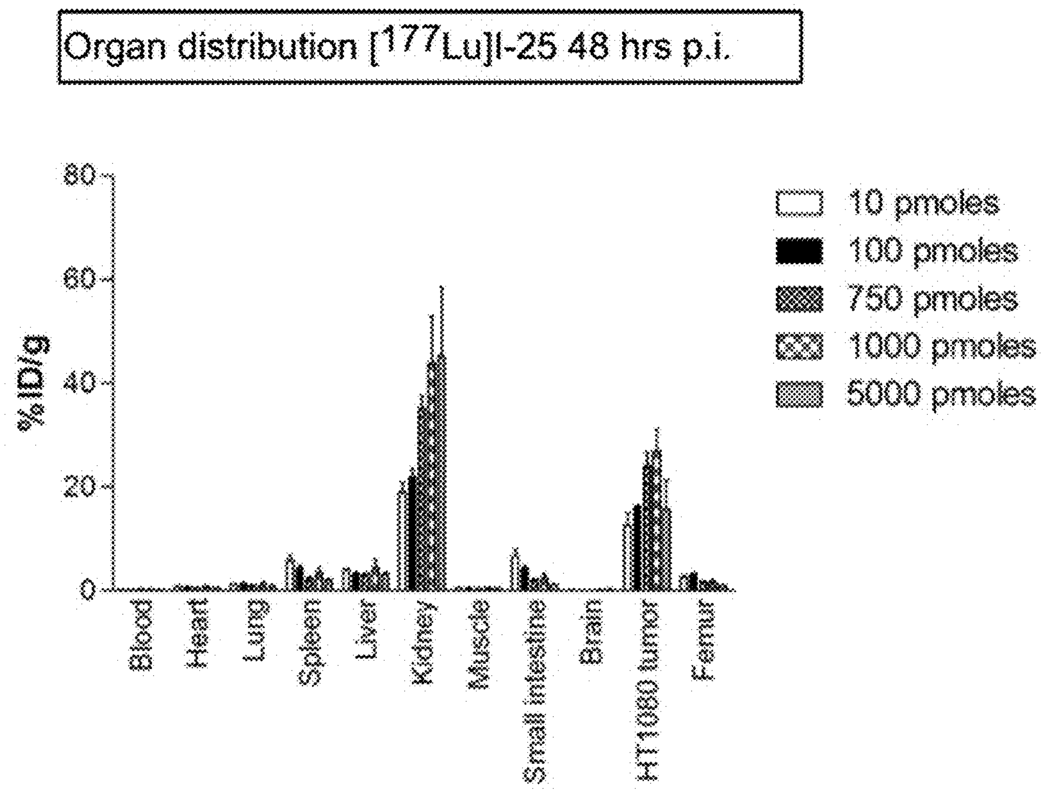
FIG. 1 depicts the organ distribution of Lu-177 labelled I-25 at different doses.

1. General Description of Certain Embodiments of the Invention

A proprietary phage display and cyclic peptide technology (Bicycle® technology) was utilized to identify high affinity binding peptides to the membrane type 1-matrix metalloproteinase (MT1-MMP/MMP14). MT1-MMP (MT1) is a cell surface membrane protease normally involved in tissue remodeling which has been found to be over-expressed in many solid tumors. Overexpression of MT1 has been linked to cancer invasiveness and poor prognosis. While attempts to target the proteolytic activity of MT1 and other MMPs in cancer were unsuccessful in clinical trials largely due to toxicity caused by insufficient selectivity, MT1-MMP remains an attractive cancer target for targeted cytotoxic delivery approaches.

Diverse selection phage libraries containing 1011 to 1013 unique peptide sequences which are post-translationally cyclized with thiol-reactive scaffolds were used to identify small (1.5-2 kDa) constrained bicyclic peptides binders (Bicycles) to the hemopexin domain of MT1. Initial binders were subject to affinity maturation by directed screens and stabilization by chemical optimization.

A bicyclic constrained peptide binder (Bicycle) was identified that binds to the hemopexin domain of MT1 with an apparent Kd of approximately 2 nM. The Bicycle peptide (N241) binds with similar affinity to the entire ectodomain of the protease but shows no binding to the catalytic domain. N241 also shows no binding toward any of the closely related MMP family members tested (MMP15, MMP16, MMP24, MMP1, Pro-MMP1, MMP2). Characterization of the pharmacologic effect of N241 on MT1 in vitro shows that the peptide has no direct impact on the catalytic activity of the protease, nor related MMP catalytic activity (MMP1, MMP2 and MMP9) nor cell migration or invasion. However, binding of fluorescently-tagged N241 to MT1 on HT1080 fibrosarcoma cells results in the rapid internalization and subsequent lysosomal localization of the compound. In addition, $^{177}$Lu-loaded N241 demonstrates rapid tumor localization when injected IV into mice bearing MT1-positive tumor xenografts, with levels as high as 15-20% injected dose per gram of tumor in less than 60 minutes. In contrast, a non-binding Bicycle peptide shows no tumor localization. These properties suggest that N241 may be a good delivery vehicle for Detectable Moieties targeting MT1-positive tumor cells. Bicycle Detectable Moiety Conjugates (BDMCs) with a variety of linkers and detectable moieties were prepared which retained binding to MT1. The imaging activity of select BDMCs was demonstrated in MT1-positive human tumor cell xenografts in mice as described in WO 2016/067035, which is hereby incorporated in its entirety by reference.

A series of Bicycle Detectable Moiety Conjugates (BDMCs) were prepared comprising a constrained bicyclic peptide that binds with high affinity and specificity to membrane type 1-matrix metalloprotease (MT1-MMP; MMP14) covalently linked via a Linker to 1,4,7,10-tetraazacyclododecane-1,4,7,10-tetraacetic acid (DOTA), a chelating ligand capable of binding radionuclides. MT1-MMP is naturally involved in tissue remodeling, however overexpression of the cell-surface protease has been tied to tumor aggressiveness and invasiveness, as well as poor patient prognosis for many cancer indications. The Bicycle binder for MT1-MMP (N241) was identified using a proprietary phage display peptide technology consisting of highly diverse phage libraries of linear amino acid sequences constrained into two loops by a central chemical scaffold. While binding with similar affinity and specificity to that observed with monoclonal antibodies, the small size of a Bicycle peptide (1.5-2 kDa) aids in its rapid extravasation and tumor penetration making it an ideal format for the targeted delivery of Detectable Moieties for imaging and treating cancer.

A series of Bicycle-Linker-Detectable Moiety BDMCs were prepared, with varying spacer format to adjust the presentation of the Bicycle and evaluated for their ability to target and image tumors in an MT1-positive tumor xenograft model.

The Bicycle Detectable Moiety conjugates (BDMCs) of the present invention show selective targeting of tumor cells in human tumor xenograft models of fibrosarcomas. Without wishing to be bound by any particular theory, it is believed that the small size of the BDMC may offer a significant advantage to other targeted imaging approaches such as antibody-detectable moiety conjugates due to rapid extravasation and improved tumor penetration.

In certain aspects, the present invention provides a method of treating certain cancers in a subject, comprising administering to the subject an effective amount of a detectable moiety conjugate comprising a high affinity binder of MT1-MMP, or a pharmaceutically acceptable salt or composition thereof.

In certain aspects, the present invention provides a method of imaging certain cancers in a subject, comprising administering to the subject an effective amount of a detectable moiety conjugate comprising a high affinity binder of MT1-MMP, or a pharmaceutically acceptable salt or composition thereof.

In a similar manner, proprietary phage display and cyclic peptide technology (Bicycle® technology) was utilized to identify high affinity binding peptides to carbonic anhydrase IX (CAIX), PSMA, CD38, EphA2, and the integrin αvβ3.

In certain aspects, the present invention provides a method of treating certain cancers in a subject, comprising administering to the subject an effective amount of a detectable moiety conjugate comprising a high affinity binder of CAIX, or a pharmaceutically acceptable salt or composition thereof.

In certain aspects, the present invention provides a method of imaging certain cancers in a subject, comprising administering to the subject an effective amount of a detectable moiety conjugate comprising a high affinity binder of CAIX, or a pharmaceutically acceptable salt or composition thereof.

In certain aspects, the present invention provides a method of treating certain cancers in a subject, comprising administering to the subject an effective amount of a detectable moiety conjugate comprising a high affinity binder of PSMA, or a pharmaceutically acceptable salt or composition thereof.

In certain aspects, the present invention provides a method of imaging certain cancers in a subject, comprising administering to the subject an effective amount of a detectable moiety conjugate comprising a high affinity binder of PSMA, or a pharmaceutically acceptable salt or composition thereof.

In certain aspects, the present invention provides a method of treating certain cancers in a subject, comprising administering to the subject an effective amount of a detectable moiety conjugate comprising a high affinity binder of CD38, or a pharmaceutically acceptable salt or composition thereof.

In certain aspects, the present invention provides a method of imaging certain cancers in a subject, comprising administering to the subject an effective amount of a detectable moiety conjugate comprising a high affinity binder of CD38, or a pharmaceutically acceptable salt or composition thereof.

In certain aspects, the present invention provides a method of treating certain cancers in a subject, comprising administering to the subject an effective amount of a detectable moiety conjugate comprising a high affinity binder of EphA2, or a pharmaceutically acceptable salt or composition thereof.

In certain aspects, the present invention provides a method of imaging certain cancers in a subject, comprising administering to the subject an effective amount of a detectable moiety conjugate comprising a high affinity binder of EphA2, or a pharmaceutically acceptable salt or composition thereof.

In certain aspects, the present invention provides a method of treating certain cancers in a subject, comprising administering to the subject an effective amount of a detectable moiety conjugate comprising a high affinity binder of αvβ3, or a pharmaceutically acceptable salt or composition thereof.

In certain aspects, the present invention provides a method of imaging certain cancers in a subject, comprising administering to the subject an effective amount of a detectable moiety conjugate comprising a high affinity binder of αvβ3, or a pharmaceutically acceptable salt or composition thereof.

In some embodiments, peptide sequences are treated with molecular scaffold reagents to form compounds of the present invention.

Compounds of the present invention, and compositions thereof, are useful as inhibitors of CAIX, MT1-MMP, PSMA, CD38, EphA2, or αvβ3. In some embodiments, a provided compound inhibits CAIX. In some embodiments, a provided compound inhibits MT1-MMP. In some embodiments, a provided compound inhibits PSMA. In some embodiments, a provided compound inhibits CD38. In some embodiments, a provided compound inhibits EphA2. In some embodiments, a provided compound inhibits αvβ3.

In certain embodiments, the present invention provides a compound of formula I:

I

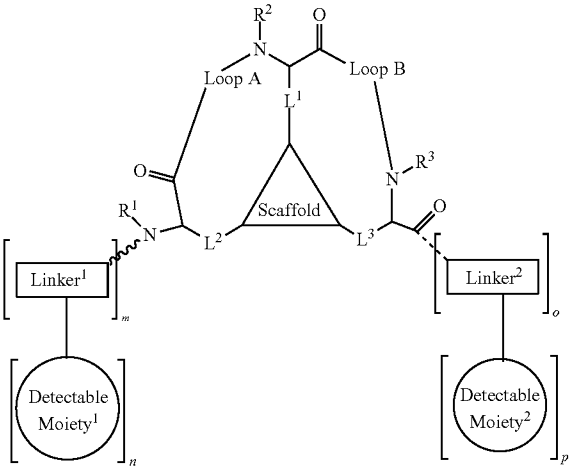

or a pharmaceutically acceptable salt thereof, wherein:

each of $L^1$, $L^2$, and $L^3$ is independently a covalent bond or a $C_{1-8}$ bivalent hydrocarbon chain wherein one, two or three methylene units of the chain are optionally and independently replaced by —S—, —N(R)—, —O—, —C(O)—, —OC(O)—, —C(O)O—, —C(O)N(R)—, —N(R)C(O)—, —S(O)—, $—S(O)_2—$ or —N(R)$CH_2C(O)$—;

each of R is independently hydrogen or $C_{1-4}$ alkyl;

each of m, n, o, and p is independently 0 or 1;

each of q and r is independently 1, 2, 3, 4, 5, 6, 7, 8, 9, 10, 11, 12, 13, 14 or 15;

$R^1$ is R or —C(O)R;

each of $R^4$ and $R^6$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each of $R^{4'}$ and $R^{6'}$ is independently hydrogen or methyl;

each of $R^2$, $R^3$, $R^5$, and $R^7$ is independently hydrogen, or $C_{1-4}$ aliphatic, or:

an $R^5$ group and its adjacent $R^4$ group are optionally taken together with their intervening atoms to form a 4-8 membered saturated or partially unsaturated monocyclic heterocyclic ring having 1-2 heteroatoms independently selected from nitrogen, oxygen, or sulfur; or an $R^7$ group and its adjacent $R^6$ group are optionally taken together with their intervening atoms to form a 4-8 membered saturated or partially unsaturated monocyclic heterocyclic ring having 1-2 heteroatoms independently selected from nitrogen, oxygen, or sulfur;

Scaffold is a trivalent group that connects and orients a cyclic peptide;

Loop A is a bivalent natural or unnatural amino acid residue or peptide attached to the amino acid residue linked to $L^2$ and the amino acid residue linked to $L^1$, wherein Loop A comprises

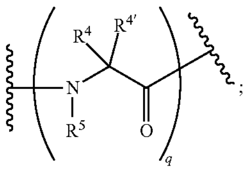

;

Loop B is a bivalent natural or unnatural amino acid residue or peptide attached to the amino acid residue linked to $L^1$ and the amino acid residue linked to $L^3$, wherein Loop B comprises

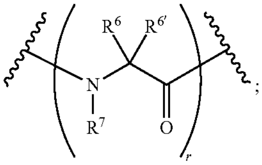

;

indicates the site of attachment to the N-terminus of the Bicycle;

indicates the site of attachment to the C-terminus of the Bicycle;

Detectable $Moiety^1$ is any moiety capable of being detected;

Detectable $Moiety^2$ is any moiety capable of being detected;

$Linker^1$ is hydrogen, —C(O)R,

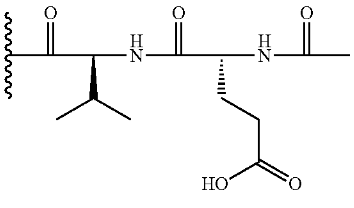

, or a bivalent moiety that connects the N-terminus of the Bicycle with Detectable $Moiety^1$, wherein when n is 0, $Linker^1$ is hydrogen, —C(O)R, or

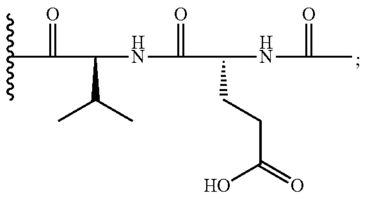 [SMILES: *C(=O)[C@H](NC(=O)[C@H](CCC(=O)O)NC(C)=O)C(C)C]

Linker$^2$ is —$NH_2$ or a bivalent moiety that connects the C-terminus of the Bicycle with Detectable Moiety$^2$, wherein when p is 0, Linker$^2$ is —$NH_2$; and Ring A is selected from the group consisting of 18-crown-6,1,7,13-triaza-18-crown-6, and a 3-12-membered saturated, partially unsaturated, bridged bicyclic, bridged tricyclic, propellane, or aromatic ring optionally substituted with 0-3 oxo, methyl, ethyl or spiroethylene groups and having 0-6 heteroatoms independently selected from nitrogen, oxygen, or sulfur.

2. Compounds and Definitions

Peptide Ligands

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å2; Wu et al. (2007), Science 330, 1066-71), a cyclic peptide with the Arg-Gly-Asp motif binding to integrin αVβ3 (355 Å2) (Xiong et al. (2002), Science 296 (5565), 151-5) or the cyclic peptide inhibitor upain-1 binding to urokinase-type plasminogen activator (603 Å2; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Phage display-based combinatorial approaches have been developed to generate and screen large libraries of bicyclic peptides to targets of interest (Heinis et al. (2009), Nat Chem Biol 5 (7), 502-7 and WO2009/098450). Briefly, combinatorial libraries of linear peptides containing three cysteine residues and two regions of six random amino acids (Cys-(Xaa)6-Cys-(Xaa)6-Cys) were displayed on phage and cyclised by covalently linking the cysteine side chains to a small molecule (tris-(bromomethyl)benzene).

A peptide ligand, as referred to herein, refers to a peptide covalently bound to a molecular scaffold. Typically, such peptides comprise two or more reactive groups (e.g. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues and form at least two loops on the scaffold. One of ordinary skill in the art will recognize that other amino acid residues capable of forming covalent bonds to the scaffold can be used (e.g. lysine, Dap or serine) to form bicyclic peptides of the present invention.

Advantages of the Peptide Ligands

Certain bicyclic peptides of the present invention have a number of advantageous properties which enable them to be considered as suitable drug-like molecules for injection, inhalation, nasal, ocular, oral or topical administration. Without being bound by any particular theory, such advantageous properties may include:

Species cross-reactivity. This is a typical requirement for preclinical pharmacodynamics and pharmacokinetic evaluation;

Protease stability. Bicyclic peptide ligands should ideally demonstrate stability to plasma proteases, epithelial ("membrane-anchored") proteases, gastric and intestinal proteases, lung surface proteases, intracellular proteases and the like. Protease stability should be maintained between different species such that a bicycle lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes;

An optimal plasma half-life in the circulation. Depending upon the clinical indication and treatment regimen, it may be required to develop a bicyclic peptide for short exposure in an acute illness management setting, or develop a bicyclic peptide with enhanced retention in the circulation, and is therefore optimal for the management of more chronic disease states. Other factors driving the desirable plasma half-life are requirements of sustained exposure for maximal therapeutic efficiency versus the accompanying toxicology due to sustained exposure of the agent; and Selectivity. Certain peptide ligands of the invention demonstrate good selectivity over other carbonic anhydrases, metalloproteases, and integrins.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

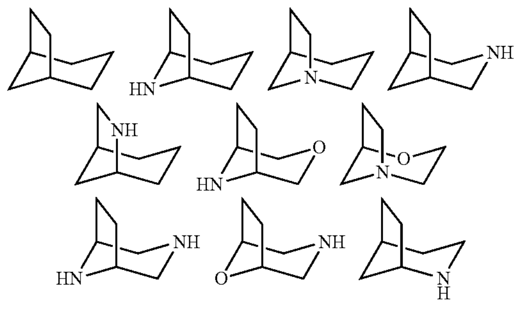

-continued

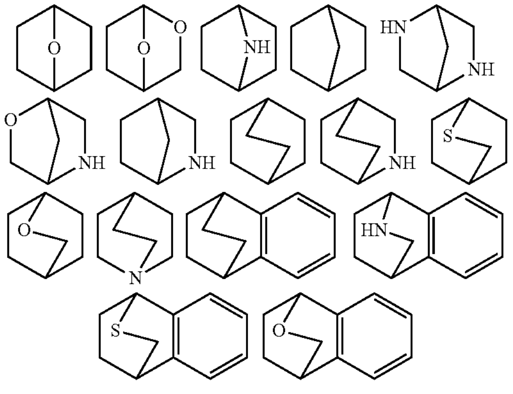

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2HI-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

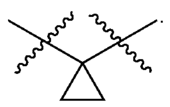 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 $\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4 oxazin-3 (4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4 dihydro-2H-pyrrolyl), NH (as in pyrrolidinyl), or $^{+}NR$ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $CH{=}CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)(O)R^\circ$; $-N(R^\circ)(S)R^\circ$; $-N(R^\circ)(NR^\circ)N(R^\circ)_2$; $-(CH_2)_{0-4}N(R^\circ)(O)NR^\circ_2$; $-N(R^\circ)(S)NR^\circ_2$; $-(CH_2)_{0-4}N(R^\circ)(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $-SC(S)SR^\circ$; $-(CH_2)_{0-4}SC(O)R^\circ$; $-(CH_2)_{0-4}C(O)NR^\circ_2$; $C(S)NR^\circ_2$; $-C(S)SR^\circ$; $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $-SiR^\circ_3$; $-(C_{1-4}$ straight or branched alkylene)$O-N(R^\circ)_2$; or $-(C_{1-4}$ straight or branched)alkylene) $C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $—(CH_2)_{0-2}R^{\bullet}$, -(halo$R^{\bullet}$), $—(CH_2)_{0-2}OH$, $—(CH_2)_{0-2}OR^{\bullet}$, $—(CH_2)_{0-2}CH(OR^{\bullet})_2$; —O(halo$R^{\bullet}$), —CN, $—N_3$, $—(CH_2)_{0-2}C(O)R^\circ$, $—(CH_2)_{0-2}C(O)OH$, $—(CH_2)_{0-2}C(O)OR^{\bullet}$, $—(CH_2)_{0-2}SR^\circ$, $—(CH_2)_{0-2}SH$, $—(CH_2)_{0-2}NH_2$, $—(CH_2)_{0-2}NHR^{\bullet}$, $—(CH_2)_{0-2}NR^{\bullet}_2$, $—NO_2$, $—SiR^{\bullet}_3$, $—OSiR^{\bullet}_3$, $—C(O)SR^{\bullet}$, —($C_{1-4}$ straight or branched alkylene) $C(O)OR^{\bullet}$, or $—SSR^{\bullet}$ wherein each $R^{\bullet}$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\bullet}$ include =O and =S.

Suitable divalent substituents on a saturated carbon atom of an "optionally substituted" group include the following: =O, =S, $=NNR^*_2$, =NNHC(O)R*, =NNHC(O)OR*, $=NNHS(O)_2R^*$, =NR*, =NOR*, $—O(C(R^*_2))_{2-3}O—$, or $—S(C(R^*_2))_{2-3}S—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $—R^{\bullet}$, -(halo$R^{\bullet}$), —OH, $—OR^{\bullet}$, —O(halo$R^{\bullet}$), —CN, —C(O) OH, $—C(O)OR^{\bullet}$, $—NH_2$, $—NHR^{\bullet}$, $—NR^{\bullet}_2$, or $—NO_2$, wherein each $R^{\bullet}$ is unsubstituted or where preceded by "halo" is substituted only with one or more halogens, and is independently $C_1$-4 aliphatic, $CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $—R^\dagger$, $—NR^\dagger_2$, $—C(O)R^\dagger$, $—C(O)OR^\dagger$, $—C(O)C(O)R^\dagger$, $—C(O)CH_2C(O)R^\dagger$, $—S(O)_2R^\dagger$, $—S(O)_2NR^\dagger_2$, $—C(S)NR^\dagger_2$, $—C(NH)NR^\dagger_2$, or $—N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $—R^\dagger$, -(halo$R^\dagger$), —OH, $—OR^\dagger$, —O(halo$R^\dagger$), —CN, —C(O) OH, $—C(O)OR^\dagger$, $—NH_2$, $—NHR^\dagger$, $—NR^\dagger_2$, or $—NO_2$, wherein each $R^\dagger$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a provided compound comprises one or more deuterium atoms.

As used herein, the term "inhibitor" is defined as a compound that binds to and/or inhibits CAIX, MT1-MMP, PSMA, CD38, EphA2, or $\alpha v\beta 3$ with measurable affinity. In certain embodiments, an inhibitor has an $IC_{50}$ and/or binding constant of less than about 50 μM, less than about 1 μM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{225}Ac$, $^{227}Ac$, $^{241}Am$, $^{72}As$, $^{74}As$, $^{211}At$, $^{198}Au$, $^{11}B$, $^{7}Be$, $^{212}Bi$, $^{213}Bi$, $^{75}Br$, $^{77}Br$, $^{11}C$, $^{14}C$, $^{48}Ca$, $^{109}Cd$, $^{139}Ce$, $^{141}Ce$, $^{252}Cf$, $^{55}Co$, $^{57}Co$, $^{60}Co$, $^{51}Cr$, $^{130}Cs$, $^{131}Cs$, $^{137}Cs$, $^{61}Cu$, $^{62}Cu$, $^{64}Cu$, $^{67}Cu$, $^{165}Dy$, $^{152}Eu$, $^{155}Eu$, $^{18}F$, $^{55}Fe$, $^{59}Fe$, $^{64}Ga$, $^{67}Ga$, $^{68}Ga$, $^{153}Gd$, $^{68}Ge$, $^{122}I$, $^{123}I$, $^{124}I$, $^{125}I$, $^{131}I$, $^{132}I$, $^{111}In$, $^{115m}In$, $^{191m}Ir$, $^{192}Ir$, $^{81m}Kr$, $^{177}Lu$, $^{51}Mn$, $^{52}Mn$, $^{99}Mo$, $^{13}N$, $^{95}Nb$, $^{15}O$, $^{191}Os$, $^{194}Os$, $^{32}P$, $^{33}P$, $^{203}Pb$, $^{212}Pb$, $^{103}Pd$, $^{109}Pd$, $^{238}Pu$, $^{223}Ra$, $^{226}Ra$, $^{82}Rb$, $^{186}Re$, $^{188}Re$, $^{105}Rh$, $^{97}Ru$, $^{103}Ru$, $^{35}S$, $^{46}Sc$, $^{47}Sc$, $^{72}Se$, $^{75}Se$, $^{28}Si$, $^{145}Sm$, $^{153}Sm$, $^{117m}Sn$, $^{85}Sr$, $^{89}Sr$, $^{90}Sr$, $^{178}Ta$, $^{179}Ta$, $^{182}Ta$, $^{149}Tb$, $^{96}Tc$, $^{99m}Tc$, $^{228}Th$, $^{229}Th$, $^{201}Tl$, $^{170}Tm$, $^{171}Tm$, $^{188}W$, $^{127}Xe$, $^{133}Xe$, $^{88}Y$, $^{90}Y$, $^{91}Y$, $^{169}Yb$, $^{62}Zn$, $^{65}Zn$, $^{89}Zr$ or $^{95}Zr$, wherein a superscripted m denotes a meta-state), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5, Cy7, Cy7.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The term "quantum dot" as used herein refers to any moiety that is a highly luminescent semiconductor nanocrystal (e.g. zincsulfide-capped cadmium selenide). The synthesis and utility of these quantum dots is described in U.S. Pat. Nos. 6,326,144, 6,468,808, 7,192,785, 7,151,047, and in the scientific literature (see: Chan and Nie (1998) Science 281 (5385) 2016-2018).

The terms "measurable affinity" and "measurably inhibit," as used herein, means a measurable change in CAIX, MT1-MMP, PSMA, CD38, EphA2, or $\alpha v\beta 3$ activity between a sample comprising a compound of the present invention, or composition thereof, and CAIX, MT1-MMP, PSMA, CD38, EphA2, or $\alpha v\beta 3$, and an equivalent sample comprising CAIX, MT1-MMP, PSMA, CD38, EphA2, or $\alpha v\beta 3$, in the absence of said compound, or composition thereof.

3. Description of Exemplary Embodiments

As described above, in certain embodiments, the present invention provides a compound of formula I:

I

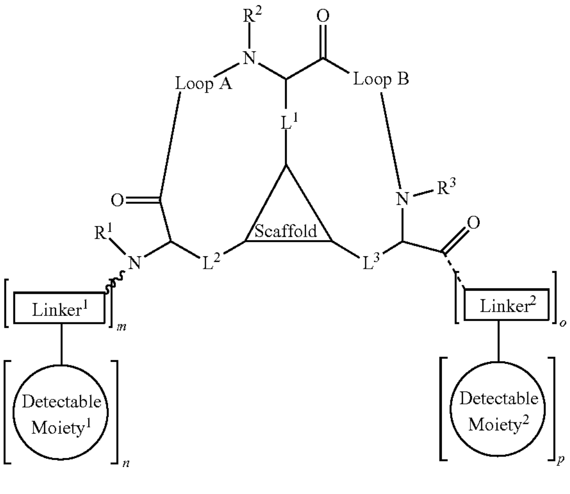

or a pharmaceutically acceptable salt thereof, wherein:

each of $L^1$, $L^2$, and $L^3$ is independently a covalent bond or a $C_{1-8}$ bivalent hydrocarbon chain wherein one, two or three methylene units of the chain are optionally and independently replaced by —S—, —N(R)—, —O—, —C(O)—, —OC(O)—, —C(O)O—, —C(O)N(R)—, —N(R) C(O)—, —S(O)—, $—S(O)_2—$ or —N(R) $CH_2C(O)—$;

each of R is independently hydrogen or $C_{1-4}$ alkyl;

each of m, n, o, and p is independently 0 or 1;

each of q and r is independently 1, 2, 3, 4, 5, 6, 7, 8, 9, 10, 11, 12, 13, 14 or 15; $R^1$ is R or —C(O)R;

each of $R^4$ and $R^6$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each of $R^{4'}$ and $R^{6'}$ is independently hydrogen or methyl;

each of $R^2$, $R^3$, $R^5$, and $R^7$ is independently hydrogen, or $C_{1-4}$ aliphatic, or:

an $R^5$ group and its adjacent $R^4$ group are optionally taken together with their intervening atoms to form a 4-8 membered saturated or partially unsaturated monocyclic heterocyclic ring having 1-2 heteroatoms independently selected from nitrogen, oxygen, or sulfur; or an $R^7$ group and its adjacent $R^6$ group are optionally taken together with their intervening atoms to form a 4-8 membered saturated or partially unsaturated monocyclic heterocyclic ring having 1-2 heteroatoms independently selected from nitrogen, oxygen, or sulfur;

Scaffold is a trivalent group that connects and orients a cyclic peptide;

Loop A is a bivalent natural or unnatural amino acid residue or peptide attached to the amino acid residue linked to $L^2$ and the amino acid residue linked to $L^1$, wherein Loop A comprises

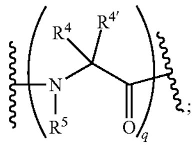

;

Loop B is a bivalent natural or unnatural amino acid residue or peptide attached to the amino acid residue linked to $L^1$ and the amino acid residue linked to $L^3$, wherein Loop B comprises

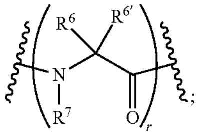

;

indicates the site of attachment to the N-terminus of the Bicycle;

indicates the site of attachment to the C-terminus of the Bicycle;

Detectable Moiety[1] is any moiety capable of being detected;

Detectable Moiety[2] is any moiety capable of being detected;

Linker[1] is hydrogen, —C(O)R,

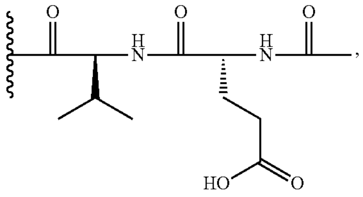 [SMILES: *C(=O)[C@H](NC(=O)[C@H](CCC(=O)O)NC(C)=O)C(C)C]

, or a bivalent moiety that connects the N-terminus of the Bicycle with Detectable Moiety[1], wherein when n is 0, Linker[1] is hydrogen, —C(O)R, or

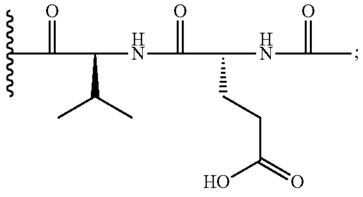 [SMILES: *C(=O)[C@H](NC(=O)[C@H](CCC(=O)O)NC(C)=O)C(C)C]

;

Linker[2] is $—NH_2$ or a bivalent moiety that connects the C-terminus of the Bicycle with Detectable Moiety[2], wherein when p is 0, Linker[2] is $—NH_2$; and Ring A is selected from the group consisting of 18-crown-6,1,7,13-triaza-18-crown-6, and a 3-12-membered saturated, partially unsaturated, bridged bicyclic, bridged tricyclic, propellane, or aromatic ring optionally substituted with 0-3 oxo, methyl, ethyl or spiroethylene groups and having 0-6 heteroatoms independently selected from nitrogen, oxygen, or sulfur.

As defined above and described herein, each of $L^1$, $L^2$, and $L^3$ is a covalent bond or a $C_{1-8}$ bivalent hydrocarbon chain wherein one, two or three methylene units of the chain are optionally and independently replaced by —S—, —N(R)—, —O—, —C(O)—, —OC(O)—, —C(O)O—, —C(O)N(R)—, —N(R) C(O)—, —S(O)—, $—S(O)_2—$ or $—N(R)CH_2C(O)—$.

In some embodiments, each of $L^1$, $L^2$, and $L^3$ is a covalent bond. In some embodiments, each of $L^1$, $L^2$, and $L^3$ is $—CH_2S—$. In some embodiments, each of $L^1$, $L^2$, and $L^3$ is $—CH_2NH—$. In some embodiments, each of $L^1$, $L^2$, and $L^3$ is $—CH_2O—$. In some embodiments, each of $L^1$, $L^2$, and $L^3$ is $—CH_2CH_2O—$. In some embodiments, each of $L^1$, $L^2$, and $L^3$ is $—CH_2CH_2CH_2CH_2NH—$. In some embodiments, each of $L^1$, $L^2$, and $L^3$ is $—CH_2N(CH_3)—$. In some embodiments, each of $L^1$, $L^2$, and $L^3$ is $—CH_2CH_2CH_2CH_2N(CH_3)—$.

In some embodiments, $L^1$ is a covalent bond. In some embodiments, $L^1$ is $—CH_2S—$. In some embodiments, $L^1$ is $—CH_2O—$. In some embodiments, $L^1$ is $—CH_2CH_2O—$. In some embodiments, $L^1$ is $—CH_2NH—$. In some embodiments, $L^1$ is $—CH_2CH_2CH_2CH_2NH—$. In some embodiments, $L^1$ is $—CH_2N(CH_3)—$. In some embodiments, $L^1$ is $—CH_2CH_2CH_2CH_2N(CH_3)—$. In some embodiments, $L^1$ is $—CH_2SCH_2—$. In some embodiments, $L^1$ is $—CH_2OCH_2—$. In some embodiments, $L^1$ is $—CH_2CH_2OCH_2—$. In some embodiments, $L^1$ is $—CH_2NHCH_2—$. In some embodiments, $L^1$ is $—CH_2N(CH_3)CH_2—$. In some embodiments, $L^1$ is $—CH_2CH_2CH_2CH_2NHCH_2—$. In some embodiments, $L^1$ is $—CH_2CH_2CH_2CH_2N(CH_3)CH_2—$. In some embodiments, $L^1$ is $—CH_2SCH_2C(O)NH—$. In some embodiments, $L^1$ is $—CH_2OCH_2C(O)NH—$. In some embodiments, $L^1$ is $—CH_2CH_2OCH_2C(O)NH—$. In some embodiments, $L^1$ is $—CH_2NHCH_2C(O)NH—$. In some embodiments, $L^1$ is $—CH_2N(CH_3)CH_2C(O)NH—$. In some embodiments, $L^1$ is $—CH_2CH_2CH_2CH_2NHCH_2C(O)NH—$. In some embodiments, $L^1$ is $CH_2CH_2CH_2CH_2N(CH_3)CH_2C(O)NH—$. In some embodiments, $L^1$ is $—CH_2SCH_2C(O)—$. In some embodiments, $L^1$ is $—CH_2OCH_2C(O)—$. In some embodiments, $L^1$ is $—CH_2CH_2OCH_2C(O)—$. In some embodiments, $L^1$ is $—CH_2NHCH_2C(O)—$. In some embodiments, $L^1$ is $—CH_2N(CH_3)CH_2C(O)—$. In some embodiments, $L^1$ is $—CH_2CH_2CH_2CH_2NHCH_2C(O)—$. In some embodiments, $L^1$ is $—CH_2CH_2CH_2CH_2N(CH_3)CH_2C(O)—$. In some embodiments, $L^1$ is $—CH_2SCH_2CH_2C(O)NH—$. In some embodiments, $L^1$ is $—CH_2OCH_2CH_2C(O)NH—$. In some embodiments, $L^1$ is $—CH_2CH_2OCH_2CH_2C(O)NH—$. In some embodiments, $L^1$ is $—CH_2NHCH_2CH_2C(O)NH—$. In some embodiments, $L^1$ is $—CH_2N(CH_3)CH_2CH_2C(O)NH—$. In some embodiments, $L^1$ is $—CH_2CH_2CH_2CH_2NHCH_2CH_2C(O)NH—$. In some embodiments, $L^1$ is $—CH_2CH_2CH_2CH_2N(CH_3)CH_2CH_2C(O)NH—$. In some embodiments, $L^1$ is $—CH_2SCH_2CH_2C(O)—$. In some embodiments, $L^1$ is $—CH_2OCH_2CH_2C(O)—$. In some embodiments, $L^1$ is $—CH_2CH_2OCH_2CH_2C(O)—$. In some embodiments, $L^1$ is $—CH_2NHCH_2CH_2C(O)—$. In some embodiments, $L^1$ is $—CH_2N(CH_3)CH_2CH_2C(O)—$. In some embodiments, $L^1$ is $—CH_2CH_2CH_2CH_2NHCH_2CH_2C(O)—$. In some embodiments, $L^1$ is $—CH_2CH_2CH_2CH_2N(CH_3)CH_2CH_2C(O)—$. In some embodiments, $L^1$ is selected from those depicted in Table 1, below. In some embodiments, $L^1$ is selected from those depicted in Table 3, below.

In some embodiments, $L^2$ is a covalent bond. In some embodiments, $L^2$ is $—CH_2S—$. In some embodiments, $L^2$ is $—CH_2O—$. In some embodiments, $L^2$ is $—CH_2CH_2O—$. In some embodiments, $L^2$ is $—CH_2NH—$. In some embodiments, $L^2$ is $—CH_2CH_2CH_2CH_2NH—$. In some embodiments, $L^2$ is $—CH_2N(CH_3)—$. In some embodiments, $L^2$ is $—CH_2CH_2CH_2CH_2N(CH_3)—$. In some embodiments, $L^2$ is $—CH_2SCH_2—$. In some embodiments, $L^2$ is $—CH_2OCH_2—$. In some embodiments, $L^2$ is $—CH_2CH_2OCH_2—$. In some embodiments, $L^2$ is $—CH_2NHCH_2—$. In some embodiments, $L^2$ is $—CH_2N(CH_3)CH_2—$. In some embodiments, $L^2$ is $—CH_2CH_2CH_2CH_2NHCH_2—$. In some embodiments, $L^2$ is $—CH_2CH_2CH_2CH_2N(CH_3)CH_2—$. In some embodiments, $L^2$ is $—CH_2SCH_2C(O)NH—$. In some embodiments, $L^2$ is $—CH_2OCH_2C(O)NH—$. In some embodiments, $L^2$ is $—CH_2CH_2OCH_2C(O)NH—$. In some embodiments, $L^2$ is $—CH_2NHCH_2C(O)NH—$. In some embodiments, $L^2$ is $—CH_2N(CH_3)CH_2C(O)NH—$. In some embodiments, $L^2$ is $—CH_2CH_2CH_2CH_2NHCH_2C(O)NH—$. In some embodiments, $L^2$ is $CH_2CH_2CH_2CH_2N(CH_3)CH_2C(O)NH—$. In some embodiments, $L^2$ is $—CH_2SCH_2C(O)—$. In some embodiments, $L^2$ is $—CH_2OCH_2C(O)—$. In some embodiments, $L^2$ is $—CH_2CH_2OCH_2C(O)—$. In some embodiments, $L^2$ is $—CH_2NHCH_2C(O)—$. In some embodiments, $L^2$ is $—CH_2N(CH_3)CH_2C(O)—$. In some embodiments, $L^2$ is $—CH_2CH_2CH_2CH_2NHCH_2C(O)—$. In some embodiments, $L^2$ is $—CH_2CH_2CH_2CH_2N(CH_3)CH_2C(O)—$. In some embodiments, $L^2$ is $—CH_2SCH_2CH_2C(O)NH—$. In some embodiments, $L^2$ is $—CH_2OCH_2CH_2C(O)NH—$. In some embodiments, $L^2$ is $—CH_2CH_2OCH_2CH_2C(O)NH—$. In some embodiments, $L^2$ is $—CH_2NHCH_2CH_2C(O)NH—$. In some embodiments, $L^2$ is $—CH_2N(CH_3)CH_2CH_2C(O)NH—$. In some embodiments, $L^2$ is $—CH_2CH_2CH_2CH_2NHCH_2CH_2C(O)NH—$. In some embodiments, $L^2$ is $—CH_2CH_2CH_2CH_2N(CH_3)CH_2CH_2C(O)NH—$. In some embodiments, $L^2$ is $—CH_2SCH_2CH_2C(O)—$. In some embodiments, $L^2$ is $—CH_2OCH_2CH_2C(O)—$. In some embodiments, $L^2$ is $—CH_2CH_2OCH_2CH_2C(O)—$. In some embodiments, $L^2$ is $—CH_2NHCH_2CH_2C(O)—$. In some embodiments, $L^2$ is $—CH_2N(CH_3)CH_2CH_2C(O)—$. In some embodiments, $L^2$ is $—CH_2CH_2CH_2CH_2NHCH_2CH_2C(O)—$. In some embodiments, $L^2$ is $—CH_2CH_2CH_2CH_2N(CH_3)CH_2CH_2C(O)—$. In some embodiments, $L^2$ is selected from those depicted in Table 1, below. In some embodiments, $L^2$ is selected from those depicted in Table 3, below.

In some embodiments, $L^3$ is a covalent bond. In some embodiments, $L^3$ is $—CH_2S—$. In some embodiments, $L^3$ is $—CH_2O—$. In some embodiments, $L^3$ is $—CH_2CH_2O—$. In some embodiments, $L^3$ is $—CH_2NH—$. In some embodiments, $L^3$ is $—CH_2CH_2CH_2CH_2NH—$. In some embodiments, $L^3$ is $—CH_2N(CH_3)—$. In some embodiments, $L^3$ is $—CH_2CH_2CH_2CH_2N(CH_3)—$. In some embodiments, $L^3$ is $—CH_2SCH_2—$. In some embodiments, $L^3$ is $—CH_2OCH_2—$. In some embodiments, $L^3$ is $—CH_2CH_2OCH_2—$. In some embodiments, $L^3$ is $—CH_2NHCH_2—$. In some embodiments, $L^3$ is $—CH_2N(CH_3)CH_2—$. In some embodiments, $L^3$ is $—CH_2CH_2CH_2CH_2NHCH_2—$. In some embodiments, $L^3$ is $—CH_2CH_2CH_2CH_2N(CH_3)CH_2—$. In some embodiments, $L^3$ is $—CH_2SCH_2C(O)NH—$. In some embodiments, $L^3$ is $—CH_2OCH_2C(O)NH—$. In some embodiments, $L^3$ is $—CH_2CH_2OCH_2C(O)NH—$. In some embodiments, $L^3$ is $—CH_2NHCH_2C(O)NH—$. In some embodiments, $L^3$ is —$CH_2N(CH_3)CH_2C(O)NH$—. In some embodiments, $L^3$ is —$CH_2CH_2CH_2CH_2NHCH_2C(O)NH$—. In some embodiments, $L^3$ is $CH_2CH_2CH_2CH_2N(CH_3)CH_2C(O)NH$—. In some embodiments, $L^3$ is —$CH_2SCH_2C(O)$—. In some embodiments, $L^3$ is —$CH_2OCH_2C(O)$—. In some embodiments, $L^3$ is —$CH_2CH_2OCH_2C(O)$—. In some embodiments, $L^3$ is —$CH_2NHCH_2C(O)$—. In some embodiments, $L^3$ is —$CH_2N(CH_3)CH_2C(O)$—. In some embodiments, $L^3$ is —$CH_2CH_2CH_2CH_2NHCH_2C(O)$—. In some embodiments, $L^3$ is —$CH_2CH_2CH_2CH_2N(CH_3)CH_2C(O)$—. In some embodiments, $L^3$ is —$CH_2SCH_2CH_2C(O)NH$—. In some embodiments, $L^3$ is —$CH_2OCH_2CH_2C(O)NH$—. In some embodiments, $L^3$ is —$CH_2CH_2OCH_2CH_2C(O)NH$—. In some embodiments, $L^3$ is —$CH_2NHCH_2CH_2C(O)NH$—. In some embodiments, $L^3$ is —$CH_2N(CH_3)CH_2CH_2C(O)NH$—. In some embodiments, $L^3$ is —$CH_2CH_2CH_2CH_2NHCH_2CH_2C(O)NH$—. In some embodiments, $L^3$ is —$CH_2CH_2CH_2CH_2N(CH_3)CH_2CH_2C(O)NH$—. In some embodiments, $L^3$ is —$CH_2SCH_2CH_2C(O)$—. In some embodiments, $L^3$ is —$CH_2OCH_2CH_2C(O)$—. In some embodiments, $L^3$ is —$CH_2CH_2OCH_2CH_2C(O)$—. In some embodiments, $L^3$ is —$CH_2NHCH_2CH_2C(O)$—. In some embodiments, $L^3$ is —$CH_2N(CH_3)CH_2CH_2C(O)$—. In some embodiments, $L^3$ is —$CH_2CH_2CH_2CH_2NHCH_2CH_2C(O)$—. In some embodiments, $L^3$ is —$CH_2CH_2CH_2CH_2N(CH_3)CH_2CH_2C(O)$—. In some embodiments, $L^3$ is selected from those depicted in Table 1, below. In some embodiments, $L^3$ is selected from those depicted in Table 3, below.

As defined above and described herein, each of R is independently hydrogen or $C_{1-4}$ alkyl.

In some embodiments, R is hydrogen. In some embodiments, R is $C_{1-4}$ alkyl.

In some embodiments, R is methyl. In some embodiments, R is ethyl. In some embodiments, R is n-propyl. In some embodiments, R is isopropyl. In some embodiments, R is n-butyl. In some embodiments, R is isobutyl. In some embodiments, R is tert-butyl.

In some embodiments, R is selected from those depicted in Table 1, below. In some embodiments, R is selected from those depicted in Table 3, below.

As defined above and described herein, each of m, n, o, and p is independently 0 or 1.

In some embodiments, m is 0. In some embodiments, m is 1. In some embodiments, m is selected from those depicted in Table 1, below. In some embodiments, m is selected from those depicted in Table 3, below.

In some embodiments, n is 0. In some embodiments, n is 1. In some embodiments, n is selected from those depicted in Table 1, below. In some embodiments, n is selected from those depicted in Table 3, below.

In some embodiments, o is 0. In some embodiments, o is 1. In some embodiments, o is selected from those depicted in Table 1, below. In some embodiments, o is selected from those depicted in Table 3, below.

In some embodiments, p is 0. In some embodiments, p is 1. In some embodiments, p is selected from those depicted in Table 1, below. In some embodiments, p is selected from those depicted in Table 3, below.

As defined above and described herein, each of q and r is independently 1, 2, 3, 4, 5, 6, 7, 8, 9, 10, 11, 12, 13, 14 or 15.

In some embodiments, q is 1. In some embodiments, q is 2. In some embodiments, q is 3. In some embodiments, q is 4. In some embodiments, q is 5. In some embodiments, q is 6. In some embodiments, q is 7. In some embodiments, q is 8. In some embodiments, q is 9. In some embodiments, q is 10. In some embodiments, q is 11. In some embodiments, q is 12. In some embodiments, q is 13. In some embodiments, q is 14. In some embodiments, q is 15. In some embodiments, q is selected from those depicted in Table 1, below. In some embodiments, q is selected from those depicted in Table 3, below.

In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10. In some embodiments, r is 11. In some embodiments, r is 12. In some embodiments, r is 13. In some embodiments, r is 14. In some embodiments, r is 15. In some embodiments, r is selected from those depicted in Table 1, below. In some embodiments, r is selected from those depicted in Table 3, below.

As defined above and described herein, $R^1$ is R or —C(O)R.

In some embodiments, $R^1$ is R. In some embodiments, $R^1$ is —C(O)R.

In some embodiments, $R^1$ is hydrogen. In some embodiments, $R^1$ is methyl. In some embodiments, $R^1$ is ethyl. In some embodiments, $R^1$ is n-propyl. In some embodiments, $R^1$ is isopropyl. In some embodiments, $R^1$ is n-butyl. In some embodiments, $R^1$ is isobutyl. In some embodiments, $R^1$ is tert-butyl.

In some embodiments, $R^1$ is —$C(O)CH_3$. In some embodiments, $R^1$ is —$C(O)CH_2CH_3$. In some embodiments, $R^1$ is —$C(O)CH_2CH_2CH_3$. In some embodiments, $R^1$ is —$C(O)CH(CH_3)_2$. In some embodiments, $R^1$ is —$C(O)CH_2CH_2CH_2CH_3$. In some embodiments, $R^1$ is —$C(O)CH_2CH(CH_3)_2$. In some embodiments, $R^1$ is —$C(O) C(CH_3)_3$. In some embodiments, $R^1$ is selected from those depicted in Table 1, below. In some embodiments, $R^1$ is selected from those depicted in Table 3, below.

As defined above and described herein, each of $R^4$ and $R^6$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, $R^4$ is hydrogen. In some embodiments, $R^4$ is an optionally substituted $C_{1-6}$ aliphatic. In some embodiments, $R^4$ is an optionally substituted 3-8 membered saturated or partially unsaturated monocyclic carbocyclic ring. In some embodiments, $R^4$ is an optionally substituted phenyl. In some embodiments, $R^4$ is an optionally substituted 8-10 membered bicyclic aromatic carbocyclic ring. In some embodiments, $R^4$ is an optionally substituted 4-8 membered saturated or partially unsaturated monocyclic heterocyclic ring having 1-2 heteroatoms independently selected from nitrogen, oxygen, or sulfur. In some embodiments, $R^4$ is an optionally substituted 5-6 membered monocyclic heteroaromatic ring having 1-4 heteroatoms independently selected from nitrogen, oxygen, or sulfur. In some embodiments, $R^4$ is an optionally substituted 8-10 membered bicyclic heteroaromatic ring having 1-5 heteroatoms independently selected from nitrogen, oxygen, or sulfur.

In some embodiments, $R^4$ is methyl. In some embodiments, $R^4$ is

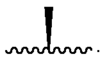

In some embodiments, $R^4$ is

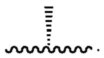

In some embodiments, $R^4$ is

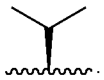

In some embodiments, $R^4$ is

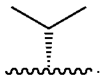

In some embodiments, $R^4$ is

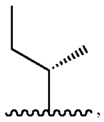

wherein the site of attachment has(S) stereochemistry. In some embodiments, $R^4$ is

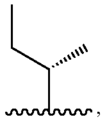

wherein the site of attachment has (R) stereochemistry. In some embodiments, $R^4$ is

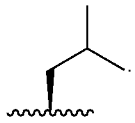

In some embodiments, $R^4$ is

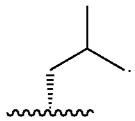

In some embodiments, $R^4$ is

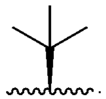

In some embodiments, $R^4$ is

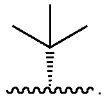

In some embodiments, $R^4$ is

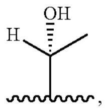

wherein the site of attachment has (S) stereochemistry. In some embodiments, $R^4$ is

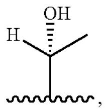

wherein the site of attachment has (R) stereochemistry.

In some embodiments, $R^4$ is

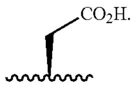

In some embodiments, $R^4$ is

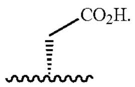

In some embodiments, $R^4$ is

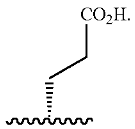

In some embodiments, $R^4$ is
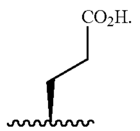
In some embodiments, $R^4$ is
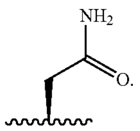
In some embodiments, $R^4$ is
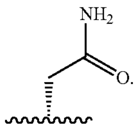
In some embodiments, $R^4$ is
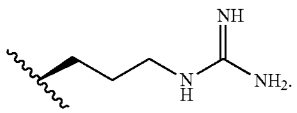
In some embodiments, $R^4$ is
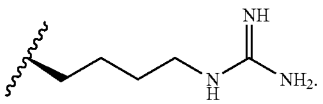
In some embodiments, $R^4$ is
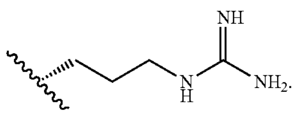
In some embodiments, $R^4$ is
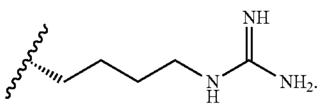
In some embodiments, $R^4$ is
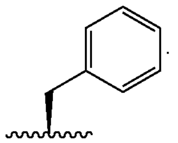
In some embodiments, $R^4$ is
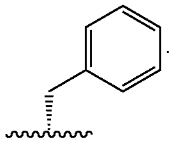
In some embodiments, $R^4$ is
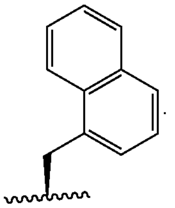
In some embodiments, $R^4$ is
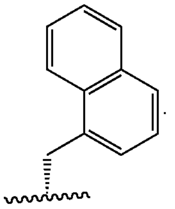
In some embodiments, $R^4$ is
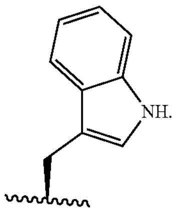
In some embodiments, $R^4$ is
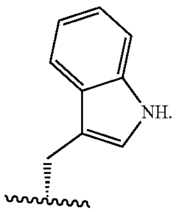

In some embodiments, $R^4$ is

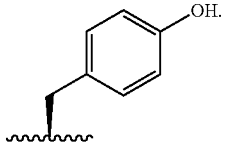

In some embodiments, $R^4$ is

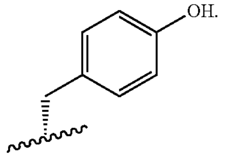

In some embodiments, $R^4$ is selected from those depicted in Table 1, below. In some embodiments, $R^4$ is selected from those depicted in Table 3, below.

In some embodiments, $R^6$ is hydrogen. In some embodiments, $R^6$ is an optionally substituted $C_{1-6}$ aliphatic. In some embodiments, $R^6$ is an optionally substituted 3-8 membered saturated or partially unsaturated monocyclic carbocyclic ring. In some embodiments, $R^6$ is an optionally substituted phenyl. In some embodiments, $R^6$ is an optionally substituted 8-10 membered bicyclic aromatic carbocyclic ring. In some embodiments, $R^6$ is an optionally substituted 4-8 membered saturated or partially unsaturated monocyclic heterocyclic ring having 1-2 heteroatoms independently selected from nitrogen, oxygen, or sulfur. In some embodiments, $R^6$ is an optionally substituted 5-6 membered monocyclic heteroaromatic ring having 1-4 heteroatoms independently selected from nitrogen, oxygen, or sulfur. In some embodiments, $R^6$ is an optionally substituted 8-10 membered bicyclic heteroaromatic ring having 1-5 heteroatoms independently selected from nitrogen, oxygen, or sulfur.

In some embodiments, $R^6$ is methyl. In some embodiments, $R^6$ is

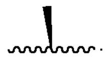

In some embodiments, $R^6$ is

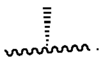

In some embodiments, $R^6$ is

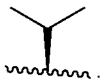

In some embodiments, $R^6$ is

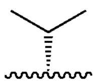

In some embodiments, $R^6$ is

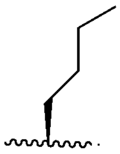

In some embodiments, $R^6$ is

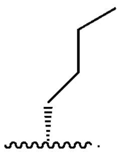

In some embodiments, $R^6$ is

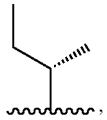 [SMILES: *[C@@H](C)CC]

wherein the site of attachment has(S) stereochemistry. In some embodiments, $R^6$ is

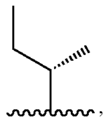 [SMILES: *[C@@H](C)CC]

wherein the site of attachment has (R) stereochemistry. In some embodiments, $R^6$ is

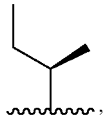 [SMILES: *[C@H](C)CC]

wherein the site of attachment has(S) stereochemistry. In some embodiments, $R^6$ is

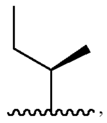

wherein the site of attachment has (R) stereochemistry. In some embodiments, $R^6$ is

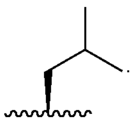

In some embodiments, $R^6$ is

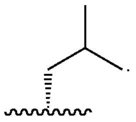

In some embodiments, $R^6$ is

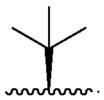

In some embodiments, $R^6$ is

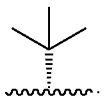

In some embodiments, $R^6$ is

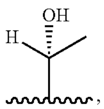

wherein the site of attachment has(S) stereochemistry. In some embodiments, $R^6$ is

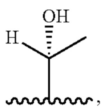

wherein the site of attachment has (R) stereochemistry.

In some embodiments, $R^6$ is

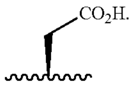

In some embodiments, $R^6$ is

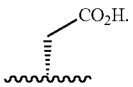

In some embodiments, $R^6$ is

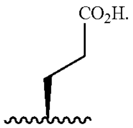

In some embodiments, $R^6$ is

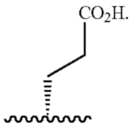

In some embodiments, $R^6$ is

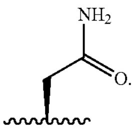

In some embodiments, $R^6$ is

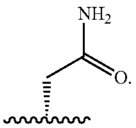

In some embodiments, $R^6$ is

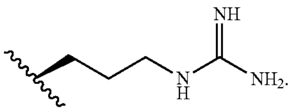

In some embodiments, $R^6$ is

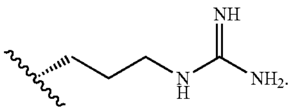

In some embodiments, $R^6$ is

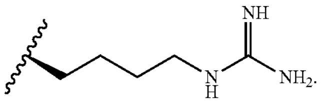

In some embodiments, $R^6$ is

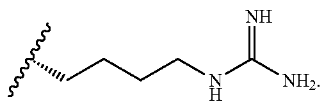

In some embodiments, $R^6$ is

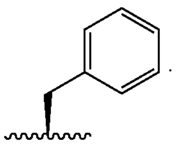

In some embodiments, $R^6$ is

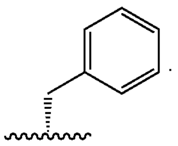

In some embodiments, $R^6$ is

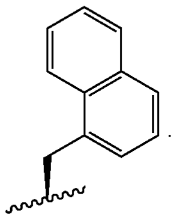

In some embodiments, $R^6$ is

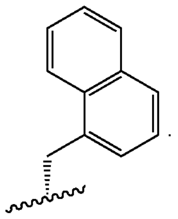

In some embodiments, $R^6$ is

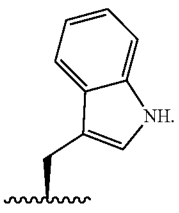

In some embodiments, $R^6$ is

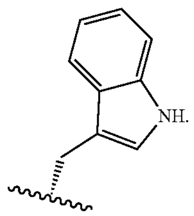

In some embodiments, $R^6$ is

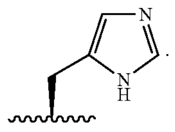

In some embodiments, $R^6$ is

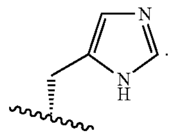

In some embodiments, $R^6$ is

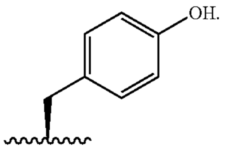

In some embodiments, $R^6$ is

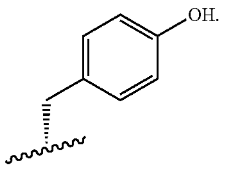

In some embodiments, $R^6$ is selected from those depicted in Table 1, below. In some embodiments, $R^6$ is selected from those depicted in Table 3, below.

As defined above and described herein, each of $R^{4'}$ and $R^{6'}$ is independently hydrogen or methyl.

In some embodiments, $R^{4'}$ is hydrogen. In some embodiments, $R^{4'}$ is methyl.

In some embodiments, $R^{4'}$ is selected from those depicted in Table 1, below. In some embodiments, $R^{4'}$ is selected from those depicted in Table 3, below.

In some embodiments, $R^{6'}$ is hydrogen. In some embodiments, $R^{6'}$ is methyl.

In some embodiments, $R^{6'}$ is selected from those depicted in Table 1, below. In some embodiments, $R^{6'}$ is selected from those depicted in Table 3, below.

As defined above and described herein, each of $R^2$, $R^3$, $R^5$, and $R^7$ is independently hydrogen, or $C_{1-4}$ aliphatic, or:

an $R^5$ group and its adjacent $R^4$ group are optionally taken together with their intervening atoms to form a 4-8 membered saturated or partially unsaturated monocyclic heterocyclic ring having 1-2 heteroatoms independently selected from nitrogen, oxygen, or sulfur; or an $R^7$ group and its adjacent $R^6$ group are optionally taken together with their intervening atoms to form a 4-8 membered saturated or partially unsaturated monocyclic heterocyclic ring having 1-2 heteroatoms independently selected from nitrogen, oxygen, or sulfur.

In some embodiments, $R^2$ is hydrogen. In some embodiments, $R^2$ is $C_1$-4 aliphatic. In some embodiments, $R^2$ is methyl. In some embodiments, $R^2$ is ethyl. In some embodiments, $R^2$ is n-propyl. In some embodiments, $R^2$ is isopropyl. In some embodiments, $R^2$ is n-butyl. In some embodiments, $R^2$ is isobutyl. In some embodiments, $R^2$ is tert-butyl.

In some embodiments, $R^2$ is selected from those depicted in Table 1, below. In some embodiments, $R^2$ is selected from those depicted in Table 3, below.

In some embodiments, $R^3$ is hydrogen. In some embodiments, $R^3$ is $C_1$-4 aliphatic. In some embodiments, $R^3$ is methyl. In some embodiments, $R^3$ is ethyl. In some embodiments, $R^3$ is n-propyl. In some embodiments, $R^3$ is isopropyl. In some embodiments, $R^3$ is n-butyl. In some embodiments, $R^3$ is isobutyl. In some embodiments, $R^3$ is tert-butyl.

In some embodiments, $R^3$ is selected from those depicted in Table 1, below. In some embodiments, $R^3$ is selected from those depicted in Table 3, below.

In some embodiments, $R^5$ is hydrogen. In some embodiments, $R^5$ is $C_1$-4 aliphatic. In some embodiments, $R^5$ is methyl. In some embodiments, $R^5$ is ethyl. In some embodiments, $R^5$ is n-propyl. In some embodiments, $R^5$ is isopropyl. In some embodiments, $R^5$ is n-butyl. In some embodiments, $R^5$ is isobutyl. In some embodiments, $R^5$ is tert-butyl.

In some embodiments, an $R^5$ group and its adjacent $R^4$ group are taken together with their intervening atoms to form

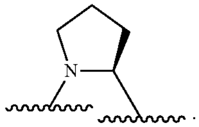 [SMILES: *[C@@H]1CCCN1*]

In some embodiments, an $R^5$ group and its adjacent $R^4$ group are taken together with their intervening atoms to form

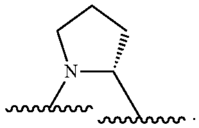 [SMILES: *[C@H]1CCCN1*]

In some embodiments, $R^5$ is selected from those depicted in Table 1, below. In some embodiments, $R^5$ is selected from those depicted in Table 3, below.

In some embodiments, $R^7$ is hydrogen. In some embodiments, $R^7$ is $C_1$-4 aliphatic. In some embodiments, $R^7$ is methyl. In some embodiments, $R^7$ is ethyl. In some embodiments, $R^7$ is n-propyl. In some embodiments, $R^7$ is isopropyl. In some embodiments, $R^7$ is n-butyl. In some embodiments, $R^7$ is isobutyl. In some embodiments, $R^7$ is tert-butyl.

In some embodiments, an $R^7$ group and its adjacent $R^6$ group are taken together with their intervening atoms to form

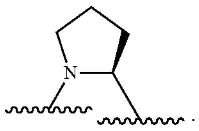 [SMILES: *[C@@H]1CCCN1*]

In some embodiments, an $R^7$ group and its adjacent $R^6$ group are taken together with their intervening atoms to form

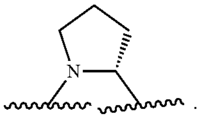 [SMILES: *[C@H]1CCCN1*]

In some embodiments, $R^7$ is selected from those depicted in Table 1, below. In some embodiments, $R^7$ is selected from those depicted in Table 3, below.

As defined above and described herein, Scaffold is a trivalent group that connects and orients a cyclic peptide.

In some embodiments, Scaffold is

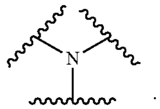 [SMILES: *N(*)*]

In some embodiments, Scaffold is

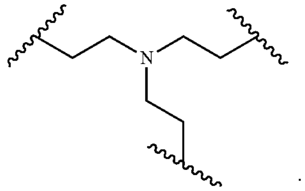 [SMILES: *CCN(CC*)CC*]

In some embodiments, Scaffold is

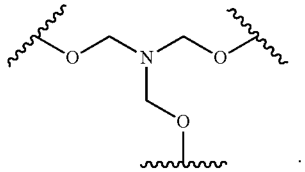 [SMILES: *OCN(CO*)CO*]

In some embodiments, Scaffold is

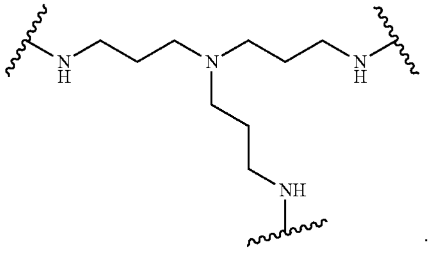 [SMILES: *NCCCN(CCCN*)CCCN*]

In some embodiments, Scaffold is
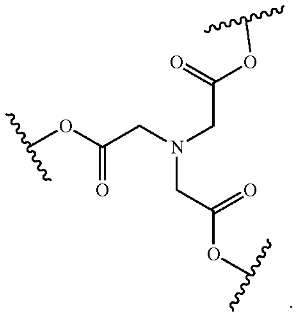 [SMILES: *OC(=O)CN(CC(=O)O*)CC(=O)O*]
In some embodiments, Scaffold is
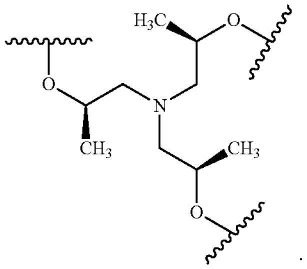 [SMILES: *O[C@H](C)CN(C[C@@H](C)O*)C[C@@H](C)O*]
In some embodiments, Scaffold is
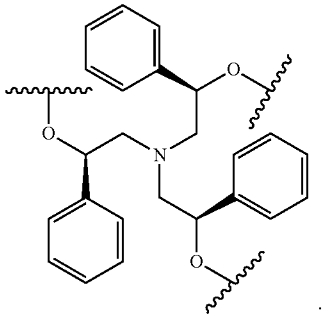 [SMILES: *O[C@@H](CN(C[C@H](O*)c1ccccc1)C[C@H](O*)c1ccccc1)c1ccccc1]
In some embodiments, Scaffold is
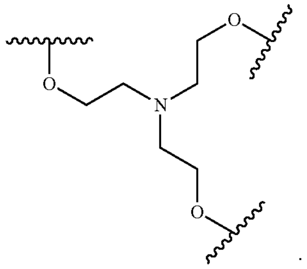 [SMILES: *OCCN(CCO*)CCO*]
In some embodiments, Scaffold is
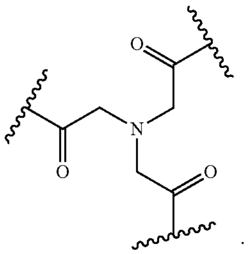 [SMILES: *C(=O)CN(CC(*)=O)CC(*)=O]
In some embodiments, Scaffold is
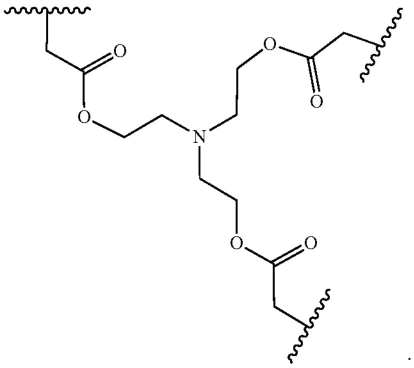 [SMILES: *CC(=O)OCCN(CCOC(=O)C*)CCOC(=O)C*]
In some embodiments, Scaffold is
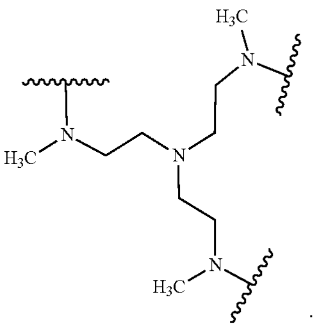 [SMILES: *N(C)CCN(CCN(*)C)CCN(*)C]

In some embodiments, Scaffold is
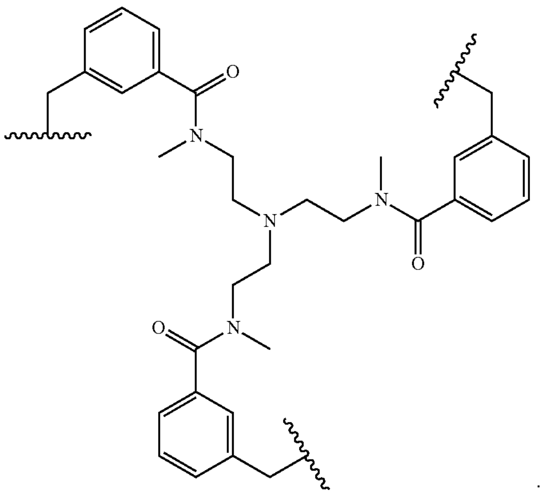 [SMILES: *Cc1cccc(C(=O)N(C)CCN(CCN(C)C(=O)c2cccc(C*)c2)CCN(C)C(=O)c2cccc(C*)c2)c1]
In some embodiments, Scaffold is
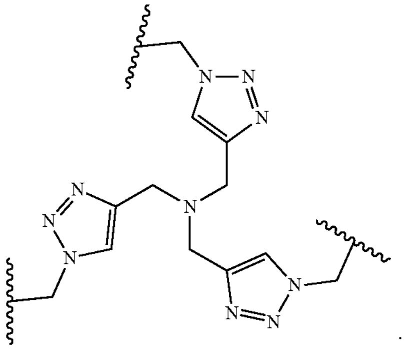 [SMILES: *Cn1cc(CN(Cc2cn(C*)nn2)Cc2cn(C*)nn2)nn1]
In some embodiments, Scaffold is
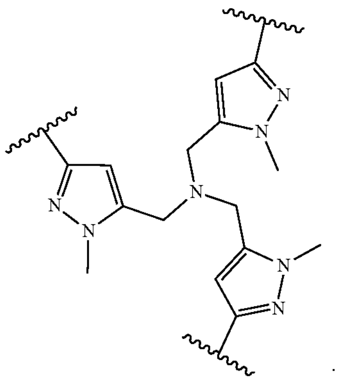
In some embodiments, Scaffold is
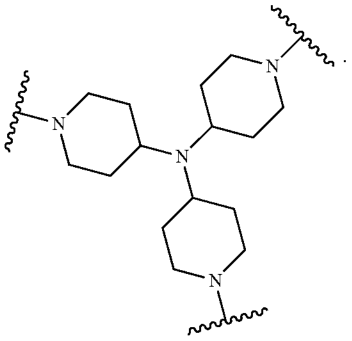 [SMILES: *N1CCC(N(C2CCN(*)CC2)C2CCN(*)CC2)CC1]
In some embodiments, Scaffold is
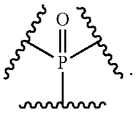 [SMILES: *P(*)(*)=O]
In some embodiments, Scaffold is
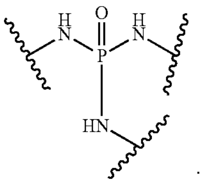 [SMILES: *NP(=O)(N*)N*]
In some embodiments, Scaffold is
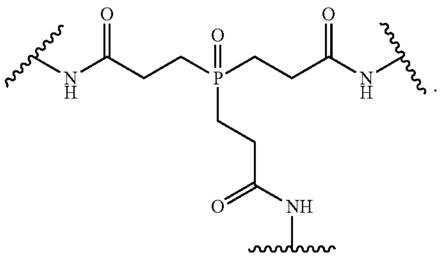 [SMILES: *NC(=O)CCP(=O)(CCC(=O)N*)CCC(=O)N*]

In some embodiments, Scaffold is
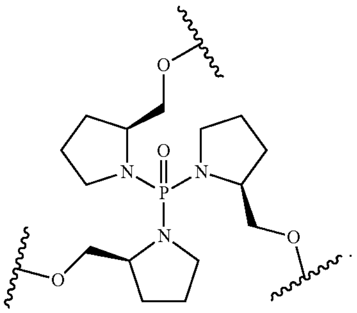 [SMILES: *OC[C@@H]1CCCN1P(=O)(N1CCC[C@H]1CO*)N1CCC[C@H]1CO*]
In some embodiments, Scaffold is
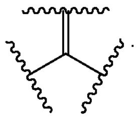 [SMILES: *C(*)=*]
In some embodiments, Scaffold is
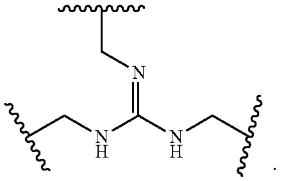 [SMILES: *CN=C(NC*)NC*]
In some embodiments, Scaffold is
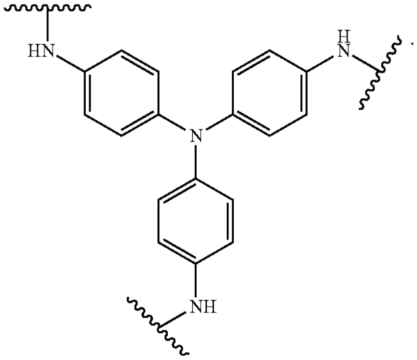 [SMILES: *Nc1ccc(N(c2ccc(N*)cc2)c2ccc(N*)cc2)cc1]
In some embodiments, Scaffold is
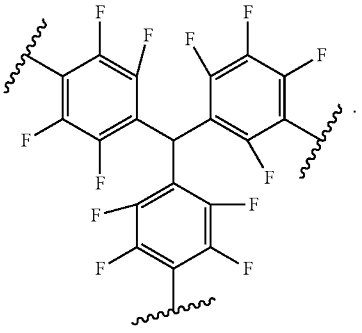 [SMILES: *c1c(F)c(F)c(C(c2c(F)c(*)c(F)c(F)c2F)c2c(F)c(F)c(*)c(F)c2F)c(F)c1F]
In some embodiments, Scaffold is
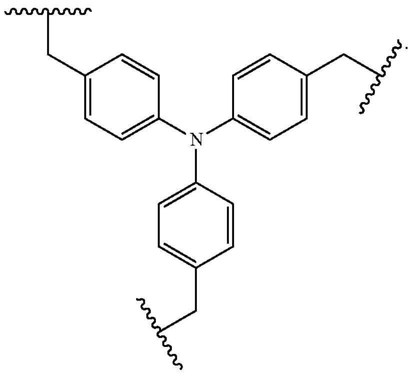 [SMILES: *Cc1ccc(N(c2ccc(C*)cc2)c2ccc(C*)cc2)cc1]
In some embodiments, Scaffold is
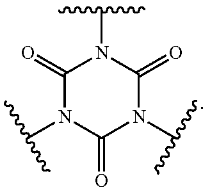 [SMILES: *n1c(=O)n(*)c(=O)n(*)c1=O]
In some embodiments, Scaffold is
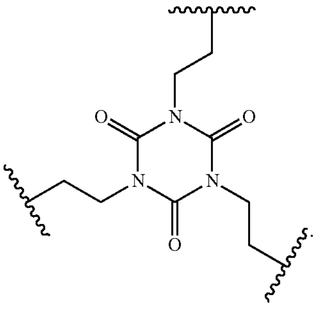 [SMILES: *CCn1c(=O)n(CC*)c(=O)n(CC*)c1=O]

In some embodiments, Scaffold is
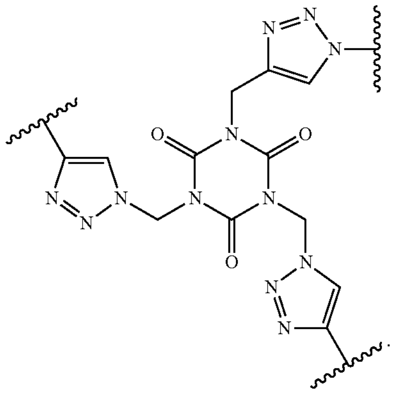 [SMILES: *c1cn(Cn2c(=O)n(Cc3cn(*)nn3)c(=O)n(Cn3cc(*)nn3)c2=O)nn1]
In some embodiments, Scaffold is
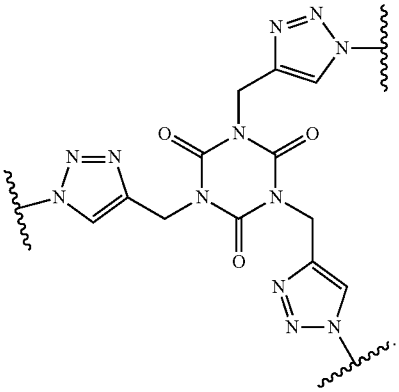 [SMILES: *n1cc(Cn2c(=O)n(Cc3cn(*)nn3)c(=O)n(Cc3cn(*)nn3)c2=O)nn1]
In some embodiments, Scaffold is
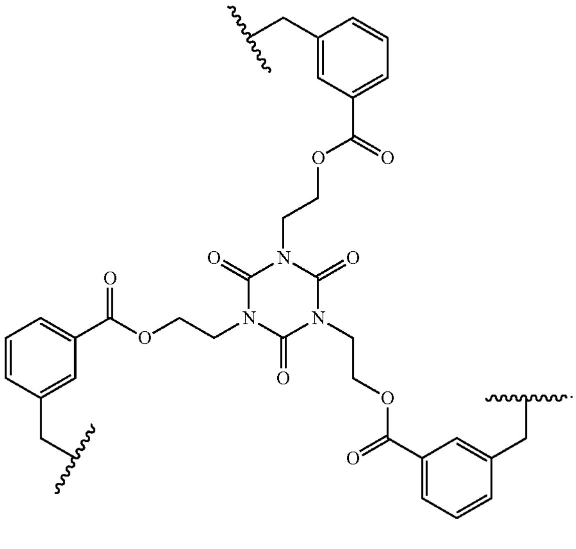 [SMILES: *Cc1cccc(C(=O)OCCn2c(=O)n(CCOC(=O)c3cccc(C*)c3)c(=O)n(CCOC(=O)c3cccc(C*)c3)c2=O)c1]
In some embodiments, Scaffold is
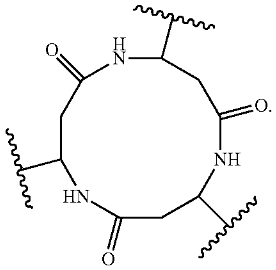 [SMILES: *C1CC(=O)NC(*)CC(=O)NC(*)CC(=O)N1]
In some embodiments, Scaffold is
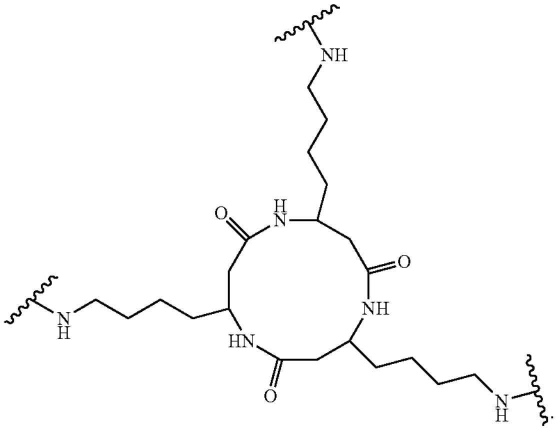 [SMILES: *NCCCCC1CC(=O)NC(CCCCN*)CC(=O)NC(CCCCN*)CC(=O)N1]
In some embodiments, Scaffold is
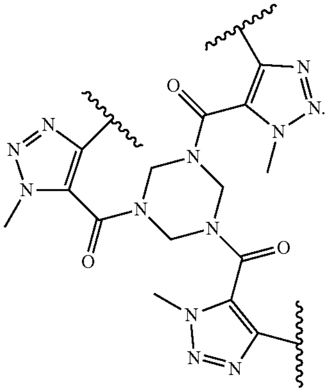 [SMILES: *c1nnn(C)c1C(=O)N1CN(C(=O)c2c(*)nnn2C)CN(C(=O)c2c(*)nnn2C)C1]

In some embodiments, Scaffold is
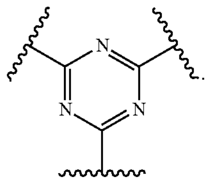 [SMILES: *c1nc(*)nc(*)n1]
In some embodiments, Scaffold is
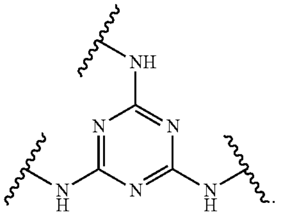 [SMILES: *Nc1nc(N*)nc(N*)n1]
In some embodiments, Scaffold is
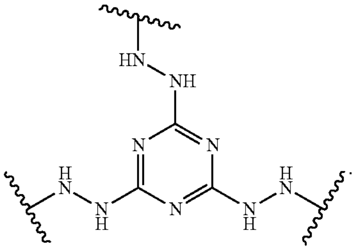 [SMILES: *NNc1nc(NN*)nc(NN*)n1]
In some embodiments, Scaffold is
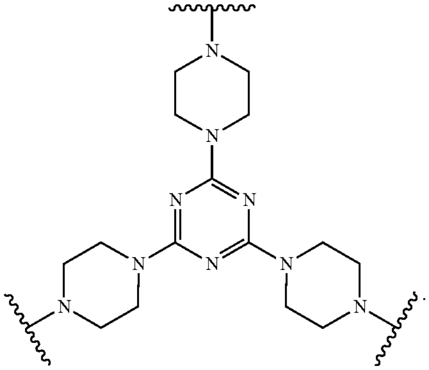 [SMILES: *N1CCN(c2nc(N3CCN(*)CC3)nc(N3CCN(*)CC3)n2)CC1]
In some embodiments, Scaffold is
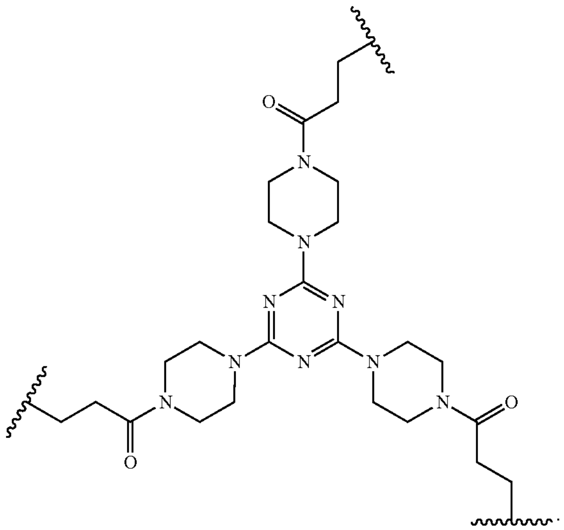 [SMILES: *CCC(=O)N1CCN(c2nc(N3CCN(C(=O)CC*)CC3)nc(N3CCN(C(=O)CC*)CC3)n2)CC1]
In some embodiments, Scaffold is
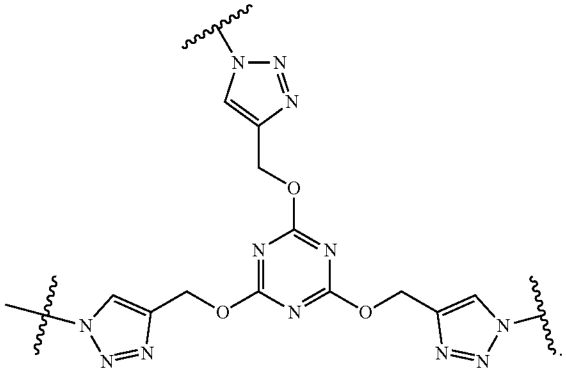 [SMILES: *n1cc(COc2nc(OCc3cn(*)nn3)nc(OCc3cn(*)nn3)n2)nn1]
In some embodiments, Scaffold is
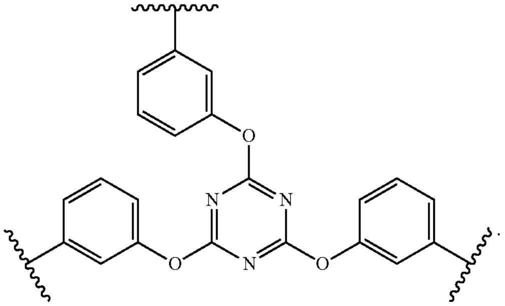 [SMILES: *c1cccc(Oc2nc(Oc3cccc(*)c3)nc(Oc3cccc(*)c3)n2)c1]

In some embodiments, Scaffold is
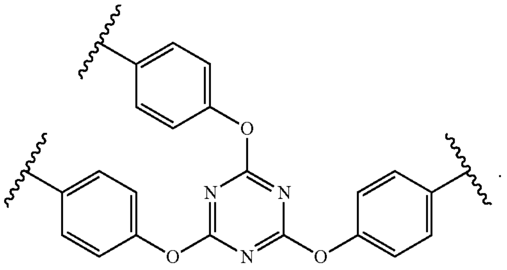 [SMILES: *c1ccc(Oc2nc(Oc3ccc(*)cc3)nc(Oc3ccc(*)cc3)n2)cc1]
In some embodiments, Scaffold is
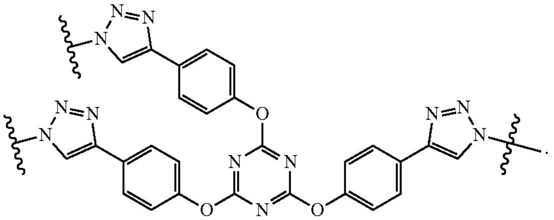 [SMILES: *n1cc(-c2ccc(Oc3nc(Oc4ccc(-c5cn(*)nn5)cc4)nc(Oc4ccc(-c5cn(*)nn5)cc4)n3)cc2)nn1]
In some embodiments, Scaffold is
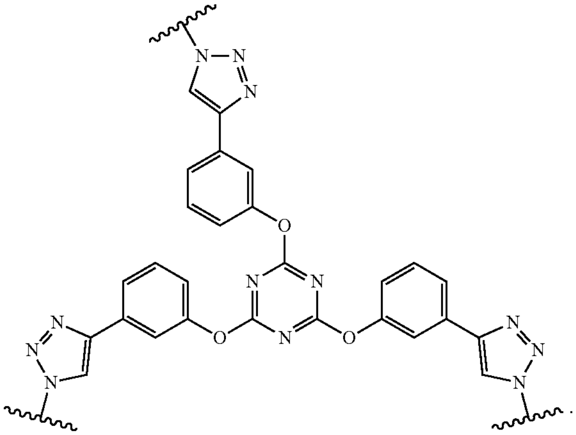 [SMILES: *n1cc(-c2cccc(Oc3nc(Oc4cccc(-c5cn(*)nn5)c4)nc(Oc4cccc(-c5cn(*)nn5)c4)n3)c2)nn1]
In some embodiments, Scaffold is
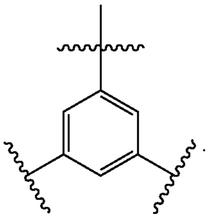 [SMILES: *c1cc(*)cc(*)c1]
In some embodiments, Scaffold is
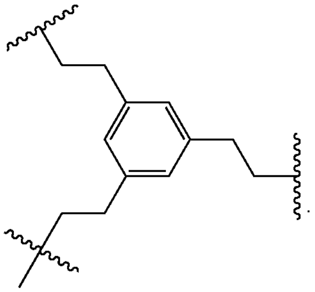 [SMILES: *CCc1cc(CC*)cc(CC*)c1]
In some embodiments, Scaffold is
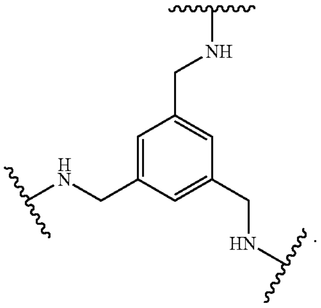 [SMILES: *NCc1cc(CN*)cc(CN*)c1]
In some embodiments, Scaffold is
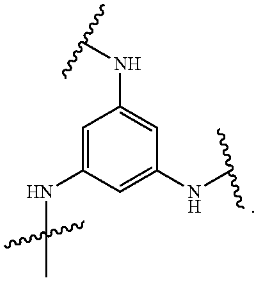 [SMILES: *Nc1cc(N*)cc(N*)c1]
In some embodiments, Scaffold is
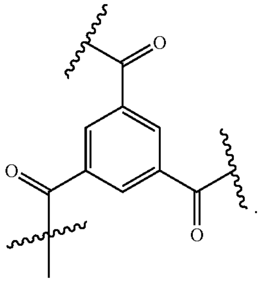 [SMILES: *C(=O)c1cc(C(*)=O)cc(C(*)=O)c1]

In some embodiments, Scaffold is
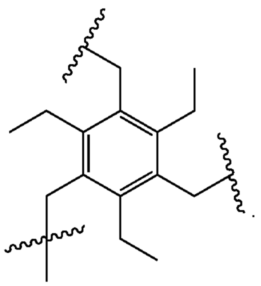 [SMILES: *Cc1c(CC)c(C*)c(CC)c(C*)c1CC]
In some embodiments, Scaffold is
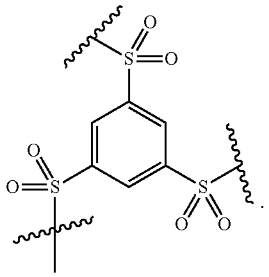 [SMILES: *S(=O)(=O)c1cc(S(*)(=O)=O)cc(S(*)(=O)=O)c1]
In some embodiments, Scaffold is
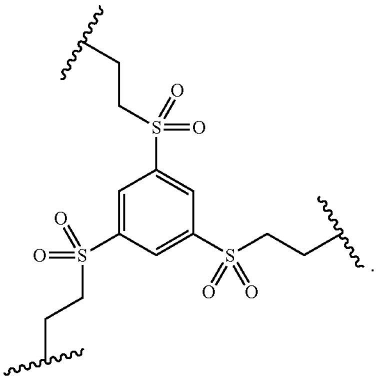 [SMILES: *CCS(=O)(=O)c1cc(S(=O)(=O)CC*)cc(S(=O)(=O)CC*)c1]
In some embodiments, Scaffold is
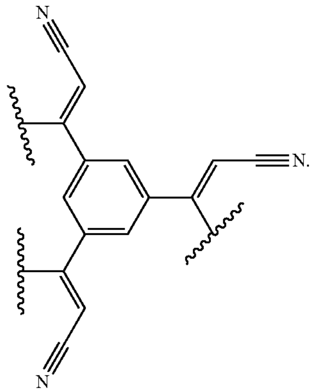 [SMILES: */C(=C\C#N)c1cc(/C(*)=C/C#N)cc(/C(*)=C/C#N)c1]
In some embodiments, Scaffold is
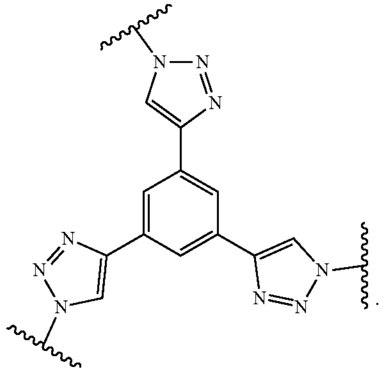 [SMILES: *n1cc(-c2cc(-c3cn(*)nn3)cc(-c3cn(*)nn3)c2)nn1]
In some embodiments, Scaffold is
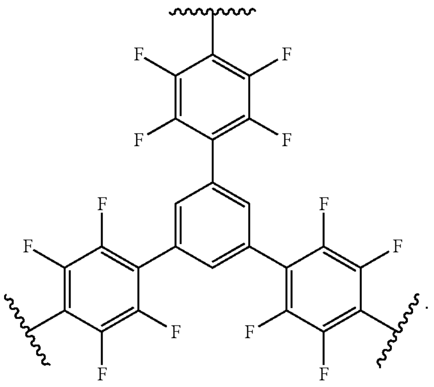 [SMILES: *c1c(F)c(F)c(-c2cc(-c3c(F)c(F)c(*)c(F)c3F)cc(-c3c(F)c(F)c(*)c(F)c3F)c2)c(F)c1F]

In some embodiments, Scaffold is
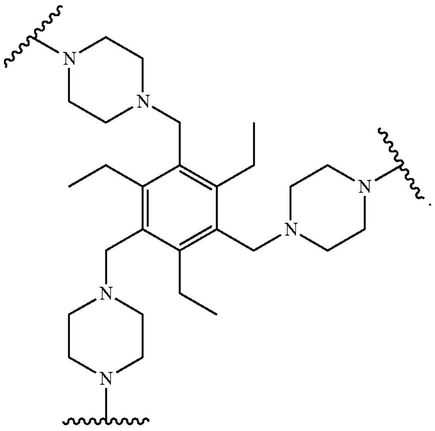 [SMILES: *N1CCN(Cc2c(CC)c(CN3CCN(*)CC3)c(CC)c(CN3CCN(*)CC3)c2CC)CC1]
In some embodiments, Scaffold is
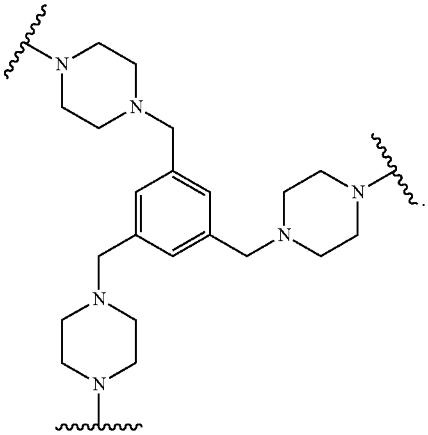 [SMILES: *N1CCN(Cc2cc(CN3CCN(*)CC3)cc(CN3CCN(*)CC3)c2)CC1]
In some embodiments, Scaffold is
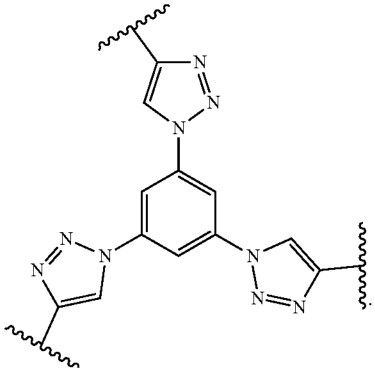 [SMILES: *c1cn(-c2cc(-n3cc(*)nn3)cc(-n3cc(*)nn3)c2)nn1]
In some embodiments, Scaffold is
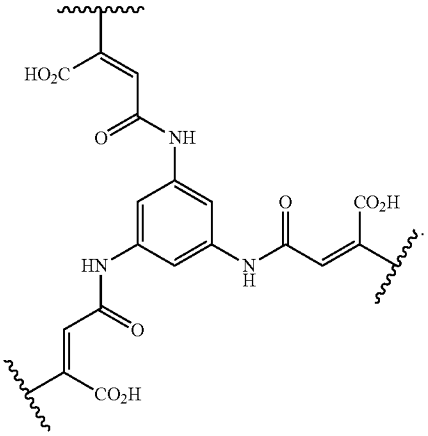 [SMILES: */C(=C/C(=O)Nc1cc(NC(=O)/C=C(/*)C(=O)O)cc(NC(=O)/C=C(/*)C(=O)O)c1)C(=O)O]
In some embodiments, Scaffold is
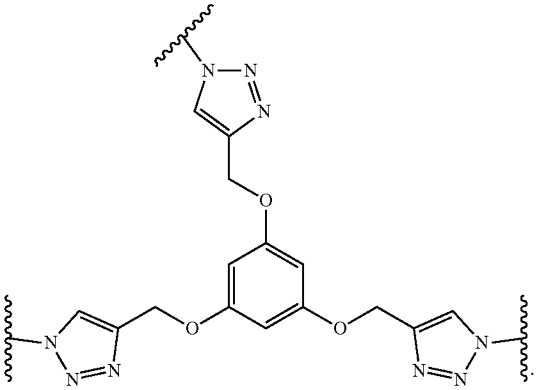 [SMILES: *n1cc(COc2cc(OCc3cn(*)nn3)cc(OCc3cn(*)nn3)c2)nn1]
In some embodiments, Scaffold is
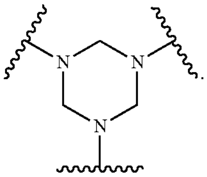 [SMILES: *N1CN(*)CN(*)C1]
In some embodiments, Scaffold is
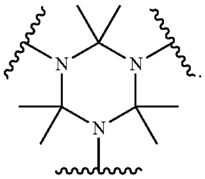

In some embodiments, Scaffold is
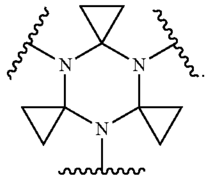 [SMILES: *N1C2(CC2)N(*)C2(CC2)N(*)C12CC2]
In some embodiments, Scaffold is
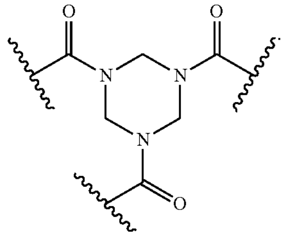 [SMILES: *C(=O)N1CN(C(*)=O)CN(C(*)=O)C1]
In some embodiments, Scaffold is
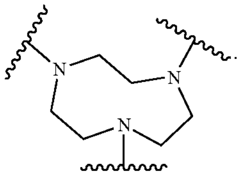 [SMILES: *N1CCN(*)CCN(*)CC1]
In some embodiments, Scaffold is
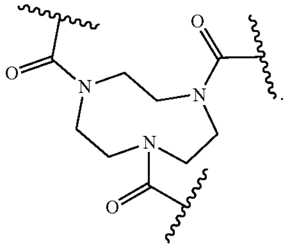 [SMILES: *C(=O)N1CCN(C(*)=O)CCN(C(*)=O)CC1]
In some embodiments, Scaffold is
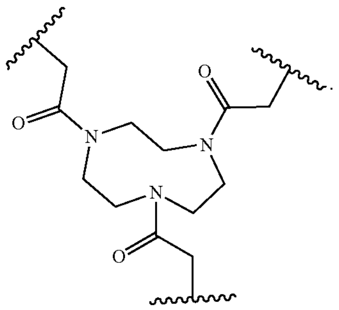 [SMILES: *CC(=O)N1CCN(C(=O)C*)CCN(C(=O)C*)CC1]
In some embodiments, Scaffold is
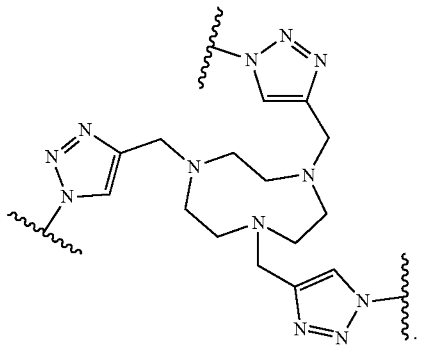 [SMILES: *n1cc(CN2CCN(Cc3cn(*)nn3)CCN(Cc3cn(*)nn3)CC2)nn1]
In some embodiments, Scaffold is
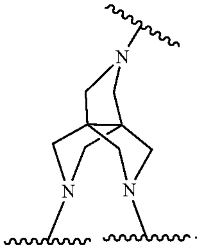 [SMILES: *N1CC23CN(*)CC2(C1)CN(*)C3]
In some embodiments, Scaffold is
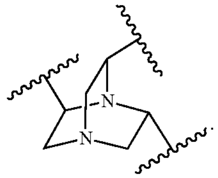 [SMILES: *C1CN2CC(*)N1C(*)C2]
In some embodiments, Scaffold is
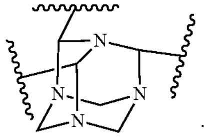 [SMILES: *C1N2CN3CN(C2)C(*)N1C3*]
In some embodiments, Scaffold is
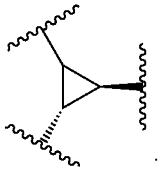 [SMILES: *C1[C@H](*)[C@H]1*]

In some embodiments, Scaffold is
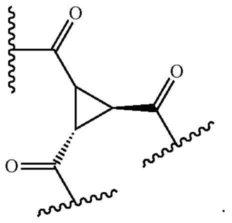 [SMILES: *C(=O)C1[C@H](C(*)=O)[C@H]1C(*)=O]
In some embodiments, Scaffold is
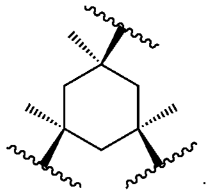
In some embodiments, Scaffold is
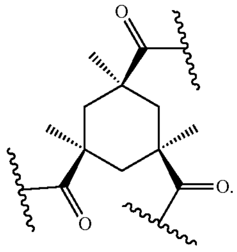 [SMILES: *C(=O)[C@]1(C)C[C@](C)(C(*)=O)C[C@](C)(C(*)=O)C1]
In some embodiments, Scaffold is
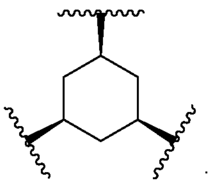 [SMILES: *[C@H]1C[C@@H](*)C[C@@H](*)C1]
In some embodiments, Scaffold is
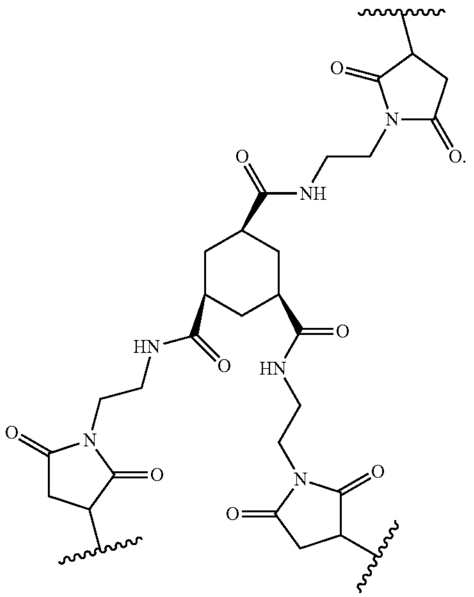 [SMILES: *C1CC(=O)N(CCNC(=O)[C@H]2C[C@@H](C(=O)NCCN3C(=O)CC(*)C3=O)C[C@@H](C(=O)NCCN3C(=O)CC(*)C3=O)C2)C1=O]
In some embodiments, Scaffold is
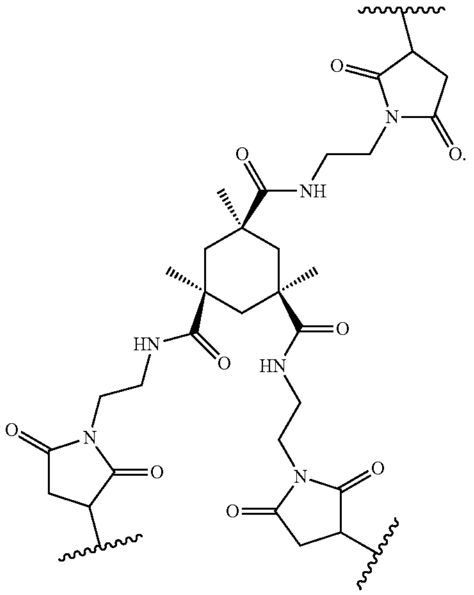 [SMILES: *C1CC(=O)N(CCNC(=O)[C@]2(C)C[C@](C)(C(=O)NCCN3C(=O)CC(*)C3=O)C[C@](C)(C(=O)NCCN3C(=O)CC(*)C3=O)C2)C1=O]

In some embodiments, Scaffold is

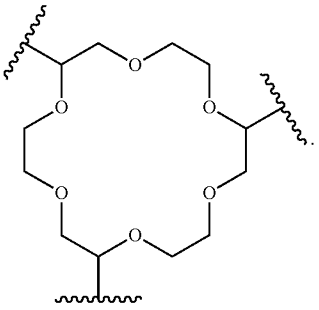 [SMILES: *C1COCCOC(*)COCCOC(*)COCCO1]

In some embodiments, Scaffold is

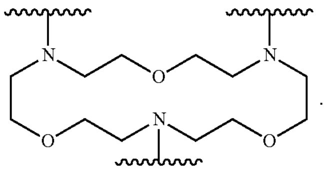 [SMILES: *N1CCOCCN(*)CCOCCN(*)CCOCC1]

In some embodiments, Scaffold is selected from those depicted in Table 1, below. In some embodiments, Scaffold is selected from those depicted in Table 3, below.

As defined above and described herein, Loop A is a bivalent natural or unnatural amino acid residue or peptide attached to the amino acid residue linked to $L^2$ and the amino acid residue linked to $L^1$, wherein Loop A comprises

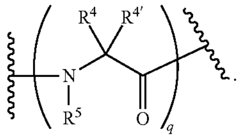

In some embodiments, Loop A is a bivalent natural amino acid residue attached to the amino acid residue linked to $L^2$ and the amino acid residue linked to $L^1$, wherein Loop A comprises

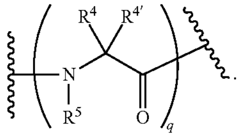

In some embodiments, Loop A is a bivalent unnatural amino acid residue attached to the amino acid residue linked to $L^2$ and the amino acid residue linked to $L^1$, wherein Loop A comprises

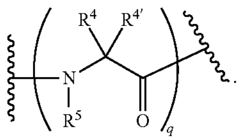

In some embodiments, Loop A is a bivalent peptide attached to the amino acid residue linked to $L^2$ and the amino acid residue linked to $L^1$, wherein Loop A comprises

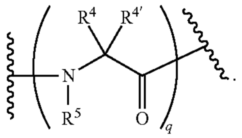

In some embodiments, Loop A is

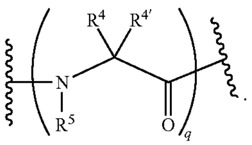

In some embodiments, Loop A is (SEQ ID NO: 9)

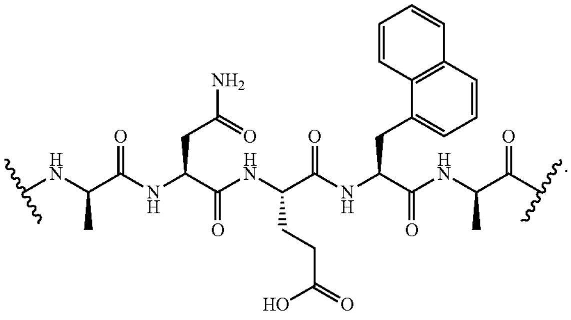

In some embodiments, Loop A is

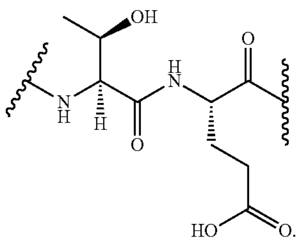 [SMILES: *N[C@H](C(=O)N[C@@H](CCC(=O)O)C(*)=O)[C@@H](C)O]

In some embodiments, Loop A is
(SEQ ID NO: 10)
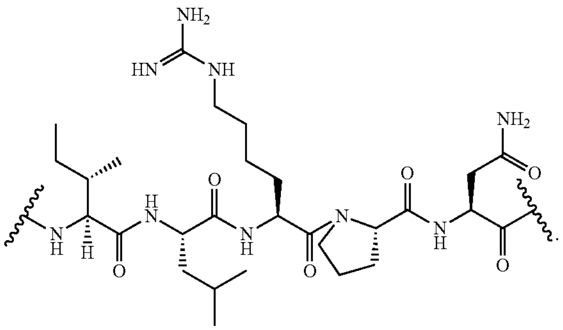
In some embodiments, Loop A is
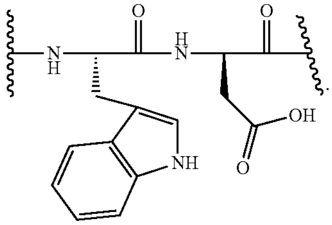 [SMILES: *N[C@H](Cc1c[nH]c2ccccc12)C(=O)N[C@@H](CC(=O)O)C(*)=O]
In some embodiments, Loop A is
(SEQ ID NO: 55)
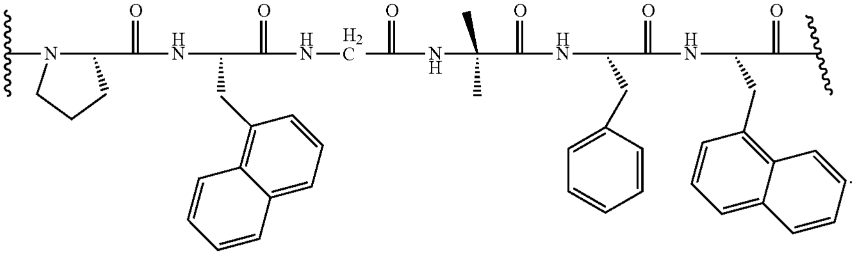
In some embodiments, Loop A is
(SEQ ID NO: 56)
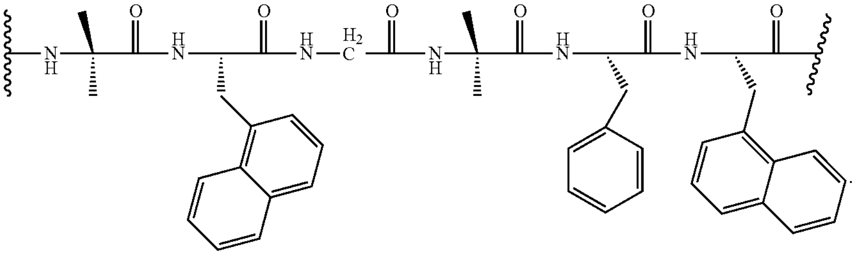
In some embodiments, Loop A is
(SEQ ID NO: 11)
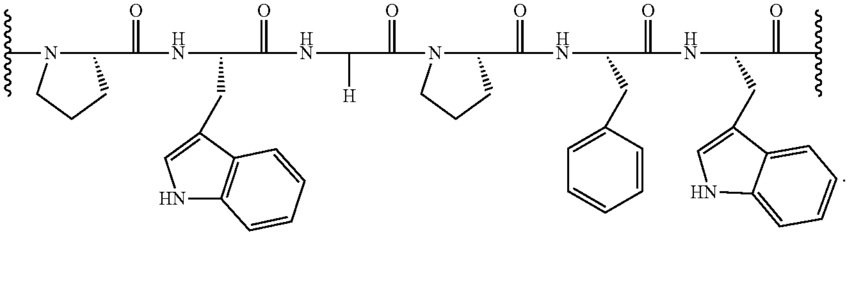

In some embodiments, Loop A is

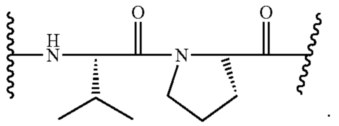

In some embodiments, Loop A is (SEQ ID NO: 12)

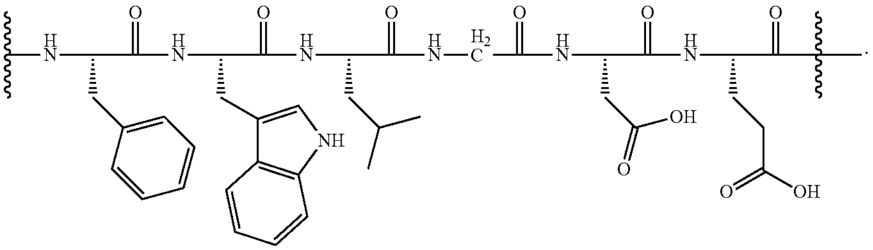

In some embodiments, Loop A is (SEQ ID NO: 9)

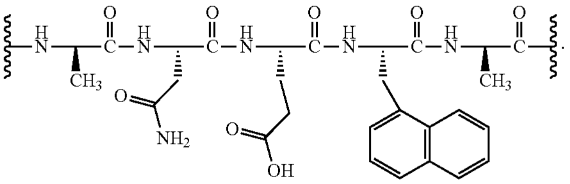

In some embodiments, Loop A is (SEQ ID NO: 13)

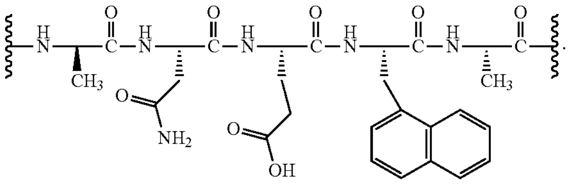

In some embodiments, Loop A is (SEQ ID NO: 57)

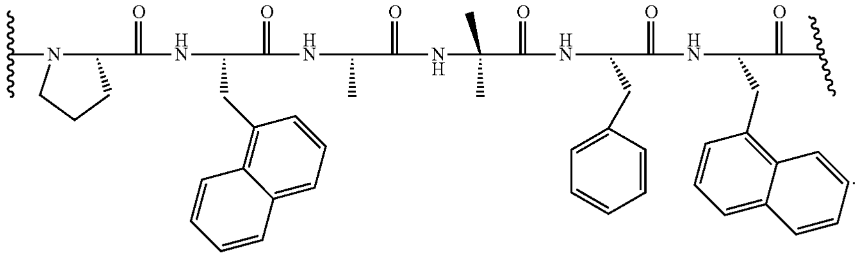

As defined above and described herein, Loop B is a bivalent natural or unnatural amino acid residue or peptide attached to the amino acid residue linked to $L^1$ and the amino acid residue linked to $L^3$, wherein Loop B comprises

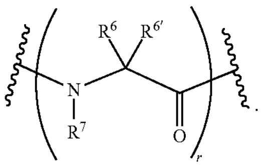

In some embodiments, Loop B is a bivalent natural amino acid residue attached to the amino acid residue linked to $L^1$ and the amino acid residue linked to $L^3$, wherein Loop B comprises

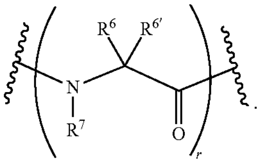

In some embodiments, Loop B is a bivalent unnatural amino acid residue attached to the amino acid residue linked to $L^1$ and the amino acid residue linked to $L^3$, wherein Loop B comprises

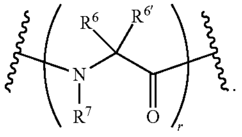

In some embodiments, Loop B is a bivalent peptide attached to the amino acid residue linked to $L^1$ and the amino acid residue linked to $L^3$, wherein Loop B comprises

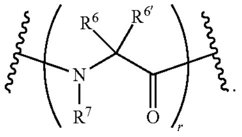

In some embodiments, Loop B is

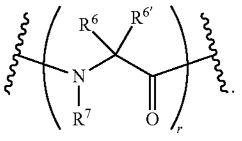

In some embodiments, Loop B is (SEQ ID NO: 14)

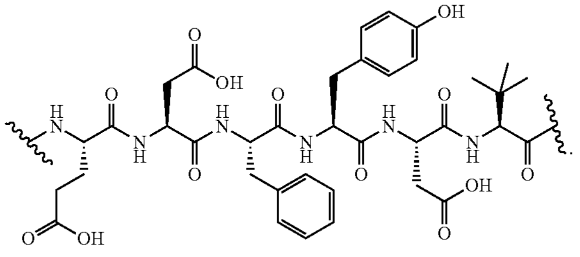

In some embodiments, Loop B is (SEQ ID NO: 15)

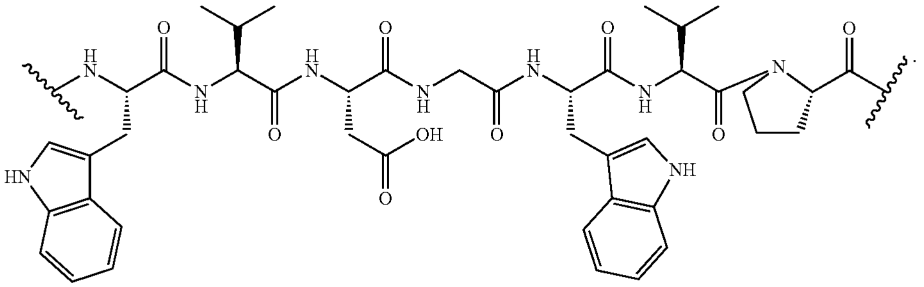

In some embodiments, Loop B is (SEQ ID NO: 16)

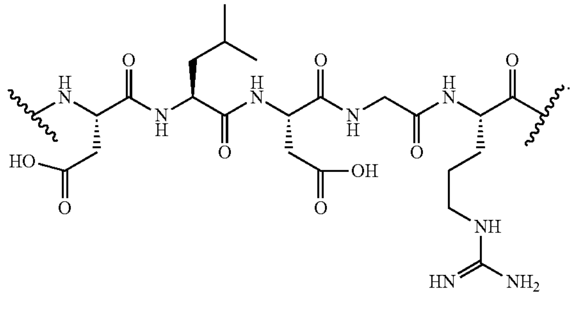

In some embodiments, Loop B is
(SEQ ID NO: 17)
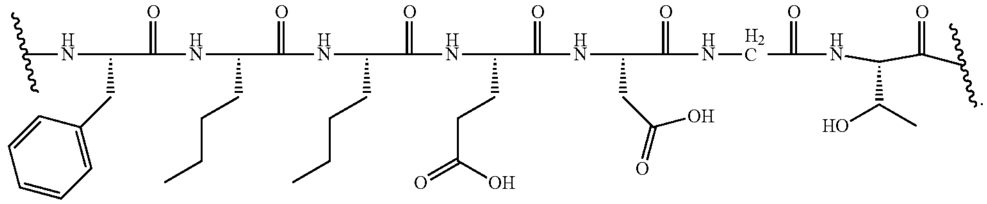
In some embodiments, Loop B is
(SEQ ID NO: 18)
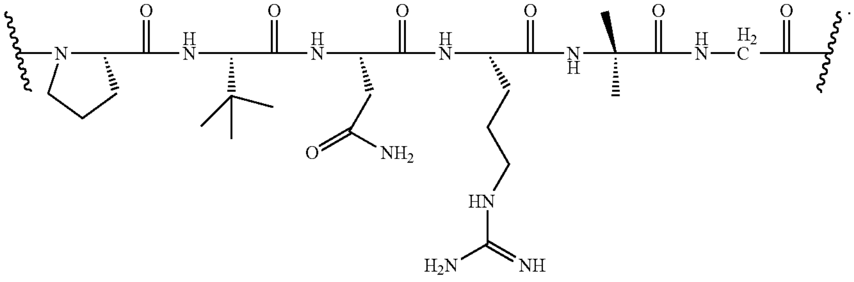
In some embodiments, Loop B is
(SEQ ID NO: 19)
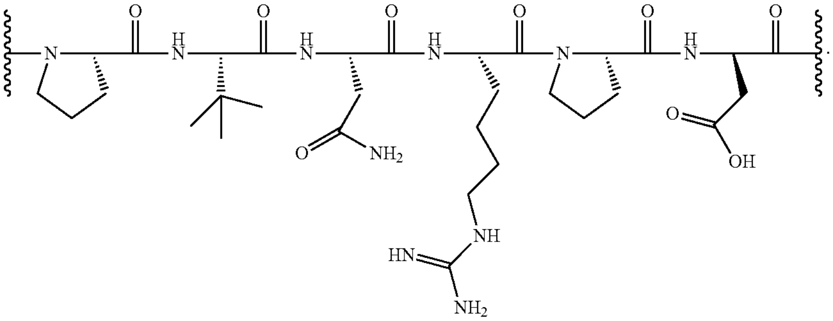
In some embodiments, Loop B is
(SEQ ID NO: 20)
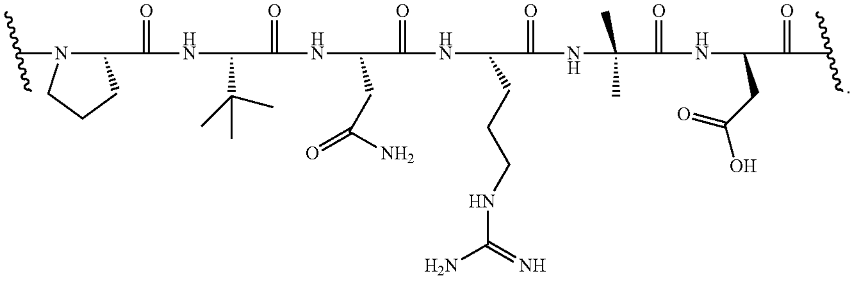

In some embodiments, Loop B is
(SEQ ID NO: 21)
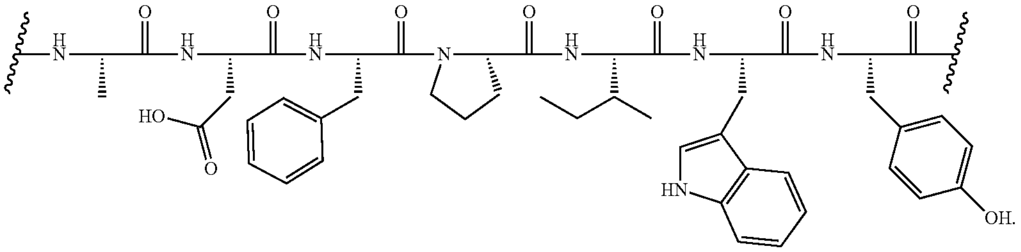
In some embodiments, Loop B is
(SEQ ID NO: 22)
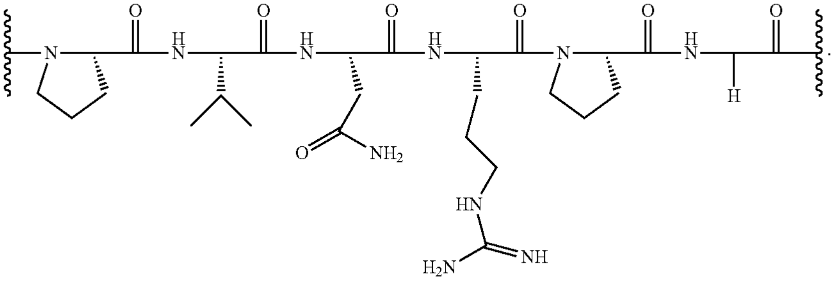
In some embodiments, Loop B is
(SEQ ID NO: 23)
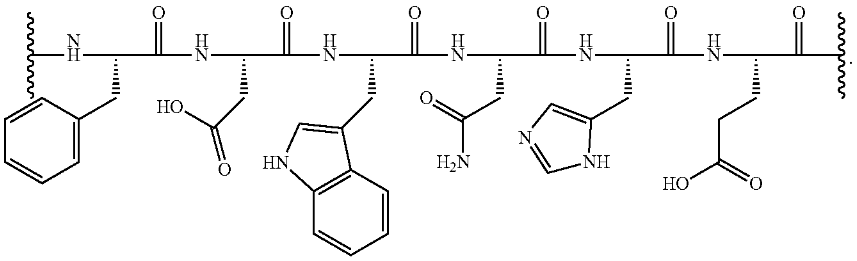
In some embodiments, Loop B is
(SEQ ID NO: 14)
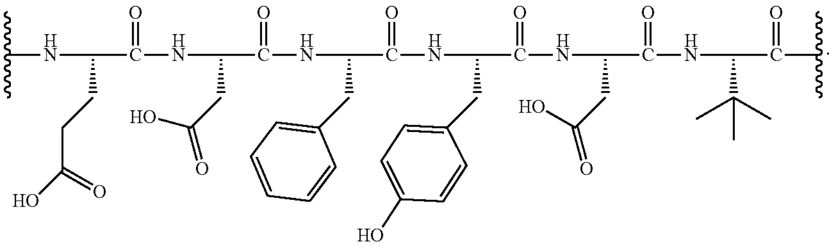

In some embodiments, Loop B is (SEQ ID NO: 24)

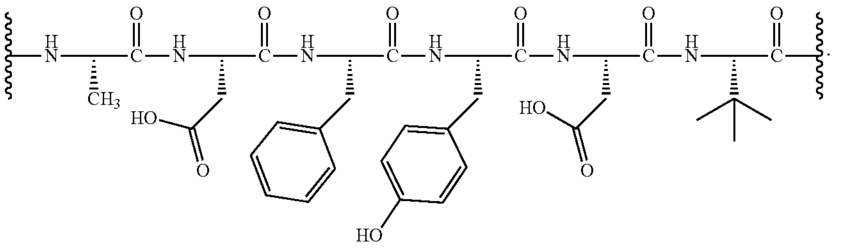

In some embodiments, Loop B is (SEQ ID NO: 25)

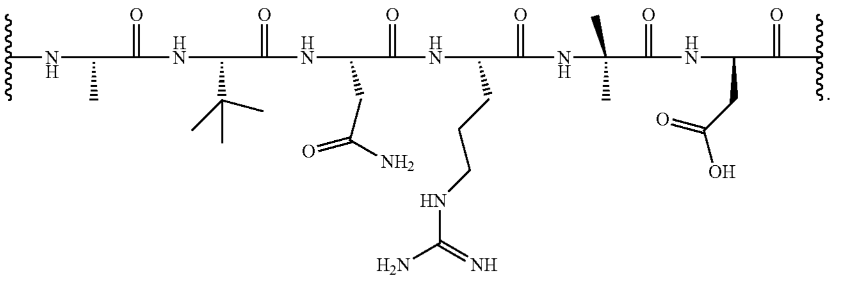

In some embodiments, Loop A comprises 1-15 amino acid residues and Loop B comprises 1-15 amino acid residues.

In some embodiments, Loop A comprises 5 amino acid residues and Loop B comprises 5 amino acid residues. In some embodiments, Loop A comprises 6 amino acid residues and Loop B comprises 5 amino acid residues. In some embodiments, Loop A comprises 2 amino acid residues and Loop B comprises 7 amino acid residues. In some embodiments, Loop A comprises 3 amino acid residues and Loop B comprises 7 amino acid residues. In some embodiments, Loop A comprises 3 amino acid residues and Loop B comprises 9 amino acid residues. In some embodiments, Loop A comprises 3 amino acid residues and Loop B comprises 6 amino acid residues. In some embodiments, Loop A comprises 2 amino acid residues and Loop B comprises 6 amino acid residues. In some embodiments, Loop A comprises 6 amino acid residues and Loop B comprises 5 amino acid residues.

In some embodiments, Loop A is selected from those depicted in Table 1, below. In some embodiments, Loop A is selected from those depicted in Table 3, below.

In some embodiments, Loop B is selected from those depicted in Table 1, below. In some embodiments, Loop B is selected from those depicted in Table 3, below.

As defined above and described herein, indicates the site of attachment to the N-terminus of the Bicycle.

As defined above and described herein, indicates the site of attachment to the C-terminus of the Bicycle.

As defined above and described herein, Detectable Moiety$^1$ is any moiety capable of being detected.

In some embodiments, Detectable Moiety$^1$ is any moiety capable of being detected.

One of ordinary skill in the art will appreciate that a variety of Detectable moieties are amenable to achieve the imaging effects of the present invention.

As used herein, "M" is a metal.

In some embodiments, Detectable Moiety$^1$ can be connected at any available position. In some embodiments, Detectable Moiety$^1$ can be connected at any available-OH, —C(O) OH, —SH, —$NH_2$, or —$NHCH_3$.

In some embodiments, Detectable Moiety$^1$ is 1,4,7,10-tetraazacyclododecane-1,4,7,10-tetraacetic acid (also known as DOTA, DotA, or tetraxetan):

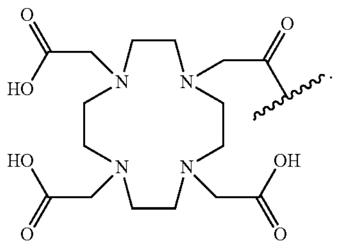 [SMILES: *C(=O)CN1CCN(CC(=O)O)CCN(CC(=O)O)CCN(CC(=O)O)CC1]

In some embodiments, Detectable Moiety$^1$ is Bn-DOTA:

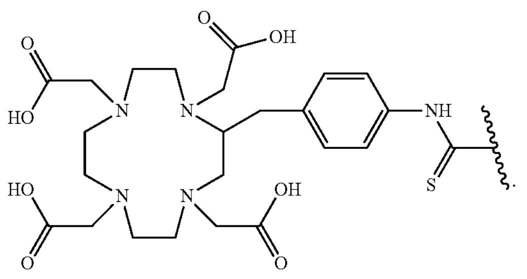 [SMILES: *C(=S)Nc1ccc(CC2CN(CC(=O)O)CCN(CC(=O)O)CCN(CC(=O)O)CCN2CC(=O)O)cc1]

In some embodiments, Detectable Moiety[1] is Bn-oxo-DOTA:
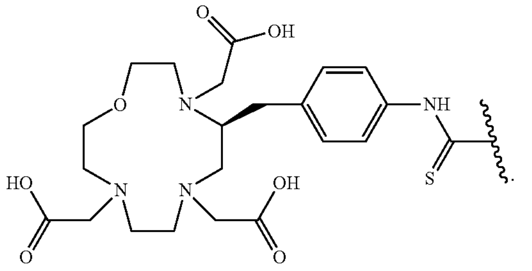 [SMILES: *C(=S)Nc1ccc(C[C@H]2CN(CC(=O)O)CCN(CC(=O)O)CCOCCN2CC(=O)O)cc1]
In some embodiments, Detectable Moiety[1] is Bn-PCTA:
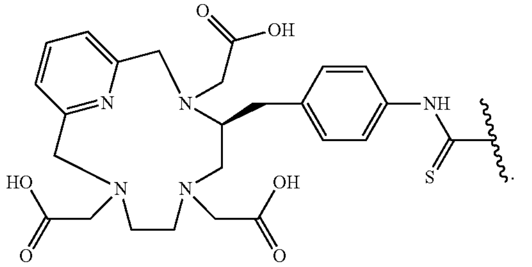 [SMILES: *C(=S)Nc1ccc(C[C@H]2CN(CC(=O)O)CCN(CC(=O)O)Cc3cccc(n3)CN2CC(=O)O)cc1]
In some embodiments, Detectable Moiety[1] is TETA:
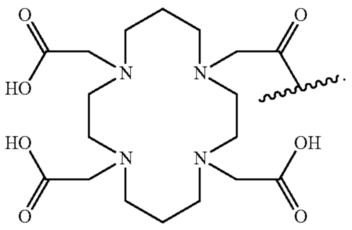 [SMILES: *C(=O)CN1CCCN(CC(=O)O)CCN(CC(=O)O)CCCN(CC(=O)O)CC1]
In some embodiments, Detectable Moiety[1] is Bn-NOTA:
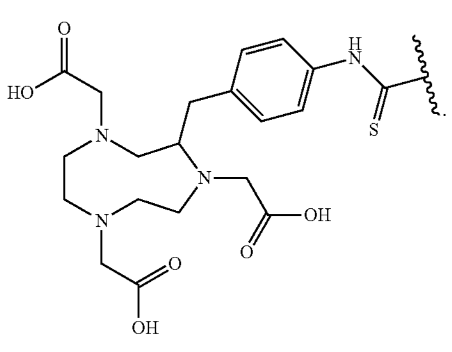 [SMILES: *C(=S)Nc1ccc(CC2CN(CC(=O)O)CCN(CC(=O)O)CCN2CC(=O)O)cc1]
In some embodiments, Detectable Moiety[1] is CHX-A"-DTPA:
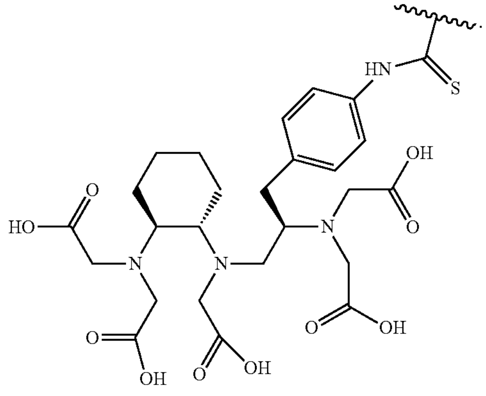 [SMILES: *C(=S)Nc1ccc(C[C@H](CN(CC(=O)O)[C@H]2CCCC[C@@H]2N(CC(=O)O)CC(=O)O)N(CC(=O)O)CC(=O)O)cc1]
In some embodiments, Detectable Moiety[1] is Bn-DTPA:
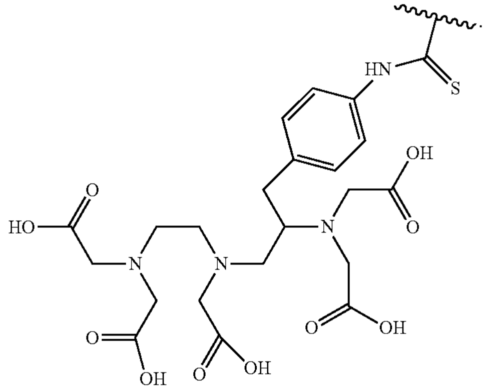 [SMILES: *C(=S)Nc1ccc(CC(CN(CCN(CC(=O)O)CC(=O)O)CC(=O)O)N(CC(=O)O)CC(=O)O)cc1]
In some embodiments, Detectable Moiety[1] is 2B3M-DTPA:
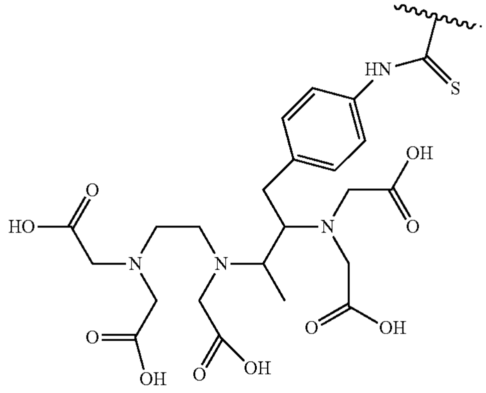 [SMILES: *C(=S)Nc1ccc(CC(C(C)N(CCN(CC(=O)O)CC(=O)O)CC(=O)O)N(CC(=O)O)CC(=O)O)cc1]

In some embodiments, Detectable Moiety[1] is a desferrioxamine (DFO):

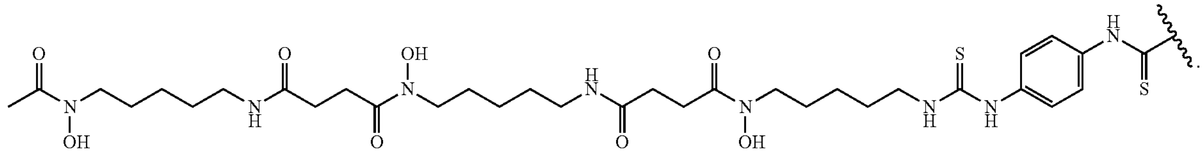 [SMILES: *C(=S)Nc1ccc(NC(=S)NCCCCCN(O)C(=O)CCC(=O)NCCCCCN(O)C(=O)CCC(=O)NCCCCCN(O)C(C)=O)cc1]

In some embodiments, Detectable Moiety[1] is a heptamethine dye:

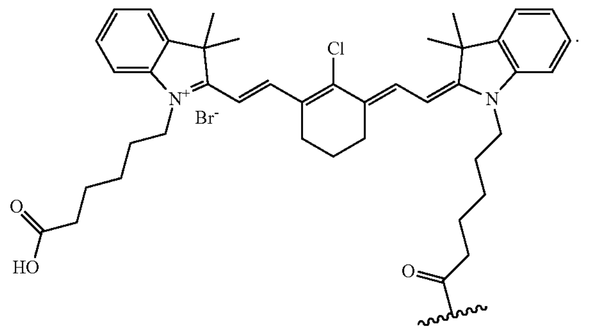 [SMILES: *C(=O)CCCCCN1/C(=C/C=C2\CCCC(/C=C/C3=[N+](CCCCCC(=O)O)c4ccccc4C3(C)C)=C2Cl)C(C)(C)c2ccccc21 ; [Br-]]

In some embodiments, Detectable Moiety[1] is Fluorescein:

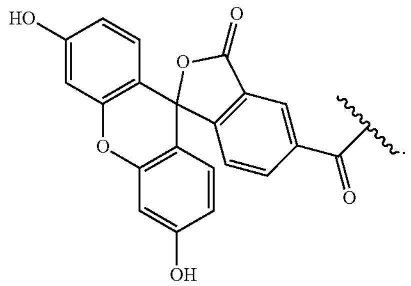 [SMILES: *C(=O)c1ccc2c(c1)C(=O)OC21c2ccc(O)cc2Oc2cc(O)ccc21]

In some embodiments, Detectable Moiety[1] is Alexafluor488:

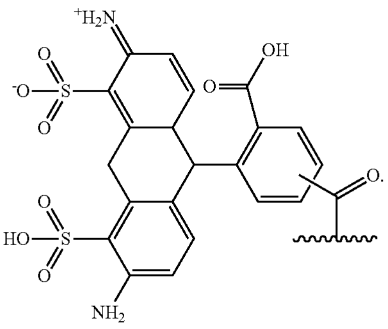

In some embodiments, Detectable Moiety[1] is a DOTA complex with a metal:

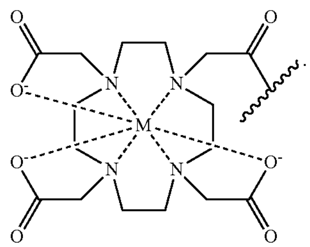

In some embodiments, Detectable Moiety[1] is a Bn-DOTA complex with a metal:

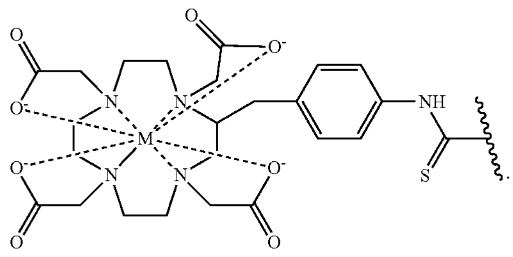

In some embodiments, Detectable Moiety[1] is a Bn-oxo-DOTA complex with a metal:

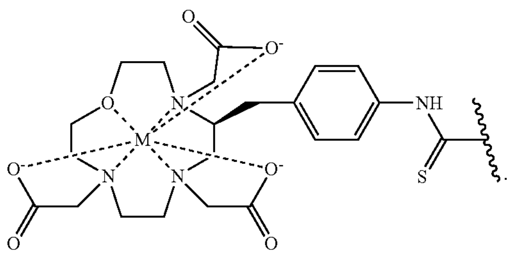

In some embodiments, Detectable Moiety[1] is a Bn-PCTA complex with a metal:

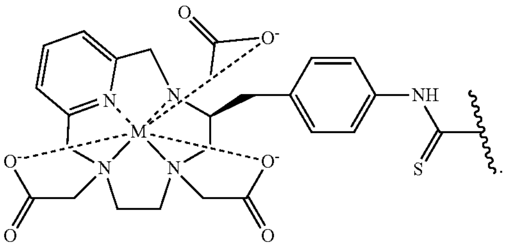

In some embodiments, Detectable Moiety[1] is a TETA complex with a metal:

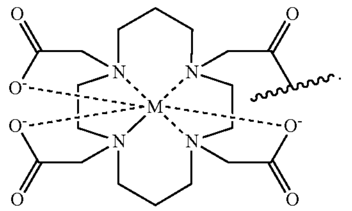

In some embodiments, Detectable Moiety[1] is a Bn-NOTA complex with a metal:

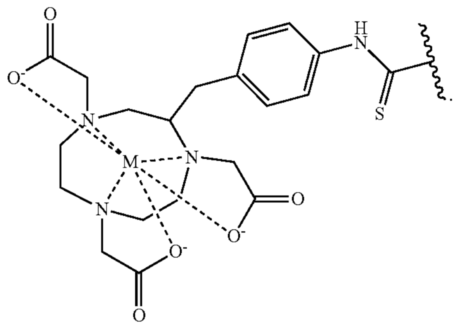

In some embodiments, Detectable Moiety[1] is a CHX-A"-DTPA complex with a metal:

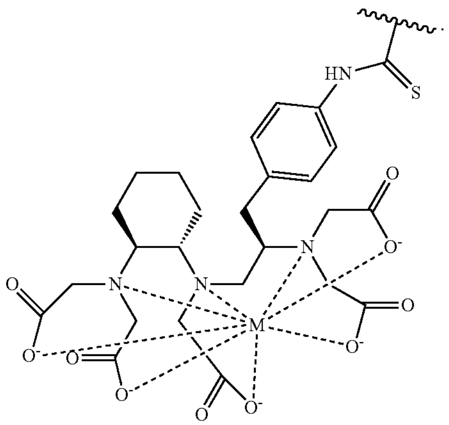

In some embodiments, Detectable Moiety[1] is a Bn-DTPA complex with a metal:

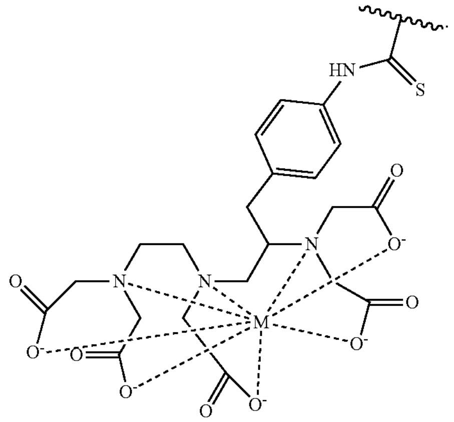

In some embodiments, Detectable Moiety[1] is a 2B3M-DTPA complex with a metal:

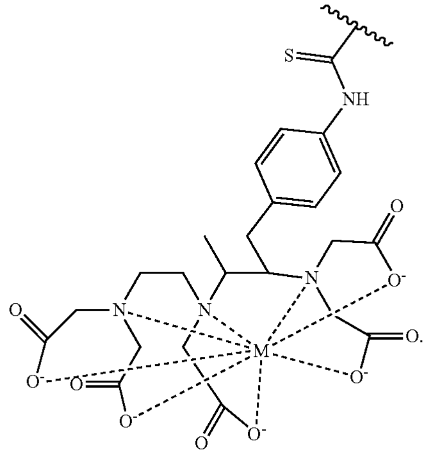

In some embodiments, Detectable Moiety[1] is a desferrioxamine (DFO) complex with a metal:

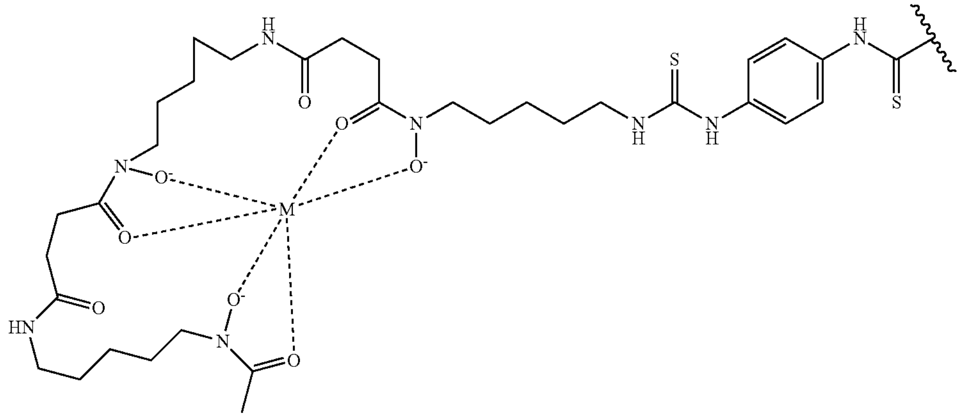

In some embodiments, Detectable Moiety[1] forms a complex with a metal.

In some embodiments, Detectable Moiety[1] is a scorpionate. In some embodiments, Detectable Moiety[1] is

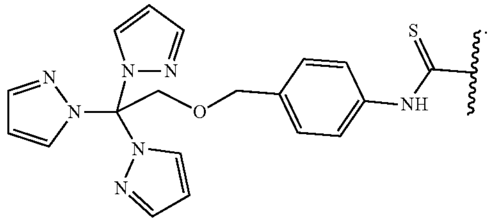 [SMILES: *C(=S)Nc1ccc(COCC(n2cccn2)(n2cccn2)n2cccn2)cc1]

In some embodiments, Detectable Moiety[1] is a nanomaterial. In some embodiments, Detectable Moiety[1] is a quantum dot.

In some embodiments, Detectable Moiety[1] is selected from those depicted in Table 1, below. In some embodiments, Detectable Moiety[1] is selected from those depicted in Table 3, below.

As defined above and described herein, Detectable Moiety[2] is any moiety capable of being detected.

In some embodiments, Detectable Moiety[2] is any moiety capable of being detected.

In some embodiments, Detectable Moiety[2] can be connected at any available position. In some embodiments, Detectable Moiety[2] can be connected at any available-OH, —C(O) OH, —SH, —$NH_2$, or —$NHCH_3$.

In some embodiments, Detectable Moiety[2] is 1,4,7,10-tetraazacyclododecane-1,4,7,10-tetraacetic acid (also known as DOTA, DotA, or tetraxetan):

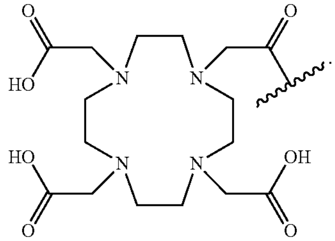 [SMILES: *C(=O)CN1CCN(CC(=O)O)CCN(CC(=O)O)CCN(CC(=O)O)CC1]

In some embodiments, Detectable Moiety[2] is Bn-DOTA:

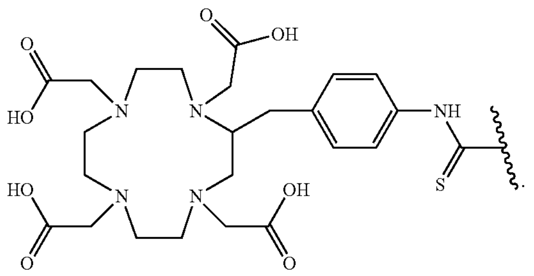 [SMILES: *C(=S)Nc1ccc(CC2CN(CC(=O)O)CCN(CC(=O)O)CCN(CC(=O)O)CCN2CC(=O)O)cc1]

In some embodiments, Detectable Moiety[2] is Bn-OXO-DOTA:

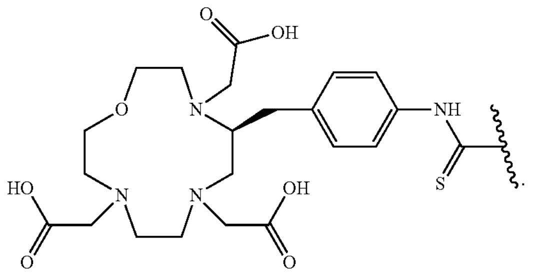 [SMILES: *C(=S)Nc1ccc(C[C@H]2CN(CC(=O)O)CCN(CC(=O)O)CCOCCN2CC(=O)O)cc1]

In some embodiments, Detectable Moiety[2] is Bn-PCTA:

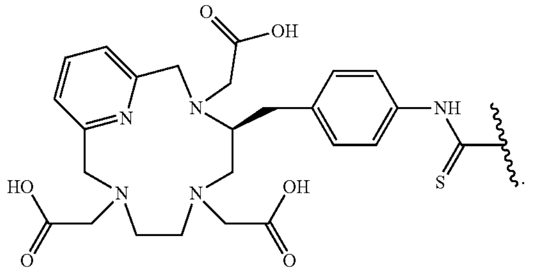 [SMILES: *C(=S)Nc1ccc(C[C@H]2CN(CC(=O)O)CCN(CC(=O)O)Cc3cccc(n3)CN2CC(=O)O)cc1]

In some embodiments, Detectable Moiety[2] is TETA:
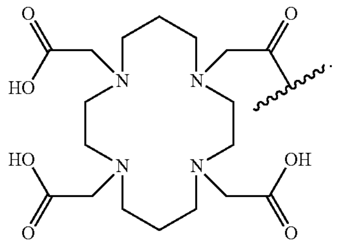 [SMILES: *C(=O)CN1CCCN(CC(=O)O)CCN(CC(=O)O)CCCN(CC(=O)O)CC1]
In some embodiments, Detectable Moiety[2] is Bn-NOTA:
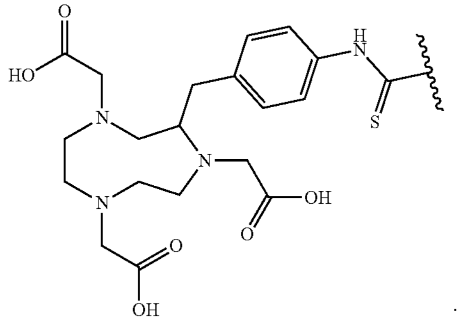 [SMILES: *C(=S)Nc1ccc(CC2CN(CC(=O)O)CCN(CC(=O)O)CCN2CC(=O)O)cc1]
In some embodiments, Detectable Moiety[2] is CHX-A"-DTPA:
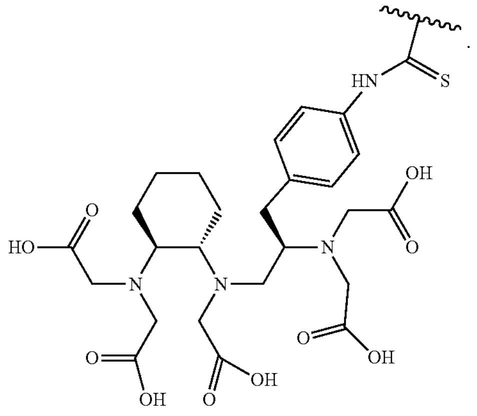 [SMILES: *C(=S)Nc1ccc(C[C@H](CN(CC(=O)O)[C@H]2CCCC[C@@H]2N(CC(=O)O)CC(=O)O)N(CC(=O)O)CC(=O)O)cc1]
In some embodiments, Detectable Moiety[2] is Bn-DTPA:
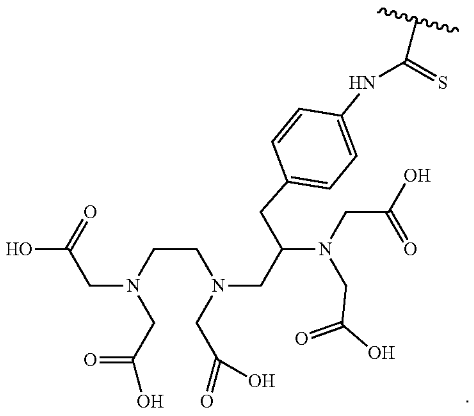 [SMILES: *C(=S)Nc1ccc(CC(CN(CCN(CC(=O)O)CC(=O)O)CC(=O)O)N(CC(=O)O)CC(=O)O)cc1]
In some embodiments, Detectable Moiety[2] is 2B3M-DTPA:
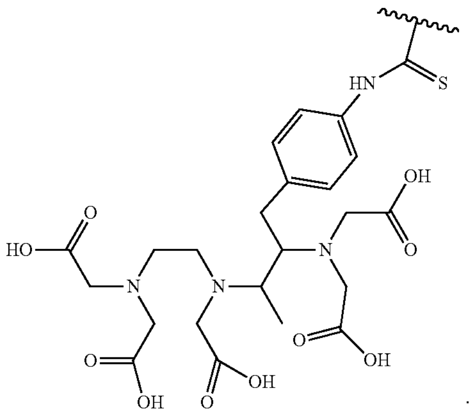 [SMILES: *C(=S)Nc1ccc(CC(C(C)N(CCN(CC(=O)O)CC(=O)O)CC(=O)O)N(CC(=O)O)CC(=O)O)cc1]
In some embodiments, Detectable Moiety[2] is a desferrioxamine (DFO):
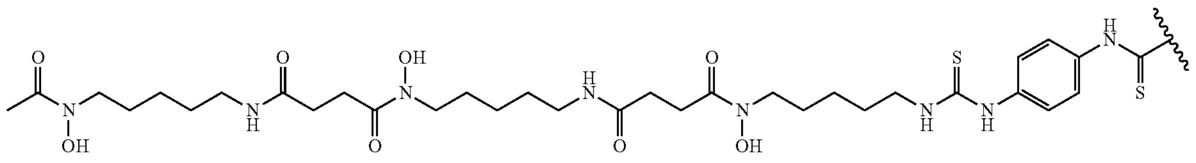 [SMILES: *C(=S)Nc1ccc(NC(=S)NCCCCCN(O)C(=O)CCC(=O)NCCCCCN(O)C(=O)CCC(=O)NCCCCCN(O)C(C)=O)cc1]

In some embodiments, Detectable Moiety$^2$ is a heptamethine dye:

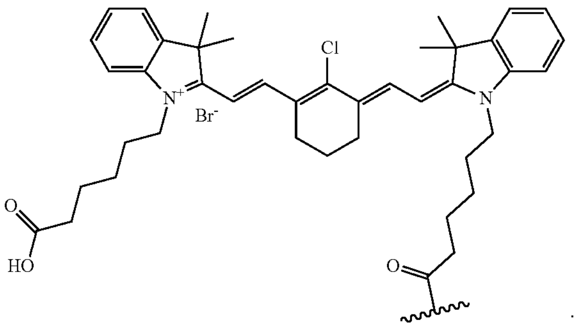 [SMILES: *C(=O)CCCCCN1/C(=C/C=C2\CCCC(/C=C/C3=[N+](CCCCCC(=O)O)c4ccccc4C3(C)C)=C2Cl)C(C)(C)c2ccccc21 ; [Br-]]

In some embodiments, Detectable Moiety$^2$ is Fluorescein:

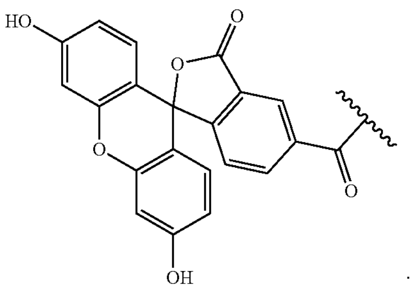 [SMILES: *C(=O)c1ccc2c(c1)C(=O)OC21c2ccc(O)cc2Oc2cc(O)ccc21]

In some embodiments, Detectable Moiety$^2$ is Alexafluor488:

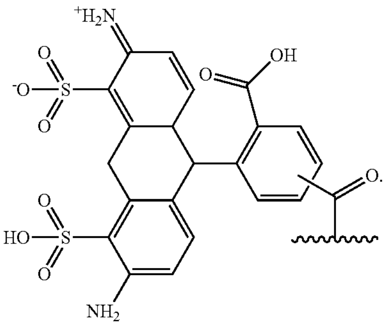

In some embodiments, Detectable Moiety$^2$ is a DOTA complex with a metal:

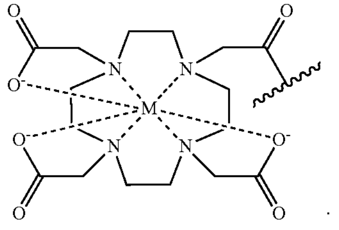

In some embodiments, Detectable Moiety$^2$ is a Bn-DOTA complex with a metal:

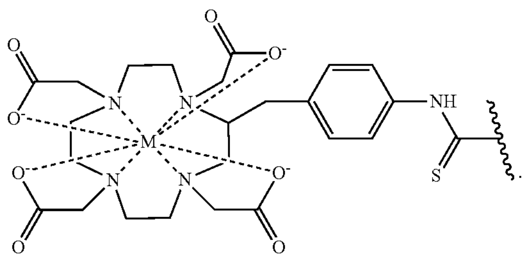

In some embodiments, Detectable Moiety$^2$ is a Bn-oxo-DOTA complex with a metal:

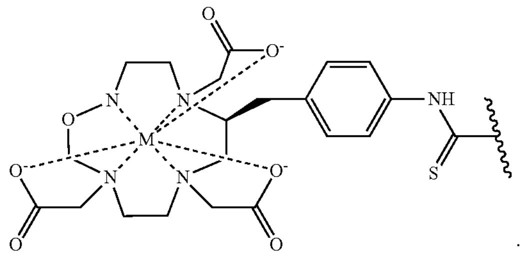

In some embodiments, Detectable Moiety$^2$ is a Bn-PCTA complex with a metal:

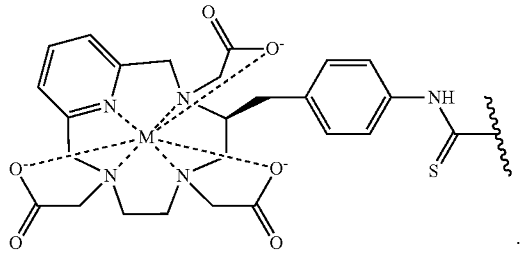

In some embodiments, Detectable Moiety$^2$ is a TETA complex with a metal:

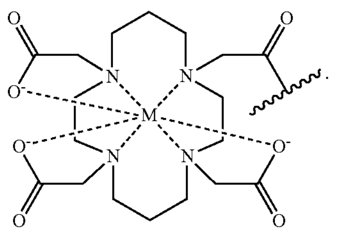

In some embodiments, Detectable Moiety[2] is a Bn-NOTA complex with a metal:

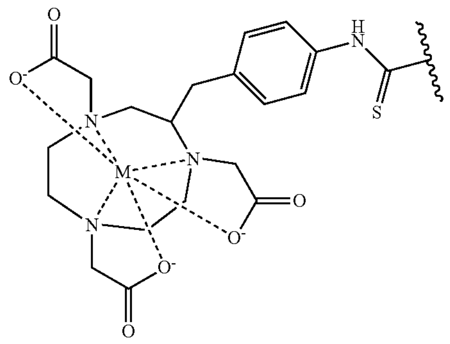

.

In some embodiments, Detectable Moiety[2] is a CHX-A"-DTPA complex with a metal:

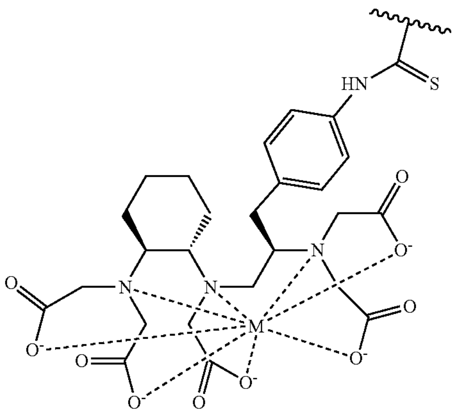

.

In some embodiments, Detectable Moiety[2] is a Bn-DTPA complex with a metal:

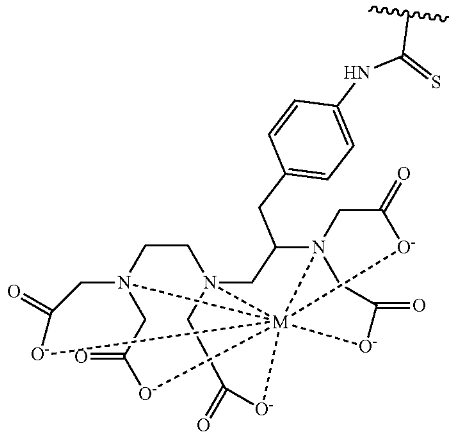

.

In some embodiments, Detectable Moiety[2] is a 2B3M-DTPA complex with a metal:

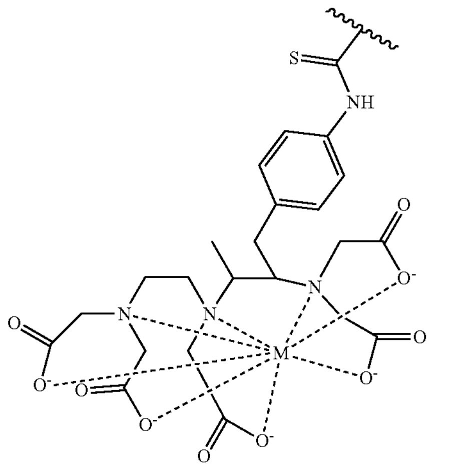

.

In some embodiments, Detectable Moiety[2] is a desferrioxamine (DFO) complex with a metal:

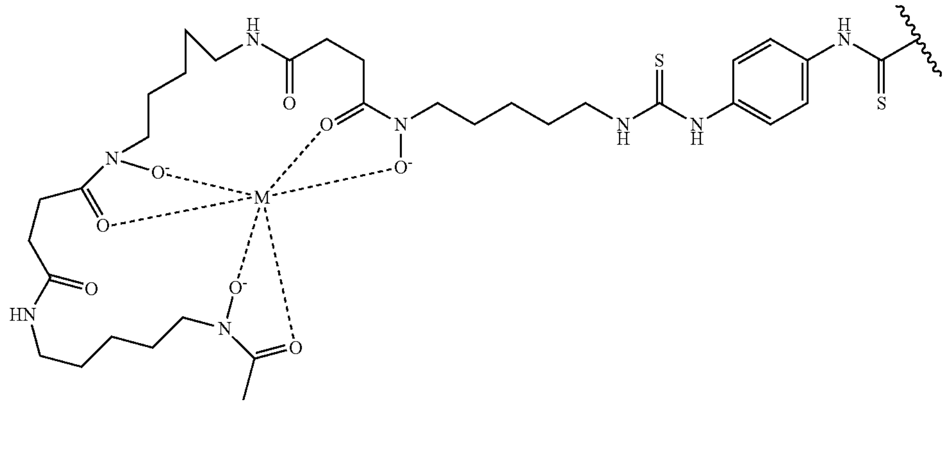

In some embodiments, Detectable Moiety[2] forms a complex with a metal.

In some embodiments, Detectable Moiety[2] is a scorpionate. In some embodiments, Detectable Moiety[2] is

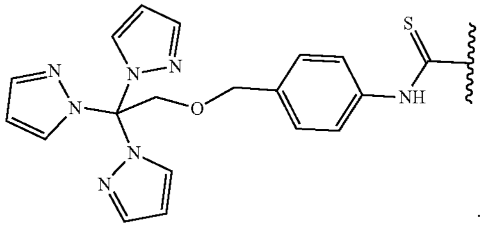 [SMILES: *C(=S)Nc1ccc(COCC(n2cccn2)(n2cccn2)n2cccn2)cc1]

.

In some embodiments, Detectable Moiety[2] is a nanomaterial. In some embodiments, Detectable Moiety[2] is a quantum dot In some embodiments, Detectable Moiety[2] is selected from those depicted in Table 1, below. In some embodiments, Detectable Moiety[2] is selected from those depicted in Table 1, below.

In some embodiments, the metal is a radiometal. In some embodiments, the metal is $^{111}$In. In some embodiments, the metal is $^{67}$Ga. In some embodiments, the metal is $^{68}$Ga. In some embodiments, the metal is $^{86}$Y. In some embodiments, the metal is $^{90}$Y. In some embodiments, the metal is $^{177}$Lu.

In some embodiments, the metal is $^{89}$Zr. In some embodiments, the metal is $^{95}$Zr.

As defined above and described herein, Linker[1] is hydrogen, —C(O)R,

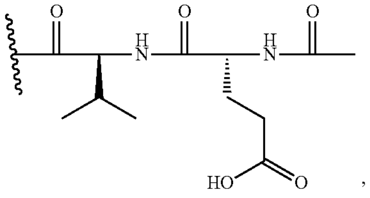 [SMILES: *C(=O)[C@H](NC(=O)[C@H](CCC(=O)O)NC(C)=O)C(C)C]

, or a bivalent moiety that connects the N-terminus of the Bicycle with Detectable Moiety[1], wherein when n is 0, Linker[1] is hydrogen, C(O)R, or

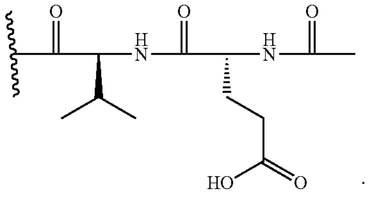 [SMILES: *C(=O)[C@H](NC(=O)[C@H](CCC(=O)O)NC(C)=O)C(C)C]

.

In some embodiments, Linker[1] is hydrogen, wherein n is 0. In some embodiments, Linker[1] is hydrogen, wherein n is 0. In some embodiments, Linker[1] is —C(O)R, wherein n is 0. In some embodiments, Linker[1] is —$C(O)CH_3$, wherein n is 0. In some embodiments, Linker[1] is

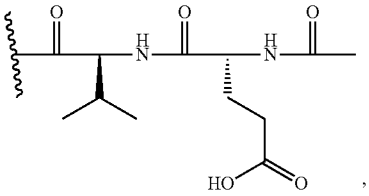

, wherein n is 0. In some embodiments, Linker[1] is a bivalent moiety that connects the N-terminus of the Bicycle with Detectable Moiety[1].

In some embodiments, Linker[1] is a covalent bond. In some embodiments, Linker[1] is

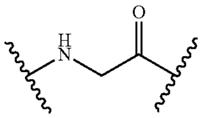

.

In some embodiments, Linker[1] is

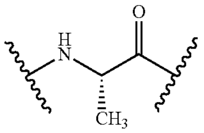

.

In some embodiments, Linker[1] is

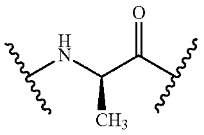

.

In some embodiments, Linker[1] is

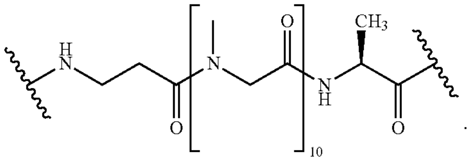

.

In some embodiments, Linker[1] is
(SEQ ID NO: 58)
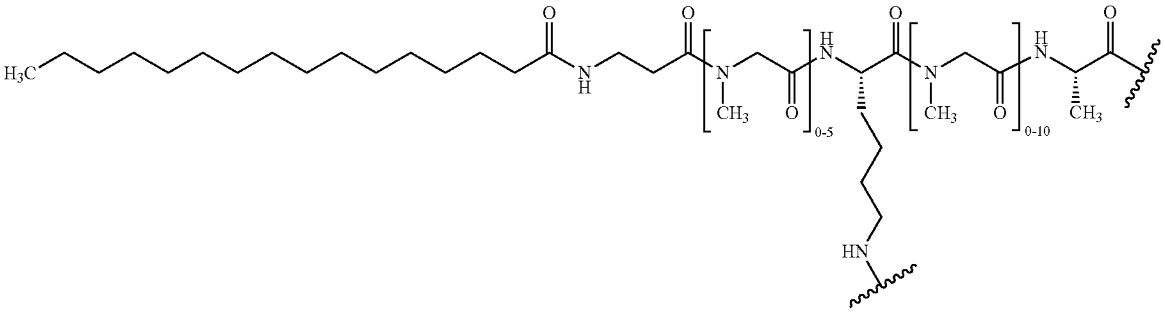
In some embodiments, Linker[1] is
(SEQ ID NO: 26)
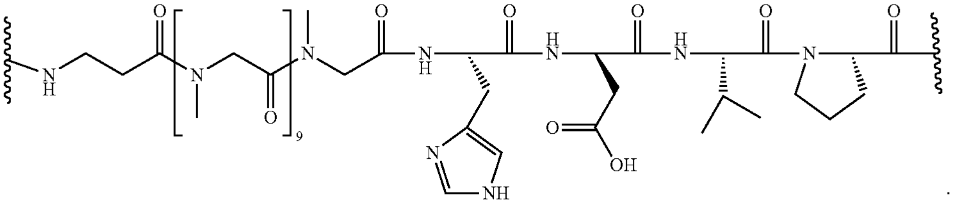
In some embodiments, Linker[1] is
(SEQ ID NO: 59)
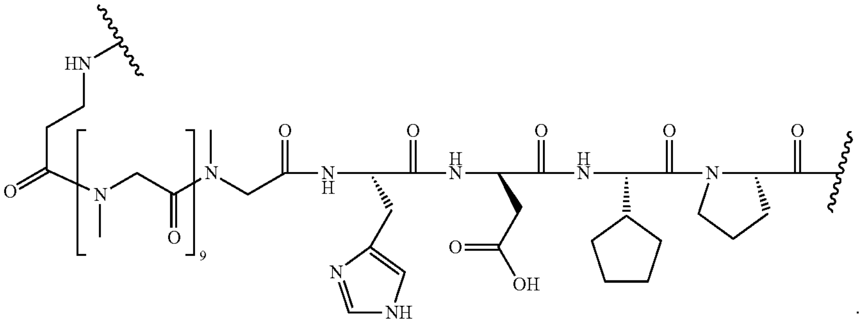
In some embodiments, Linker[1] is
(SEQ ID NO: 60)
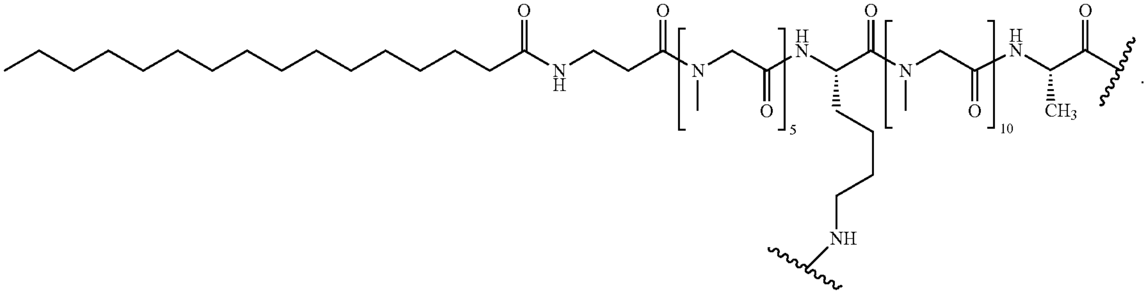

In some embodiments, $Linker^1$ is selected from those depicted in Table 1, below. In some embodiments, $Linker^1$ is selected from those depicted in Table 3, below.

As defined above and described herein, $Linker^2$ is —$NH_2$ or a bivalent moiety that connects the C-terminus of the Bicycle with Detectable $Moiety^2$, wherein when p is 0, $Linker^2$ is —$NH_2$.

In some embodiments, $Linker^2$ is —$NH_2$, wherein p is 0. In some embodiments, $Linker^2$ is a bivalent moiety that connects the C-terminus of the Bicycle with Detectable $Moiety^2$.

In some embodiments, $Linker^2$ is

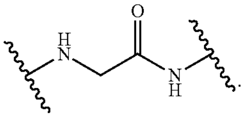 [SMILES: *NCC(=O)N*]

In some embodiments, $Linker^2$ is

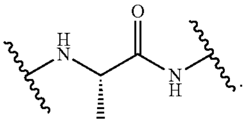 [SMILES: *NC(=O)[C@H](C)N*]

In some embodiments, $Linker^2$ is

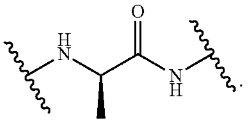 [SMILES: *NC(=O)[C@@H](C)N*]

In some embodiments, $Linker^2$ is

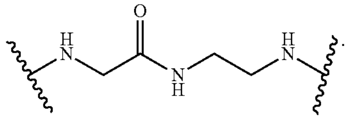 [SMILES: *NCCNC(=O)CN*]

In some embodiments, $Linker^2$ is

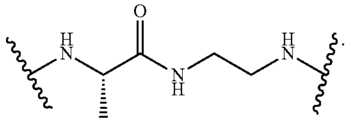 [SMILES: *NCCNC(=O)[C@H](C)N*]

In some embodiments, $Linker^2$ is

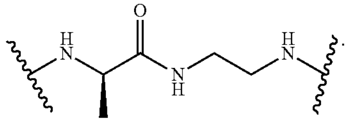 [SMILES: *NCCNC(=O)[C@@H](C)N*]

In some embodiments, $Linker^2$ is (SEQ ID NO: 61)

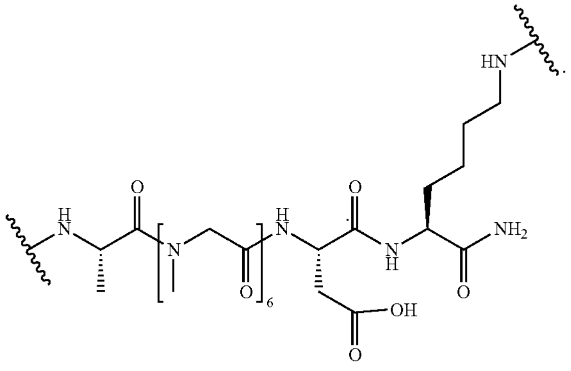

In some embodiments, $Linker^2$ is (SEQ ID NO: 62)

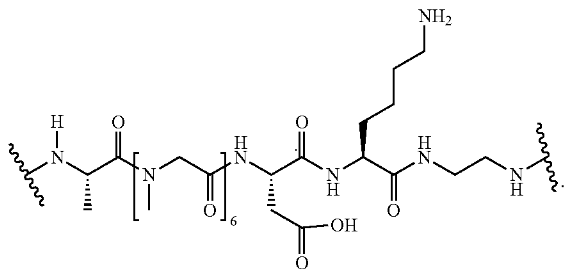

In some embodiments, $Linker^2$ is (SEQ ID NO: 63)

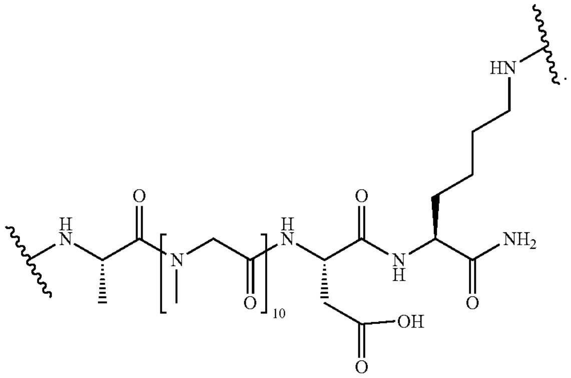

In some embodiments, $Linker^2$ is (SEQ ID NO: 64)

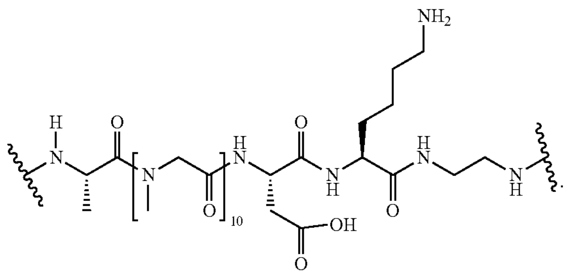

In some embodiments, $Linker^2$ is (SEQ ID NO: 65)

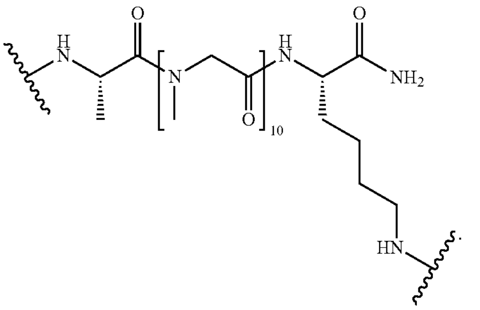

In some embodiments, $Linker^2$ is (SEQ ID NO: 66)

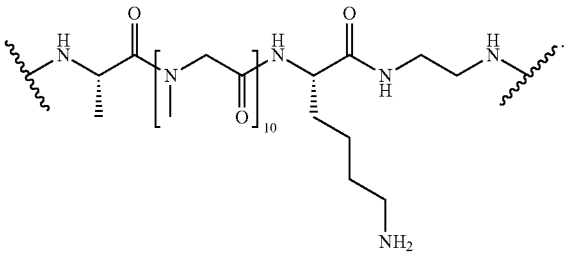

In some embodiments, $Linker^2$ is (SEQ ID NO: 67)

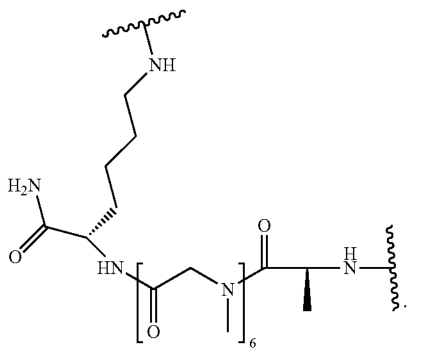

In some embodiments, $Linker^2$ is selected from those depicted in Table 1, below. In some embodiments, $Linker^2$ is selected from those depicted in Table 3, below.

As defined above and described herein, Ring A is selected from the group consisting of 18-crown-6,1,7,13-triaza-18-crown-6, and a 3-12-membered saturated, partially unsaturated, bridged bicyclic, bridged tricyclic, propellane, or aromatic ring optionally substituted with 0-3 oxo, methyl, ethyl or spiroethylene groups and having 0-6 heteroatoms independently selected from nitrogen, oxygen, or sulfur.

In some embodiments, Ring A is 18-crown-6. In some embodiments, Ring A is 1,7,13-triaza-18-crown-6. In some embodiments, Ring A is a 3-12-membered saturated, partially unsaturated, bridged bicyclic, bridged tricyclic, propellane, or aromatic ring optionally substituted with 0-3 oxo, methyl, ethyl or spiroethylene groups and having 0-6 heteroatoms independently selected from nitrogen, oxygen, or sulfur.

In some embodiments, Ring A is

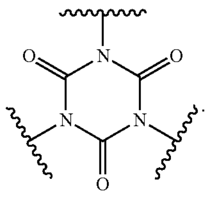 [SMILES: *n1c(=O)n(*)c(=O)n(*)c1=O]

In some embodiments, Ring A is

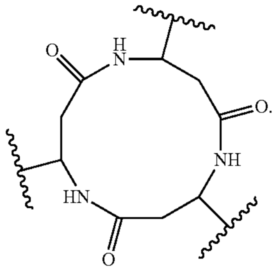 [SMILES: *C1CC(=O)NC(*)CC(=O)NC(*)CC(=O)N1]

In some embodiments, Ring A is

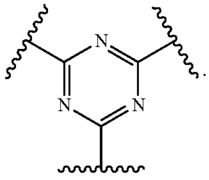 [SMILES: *c1nc(*)nc(*)n1]

In some embodiments, Ring A is

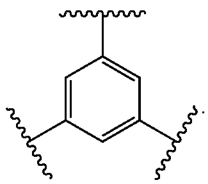 [SMILES: *c1cc(*)cc(*)c1]

In some embodiments, Ring A is
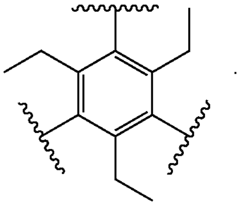 [SMILES: *c1c(CC)c(*)c(CC)c(*)c1CC]
In some embodiments, Ring A is
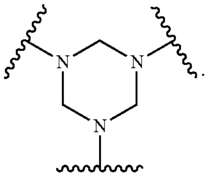 [SMILES: *N1CN(*)CN(*)C1]
In some embodiments, Ring A is
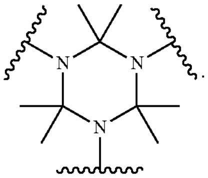
In some embodiments, Ring A is
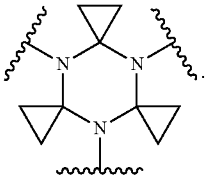 [SMILES: *N1C2(CC2)N(*)C2(CC2)N(*)C12CC2]
In some embodiments, Ring A is
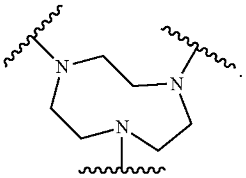 [SMILES: *N1CCN(*)CCN(*)CC1]
In some embodiments, Ring A is
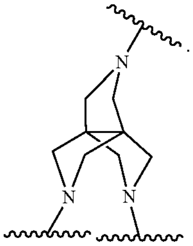 [SMILES: *N1CC23CN(*)CC2(C1)CN(*)C3]
In some embodiments, Ring A is
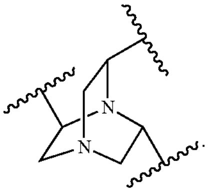 [SMILES: *C1CN2CC(*)N1C(*)C2]
In some embodiments, Ring A is
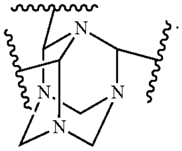 [SMILES: *C1N2CN3CN(C2)C(*)N1C3*]
In some embodiments, Ring A is
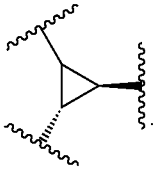 [SMILES: *C1[C@H](*)[C@H]1*]
In some embodiments, Ring A is
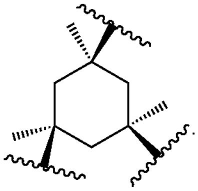

In some embodiments, Ring A is

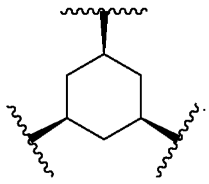 [SMILES: *[C@H]1C[C@@H](*)C[C@@H](*)C1]

In some embodiments, Ring A is

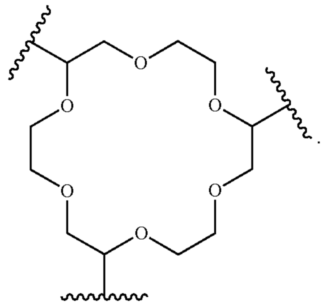 [SMILES: *C1COCCOC(*)COCCOC(*)COCCO1]

In some embodiments, Ring A is

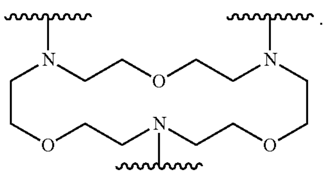 [SMILES: *N1CCOCCN(*)CCOCCN(*)CCOCC1]

In some embodiments, Ring A is selected from those depicted in Table 1, below. In some embodiments, Ring A is selected from those depicted in Table 3, below.

In certain embodiments, the present invention provides a Bicycle of formula I, wherein Scaffold is Ring A, thereby forming a compound of formula I-a:

I-a

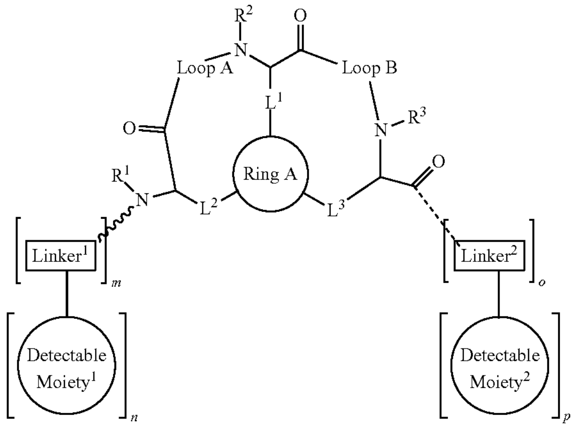

or a pharmaceutically acceptable salt thereof, wherein each of Loop A, Loop B, Ring A, $L^1$, $L^2$, $L^3$, Linker[1], Linker[2], Detectable Moiety[1], Detectable Moiety[2], $R^1$, $R^2$, $R^3$, m, n, o, and p is as defined above and described in embodiments herein, both singly and in combination.

In certain embodiments, the present invention provides a Bicycle of formula I, wherein Loop A is

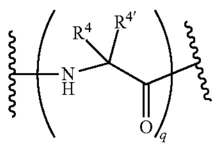

and Loop B is

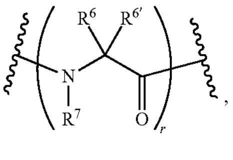

thereby forming a Bicycle of formula II:

II

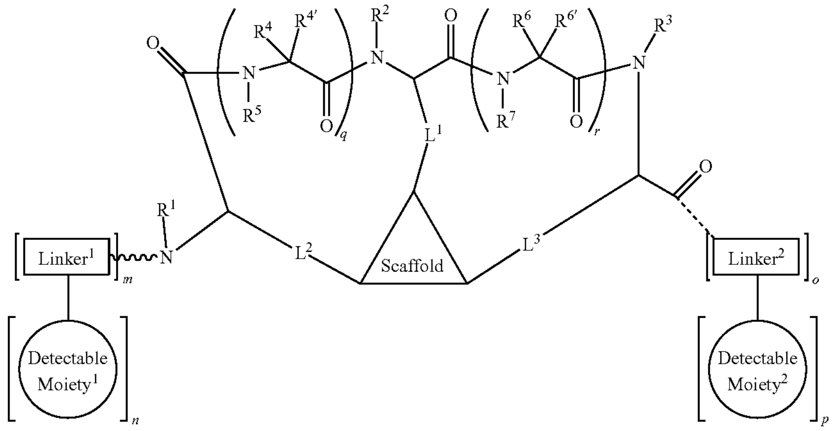

or a pharmaceutically acceptable salt thereof, wherein each of $L^1$, $L^2$, $L^3$, Scaffold, $R^1$, $R^2$, $R^3$, $R^4$, $R^{4'}$, $R^5$, $R^6$, $R^{6'}$, $R^7$, $Linker^{11}$, $Linker^2$, Detectable $Moiety^1$, Detectable $Moiety^2$, m, n, o, p, q and r is as defined above and described in embodiments herein, both singly and in combination.

In certain embodiments, the present invention provides a Bicycle of formula II, wherein p is 0, thereby forming a Bicycle of formula II-a:

II-a

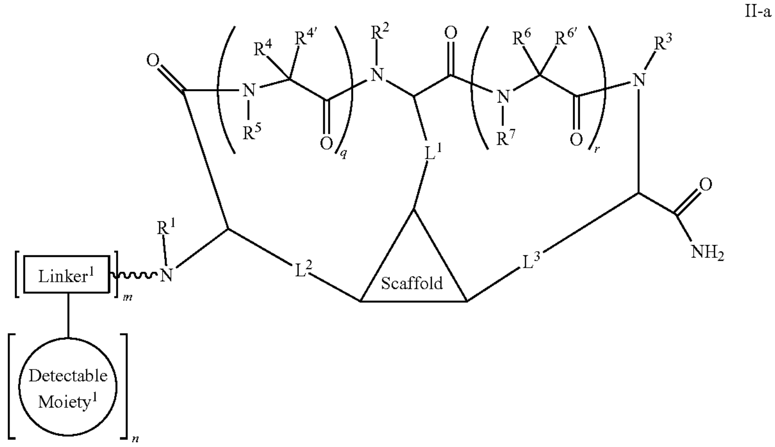

or a pharmaceutically acceptable salt thereof, wherein each of $L^1$, $L^2$, $L^3$, Scaffold, $R^1$, $R^2$, $R^3$, $R^4$, $R^{4'}$, $R^5$, $R^6$, $R^{6'}$, $R^7$, $Linker^{11}$, Detectable $Moiety^1$, m, n, q and r is as defined above and described in embodiments herein, both singly and in combination.

In certain embodiments, the present invention provides a Bicycle of formula II, wherein n is 0, thereby forming a Bicycle of formula II-b:

II-b

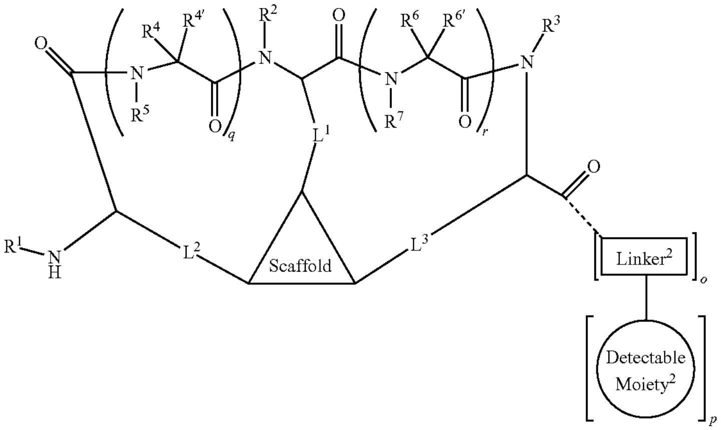

or a pharmaceutically acceptable salt thereof, wherein each of $L^1$, $L^2$, $L^3$, Scaffold, $R^1$, $R^2$, $R^3$, $R^4$, $R^{4'}$, $R^5$, $R^6$, $R^{6'}$, $R^7$, $Linker^2$, Detectable $Moiety^2$, o, p, q and r is as defined above and described in embodiments herein, both singly and in combination.

Exemplary compounds of the invention are set forth in Table 1, below.

TABLE 1

| Exemplary compounds |
|---|
| (SEQ ID NO: 28)<br>I-1<br>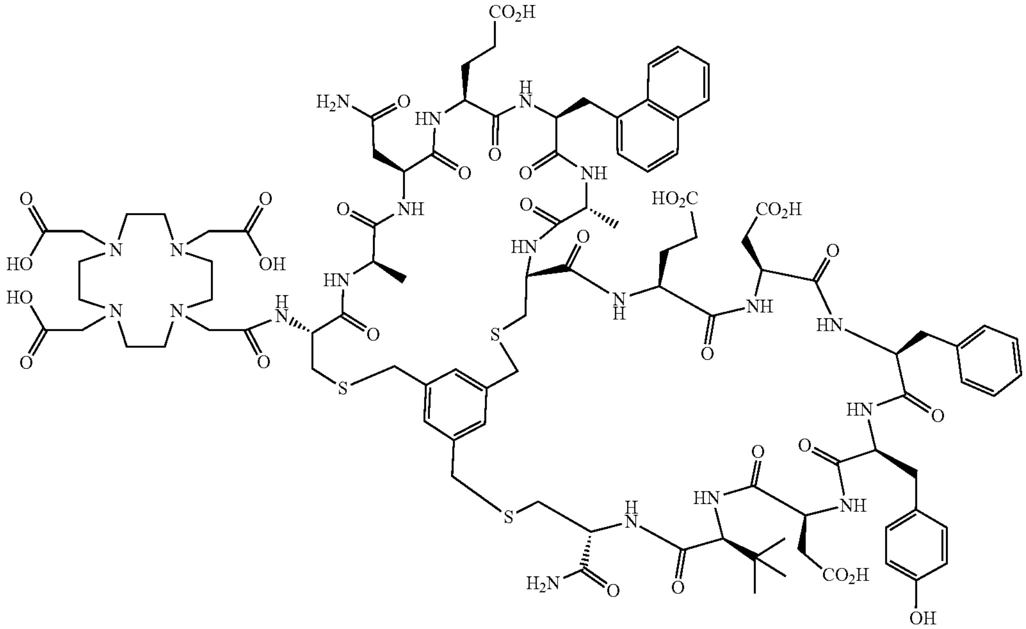 [SMILES: C[C@H]1NC(=O)[C@@H](NC(=O)CN2CCN(CC(=O)O)CCN(CC(=O)O)CCN(CC(=O)O)CC2)CSCc2cc3cc(c2)CSC[C@H](NC(=O)[C@@H](C)NC(=O)[C@H](Cc2cccc4ccccc24)NC(=O)[C@H](CCC(=O)O)NC(=O)[C@H](CC(N)=O)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSC3] |

TABLE 1-continued
| Exemplary compounds |
| --- |
(SEQ ID NO: 29)
I-2
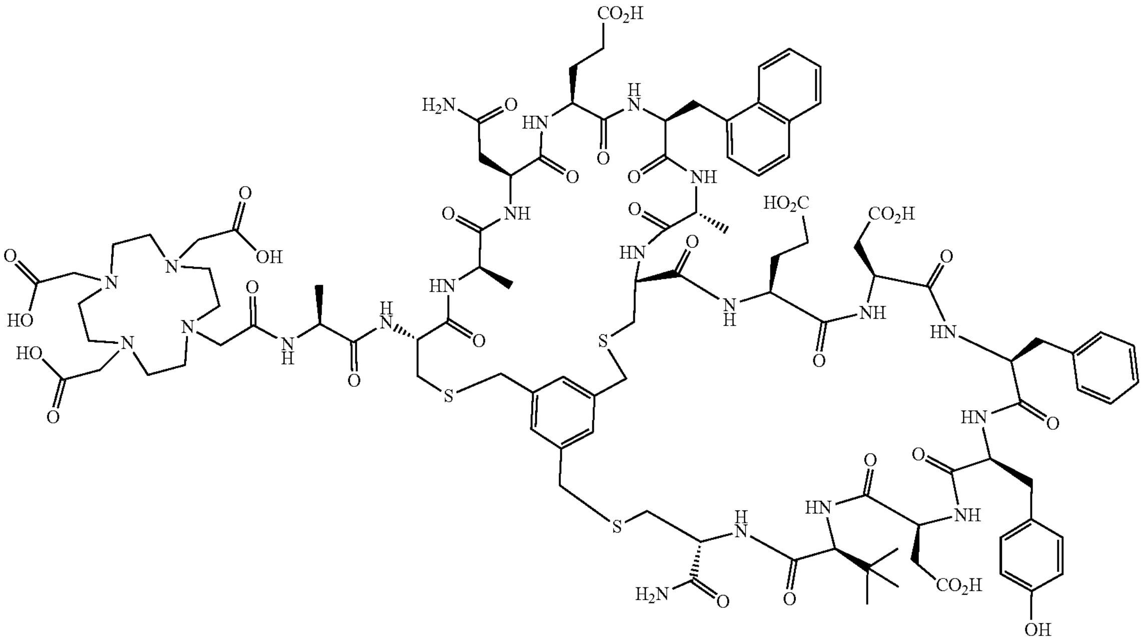 [SMILES: C[C@H](NC(=O)CN1CCN(CC(=O)O)CCN(CC(=O)O)CCN(CC(=O)O)CC1)C(=O)N[C@H]1CSCc2cc3cc(c2)CSC[C@H](NCC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSC3]
(SEQ ID NO: 30)
I-3
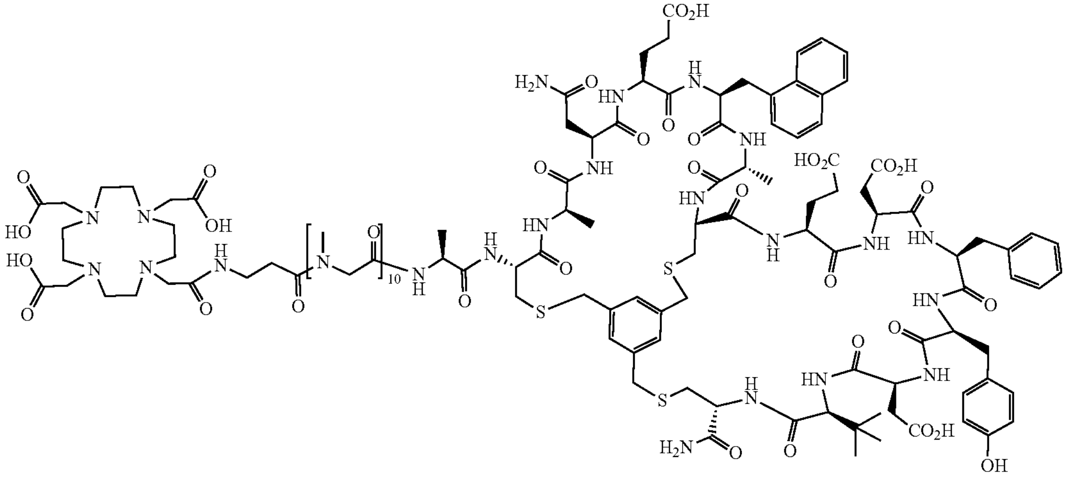

TABLE 1-continued
| Exemplary compounds |
| --- |
(SEQ ID NO: 31)
I-4
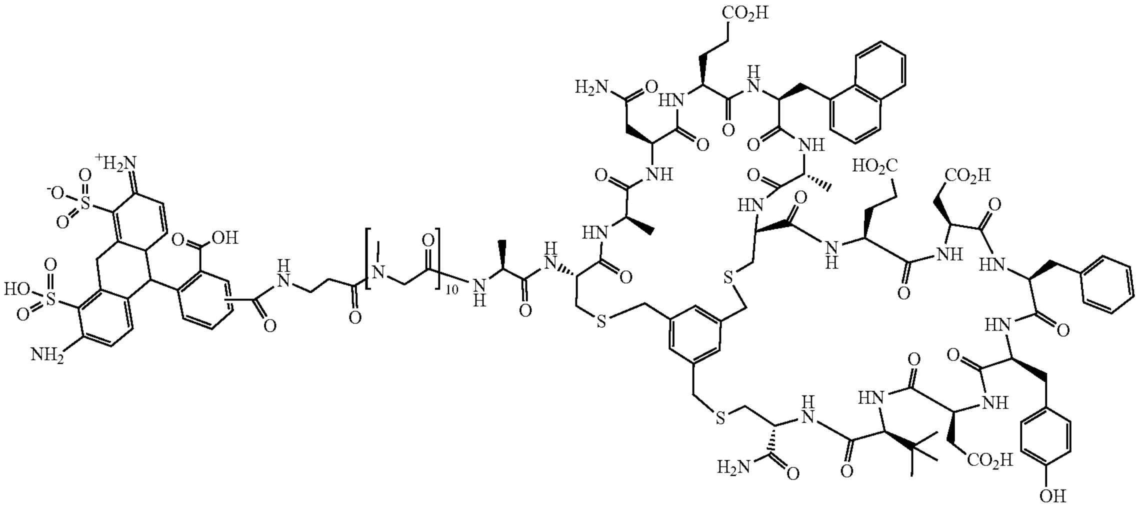
(SEQ ID NO: 32)
I-5
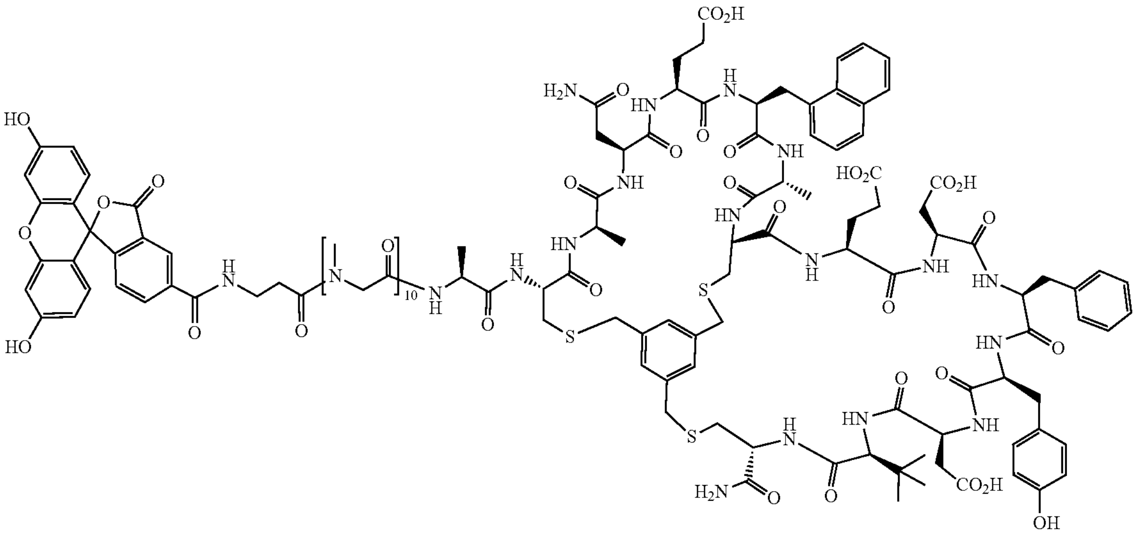

TABLE 1-continued
| Exemplary compounds |
| --- |
(SEQ ID NO: 33)
I-6
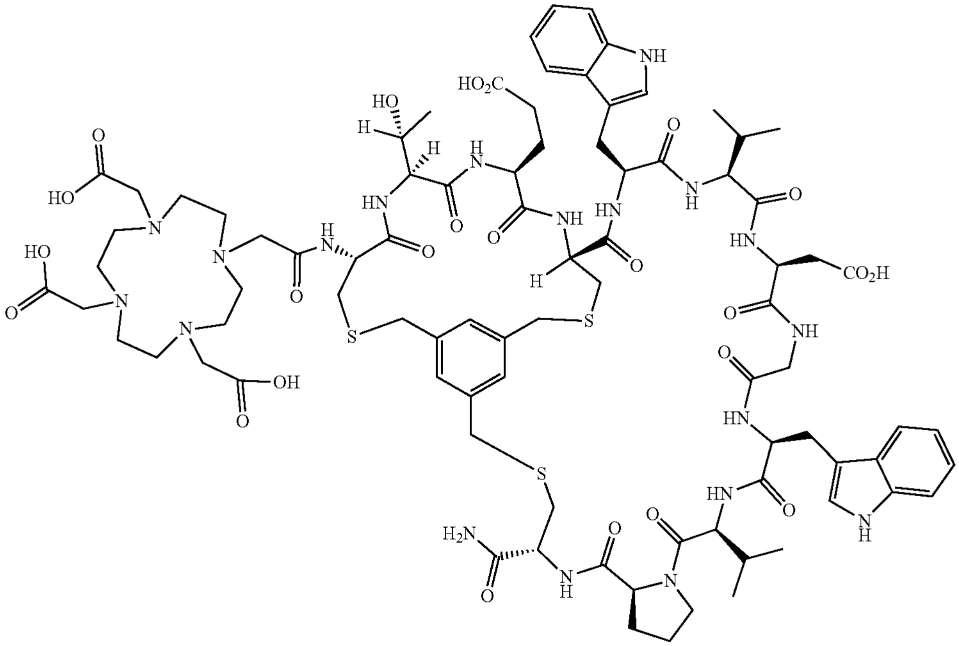 [SMILES: CC(C)[C@@H]1NC(=O)[C@H](Cc2c[nH]c3ccccc23)NC(=O)[C@@H]2CSCc3cc(cc(c3)CSC[C@H](NC(=O)CN3CCN(CC(=O)O)CCN(CC(=O)O)CCN(CC(=O)O)CC3)C(=O)N[C@@H]([C@@H](C)O)C(=O)N[C@@H](CCC(=O)O)C(=O)N2)CSC[C@@H](C(N)=O)NC(=O)[C@@H]2CCCN2C(=O)[C@H](C(C)C)NC(=O)[C@H](Cc2c[nH]c3ccccc23)NC(=O)CNC(=O)[C@H](CC(=O)O)NC1=O]
(SEQ ID NO: 34)
I-7
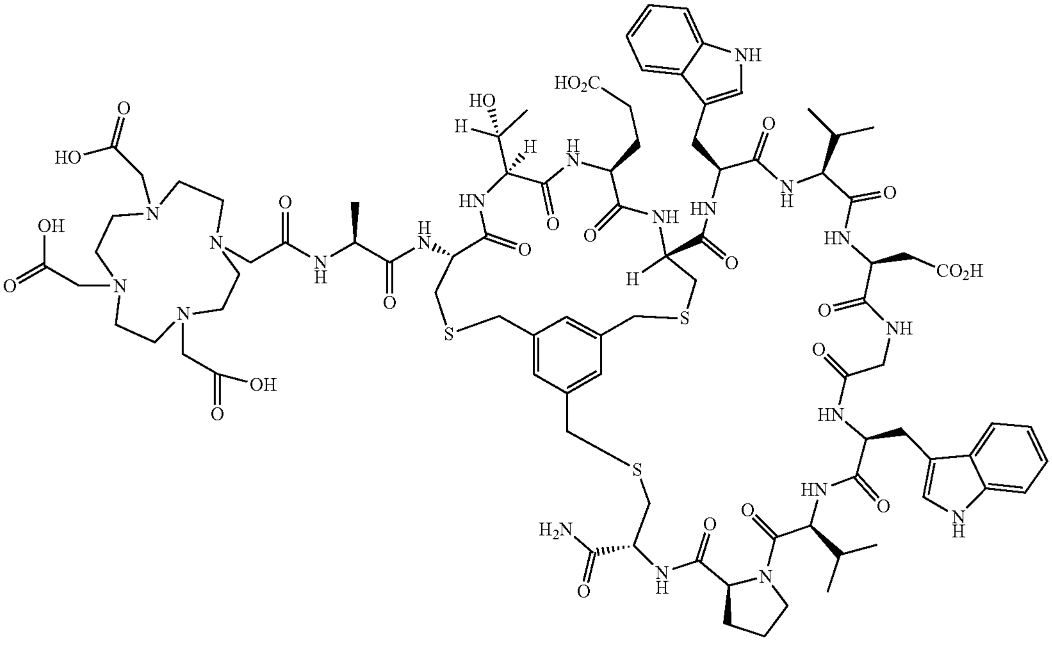 [SMILES: CC(C)[C@@H]1NC(=O)[C@H](Cc2c[nH]c3ccccc23)NC(=O)[C@@H]2CSCc3cc(cc(c3)CSC[C@H](NC(=O)[C@H](C)NC(=O)CN3CCN(CC(=O)O)CCN(CC(=O)O)CCN(CC(=O)O)CC3)C(=O)N[C@@H]([C@@H](C)O)C(=O)N[C@@H](CCC(=O)O)C(=O)N2)CSC[C@@H](C(N)=O)NC(=O)[C@@H]2CCCN2C(=O)[C@H](C(C)C)NC(=O)[C@H](Cc2c[nH]c3ccccc23)NC(=O)CNC(=O)[C@H](CC(=O)O)NC1=O]

TABLE 1-continued
| Exemplary compounds |
| --- |
(SEQ ID NO: 35)
I-8
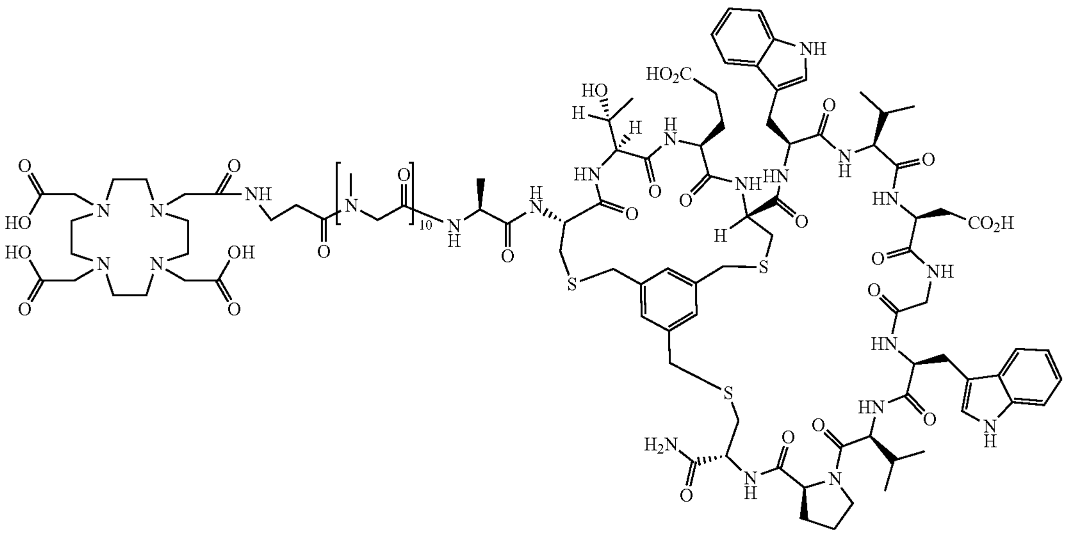
(SEQ ID NO: 36)
I-9
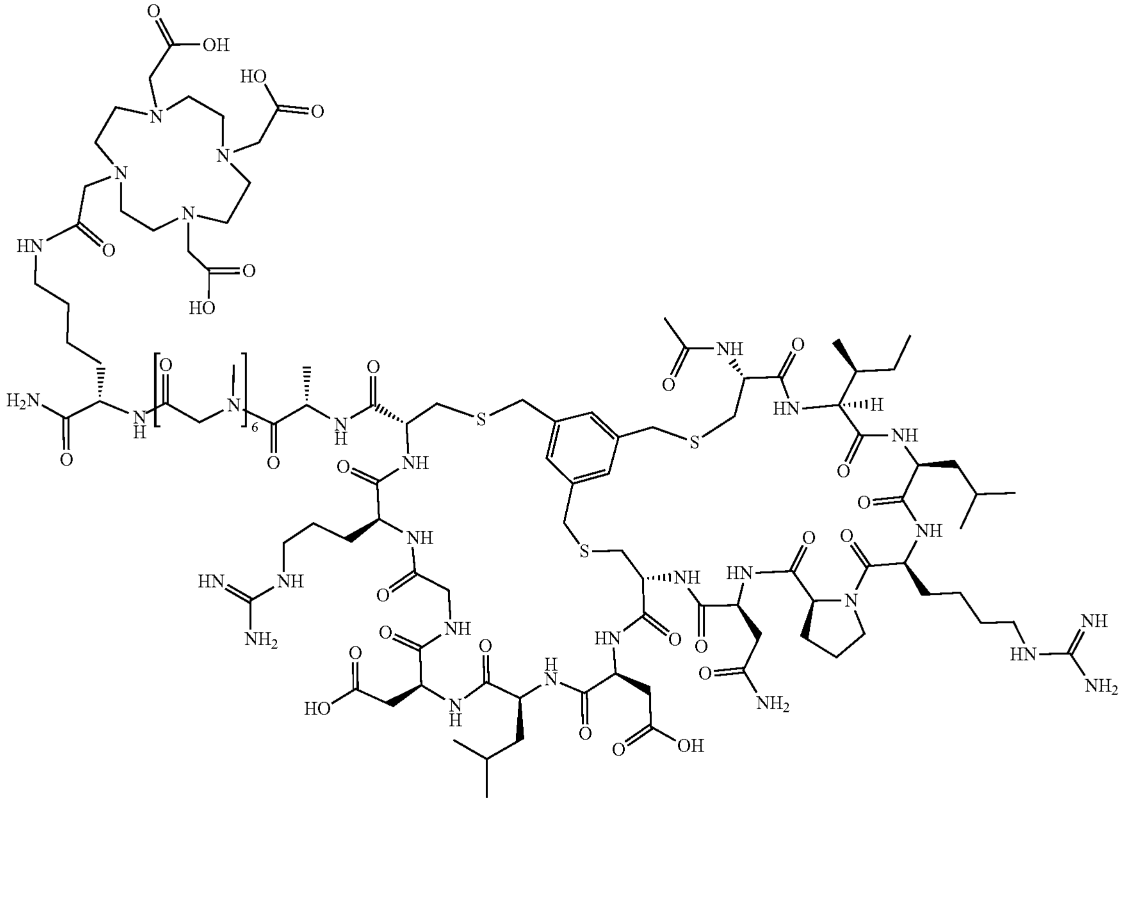

TABLE 1-continued
| Exemplary compounds |
| --- |
(SEQ ID NO: 37)
I-10
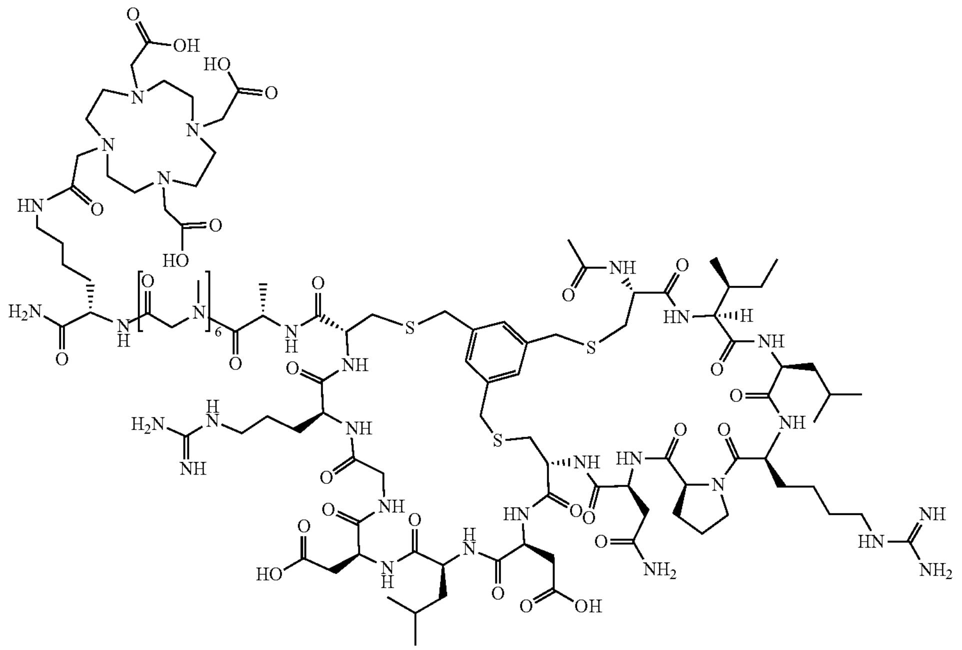
(SEQ ID NO: 38)
I-11
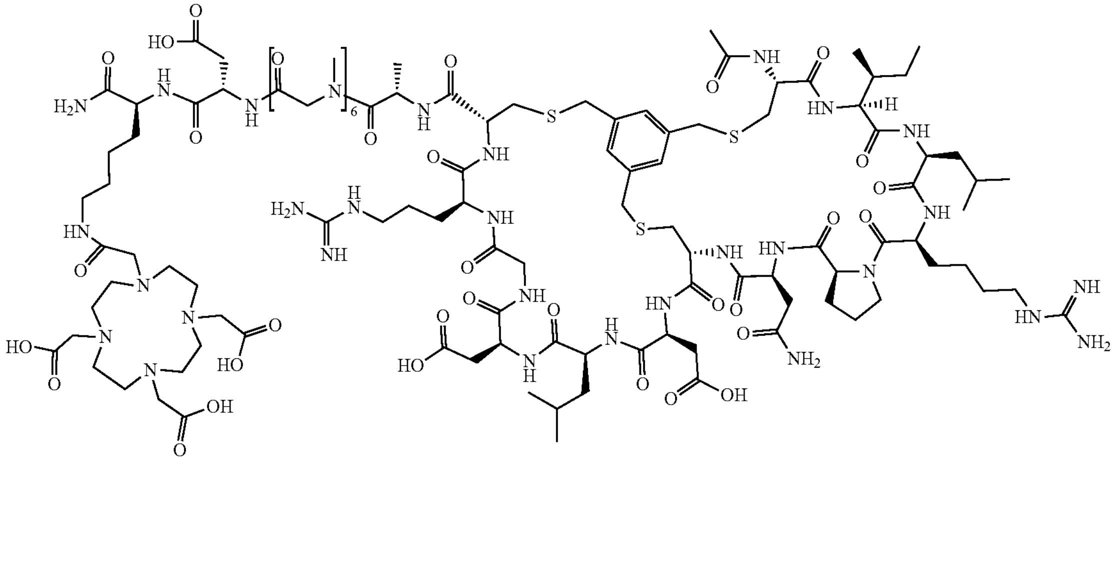

TABLE 1-continued
Exemplary compounds
(SEQ ID NO: 39)
I-12
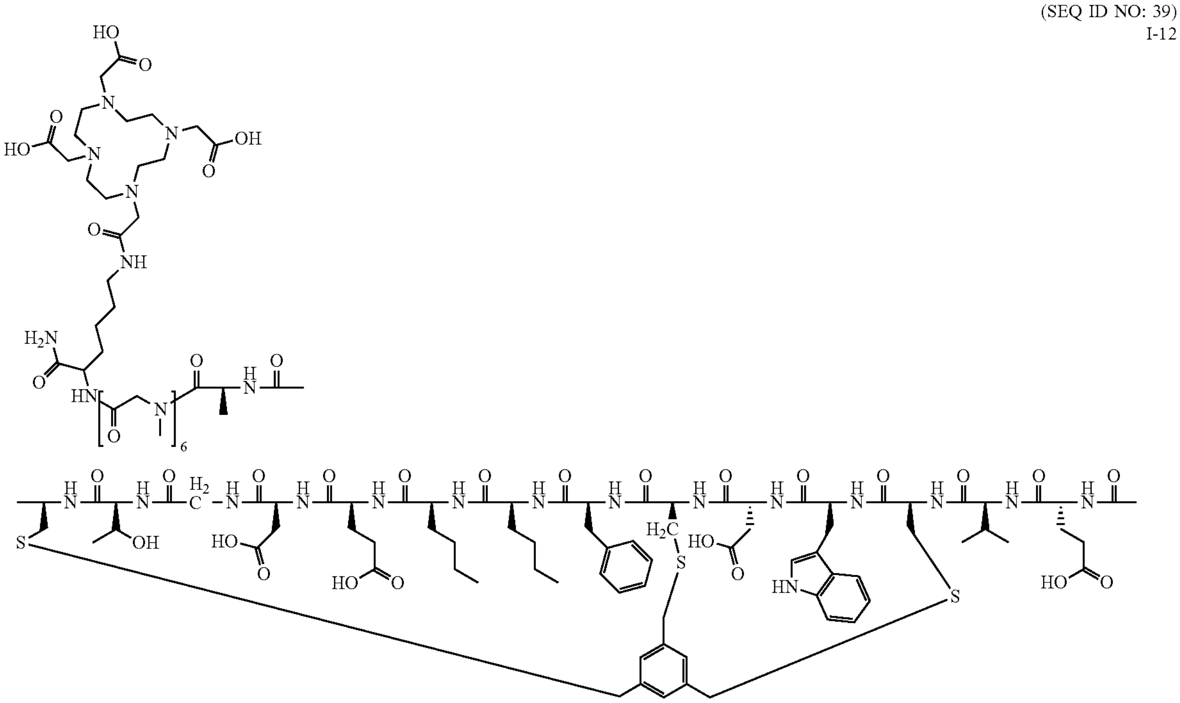
(SEQ ID NO: 40)
I-13
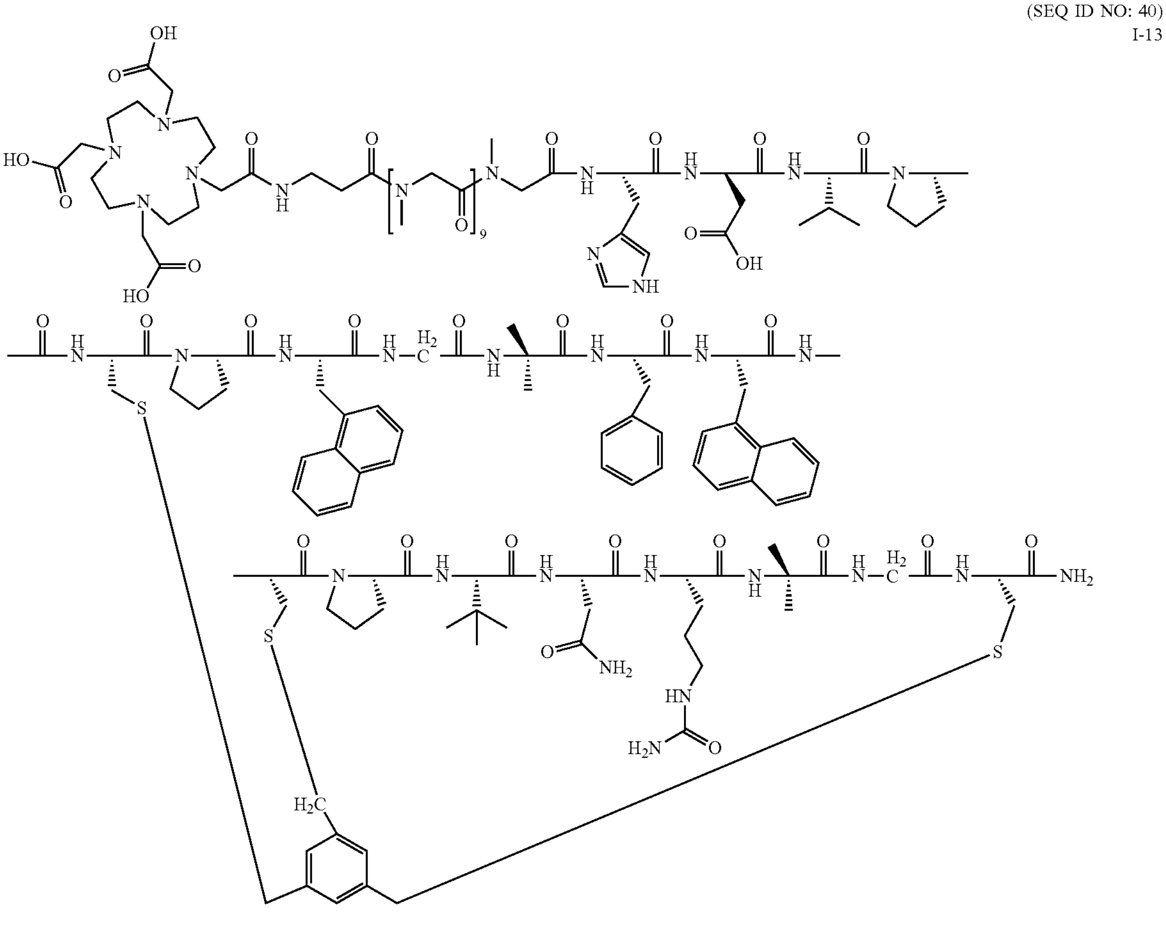

TABLE 1-continued
| Exemplary compounds |
| --- |
(SEQ ID NO: 41)
I-14
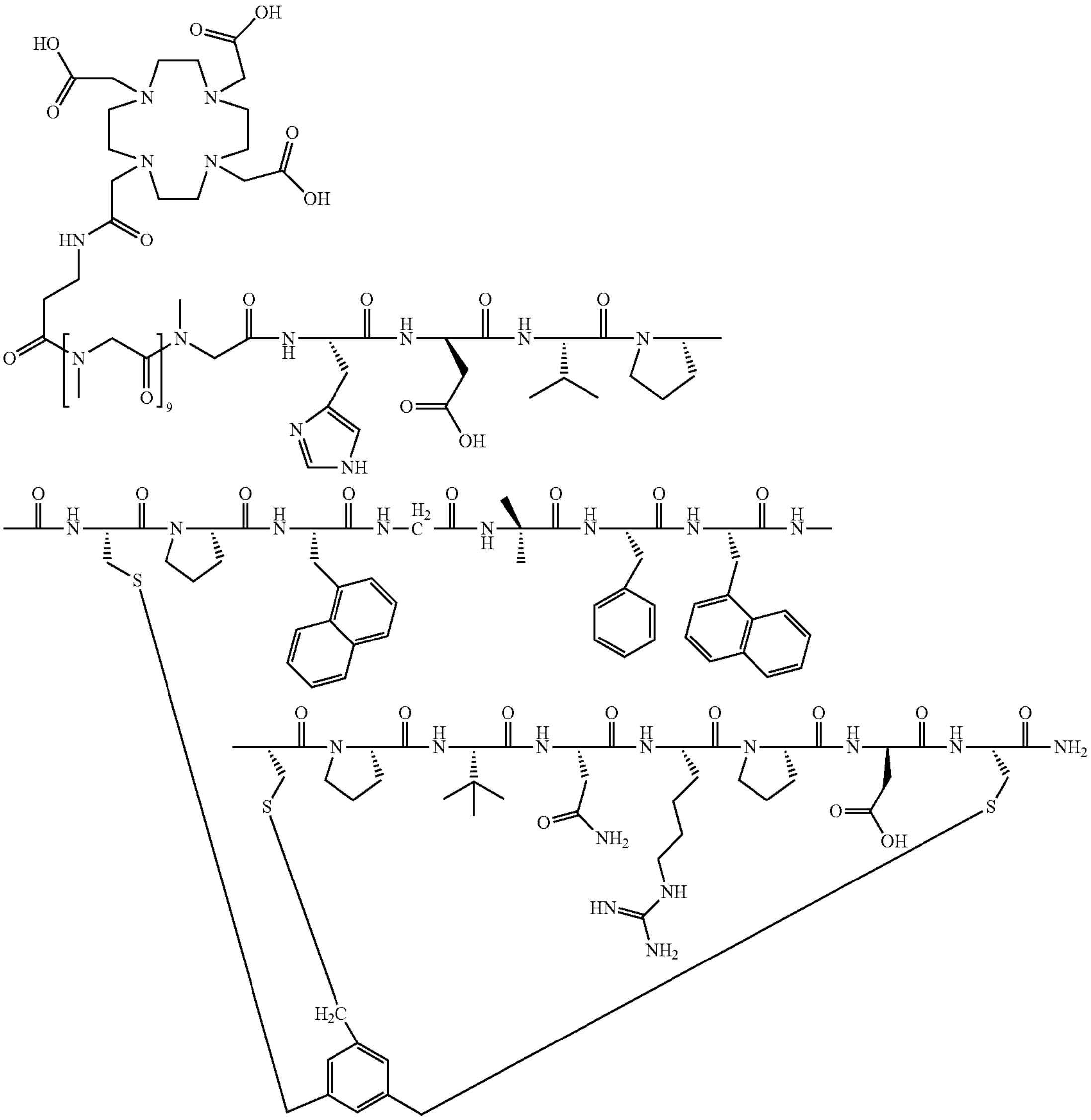

TABLE 1-continued
| Exemplary compounds |
| --- |
(SEQ ID NO: 42)
I-15
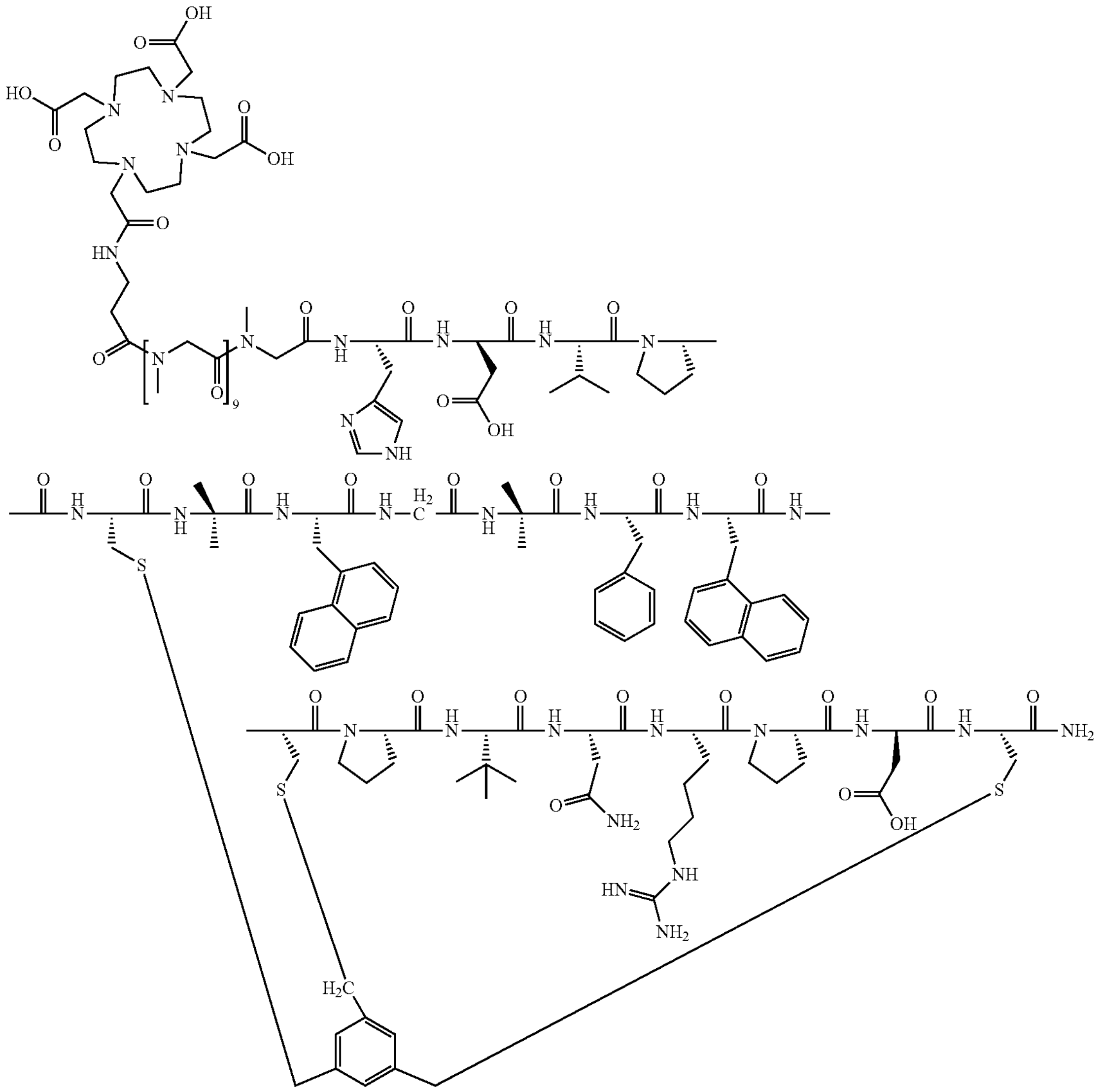

TABLE 1-continued
| Exemplary compounds |
| --- |
(SEQ ID NO: 43)
I-16
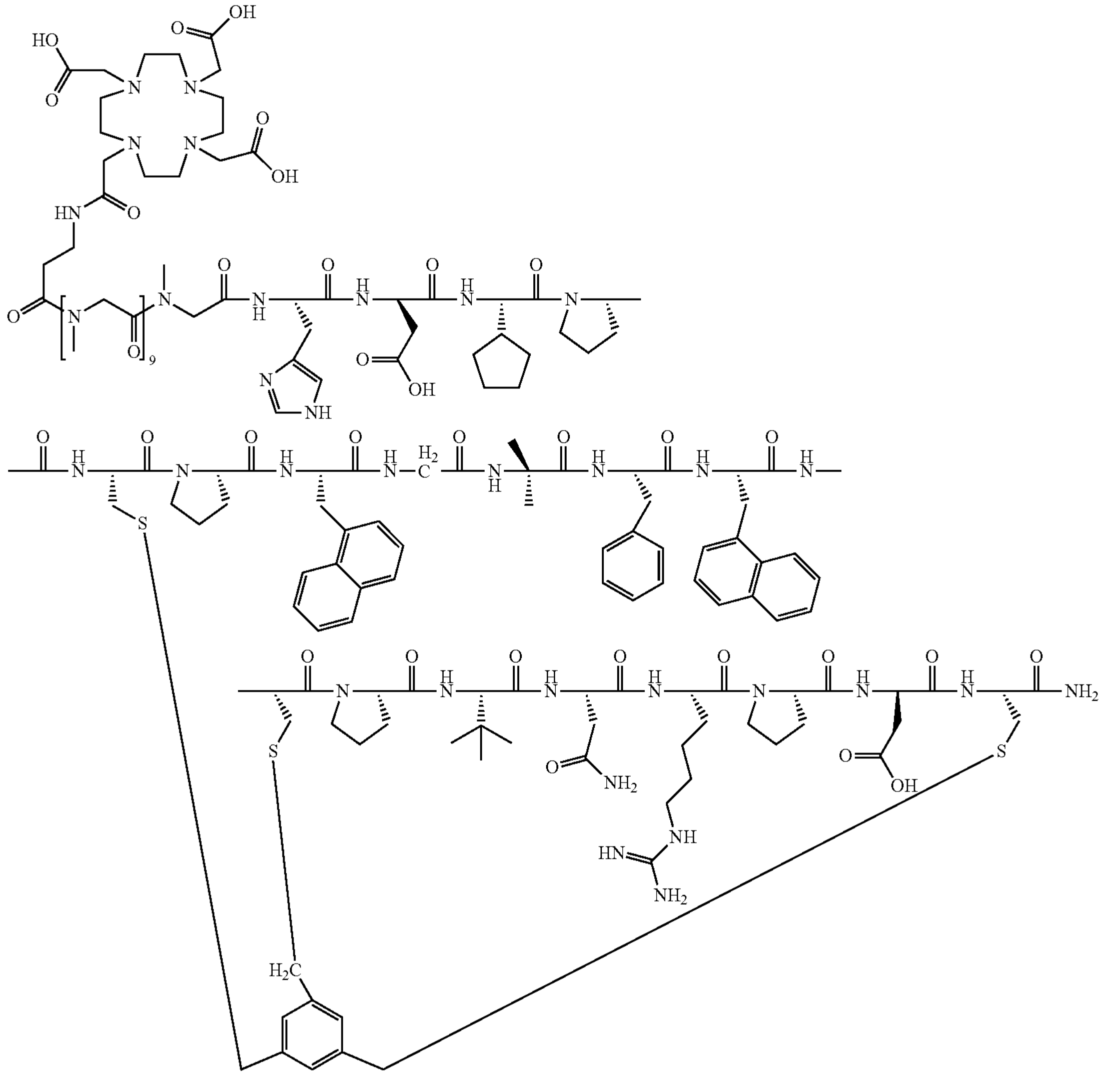

TABLE 1-continued
| Exemplary compounds |
| --- |
(SEQ ID NO: 44)
I-17
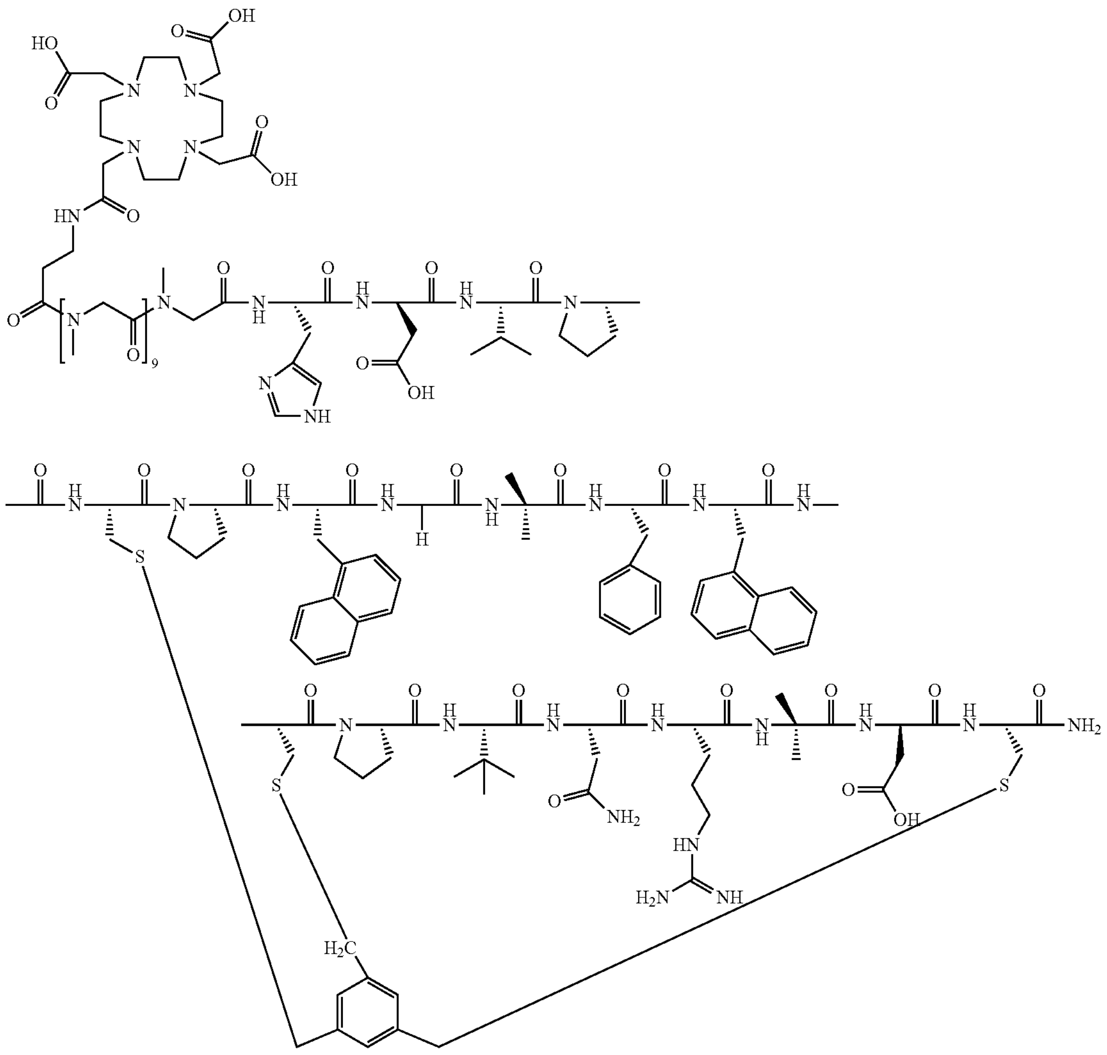

TABLE 1-continued
| Exemplary compounds |
| --- |
(SEQ ID NO: 45)
I-18
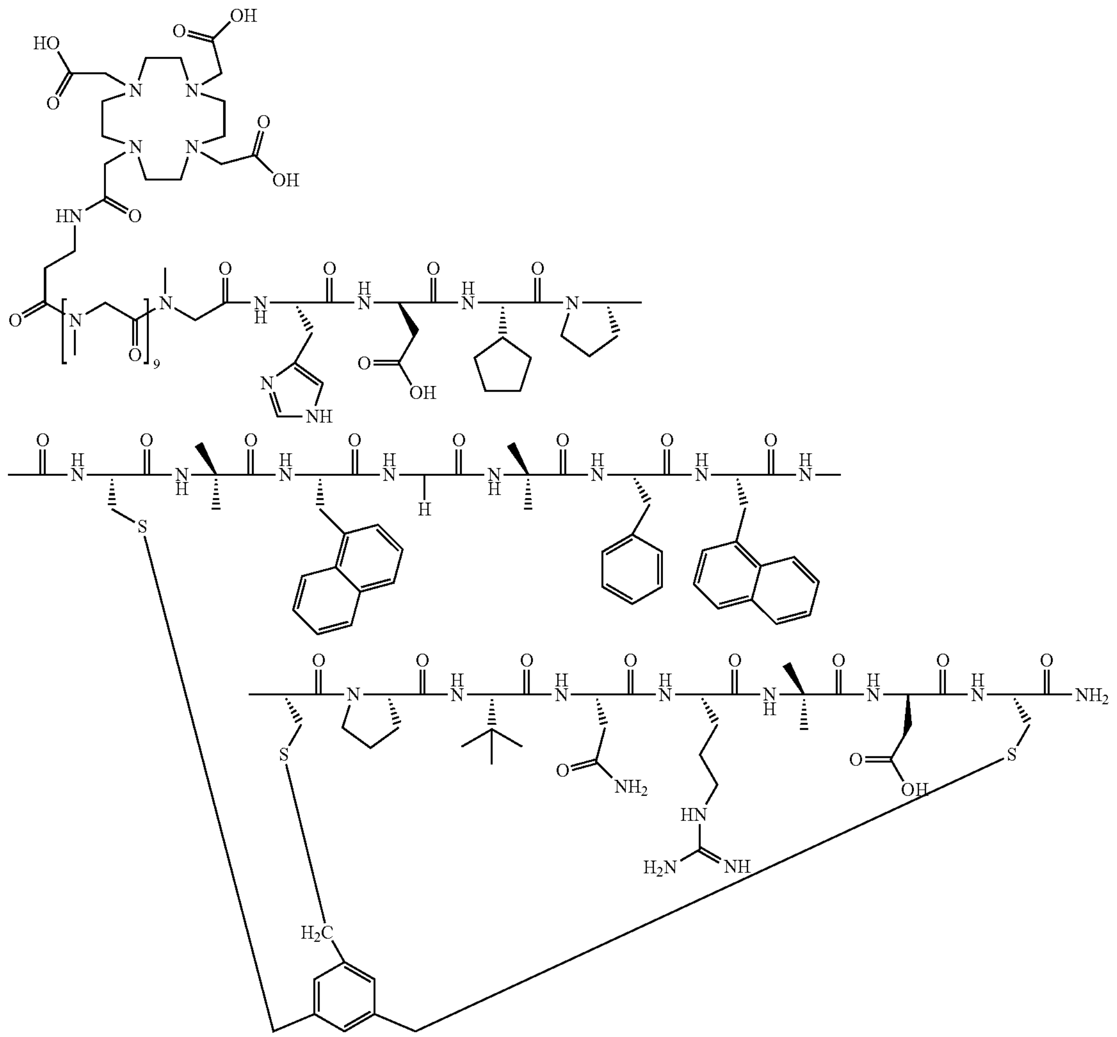

TABLE 1-continued
| Exemplary compounds |
| --- |
(SEQ ID NO: 46)
I-19
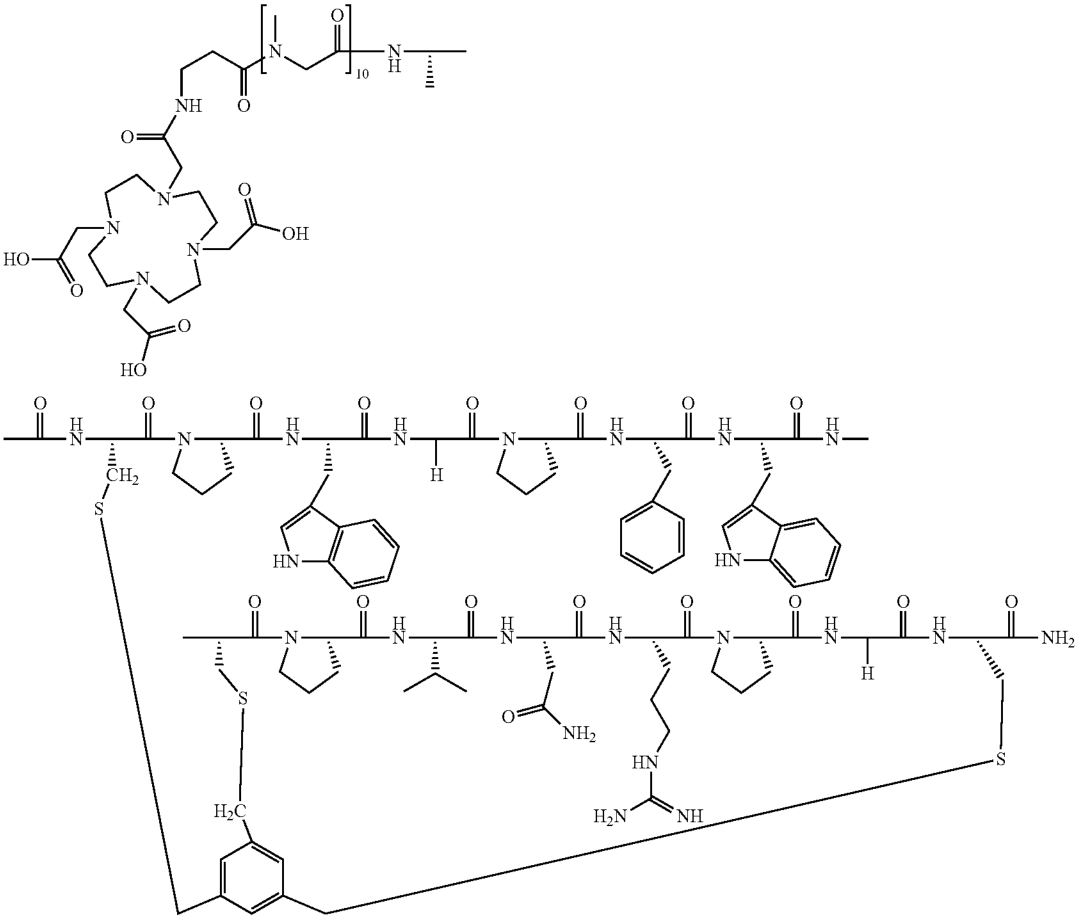

TABLE 1-continued
| Exemplary compounds |
|---|
(SEQ ID NO: 47)
I-20
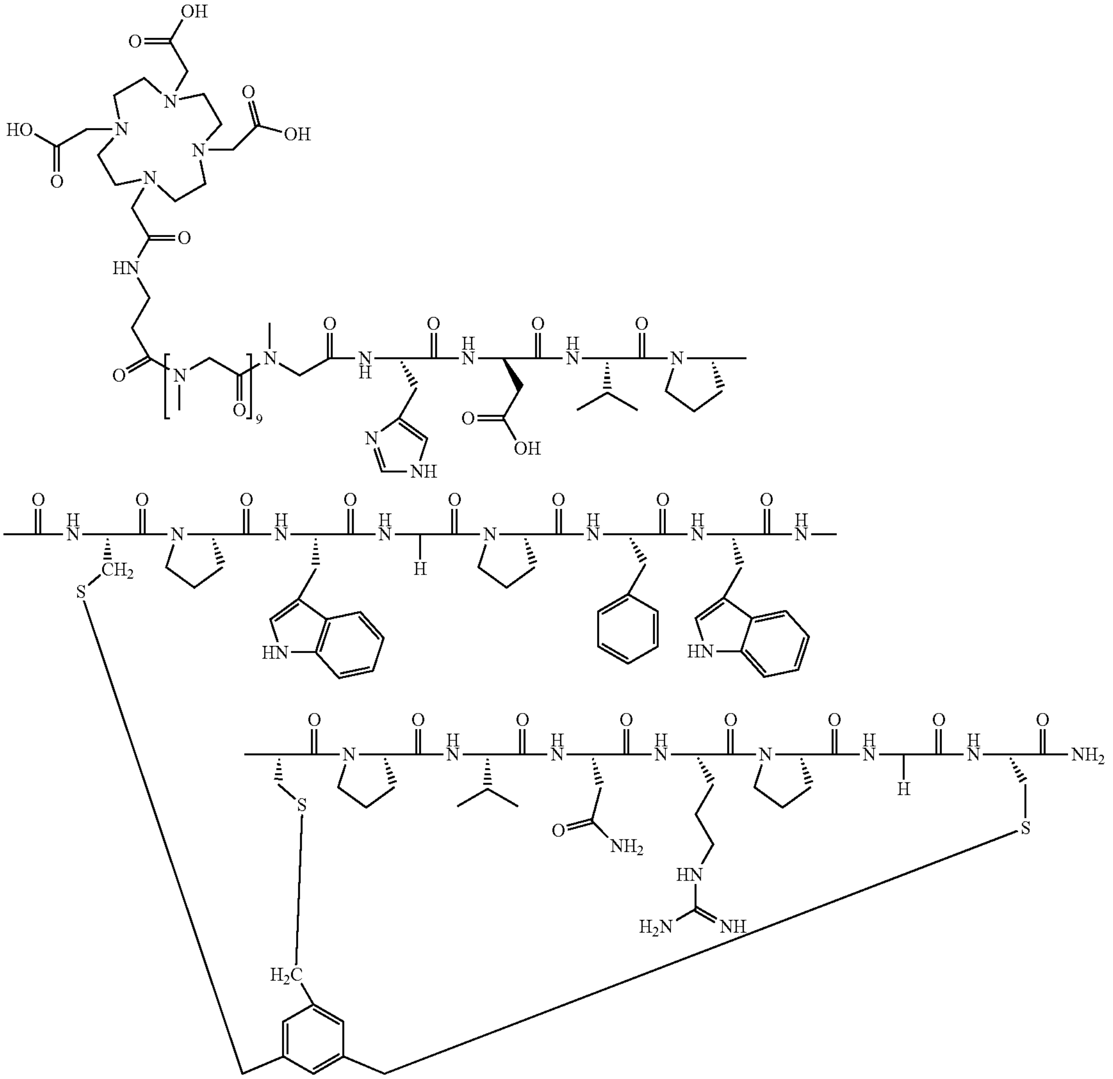

TABLE 1-continued
| Exemplary compounds |
| --- |
(SEQ ID NO: 48)
I-21
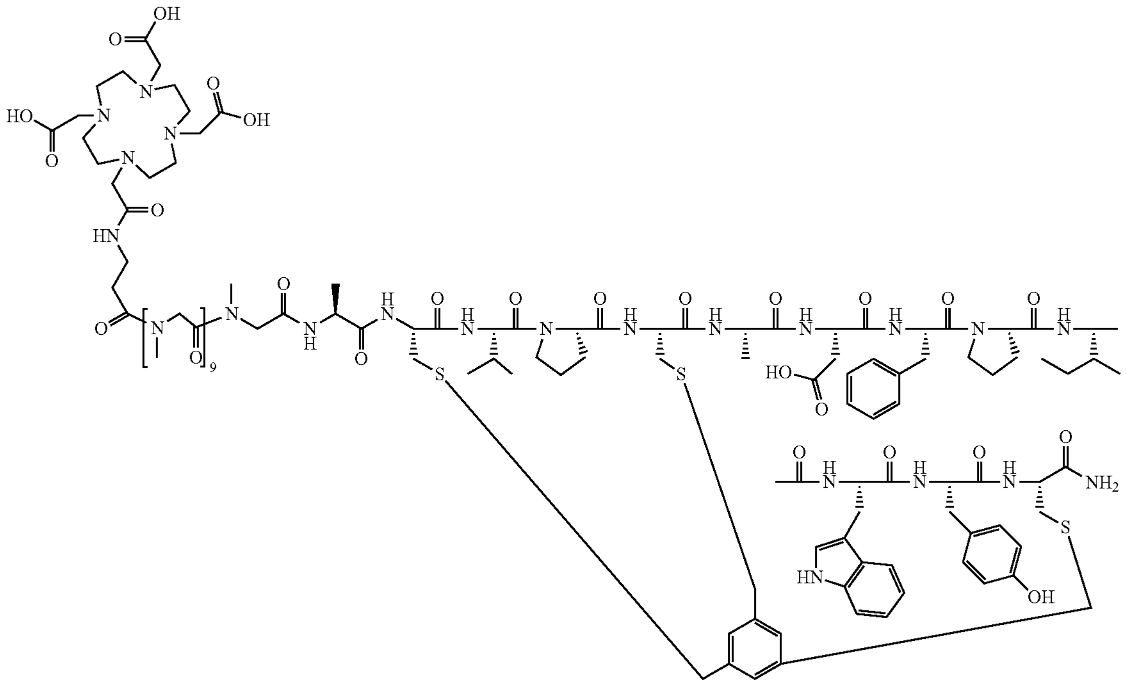
(SEQ ID NO: 49)
I-22
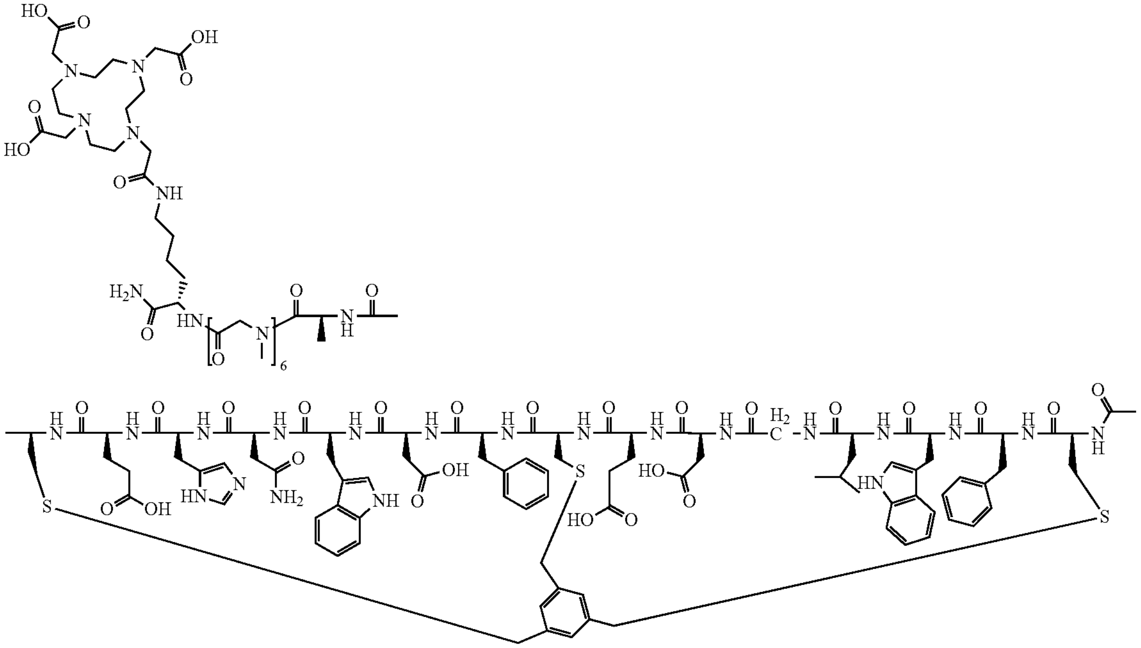

TABLE 1-continued
| Exemplary compounds |
|---|
(SEQ ID NO: 50)
I-23
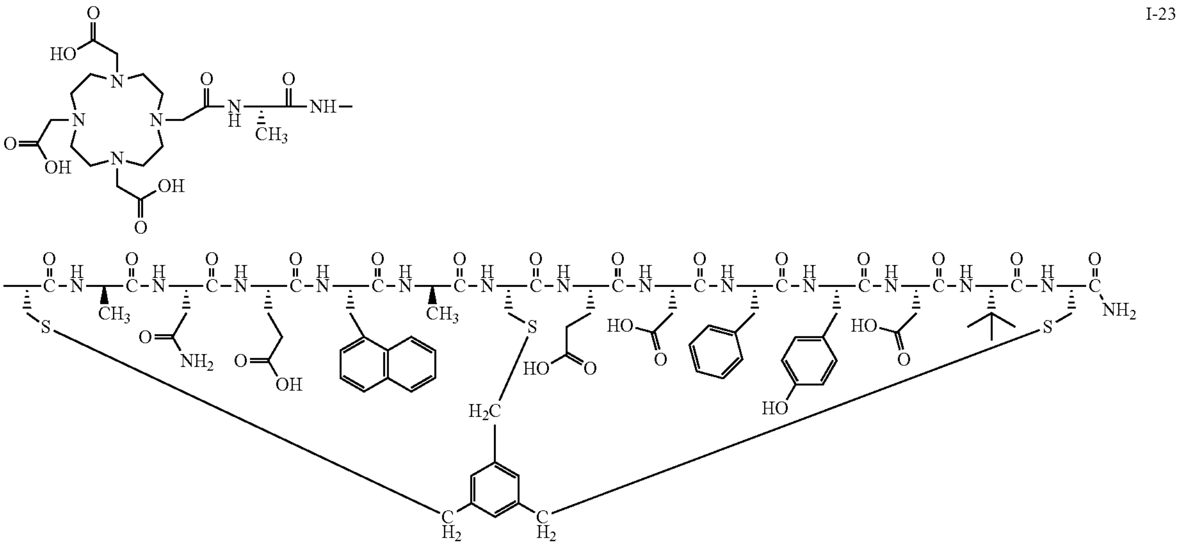
(SEQ ID NO: 51)
I-24
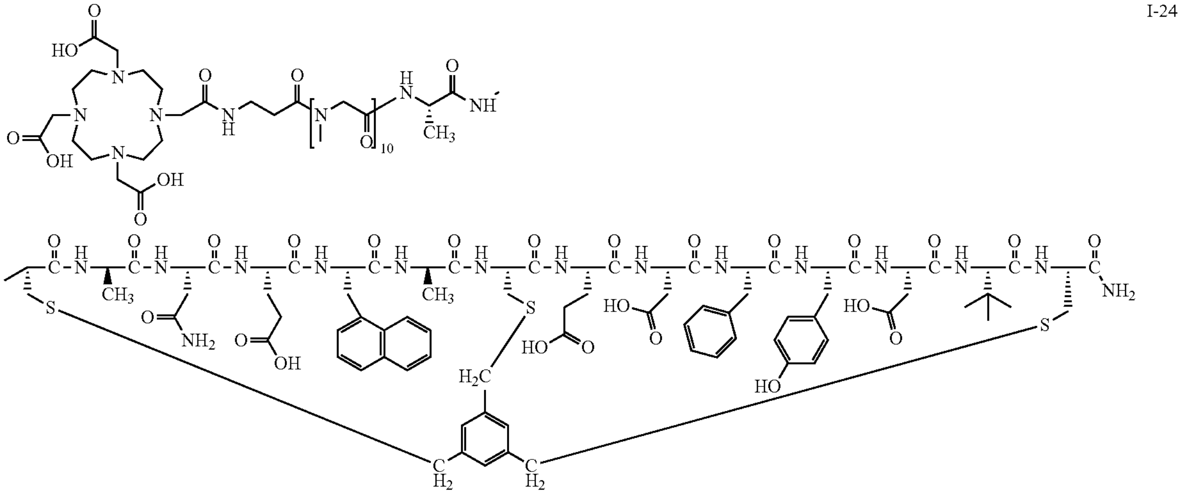

TABLE 1-continued

| Exemplary compounds |
|---|
| (SEQ ID NO: 52) I-25 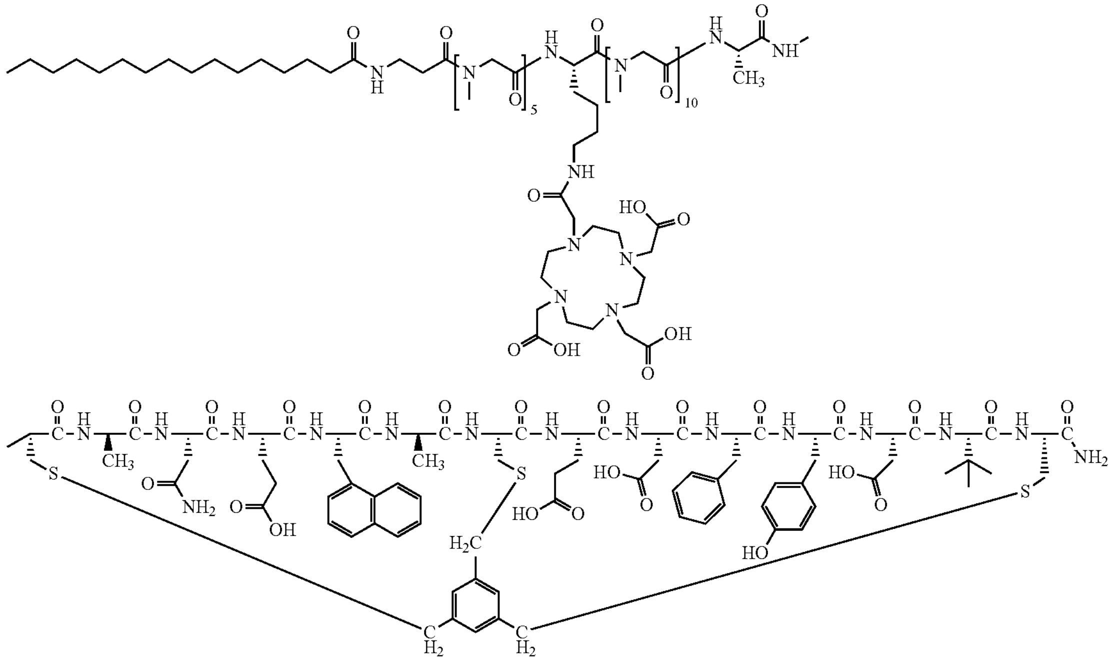 |

In some embodiments, the present invention provides a compound set forth in Table 1, above, or a pharmaceutically acceptable salt thereof.

In some embodiments, the present invention provides a compound of formula I, wherein the compound is not any of compounds described in Table 2, below.

In some embodiments, the present invention provides a compound of formula I, wherein the compound is not any of compounds from WO 2013/050617 described in Table 2, below.

In some embodiments, the present invention provides a compound of formula I, wherein the compound is not any of compounds from WO 2016/067035 described in Table 2, below.

TABLE 2

| Compounds | |
|---|---|
| Publication | Compound Code |
| WO 2013/050617 | DOTA-GSar6-(06-34-18)-NH2 |
| WO 2013/050617 | [$^{89}$Y]•DOTA-GSar6-(06-34-18)-NH2 |
| WO 2013/050617 | Palm-G-Sar6-PK15(TMB)K-(Fluo) |
| WO 2013/050617 | Palm-G-Hyp6-PK15(TMB)K-(Fluo) |
| WO 2013/050617 | Palm-G-Hyp12-UK18(TMB)K-(Fluo) |
| WO 2016/067035 | 17-69-07-N144 |
| WO 2016/067035 | 17-69-07-N147 |
| WO 2016/067035 | 17-69-07-N246 |
| WO 2016/067035 | 17-69-07-N248 |

In some embodiments, the present invention is not a compound set forth in Table 2, above.

Exemplary compounds of the invention are set forth in Table 3, below.

TABLE 3
| Exemplary Compounds |
| --- |
(SEQ ID NO: 53)
I-26
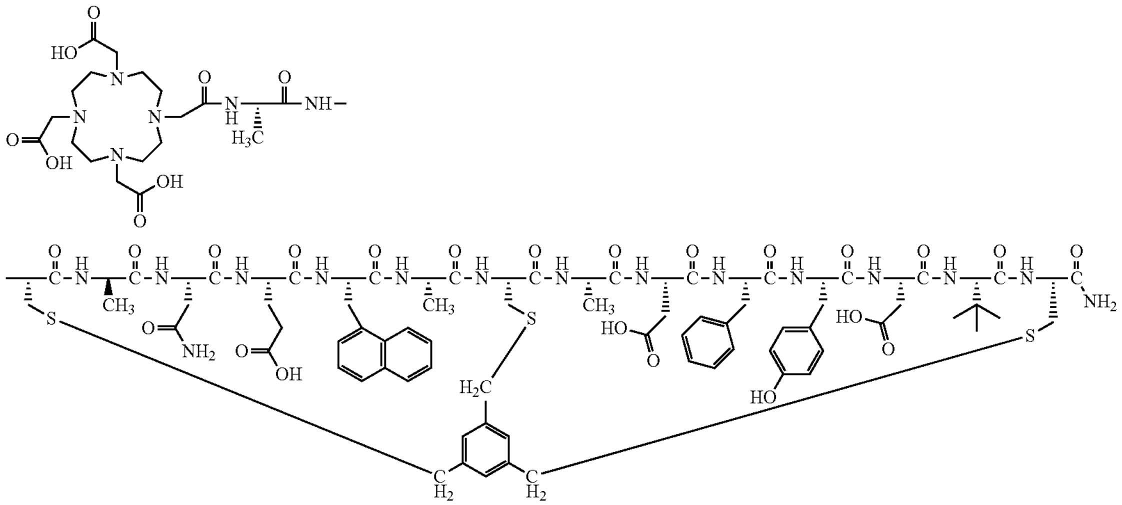
(SEQ ID NO: 54)
I-27
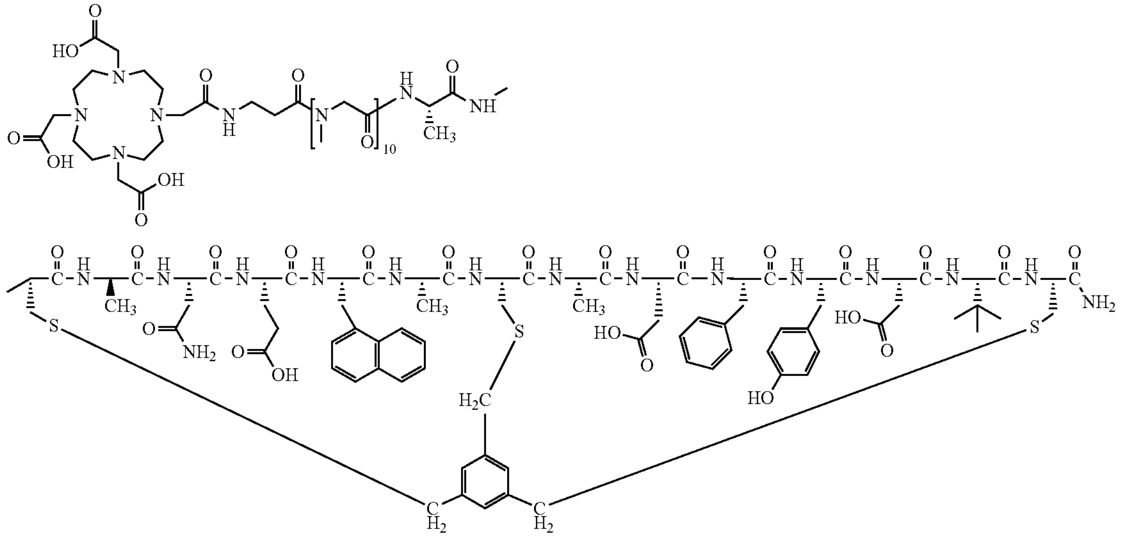

TABLE 3-continued

Exemplary Compounds (SEQ ID NO: 27)
I-28

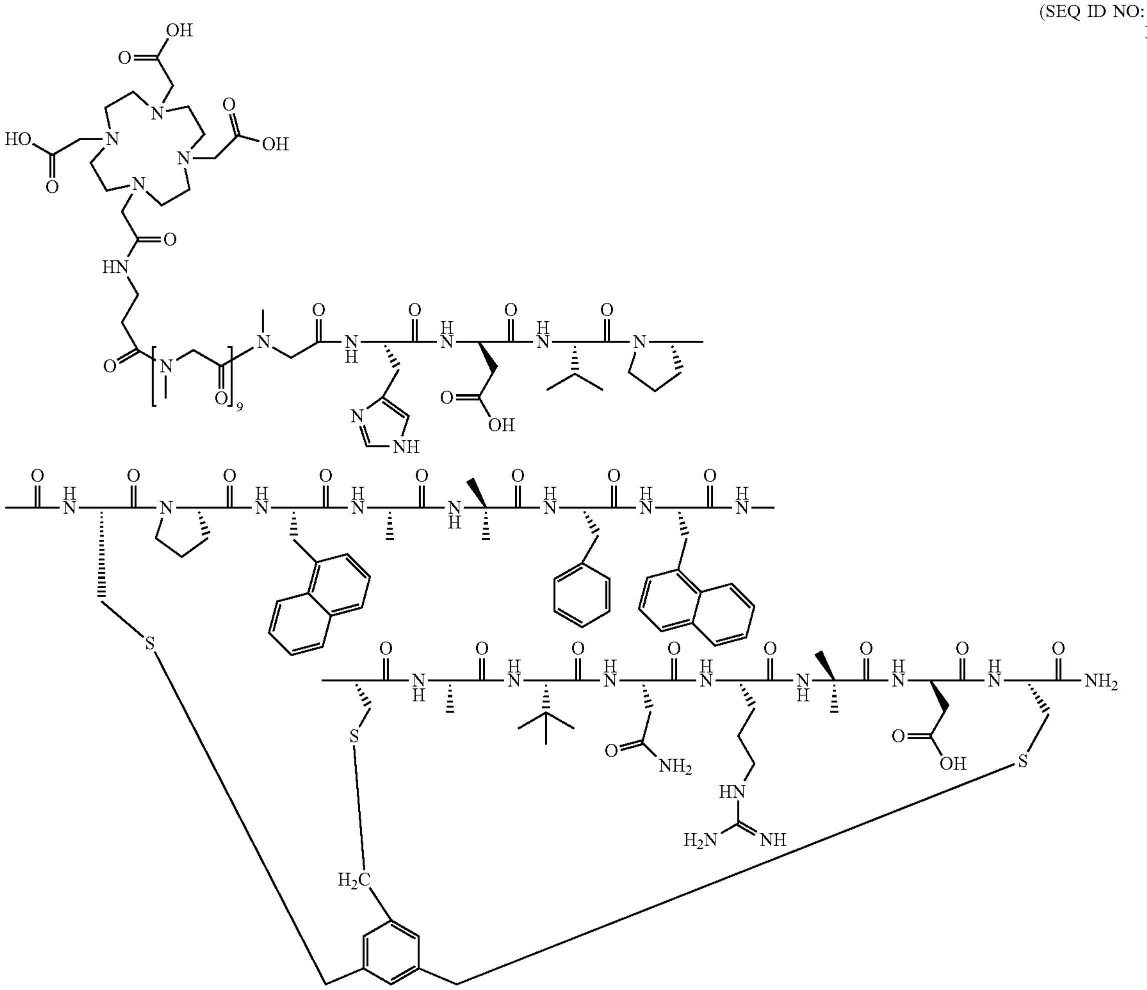

In some embodiments, the present invention provides a compound set forth in Table 3, above, or a pharmaceutically acceptable salt thereof.

The compounds of Table 3 are useful as negative controls of the compounds of Table 1. For example, I-26 ($K_d$ to MT1-MMP of >5,000 nM) serves as a negative control of I-23 ($K_d$ to MT1-MMP of 0.52±0.24 nM) as I-26 is an I-23 analog that has alanine residues flanking the central cysteine residue, thereby rendering it inactive at MT1-MMP. I-27 ($K_d$ to MT1-MMP of >5,000 nM) serves as a negative control of I-24 ($K_d$ to MT1-MMP of 1.37±0.53 nM) as I-27 is an I-24 analog that has alanine residues flanking the central cysteine residue, thereby rendering it inactive at MT1-MMP. Such control compounds can be useful, for example, in biodistribution studies of active MT1-MMP binders.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

The compounds of this invention may be prepared by treating a peptide with a molecular scaffold reagent. The molecular scaffold reagent comprises the Scaffold and reactive functionality such as leaving groups ("LG") or Michael acceptors ("MA"), that allow the peptide to form covalent bonds with the molecular scaffold via displacement of the leaving group or addition to the Michael acceptor group followed by subsequent protonation of the addition complex.

Compounds of the present invention are formed by treating peptides with various molecular scaffold reagents to form a Bicycle intermediate which is then coupled to a Detectable Moiety using standard amide formation methodology.

One such peptide is peptide 1 (17-69-07-N241), which has the following amino acid sequence:

(SEQ ID NO: 1)
βAla-Sar10-A-C(D-Ala)NE(1Nal)(D-Ala)CEDFYD(tBuGLy)C

The bicyclic peptide formed by treating 17-69-07-N241 with the molecular scaffold reagent 1,3,5-tris(bromomethyl) benzene ("TBMB") as described in WO 2016/067035 affords an MT1-MMP binder with a $K_d$ of 1.2 nM.

Another such peptide is peptide 2, which contains only the amino acid residues corresponding to the Bicyclic portion of peptide 1 and has the following amino acid sequence:

(SEQ ID NO: 2)
C(D-Ala)NE(1Nal)(D-Ala)CEDFYD(tBuGLy)C

Another such peptide is peptide 3, which has the following amino acid sequence:

(SEQ ID NO: 3)
βAla-Sar10-A-CTECWVDGWVPC.

The bicyclic peptide formed by treating 3 with the molecular scaffold reagent 1,3,5-tris(bromomethyl)benzene ("TBMB") as described in the UK provisional application P2120 affords a CAIX binder with a $K_d$ of 10 nM.

Another such peptide is peptide 4, which contains only the amino acid residues corresponding to the Bicyclic portion of peptide 3 and has the following amino acid sequence:

(SEQ ID NO: 4)
CTECWVDGWVPC.

Another such peptide is peptide 5, which has the following amino acid sequence:

(SEQ ID NO: 5)
Ac-CIL(HArg)PNCDLDGRCA-Sar6-(D-K).

The bicyclic peptide formed by treating 5 with the molecular scaffold reagent 1,3,5-tris(bromomethyl)benzene ("TBMB") as described in the UK provisional application P2122 affords a αvβ3_binder with a $K_i$ of 15 nM.

Another such peptide is peptide 6, which contains a subset of the amino acid residues corresponding to peptide 5 including the Bicyclic portion, the acetyl residue at the N-terminus and an Alanine C-terminal extension and has the following amino acid sequence:

(SEQ ID NO: 6)
Ac-CIL(HArg)PNCDLDGRCA.

In the Schemes below, where a particular Michael acceptor ("MA"), leaving group ("LG"), or transformation condition is depicted, one of ordinary skill in the art will appreciate that other Michael acceptors, leaving groups, and transformation conditions are also suitable and are contemplated. Such acceptors, groups and transformations are described in detail in *March's Advanced Organic Chemistry: Reactions, Mechanisms, and Structure*, M. B. Smith and J. March, 5th Edition, John Wiley & Sons, 2001, *Comprehensive Organic Transformations*, R. C. Larock, 2nd Edition, John Wiley & Sons, 1999, and *Protecting Groups in Organic Synthesis*, T. W. Greene and P. G. M. Wuts, 3rd edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "activated ester" (AE) includes, but is not limited to, acyl halides (e.g. acyl fluoride, acyl chloride, acyl bromide, acyl iodide), N-succinimidyl esters, uronium esters (e.g. 1-hydroxy-7azabenzotriazole, —OAt), and the like.

In certain embodiments, compounds of the present invention of formula I are generally prepared according to Scheme I set forth below:

Scheme I

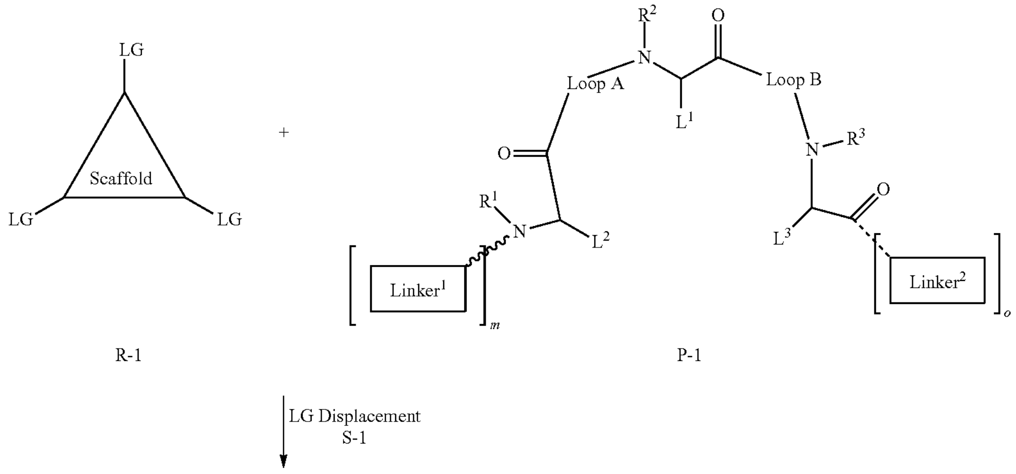

R-1 P-1

-continued

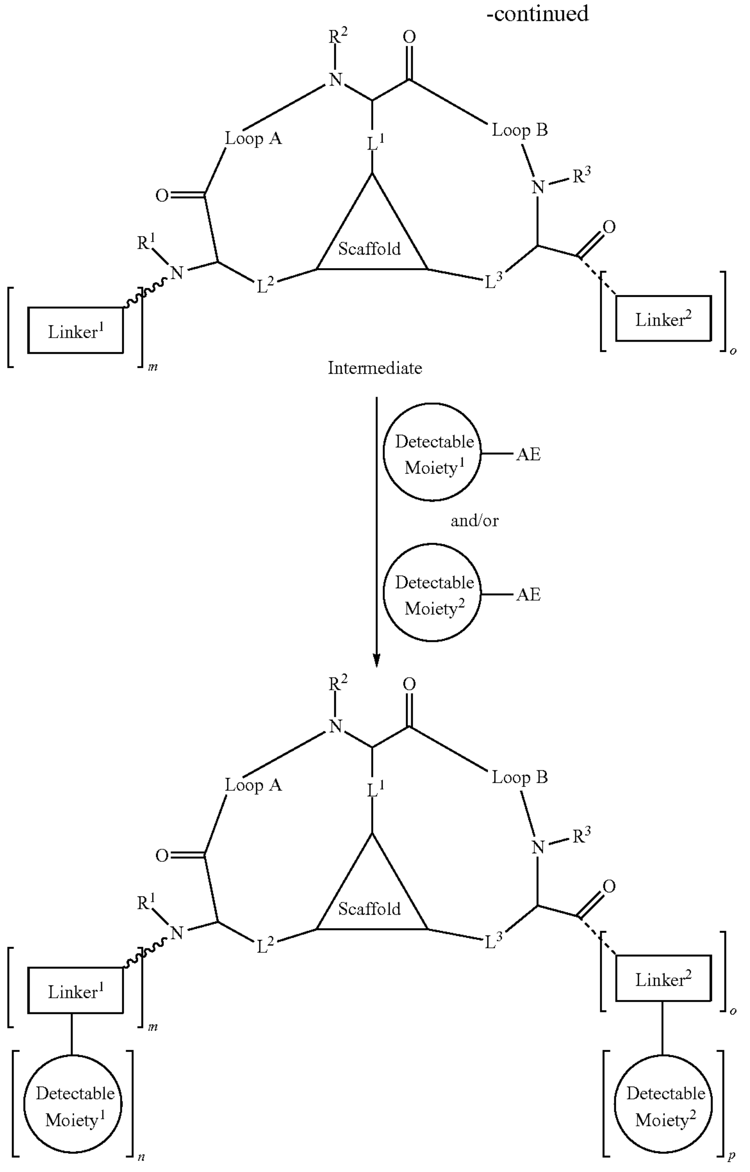

I

In Scheme I above, each of LG, $L^1$, $L^2$, $L^3$, Scaffold, $Linker^1$, $Linker^2$, $R^1$, $R^2$, $R^3$, Loop A, Loop B, Detectable $Moiety^1$, Detectable $Moiety^2$, AE, m, n, o and p is as defined above and below and in classes and subclasses as described herein.

In one aspect, the present invention provides methods for preparing compounds of formula I according to the steps depicted in Scheme I, above. In some embodiments, step S-1 comprises contacting the scaffold reagent R-1 with a peptide P-1 to displace the leaving group LG, thereby forming an intermediate which is further treated with an activated ester of a Detectable Moiety to afford a compound of formula I. In some embodiments, LG is a halogen. In some embodiments, LG is chlorine. In some embodiments, LG is a sulfonate. In some embodiments, AE is a N-succinimidyl ester. In some embodiments, a base is added to promote the displacement. In some embodiments, the base is ammonium carbonate. In some embodiments, the base is an amine. In some embodiments, the base is N,N-diisopropylethylamine.

In certain embodiments, step S-1 comprises contacting a compound of formula P-1 with a compound of the formula

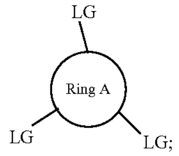

wherein

LG and Ring A are defined above and below and in classes and subclasses as described herein.

In some embodiments the reaction further comprises a solvent. In some embodiments the solvent is acetonitrile. In some embodiments the reaction further comprises a solvent.

In some embodiments the solvent is DMSO. In some embodiments the solvent is a mixture of water and acetonitrile.

In some embodiments, LG is a halogen. In some embodiments, LG is chlorine. In some embodiments, LG is a sulfonate. In some embodiments, a catalyst is added to promote the displacement. In some embodiments, the catalyst is generated from $3^{rd}$ Generation XPhos precatalyst. In some embodiments, the solvent is tert-butanol. In some embodiments, the solvent is a mixture of water and tert-butanol.

In certain embodiments, compounds of the present invention of formula I are generally prepared according to Scheme II set forth below:

Scheme II

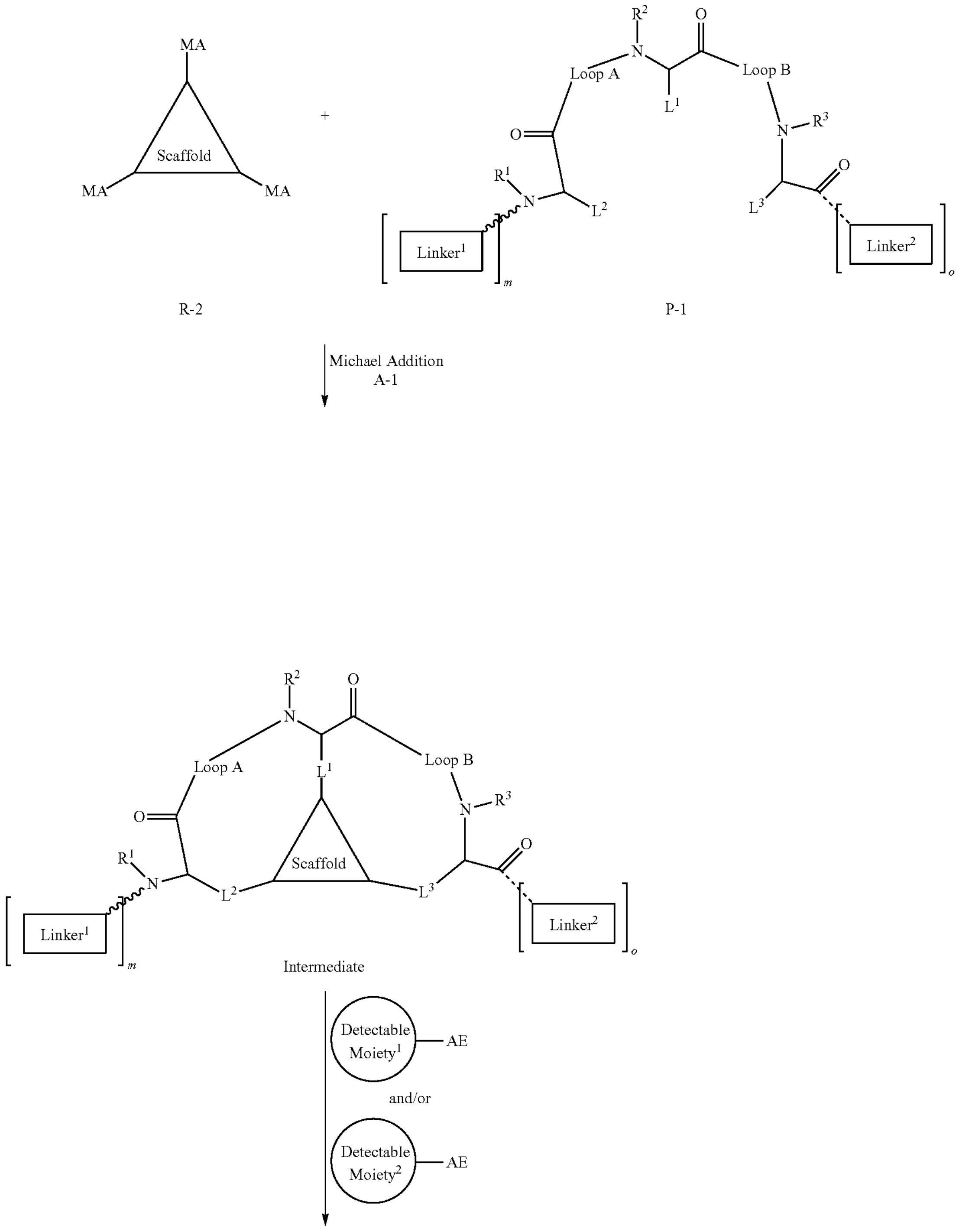

R-2

P-1

Intermediate

-continued

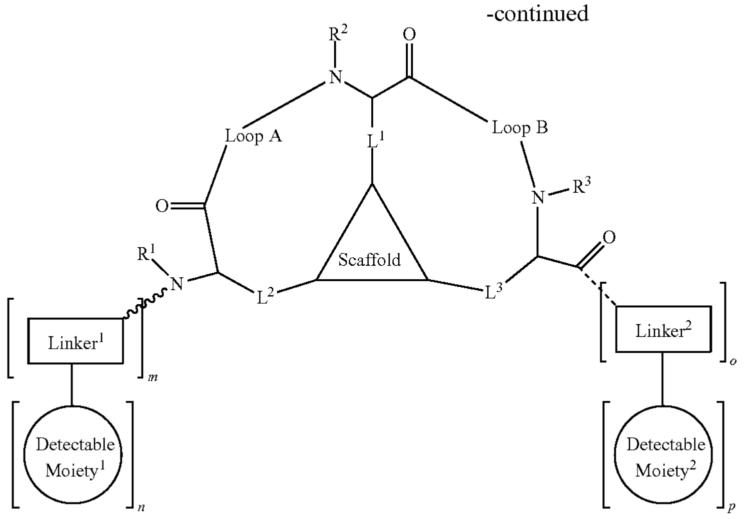

I

In Scheme II above, each of MA, $L^1$, $L^2$, $L^3$, Scaffold, $Linker^1$, $Linker^2$, $R^1$, $R^2$, $R^3$, Loop A, Loop B, Detectable $Moiety^1$, Detectable $Moiety^2$, AE, m, n, o, and p is as defined above and below and in classes and subclasses as described herein.

In one aspect, the present invention provides methods for preparing compounds of formula I according to the steps depicted in Scheme II, above. In some embodiments, step A-1 comprises contacting the scaffold reagent R-2 with a peptide P-1 to affect a Michael addition to MA, thereby forming a an intermediate which is further treated with an activated ester of a Detectable Moiety to afford a compound of formula I. In some embodiments, MA is an α,β-unsaturated amide. In some embodiments, MA is an α,β-unsaturated ketone. In some embodiments, MA is an α,β-unsaturated ester. In some embodiments, MA is an α,β-unsaturated sulfone. In some embodiments, MA is an α,β-unsaturated nitrile. In some embodiments, a base is added to promote the Michael addition. In some embodiments, AE is a N-succinimidyl ester. In some embodiments, the base is ammonium carbonate. In some embodiments, the base is an amine. In some embodiments, the base is N,N-diisopropylethylamine.

In certain embodiments, step A-1 comprises contacting a compound of formula P-1 with a compound of the formula

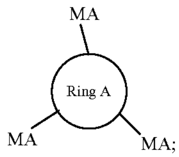

wherein

MA and Ring A are defined above and below and in classes and subclasses as described herein.

In some embodiments the reaction further comprises a solvent. In some embodiments the solvent is acetonitrile. In some embodiments the reaction further comprises a solvent. In some embodiments the solvent is DMSO. In some embodiments the solvent is a mixture of water and acetonitrile.

In some embodiments, MA is an α,β-unsaturated amide. In some embodiments, MA is an α,β-unsaturated ketone. In some embodiments, MA is an α,β-unsaturated ester. In some embodiments, MA is an α,β-unsaturated sulfone. In some embodiments, MA is an α,β-unsaturated nitrile. In some embodiments, a base is added to promote the Michael addition. In some embodiments, the base is ammonium carbonate. In some embodiments, the base is an amine. In some embodiments, the base is N,N-diisopropylethylamine.

One of skill in the art will appreciate that compounds of formula I may contain one or more stereocenters, and may be present as an racemic or diastereomeric mixture. One of skill in the art will also appreciate that there are many methods known in the art for the separation of isomers to obtain stereoenriched or stereopure isomers of those compounds, including but not limited to HPLC, chiral HPLC, fractional crystallization of diastereomeric salts, kinetic enzymatic resolution (e.g. by fungal-, bacterial-, or animal-derived lipases or esterases), and formation of covalent diastereomeric derivatives using an enantioenriched reagent.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. "March's Advanced Organic Chemistry", $5^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit CAIX, MT1-MMP, PSMA, CD38, EphA2, or αvβ3, or a mutant thereof, in a biological sample or in a patient. In certain embodiments, the amount of compound in compositions of this invention is such that is effective to measurably inhibit CAIX, MT1-MMP, PSMA, CD38, EphA2, or αvβ3, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of CAIX, MT1-MMP, PSMA, CD38, EphA2, or αvβ3, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation.

Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Certain bicyclic peptides of the invention have specific utility as CAIX binding agents.

Various forms of the enzyme carbonic anhydrase (CA) catalyze hydration of carbon dioxide to generate bicarbonate anion ($HCO_3^-$) and a proton. Substrates of the reaction which is catalyzed by CA regulate a number of physiological processes, including formation and transport of $CO_2$, protons and bicarbonate anion, such as respiration, maintenance of pH levels, bone development and other processes. In the human organism, 12 catalytically active CA isoenzymes were identified which differ in their cellular localization and their expression in various tissues.

Clinical regulation of the activity of human carbonic anhydrase (hCA) by small molecular inhibitors proved to be reliable therapeutic method for a number of human diseases and already for several decades it remains a major component of therapy for high blood pressure, glaucoma, hyperthyrosis and hypoglycemia (Supuran (2008) Nat. Rev. Drug Discov. 7, 168). Classical inhibitors of carbonic anhydrases, binding into the active site of CA, are aromatic or heteroaromatic sulfonamides.

Human carbonic anhydrase IX (hCAIX) is an isoform bound to the outer cell membrane (its catalytic domain is located in the extracellular space). At physiological conditions, hCAIX is expressed only in specific tissues of gastrointestinal tract. Its overexpression was shown during hypoxia in cancer cells both in vitro and in vivo. Expression of hCAIX was detected in carcinomas of cervix, ovaries, kidneys, esophagus, lungs, breasts and brain. In tumors, hCAIX is a molecule crucial for the maintenance of intracellular pH on normal level and its expression provides the hypoxic tumor cells with an advantage in growth at acidic conditions (Chiche et al. (2009) Cancer Res 69, 358). hCAIX enzyme is thus a convenient target for development of specific inhibitors used as anti-cancer therapeutics with new mechanism of action (Neri and Supuran (2011) Nature Reviews 10, 767).

According to a further aspect of the invention, there is provided a compound or composition as defined herein, for use in preventing, suppressing or treating a disease or disorder mediated by CAIX.

According to a further aspect of the invention, there is provided a method of preventing, suppressing or treating a disease or disorder mediated by CAIX, which comprises administering to a patient in need thereof a compound or composition as defined herein.

In one embodiment, the CAIX is mammalian CAIX. In a further embodiment, the mammalian CAIX is human CAIX (hCAIX).

In one embodiment, the disease or disorder mediated by CAIX is selected from cancer.

In another aspect, certain bicyclic peptides of the invention have specific utility as high affinity binders of membrane type 1 metalloprotease (MT1-MMP, also known as MMP14). MT1-MMP is a transmembrane metalloprotease that plays a major role in the extracellular matrix remodeling, directly by degrading several of its components and indirectly by activating pro-MMP2. MT1-MMP is crucial for tumor angiogenesis (Sounni et al (2002) FASEB J. 16 (6), 555-564) and is over-expressed on a variety of solid tumors, therefore the MT1-MMP-binding bicycle peptides of the present invention have particular utility in the targeted treatment of cancer, in particular solid tumors such as non-small cell lung carcinomas. In one embodiment, the bicyclic peptide of the invention is specific for human MT1-MMP. In a further embodiment, the bicyclic peptide of the invention is specific for mouse MT1-MMP. In a yet further embodiment, the bicyclic peptide of the invention is specific for human and mouse MT1-MMP. In a yet further embodiment, the bicyclic peptide of the invention is specific for human, mouse and dog MT1-MMP.

In another aspect, certain bicyclic peptides of the invention have specific utility as high affinity binders of prostate-specific membrane antigen (PSMA).

In one embodiment, the disease or disorder mediated by CAIX is selected from PSMA is a type II integral membrane protein that has abundant and restricted expression on the surface of prostate cancer, particularly in androgen-independent, advanced and metastatic disease (Schulke, N.; et al. *Proc Natl Acad Sci USA* 2003, 100, 12590-12595). The latter is important since almost all PCa becomes androgen independent. It is also expressed within the endothelium of most solid tumors other than prostate (Chang, S. S.; et al. *Cancer Res* 1999, 59, 3192-3198). PSMA possesses the criteria of a promising target for therapy, i.e., abundant and restricted (to prostate) expression at all stages of the disease, presentation at the cell surface but not shed into the circulation, and association with enzymatic or signaling activity (Schulke, N.; et al. *Proc Natl Acad Sci USA* 2003, 100, 12590-12595). The PSMA gene is located on the short arm of chromosome 11 and functions both as a folate hydrolase and neuropeptidase. It is the neuropeptidase function that is equivalent to glutamate carboxypeptidase II (GCPII), which is referred to as the "brain PSMA", and may modulate glutamatergic transmission by cleaving N-acetylaspartylglutamate (NAAG) to N-acetylaspartate (NAA) and glutamate (Nan, F.; et al. *J Med Chem* 2000, 43, 772-774). There are up to $10^6$ PSMA molecules per cancer cell, further suggesting it as an ideal target for imaging and therapy with radionuclide-based techniques (Tasch, J.; et al. *Crit Rev Immunol* 2001, 21, 249-261).

In another aspect, certain bicyclic peptides of the invention have specific utility as CD38 binding agents.

CD38 is a 45 kD type II transmembrane glycoprotein with a long C-terminal extracellular domain and a short N-terminal cytoplasmic domain. The CD38 protein is a bifunctional ectoenzyme that can catalyze the conversion of NAD+ into cyclic ADP-ribose (cADPR) and also hydrolyze cADPR into ADP-ribose. During ontogeny, CD38 appears on CD34+ committed stem cells and lineage-committed progenitors of lymphoid, erythroid and myeloid cells. CD38 expression persists mostly in the lymphoid lineage with varying expression levels at different stages of T and B cell development.

CD38 is upregulated in many hematopoeitic malignancies and in cell lines derived from various hematopoietic malignancies, including non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML). On the other hand, most primitive pluripotent stem cells of the hematopoietic system are CD38−. CD38 expression in hematopoietic malignancies and its correlation with disease progression makes CD38 an attractive target for antibody therapy.

CD38 has been reported to be involved in $Ca^{2+}$ mobilization (Morra et al. (1998) FASEB J. 12; 581-592; Zilber et al. (2000) Proc Natl Acad Sci USA 97, 2840-2845) and in the signal transduction through tyrosine phosphorylation of numerous signaling molecules, including phospholipase C-γ, ZAP-70, syk, and c-cbl, in lymphoid and myeloid cells or cell lines (Funaro et al. (1993) Eur J Immunol 23, 2407-2411; Morra et al. (1998), supra; Funaro et al. (1990) J Immunol 145, 2390-2396; Zubiaur et al. (1997) J Immunol 159, 193-205; Deaglio et al. (2003) Blood 102, 2146-2155; Todisco et al. (2000) Blood 95, 535-542; Konopleva et al. (1998) J Immunol 161, 4702-4708; Zilber et al. (2000) Proc Natl Acad Sci USA 97, 2840-2845; Kitanaka et al. (1997) J Immunol 159, 184-192; Kitanaka et al. (1999) J Immunol 162, 1952-1958; Mallone et al. (2001) Int Immunol 13, 397-409). On the basis of these observations, CD38 was proposed to be an important signaling molecule in the maturation and activation of lymphoid and myeloid cells during their normal development.

The exact role of CD38 in signal transduction and hematopoiesis is still not clear, especially since most of these signal transduction studies have used cell lines ectopically overexpressing CD38 and anti-CD38 monoclonal antibodies, which are non-physiological ligands. Because the CD38 protein has an enzymatic activity that produces cADPR, a molecule that can induce $Ca^{2+}$ mobilization (Lee et al. (1989) J Biol Chem 264, 1608-1615; Lee and Aarhus (1991) Cell Regul 2, 203-209), it has been proposed that CD38 ligation by monoclonal antibodies triggers $Ca^{2+}$ mobilization and signal transduction in lymphocytes by increasing production of cADPR (Lee et al. (1997) Adv Exp Med Biol 419, 411-419). Contrary to this hypothesis, the truncation and point-mutation analysis of CD38 protein showed that neither its cytoplasmic tail nor its enzymatic activity is necessary for the signaling mediated by anti-CD38 antibodies (Kitanaka et al. (1999) J Immunol 162, 1952-1958; Lund et al. (1999) J Immunol 162, 2693-2702; Hoshino et al. (1997) J Immunol 158, 741-747).

The best evidence for the function of CD38 comes from CD38−/− knockout mice, which have a defect in their innate immunity and a reduced T-cell dependent humoral response due to a defect in dendritic cell migration (Partida-Sanchez et al. (2004) Immunity 20, 279-291; Partida-Sanchez et al. (2001) Nat Med 7, 1209-1216). Nevertheless, it is not clear if the CD38 function in mice is identical to that in humans since the CD38 expression pattern during hematopoiesis differs greatly between human and mouse: a) unlike immature progenitor stem cells in humans, similar progenitor stem cells in mice express a high level of CD38 (Randall et al. (1996) Blood 87, 4057-4067; Dagher et al. (1998) Biol Blood Marrow Transplant 4, 69-74), b) while during the human B cell development, high levels of CD38 expression are found in germinal center B cells and plasma cells (Uckun (1990) Blood 76, 1908-1923; Kumagai et al. (1995) J Exp Med 181, 1101-1110), in the mouse, the CD38 expression levels in the corresponding cells are low (Oliver et al. (1997) J Immunol 158, 1108-1115; Ridderstad and Tarlinton (1998) J Immunol 160, 4688-4695).

Several anti-human CD38 antibodies with different proliferative properties on various tumor cells and cell lines have been described in the literature. For example, a chimeric OKT10 antibody with mouse Fab and human IgG1 Fc mediates antibody-dependent cell-mediated cytotoxicity (ADCC) very efficiently against lymphoma cells in the presence of peripheral blood mononuclear effector cells from either MM patients or normal individuals (Stevenson et al. (1991) Blood 77, 1071-1079). A CDR-grafted humanized version of the anti-CD38 antibody AT13/5 has been shown to have potent ADCC activity against CD38-positive cell lines (U.S. patent application Ser. No. 09/797,941). Human monoclonal anti-CD38 antibodies have been shown to mediate the in vitro killing of CD38-positive cell lines by ADCC and/or complement-dependent cytotoxicity (CDC), and to delay the tumor growth in SCID mice bearing MM cell line RPMI-8226 (WO 2005/103083). On the other hand, several anti-CD38 antibodies, IB4, SUN-4B7, and OKT10, but not IB6, AT1, or AT2, induced the proliferation of peripheral blood mononuclear cells (PBMC) from normal individuals (Ausiello et al. (2000) Tissue Antigens 56, 539-547).

Some of the antibodies of the prior art have been shown to be able to trigger apoptosis in CD38+ B cells. However, they can only do so in the presence of stroma cells or stroma-derived cytokines. An agonistic anti-CD38 antibody (IB4) has been reported to prevent apoptosis of human germinal center (GC) B cells (Zupo et al. (1994) Eur J Immunol 24, 1218-1222), and to induce proliferation of KG-1 and HL-60 AML cells (Konopleva et al. (1998) J Immunol 161, 4702-4708), but induces apoptosis in Jurkat T lymphoblastic cells (Morra et al. (1998) FASEB J 12, 581-592). Another anti-CD38 antibody T16 induced apoptosis of immature lymphoid cells and leukemic lymphoblast cells from an ALL patient (Kumagai et al. (1995) J Exp Med 181, 1101-1110), and of leukemic myeloblast cells from AML patients (Todisco et al. (2000) Blood 95, 535-542), but T16 induced apoptosis only in the presence of stroma cells or stroma-derived cytokines (IL-7, IL-3, stem cell factor).

In another aspect, certain bicyclic peptides of the invention have specific utility as EphA2 binding agents.

Eph receptor tyrosine kinases (Ephs) belong to a large group of receptor tyrosine kinases (RTKs), kinases that phosphorylate proteins on tyrosine residues. Ephs and their membrane bound ephrin ligands (ephrins) control cell positioning and tissue organization (Poliakov et al. (2004) Dev Cell 7, 465-80). Functional and biochemical Eph responses occur at higher ligand oligomerization states (Stein et al. (1998) Genes Dev 12, 667-678).

Among other patterning functions, various Ephs and ephrins have been shown to play a role in vascular development. Knockout of EphB4 and ephrin-B2 results in a lack of the ability to remodel capillary beds into blood vessels (Poliakov et al., supra) and embryonic lethality. Persistent expression of some Eph receptors and ephrins has also been observed in newly-formed, adult micro-vessels (Brantley-Sieders et al. (2004) Curr Pharm Des 10, 3431-42; Adams (2003) J Anat 202, 105-12).

The de-regulated re-emergence of some ephrins and their receptors in adults also has been observed to contribute to tumor invasion, metastasis and neo-angiogenesis (Nakamoto et al. (2002) Microsc Res Tech 59, 58-67; Brantley-Sieders et al., supra). Furthermore, some Eph family members have been found to be over-expressed on tumor cells from a variety of human tumors (Brantley-Sieders et al., supra); Marme (2002) Ann Hematol 81 Suppl 2, S66; Booth et al. (2002) Nat Med 8, 1360-1).

EPH receptor A2 (ephrin type-A receptor 2) is a protein that in humans is encoded by the EPHA2 gene.

EphA2 is upregulated in multiple cancers in man, often correlating with disease progression, metastasis and poor prognosis e.g.: breast (Zelinski et al (2001) Cancer Res. 61, 2301-2306; Zhuang et al (2010) Cancer Res. 70, 299-308; Brantley-Sieders et al (2011) PLOS One 6, e24426), lung (Brannan et al (2009) Cancer Prev Res (Phila) 2, 1039-1049; Kinch et al (2003) Clin Cancer Res. 9, 613-618; Guo et al (2013) J Thorac Oncol. 8, 301-308), gastric (Nakamura et al (2005) Cancer Sci. 96, 42-47; Yuan et al (2009) Dig Dis Sci 54, 2410-2417), pancreatic (Mudali et al (2006) Clin Exp Metastasis 23, 357-365), prostate (Walker-Daniels et al (1999) Prostate 41, 275-280), liver (Yang et al (2009) Hepatol Res. 39, 1169-1177) and glioblastoma (Wykosky et al (2005) Mol Cancer Res. 3, 541-551; Li et al (2010) Tumour Biol. 31, 477-488).

The full role of EphA2 in cancer progression is still not defined although there is evidence for interaction at numerous stages of cancer progression including tumour cell growth, survival, invasion and angiogenesis. Downregulation of EphA2 expression suppresses tumour cancer cell propagation (Binda et al (2012) Cancer Cell 22, 765-780), whilst EphA2 blockade inhibits VEGF induced cell migration (Hess et al (2001) Cancer Res. 61, 3250-3255), sprouting and angiogenesis (Cheng et al (2002) Mol Cancer Res. 1, 2-11; Lin et al (2007) Cancer 109, 332-40) and metastatic progression (Brantley-Sieders et al (2005) FASEB J. 19, 1884-1886).

An antibody drug conjugate to EphA2 has been shown to significantly diminish tumour growth in rat and mouse xenograft models (Jackson et al (2008) Cancer Research 68, 9367-9374) and a similar approach has been tried in man although treatment had to be discontinued for treatment related adverse events (Annunziata et al (2013) Invest New drugs 31, 77-84).

In another aspect, certain bicyclic peptides of the invention have specific utility as integrin αvβ3 binding agents.

Integrins are heterodimeric matrix receptors that anchor cells to substrates and transmit externally derived signals across the plasma membrane. Integrin αvβ3 is involved in the osteoclast-mediated bone resorption, both in vivo and in vitro. This heterodimer molecule recognizes the amino acid motif Arg-Gly-Asp (RGD) contained in bone matrix proteins such as osteopontin and bone sialoprotein. Integrin αvβ3 is expressed in an osteoclast and its expression is modulated by resorptive steroids and cytokines. Based on blocking experiments, αvβ3 integrin has been identified as a major functional adhesion receptor on osteoclasts. Inhibitors of integrin αvβ3 reduce the capacity of osteoclasts to bind to and resorb bone. Integrin αvβ3 plays a major role in the function of osteoclasts and inhibitors of this integrin are being considered for treating or preventing osteoporosis, osteolytic metastases, and malignancy-induced hypercalcemia.

There are many bone diseases that are related to osteolysis that is mediated by osteoclasts. Osteoporosis is the most common one that is induced when resorption and formation of bone are not coordinated and bone breakdown overrides bone building. Osteoporosis is also caused by other conditions, such as hormonal imbalance, diseases, or medications (e.g., corticosteroids or anti-epileptic agents). Bone is one of the most common sites of metastasis by human breast, prostate, lung and thyroid cancers, as well as other cancers. Osteoporosis may also result from post-menopausal estrogen deficiency. Secondary osteoporosis may be associated with rheumatoid arthritis. Bone metastasis shows a very unique step of osteoclastic bone resorption that is not seen in metastasis of other organs. It is widely accepted that osteolysis that is associated with cancer is essentially mediated by osteoclasts, which seem to be activated and may be indirectly activated through osteoblasts or directly by tumor products. In addition, hypercalcemia (increased blood-calcium concentration) is an important complication of osteolytic bone diseases. It occurs relatively frequently in patients with extensive bone destruction, and is particularly common in breast, lung, renal, ovarian and pancreatic carcinomas and in myeloma.

Disintegrins are a family of low-molecular-weight RGD-containing peptides that bind specifically to integrins αIIbβ3, α5β1 and αvβ3 expressed on platelets and other cells including vascular endothelial cells and some tumor cells. In addition to their potent antiplatelet activity, studies of disintegrins have revealed new uses in the diagnosis of cardiovascular diseases and the design of therapeutic agents in arterial thrombosis, osteoporosis and angiogenesis-related tumor growth and metastasis. Rhodostomin (Rho), a disintegrin derived from the venom of Colloselasma rhodostoma, has been found to inhibit platelet aggregation in vivo and in vitro through the blockade of platelet glycoprotein αIIbβ3.

The role of αvβ3 integrin in bone diseases has been well documented (Ross et al (2006) Journal of Clinical Investigation 116 (5); Rodan et al (1997) Journal of Endocrinology 154, S47-S56; Teitelbaum (2005) Journal of Clinical Endocrinology and Metabolism 90 (4), 2466-2468; Teitelbaum (2000) Journal of Bone and Mineral Metabolism 18, 344-349; Nakamura et al (2007) Journal of Bone and Mineral Metabolism 25, 337-344; Duong et al (1999) Journal of Bone and Mineral Metabolism 17, 1-6; and Teti et al (2002) Calcified Tissue International 71, 293-299). In addition to bone diseases, αvβ3 integrin plays an important role in angiogenesis and tumor growth in conditions not related to bone diseases.

According to a further aspect of the invention, there is provided a peptide ligand as defined herein, for use in preventing, suppressing or treating a disease or disorder mediated by integrin αvβ3.

According to a further aspect of the invention, there is provided a method of preventing, suppressing or treating a disease or disorder mediated by integrin αvβ3, which comprises administering to a patient in need thereof a peptide ligand as defined herein.

In one embodiment, the integrin αvβ3 is mammalian integrin αvβ3. In a further embodiment, the mammalian integrin αvβ3 is human integrin αvβ3.

In one embodiment, the disease or disorder mediated by integrin αvβ3 is selected from bone disease (such as osteoporosis), cancer, and diseases involving angiogenesis.

In a further embodiment, the disease or disorder mediated by integrin αvβ3 is selected from cancer.

Compounds and compositions described herein are generally useful for the inhibition of carbonic anhydrase, metalloprotease, carboxypeptidase, hydrolase, kinase, or integrin activity of one or more enzymes.

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The activity of a compound utilized in this invention as an inhibitor of CAIX, MT1-MMP, PSMA, CD38, EphA2, or αvβ3, or a mutant thereof, may be assayed in vitro, in vivo or in a cell line. Alternative in vitro assays quantitate the ability of the inhibitor to bind to CAIX, MT1-MMP, PSMA, CD38, EphA2, or αvβ3. Inhibitor binding may be measured by radiolabeling the inhibitor prior to binding, isolating the inhibitor/CAIX, inhibitor/MT1-MMP, inhibitor/PSMA, inhibitor/CD38, inhibitor/EphA2, or inhibitor/αvβ3 complex and determining the amount of radiolabel bound. Alternatively, inhibitor binding may be determined by running a competition experiment where new inhibitors are incubated with CAIX, MT1-MMP, PSMA, CD38, EphA2, or αvβ3 bound to known radioligands. Representative in vitro and in vivo assays useful in assaying an MT1-MMP inhibitor include those described and disclosed in: Pietraszek et al., (2014) FEBS Letters 588 (23), 4319-4324; Cheltsov et al., (2012) Cancer Res. 72 (9), 2339-49; and WO 2009/098450, each of which is herein incorporated by reference in its entirety. Representative in vitro and in vivo assays useful in assaying a CAIX inhibitor include those described and disclosed in: Wind et al., (2011) Ann Clin Biochem. 48 (2), 112-120; Gandhi et al., (2015) J. Urology 193 (4), e870-e871; and WO 2004/005348, each of which is herein incorporated by reference in its entirety. Representative in vitro and in vivo assays useful in assaying a αvβ3 inhibitor include those described and disclosed in: Wang et al (2005) Bioconjug Chem 16 (3), 729-34. Detailed conditions for assaying a compound utilized in this invention as an inhibitor of CAIX, MT1-MMP, PSMA, CD38, EphA2, or αvβ3, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of CAIX, MT1-MMP, PSMA, CD38, EphA2, or αvβ3 and are therefore useful for treating one or more disorders associated with activity of CAIX, MT1-MMP, PSMA, CD38, EphA2, or αvβ3. Thus, in certain embodiments, the present invention provides a method for treating a CAIX-mediated, a MT1-MMP-mediated, PSMA-mediated, CD38-mediated, EphA2-mediated, or αvβ3-mediated disorder comprising the step of administering to a patient in need thereof a compound of the present invention, or pharmaceutically acceptable composition thereof.

As used herein, the terms "CAIX-mediated", "MT1-MMP-mediated", "PSMA-mediated", "CD38-mediated", "EphA2-mediated", or "αvβ3-mediated" disorders, diseases, and/or conditions as used herein means any disease or other deleterious condition in which CAIX, MT1-MMP, PSMA, CD38, EphA2, or αvβ3, or a mutant thereof, are known to play a role. Accordingly, another embodiment of the present invention relates to treating or lessening the severity of one or more diseases in which CAIX, MT1-MMP, PSMA, CD38, EphA2, or αvβ3, or a mutant thereof, are known to play a role.

Examples of cancers (and their benign counterparts) which may be treated (or inhibited) include, but are not limited to tumors of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); hematological malignancies (i.e. leukemias, lymphomas) and premalignant hematological disorders and disorders of borderline malignancy including hematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukemias, natural killer [NK] cell lymphomas, Hodgkin's lymphomas, hairy cell leukemia, monoclonal gammopathy of uncertain significance, plasmacytoma, multiple myeloma, and post-transplant lymphoproliferative disorders), and hematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumors of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumors, benign and malignant histiocytomas, and dermatofibrosarcomaprotuberans; tumors of the central or peripheral nervous system (for example astrocytomas, gliomas and glioblastomas, meningiomas, ependymomas, pineal tumors and schwannomas); endocrine tumors (for example pituitary tumors, adrenal tumors, islet cell tumors, parathyroid tumors, carcinoid tumors and medullary carcinoma of the thyroid); ocular and adnexal tumors (for example retinoblastoma); germ cell and trophoblastic tumors (for example teratomas, seminomas, dysgerminomas, hydatidiform moles and choriocarcinomas); and pediatric and embryonal tumors (for example medulloblastoma, neuroblastoma, Wilms tumor, and primitive neuroectodermal tumors); or syndromes, congenital or otherwise, which leave the patient susceptible to malignancy (for example Xeroderma Pigmentosum).

In a further embodiment, the cancer is selected from cancer of the cervix, ovary, kidney, esophagus, lung, breast and brain.

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

Furthermore, the invention provides the use of a compound according to the definitions herein, or a pharmaceutically acceptable salt, or a hydrate or solvate thereof for the preparation of a medicament for the treatment of a proliferative disease.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL)

comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenström's macroglobulinemia comprising administering to a patient in need thereof a compound of formula I and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a compound of formula I and a BTK inhibitor, wherein the disease is selected from inflammatory bowel disease, arthritis, systemic lupus erythematosus (SLE), vasculitis, idiopathic thrombocytopenia purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenia states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenia purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleroderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting carbonic anhydrase activity in a biological sample comprising the step of contacting said biological sample with a compound of this invention, or a composition comprising said compound.

According to another embodiment, the invention relates to a method of inhibiting metalloprotease activity in a biological sample comprising the step of contacting said biological sample with a compound of this invention, or a composition comprising said compound.

According to another embodiment, the invention relates to a method of inhibiting integrin activity in a biological sample comprising the step of contacting said biological sample with a compound of this invention, or a composition comprising said compound.

According to another embodiment, the invention relates to a method of inhibiting CAIX, MT1-MMP, PSMA, CD38, EphA2, or αvβ3, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of CAIX, MT1-MMP, PSMA, CD38, EphA2, or αvβ3, or a mutant thereof, activity in a biological sample is useful for a variety of purposes that are known to one of skill in the art. Examples of such purposes include, but are not limited to, biological assays.

Another embodiment of the present invention relates to a method of inhibiting carbonic anhydrase, metalloprotease or integrin activity in a patient comprising the step of administering to said patient a compound of the present invention, or a composition comprising said compound.

According to another embodiment, the invention relates to a method of inhibiting CAIX, MT1-MMP, PSMA, CD38, EphA2, or αvβ3, or a mutant thereof, activity in a patient comprising the step of administering to said patient a compound of the present invention, or a composition comprising said compound. In other embodiments, the present invention provides a method for treating a disorder mediated by CAIX, MT1-MMP, PSMA, CD38, EphA2, or αvβ3, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtubulin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; colchicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; Ilmofosine; RO 318220 and RO 320432; GO 6976; Isis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases ($EGFR_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., $4^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl) phthalazine or a pharmaceutically acceptable salt thereof, 1-(4-chloroanilino)-4-(4-pyridylmethyl) phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Materials and Methods

Example 1: Peptide Synthesis—Molecular Scaffold Reagent with Leaving Groups

Peptide synthesis was based on Fmoc chemistry, using a Symphony peptide synthesizer manufactured by Peptide Instruments and a Syro II synthesizer by MultiSynTech. Standard Fmoc-amino acids were employed (Sigma, Merck), with appropriate side chain protecting groups: where applicable standard coupling conditions were used in each case, followed by deprotection using standard methodology. Peptides were purified using HPLC and following isolation they were modified with a molecular scaffold reagent with leaving groups. For this, linear peptide was diluted with $H_2O$ up to ~35 mL, ~500 μL of 100 mM molecular scaffold reagent in acetonitrile was added, and the reaction was initiated with 5 mL of 1 M $NH_4$ $HCO_3$ in $H_2O$. The reaction was allowed to proceed for ~30-60 min at RT, and lyophilized once the reaction had completed (as judged by MALDI). Following lyophilization, the reaction mixture was loaded onto a Gemini C18 column (Phenomenex). Solvents ($H_2O$, acetonitrile) were acidified with 0.1% trifluoroacetic acid. The gradient ranged from 30-70% acetonitrile in 15 minutes, at a flowrate of 15-20 mL/min, using a Gilson preparative HPLC system. Pure fractions containing the desired product were pooled, lyophilized and kept at −20° C. for storage.

Example 2: Peptide Synthesis—Molecular Scaffold Reagent Containing Michael Acceptors Alternatively, peptides were purified using HPLC and following isolation they were modified with a molecular scaffold reagent containing Michael acceptors. For this, linear peptide was diluted with 50:50 MeCN:$H_2O$ up to ~35 mL, ~500 μL of 100 mM molecular scaffold reagent containing Michael acceptors in acetonitrile was added, and the reaction was initiated with 5 mL of 1 M $NH_4HCO_3$ in $H_2O$. The reaction was allowed to proceed for ~30-60 min at RT, and lyophilized once the reaction had completed (as judged by MALDI). Once completed, 1 mL of 1M L-Cysteine hydrochloride monohydrate (Sigma) in $H_2O$ was added to the reaction for ~60 min at RT to quench any excess molecular scaffold reagent containing Michael acceptors.

Following lyophilization, the modified peptide was purified as above, while replacing the Luna C8 with a Gemini C18 column (Phenomenex), and changing the acid to 0.1% trifluoroacetic acid. Pure fractions containing the correct desired product were pooled, lyophilized and kept at −20° C. for storage.

All amino acids, unless noted otherwise, were used in the L-configurations.

Example 3: Conjugation of Bicycle Peptides with DOTA (1,4,7,10 tetraazacyclododecane-1,4,7,10-tetraacetic acid)

1,4,7,10-tetraazacyclododecane-1,4,7,10-tetraacetic acid (DOTA) is a complexing agent, it can be conjugate with Bicycles in order to obtain constructs which, after being labelled with radioactive isotopes (i.e. $Lu^{3+}$) or MRI contrast agents (i.e. $Gd^{3+}$), are used for biodistribution studies in animal models. Commercially available N-succinimidyl ester of DOTA is coupled to an amino group, generally the N-terminal amino group, of the Bicycle peptide.

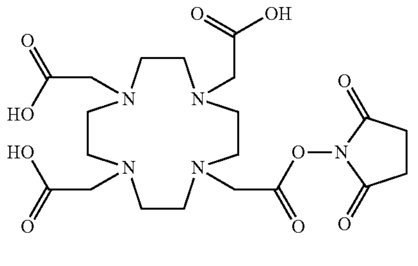 [SMILES: O=C(O)CN1CCN(CC(=O)O)CCN(CC(=O)ON2C(=O)CCC2=O)CCN(CC(=O)O)CC1]

| Name | CAS number | Mw |
|---|---|---|
| DOTA N-succinimidyl ester | 170908-81-3 | 761.48 |

Material and Methods

Equipment
- LCMS
- MALDI Mass Spectrometer

Solvents and Compounds and Consumables
- Dry dimethyl sulfoxide (DMSO)
- DOTA N-succinimidyl ester
- N,N-diisopropylethylamine (DIPEA)
- 100 mM tris(hydroxymethyl)aminomethane (TRIS) pH 9

Full Procedure

Prepare 20 mM solution of the Bicycle peptide in dry DMSO.

Prepare 100 mM solution of DOTA N-Succinimidyl ester in dry DMSO. N-Succinimidyl esters are moisture sensitive and are kept under nitrogen in a desiccator in −20° C. freezer.

Add the DOTA N-Succinimidyl ester solution to the peptide solution in order to have a 5-fold excess of the former over the peptide. Mix well the resulting reaction mix and spin down any droplets on the wall.

Add neat DIPEA to the mixture to have a 20-fold excess of the DIPEA over the peptide. Mix well the resulting solution and spin down any droplets on the wall. Thus, the approximate initial concentrations of the reactants are:
- Bicycle peptide 15 mM
- DOTA N-succinimidyl ester 19 mM
- DIPEA 300 mM.

Stir or shake the reaction mix are room temperature and follow the progression of the reaction using LC/MS or MALDI-TOF.

When the reaction is complete quench the mixture with 100 mM TRIS pH 9, dilute to 10 mL with 6 M guanidine hydrochloride and purify the mixture by RP-HPLC.

Example 4: Conjugation of Bicycle Peptides with 5(6)-Carboxyfluorescein

The commercially available N-succinimidyl ester of the 5(6)-Carboxyfluorescein (CAS number: 92557-80-7) is coupled to an amino group, generally the N-terminal amino group, of the Bicycle peptide.

Materials and Methods

Equipment
- MALDI Mass Spectrometer.

Procedure

In an Eppendorf tube prepare a 20 mM solution of the Bicycle peptide in dry DMSO. In an Eppendorf tube prepare 100 mM solution of 5(6)-Carboxyfluorescein N-Succinimidyl ester in dry DMSO. N-Succinimidyl esters are moisture sensitive and are kept under nitrogen in a desiccator in −20° C. freezer. 5(6)-Carboxyfluorescein is light sensitive, handle it and peptides labelled with it in amber glassware/plasticware and keep light irradiation as low as possible. Add the Fluorescent dye solution to the peptide solution in order to have a 5-fold excess of dye over the peptide. Mix resulting reaction mixture well and spin down any droplets on the wall. Add neat DIPEA to the mixture to have a 20 fold excess of the DIPEA over the peptide. Mix well the resulting solution and spin down any droplets on the wall. Thus, the approximate initial concentrations of the reactants are: Bicycle peptide (10 mM), fluorescent dye N-Succinimidyl ester (50 mM), and DIPEA (200 mM). Stir or shake the reaction mix at room temperature and follow the progression of the reaction using MALDI-TOF. When the reaction is complete quench the mixture with 100 mM TRIS pH 9, transfer the mixture into a 50 mL Falcon tube, dilute to 10 mL with 6 M guanidine hydrochloride and purify the mixture by RP-HPLC.

Example 5: Conjugation of Bicycle Peptides with Alexa Fluor® Fluorescent Dyes Alexa Fluor® dyes are a family of fluorescent dyes produced by Molecular Probes, Inc. They are commercially available as N-succinimidyl esters, which can be coupled to an amino group, generally the N-terminal amino group, of the Bicycle peptide.

The Alexa Fluor® N-succinimidyl esters used are as follows: Alexa Fluor 488 N-succinimidyl ester and Alexa Fluor 680 N-succinimidyl ester.

Materials and Methods

Equipment
- MALDI Mass Spectrometer.

Procedure

In an Eppendorf tube prepare 20 mM solution of the Bicycle peptide in dry DMSO. In an Eppendorf tube prepare 15 mM solution of Alexa Fluor® N-Succinimidyl ester in dry DMSO. N-Succinimidyl esters are moisture sensitive and are kept under nitrogen in a desiccator in −20° C. freezer. Alexa Fluor® dyes are light sensitive, handle them and peptides labelled with them in amber glassware/plasticware and keep light irradiation as low as possible. Add the Fluorescent dye solution to the peptide solution in order to have a 2.5 fold excess of dye over the peptide. Mix well the resulting reaction mix and spin down any droplets on the wall. Add neat DIPEA to the mixture to have a 20 fold excess of the DIPEA over the peptide. Mix well the resulting solution and spin down any droplets on the wall. Thus, the approximate initial concentrations of the reactants are: Bicycle peptide (5 mM); Fluorescent dye N-Succinimidyl ester (12.5 mM); and DIPEA (100 mM). Stir or shake the reaction mix at room temperature and follow the progression of the reaction using MALDI-TOF. When the reaction is complete quench the mixture with 100 mM TRIS pH 9, transfer the mixture in a 50 mL Falcon tube, dilute to 10 mL with 6 M guanidine hydrochloride and purify the mixture by RP-HPLC.

Example 6: CAIX Assay

CAIX Competition Binding Assay Affinity of the peptides of the invention for human CAIX (Ki) was determined using a competition fluorescence polarization assay analogous to that described in Dubois et al. (2011) Radiotherapy and Oncology 99 (3), 424-43 using A-(CAECWIDGWVPC)-A-Sar6-K (Fl) (SEQ ID NO: 7) as the fluorescent ligand.

Example 7: Dissociation Rate Constant Determination of Bicyclic Binders to MT1-MMP Direct Binding Fluorescence Polarization (Anisotropy) Assays Direct Binding Fluorescence Polarization or Anisotropy Assays are performed by titrating a constant concentration of fluorescent tracer (here, the fluoresceinated bicyclic peptide to be studied) with its binding partner (here, the MT1-MMP hemopexin domain). As the concentration of binding partner increases during the titration, the polarization signal changes in proportion to the fraction of bound and unbound material. This allows determination of dissociation rates ($K_d$) quantitatively. Assay data can be fit using standard ligand binding equations.

Typically, concentrations of the tracer are ideally well below the $K_d$ of the tracer: titrant pair, and concentrations chosen are usually at ~1 nM or less. The titrant (binding partner) concentration is varied from 0.1 nM up to typically 5 μM. The range is chosen such that the maximum change in fluorescent polarization can be observed. Buffers employed are phosphate buffered saline in the presence of 0.01% Tween. Experiments were run in black 384 well low-bind/low volume plates (Corning 3820), and the fluorescent polarization signal was measured using a BMG Pherastar FS plate reader. Fluorescent tracers referred to in the text are bicyclic peptides that have been fluoresceinated using 5,6-carboxyfluorescein. Fluoresceination may be performed on the N-terminal amino group of the peptide, which is separated from the bicycle core sequence by a sarcosine spacer (usually Sar10 (SEQ ID NO: 73)). This can be done during Fmoc solid phase synthesis or post-synthetically (after cyclization with the molecular scaffold reagent and purification) if the N-terminal amino group is unique to the peptide. Fluoresceination can also be performed on the C-terminus, usually on a Lysine introduced as the first C-terminal residue, which is then separated from the bicycle core sequence by a sarcosine spacer (usually Sar6 (SEQ ID NO: 69)). Thus, N-terminal tracers can have a molecular format described as Fluo-Ala-Sar10-A (SEQ ID NO: 72) (BicycleCoreSequence), and (BicycleCoreSequence)-A-Sar6-K (Fluo) (SEQ ID NO: 67) for a C-terminally fluoresceinated construct.

Fluorescent tracers used in the Examples are A-(17-69)-A-Sar6-K (Fluo) (SEQ ID NO: 67), A-(17-69-07)-A-Sar6-K (Fluo) (SEQ ID NO: 67), and A-(17-69-12)-A-Sar6-K (Fluo) (SEQ ID NO: 67). Due to the acidic nature of the 17-69 fluorescent peptides, they were typically prepared as concentrated DMSO stocks, from which dilution were prepared in 100 mM Tris pH 8 buffer.

Example 8: Competition Assays Using Fluorescence Polarization (Anisotropy)

Due to their high affinities to the MT1-MMP Hemopexin domain (PEX), the fluoresceinated derivatives of 17-69-07 and 17-69-12 (denoted as 17-69-07-N040 and 17-69-12-N005, respectively) can be used for competition experiments (using FP for detection). Here, a preformed complex of PEX with the fluorescent PEX-binding tracer is titrated with free, non-fluoresceinated bicyclic peptide. Since all 17-69-based peptides are expected to bind at the same site, the titrant will displace the fluorescent tracer from PEX. Dissociation of the complex can be measured quantitatively, and the $K_d$ of the competitor (titrant) to the target protein determined. The advantage of the competition method is that the affinities of non-fluoresceinated bicyclic peptides can be determined accurately and rapidly.

Concentrations of tracer are usually at the $K_d$ or below (here, 1 nM), and the binding protein (here, hemopexin of MT1-MMP) is at a 15-fold excess such that >90% of the tracer is bound. Subsequently, the non-fluorescent competitor bicyclic peptide (usually just the bicycle core sequence) is titrated, such that it displaces the fluorescent tracer from the target protein. The displacement of the tracer is measured and associated with a drop in fluorescence polarization. The drop in fluorescence polarization is proportional to the fraction of target protein bound with the non-fluorescent titrant, and thus is a measure of the affinity of titrant to target protein.

The raw data is fit to the analytical solution of the cubic equation that describes the equilibria between fluorescent tracer, titrant, and binding protein. The fit requires the value of the affinity of fluorescent tracer to the target protein, which can be determined separately by direct binding FP experiments (see previous section). The curve fitting was performed using Sigmaplot 12.0 and used an adapted version of the equation described by Zhi-Xin Wang (FEBS Letters 360 (1995) 1 11-1 14).

Example 9: Integrin αvβ3 Competition Binding Assay

Affinity of the peptides of the invention for integrin αvβ3 (Ki) was determined using a competition fluorescence polarization assay analogous to that described in Wang et al (2005) Bioconjug Chem 16 (3), 729-34 using 5 nM peptide with the sequence: FITC-LC-GRGDSP (SEQ ID NO: 8) as the ligand.

Example 10. I-25 (a Palmitoylated, MT1-MMP Specific Bicyclic Peptide) Organ Distribution and Dose Study General procedure for radiolabelling with Lu-177.

Labeling Reaction Reactants:

50 μL 0.25 M Na-Acetate buffer pH 5.2+0.1% Tween 20;

10 μL [Lu-177]$LuCl_3$ in 0.05 M HCl; and

2 μL of the diluted peptide (2 nmols).

The reaction mixture was incubated at 98° C. for 2, 10, 30, 45 minutes and for 5 h. At each time point the heating was stopped and 5 μL of the labeling reaction were diluted in 100 μL INJECTION BUFFER (0.25 M Na-Acetate pH 7+0.05% Tween20) and subsequently analyzed in radio-HPLC. TLC was done in parallel and confirmed the results of the radio-HPLC.

Organ distribution studies, general method: For organ distribution, the respective dose is prepared by dilution of the labeling reaction mixture in injection buffer (0.25 M Na-Acetate pH 7+0.05% Tween20). The $^{177}$Lu-radiolabeled peptide was injected via the tail vein of the nu/nu mice (50 kBq per mouse), transplanted with the respective cell line. At indicated time points after injection the animals were sacrificed. Blood, heart, lung, spleen, liver, kidney, muscle, brain, femur, and the tumor were dissected, blotted dry, and weighed. The radioactivity was measured with a γ-counter (CobraII; Canberra Packard) along with a sample of the injection solution to calculate the percentage injected dose per gram of tissue (% ID/g).

Exemplary Procedure for Radiolabelling with Lu-177

The γ- and β-emitter $^{177}LuCl_3$ (NEZ307D, Perkin Elmer, in 0.04 M HCl), with a $t_{1/2}$ of 6.7 days was used for both in vivo biodistribution and internalization studies. Labeling reactions were performed by adding 10 μL $^{177}LuCl_3$ (~10 MBq) in 50 mM HCl, 2 μL of the diluted peptide (1 mM solution in 50 mM HEPES buffer pH 7+0.1% Tween 20 diluted from a 10 mM DMSO stock) to 50 μL 50 mM HEPES buffer pH 7 supplemented with 0.1% Tween 20. The reaction mixture was incubated at 98° C. for 10 minutes. The radiochemical yield (RCY) was determined using high performance liquid chromatography (HPLC) system equipped with a Latek P402 (Latek, Eppelheim, Germany), a HITACHI variable UV detector (absorbance was measured at 214 and 254 nm) and a gamma detector (Bioscan, WA, USA), using a Chromolith RP-18 column (100×4.6 mm; Merck). The analytical HPLC run was performed at 4 mL/min, using a linear A (0.1% trifluoroacetic acid (TFA) in water) to B (0.1% TFA in acetonitrile) gradient (0% B to 100% B in 6 min). Thin-layer chromatography was performed in parallel to confirm the results of the radio-HPLC. The RCY was generally >95%, and thus, the output of labelling reactions was directly diluted with the appropriate buffer and further unlabeled peptide if required, to use in subsequent experiments.

Exemplary Procedure for Organ Distribution Studies $5\times10^6$ cells of HT1080 were subcutaneously inoculated into the right trunk of male 6-week-old BALB/c nu/nu mice (Charles River Laboratories). The tumors were grown for approximately 1 week, to a maximum size of ~200 $mm^3$. Respective doses were prepared by mixing a fixed quantity of 5 pmoles $^{177}$Lu labelled peptides (at approx. 50 kBq) with different quantities of non-labelled peptide (derived from 1 mM stock solution in 0.25 M sodium acetate pH 7+0.05% Tween20) in 100 μL injection buffer (0.25 M sodium acetate pH 7+0.05% Tween20). 3 animals were used per dose and timepoint. Radiolabelled peptide solutions were injected via the tail vein, followed by sacrifice at various time points. Organs of interest (blood, heart, lung, spleen, liver, kidney, muscle, small intestine, brain, HT1080 tumor) were dissected, blotted dry, and weighed. The radioactivity was measured using a gamma counter and calculated as % ID/g.

Results: Lipidation of biomolecules is known to increase serum half-life through serum albumin binding in the circulation (Di, L. (2015) *Strategic approaches to optimizing peptide ADME properties. AAPS J* 17, 134-43) and could offer a potential modification to the MT1 Bicyclic Peptide I-23 to further increase the tumor-specific signal through prolonged exposure in vivo. A palmitoylated bicyclic peptide derivative I-25 was generated based on stabilised I-23, where its N-terminus was modified with an extended sarcosine oligomer spacer terminated with palmitoic acid, and where a lysine modified with DOTA was placed within the sarcosine spacer. Oligosarcosine was chosen as a spacer due to its extended, non-globular structure, high aqueous solubility and ease of synthesis (Teufel, D. P., Johnson, C. M., Lum, J. K., and Neuweiler, H. (2011) *Backbone-driven collapse in unfolded protein chains. J Mol Biol* 409, 250-62). The overall spacer length was set at 15 sarcosines, so as to ensure that the bicyclic peptide and its MT1-MMP binding activity are spatially well separated from the albumin-binding palmitoic acid. The molecular design should in principle allow formation of a ternary complex between albumin, fatty acid-modified radio-labelled bicyclic peptide and MT1-MMP. Indeed, despite the extended modification on the peptide's N-terminus, I-25 retained its affinity to MT1-MMP (Kd=2.25±0.5 nM).

A biodistribution study using $^{177}$Lu-labelled I-25 was conducted, choosing the 48 hr timepoint p.i. to assess the optimal dose for high tumour-to-organ contrast by administering a range of dose levels (10, 100, 750, 1000, 5000 pmole/mouse; FIG. 1). A striking tumour signal of ~26% ID/g is observed at 750-1000 pmole/mouse. Further signals at <4.5% are observed in spleen, liver and small intestine.

A dose of 750 pmol I-25 was found to be optimal. As shown in FIG. 1, using 750 pmoles as the injected dose, the background activity is quite low in all organs except the kidneys while the tumor accumulation in HT1080 xenografts is extremely high even after 48 h p.i. (24.1±2.5% ID/g).

Example 11. I-23 (an MT1-MMP Specific Proteolytically Stabilized Bicyclic Peptide) Organ Distribution and Dose Study The non-PA and stabilized derivative I-23 was produced to increase resistance to proteolytic degradation in vivo. I-23 sequence differs from 17-69-07-N144 sequence in that I-23 sequence comprises four modifications: D-Ala1, 1NA14, D-Ala5, and tBuGly11. Using varying quantities of I-23 and a constant quantity of $^{177}$Lu (approx. 50 kBq/mouse), a variety of doses were assessed in biodistribution studies using HT1080 xenograft mice. Biodistribution was performed at 1 h post injection.

Figure 2:
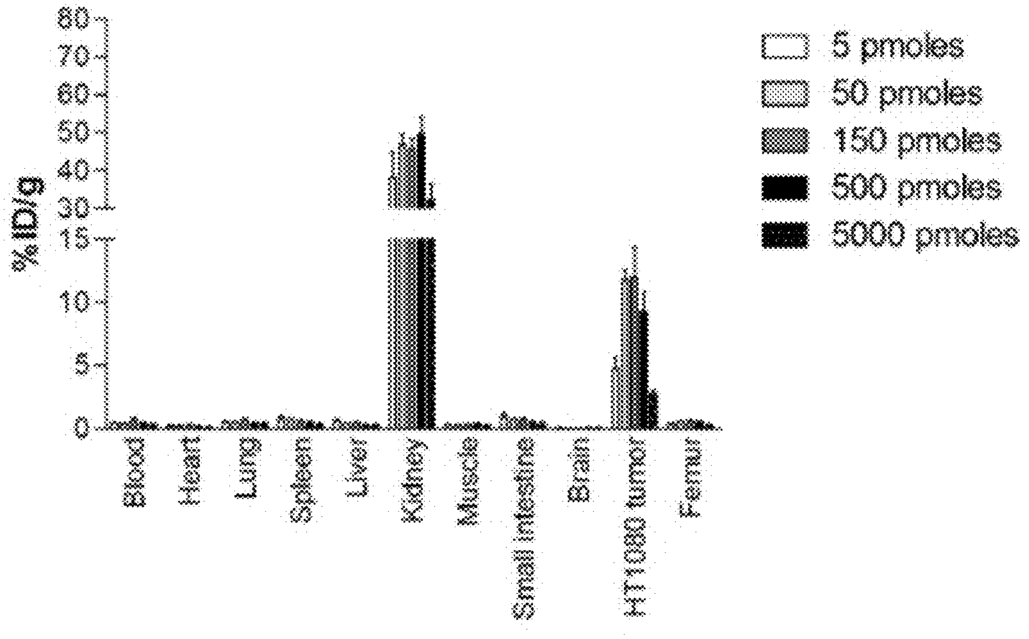
FIG. 2 depicts the organ distribution of Lu-177 labelled I-23 at different doses.

A dose of 50 to 150 pmol/mouse was found to be optimal as shown in FIG. 2. As compared to the molecule 17-69-07-N144, all doses of the stabilized I-23 showed significantly higher tumor uptake as shown in FIGS. 3A and 3B. The tumor uptake was slightly blocked at a dose of 500 pmoles and nearly completely blocked using 5 nmoles of I-23.

Figure 3:
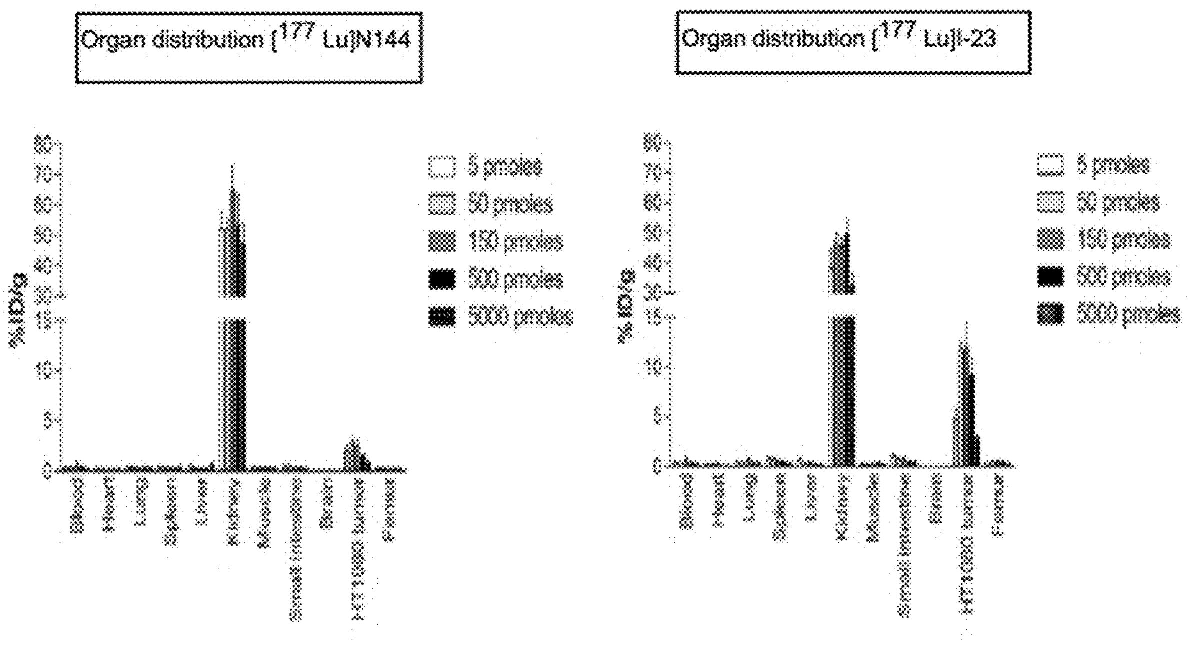
FIG. 3 depicts the comparison between Lu-177 labelled I-23 and 17-69-07-N144 at different doses.

The results demonstrate that proteolytic stabilization of the molecules leads to an improvement in tumor signal for I-23 compared to 17-69-07-N144 and makes the molecules suitable probes for molecular imaging (12.4% ID/g at the 1 hour timepoint for I-23, FIG. 3).

Example 12. I-24 Organ Distribution and Dose Study

I-24 comprises I-23 and the Sar10 (SEQ ID NO: 73) spacer. Using varying quantities of I-24 and a constant quantity of $^{177}$Lu (approx. 50 kBq/mouse), a variety of doses were assessed in biodistribution studies using HT1080 xenograft mice. Biodistribution was performed at 1 h post injection.

Figure 4:
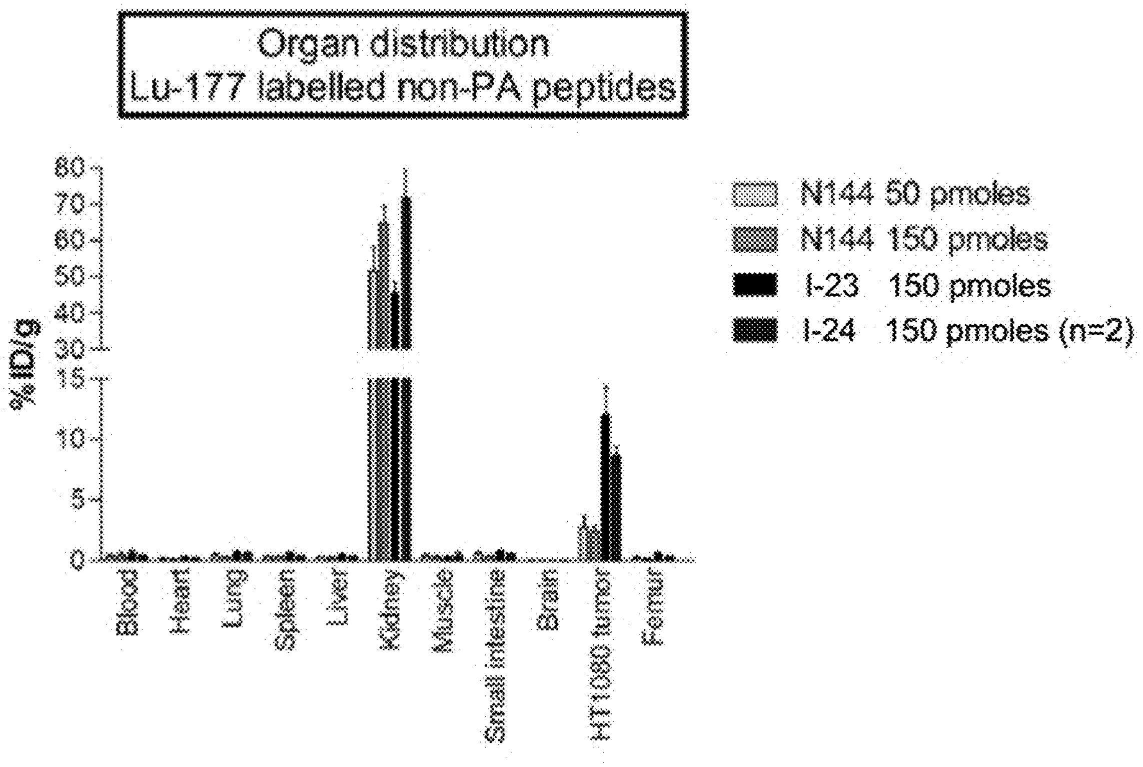
FIG. 4 depicts the comparison of the Lu-177 labelled 17-69-07-N144 (50 and 150 pmoles) with the stabilized variants I-23 and I-24 at 150 pmoles.

A dose of 150 pmol was found to be optimal. The signal in the tumor is slightly lower than I-23, but significantly greater than the non-stabilized 17-69-07-N144 (FIG. 4). The tumor uptake was slightly blocked at a dose of 500 pmoles and nearly completely blocked using 5 nmoles of I-24.

Figure 5:
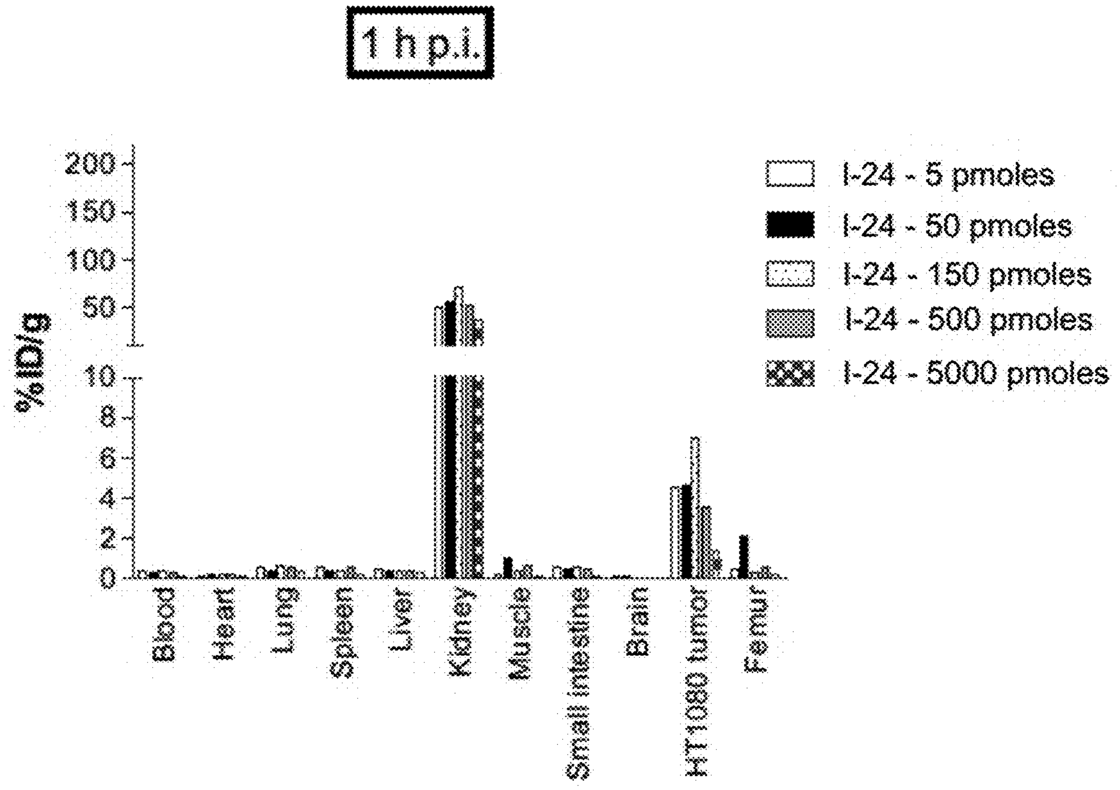
FIG. 5 depicts the organ distribution of Lu-177 labelled I-24 at different doses.
Figure 6:
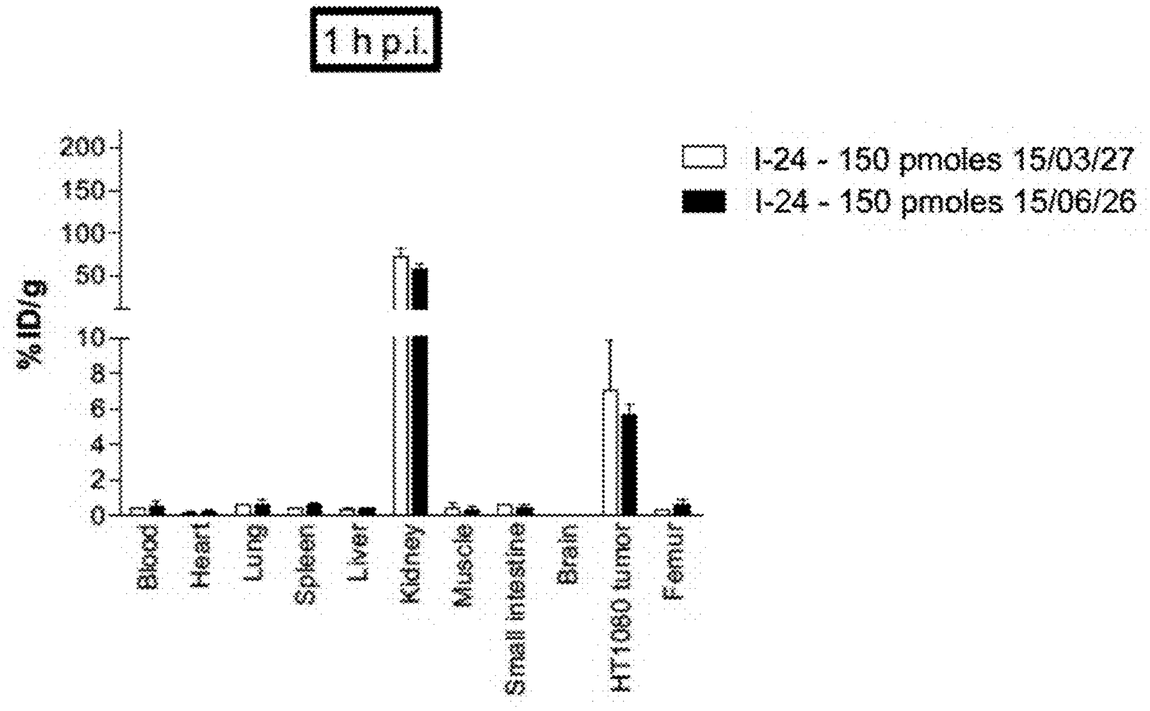
FIG. 6 depicts the comparative organ distribution of the Lu-177 labelled I-24 investigated at different days. The results indicate a high reproducibility.

Results of these studies are shown in FIGS. 5 and 6.

Example 13. Specificity of Tumor Uptake of the Stabilized Non-PA Variants

Figure 7:
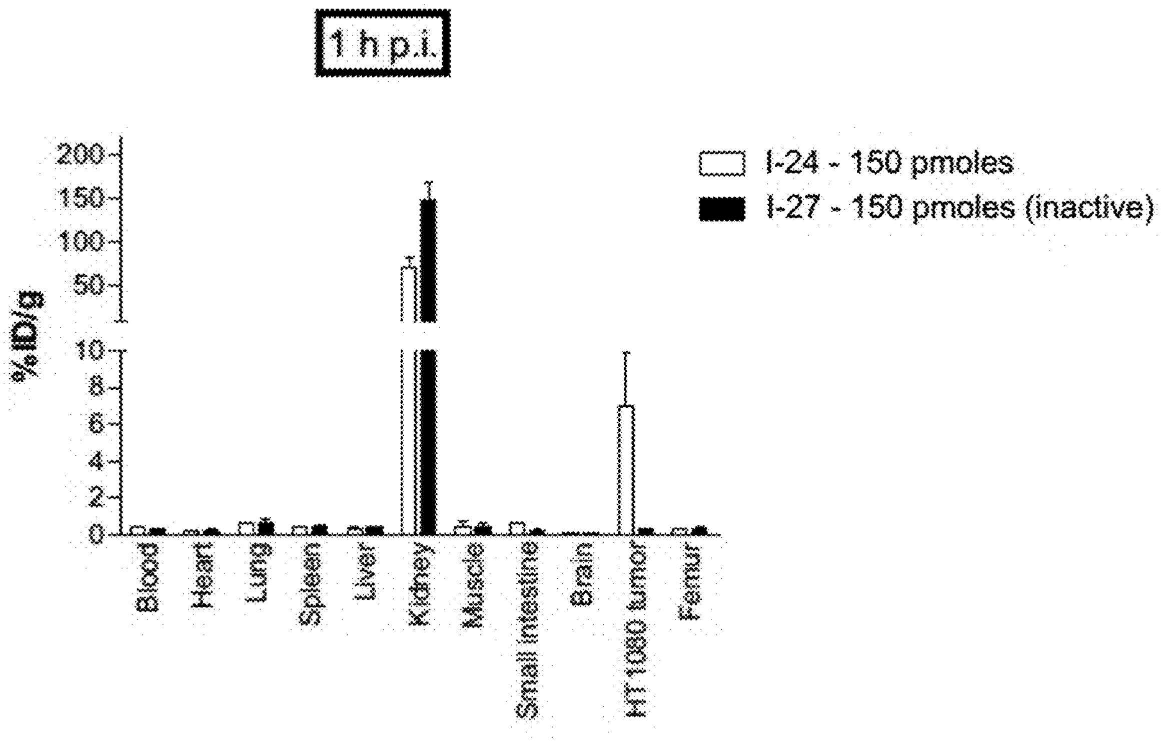
FIG. 7 depicts the organ distribution of the inactive variant I-27 1 h p.i. of 150 pmoles.

I-27 represents the MT1-MMP inactive variant of I-24. An organ distribution of I-27 showed that the tumor uptake was reduced clearly by a factor of 25 from 7.04±2.83% ID/g tumor to 0.28±0.05% ID/g tumor as shown in FIG. 7.

Figure 8:
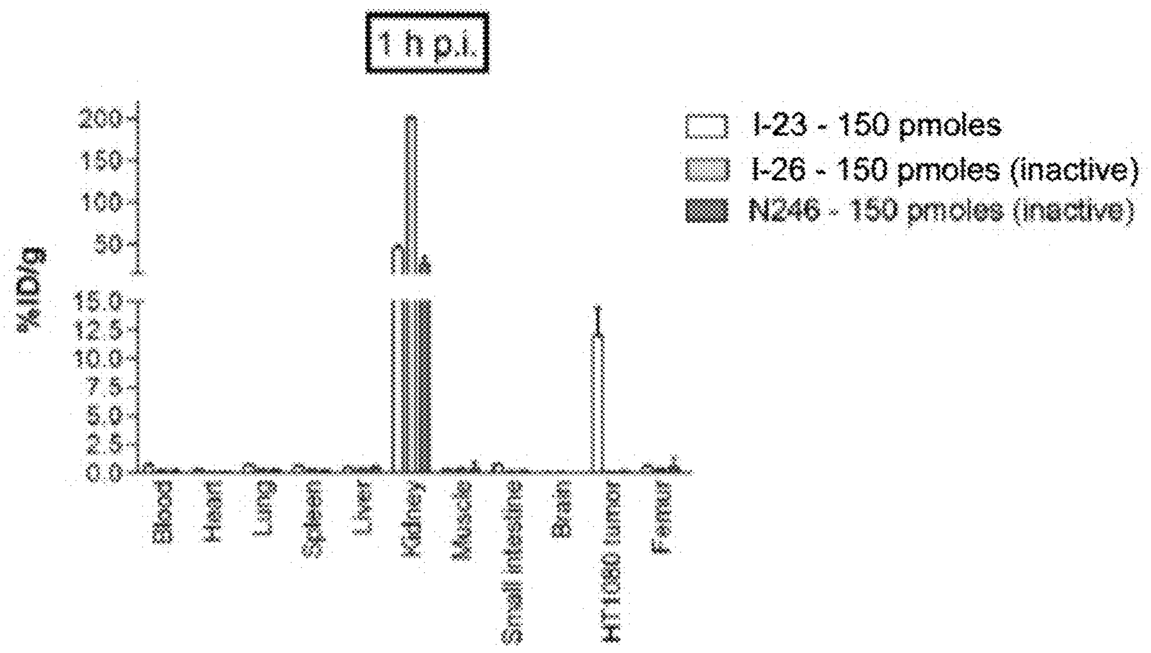
FIG. 8 depicts the analysis of tumor specificity. I-23 represents the active spacer-less variant, I-26 the inactive mutant and 17-69-07-N246 the all D variant.

In addition, two different inactive variants of the spacerless I-23, I-26 and 17-69-07-N246 have been characterized in organ distribution. Again, in both cases the tumor uptake was shown to essentially absent as compared with the binding variant I-23 as shown in FIG. 8.

Example 14. Organ Distribution of I-23 at Different Time Points p.i.

Figure 9:
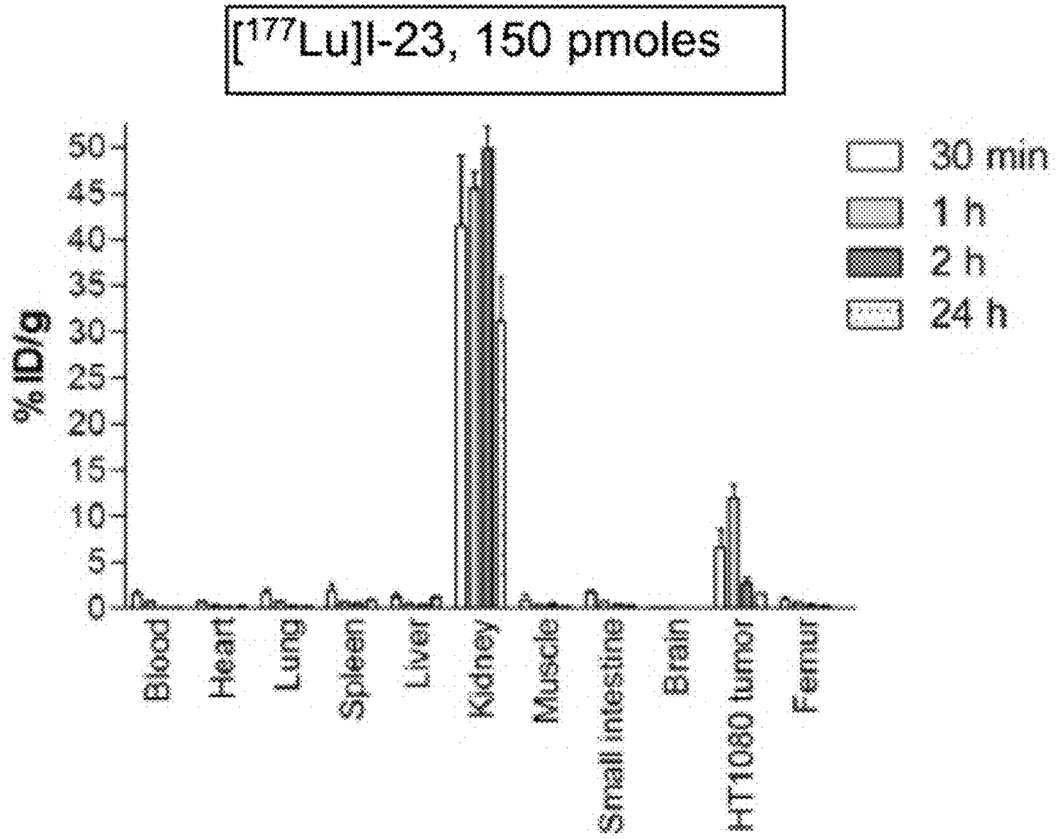
FIG. 9 depicts the organ distribution of I-23 at different time points p.i.

The distribution of the I-23 molecule at different time points was performed. It showed that the tumor localization decreases significantly after 1 h p.i. At 24 h p.i. the tumor uptake is reduced from 12.02±2.37% ID/g (1 h p.i.) to 1.54±0.06% ID/g as shown in FIG. 9.

Example 15. PET Imaging Studies of I-23

General method for μPET imaging: the mice were anaesthetized (2% sevoflurane, Abbott), placed into the small animal PET scanner (Inveon PET, Siemens) and injected with 68Ga-labeled Bicycle peptides. A 20 min transmission scan, a 50 min dynamic scan and a static scan from 100 to 120 min p.i. were performed. Images were reconstructed iteratively using the space alternating generalized expectation maximization method (SAGE, 16 subsets, 4 iterations) applying median root prior correction and were converted to standardized uptake value (SUV) images. Quantitation was done using a ROI (region of interest) technique and expressed as SUVmean.

General method for radiolabeling with Ga-68: $^{68}$Ga (half-life 68 min; $\beta^+$ 89%; E$\beta$+max. 1.9 MeV) was obtained from a in house $^{68}$Ge/$^{68}$Ga generator based on pyrogallol resin support. 1 GBq $^{68}$Ga was eluted using 5.5 M HCl. The activity was trapped on a small anion-exchanger cartridge (AG1X8, Biorad, Richmond, CA, USA) as [$^{68}$Ga]GaCl4$^-$. The radiogallium was eluted from the cartridge in a final volume of 300 μL ultrapure water (Merck, Darmstadt, Germany) as [$^{68}$Ga]$GaCl_3$.

1 nmol Bicycle peptide in 1 μL DMSO was added to a mixture of 50 μL 0.05 M HEPES, 0.1% Tween-20, and 80 μL [$^{68}$Ga]$Ga^{3+}$ eluate (~200 MBq). The pH of the labelling solution was adjusted to 4.2 using 30% NaOH. The reaction mixture was incubated at 98° C. for 10 minutes. The radiochemical yield (RCY) was determined using reversed-phase high performance liquid chromatography (RP-HPLC; Chromolith RP-18e, 100×4.6 mm; Merck, Darmstadt, Germany). The analytical HPLC run was performed using a linear A-B gradient (0% B to 100% B in 6 min) at a flow rate of 4 mL/min. Solvent A consisted of 0.1% aqueous TFA and solvent B was 0.1% TFA in $CH_3CN$.

Figure 10:
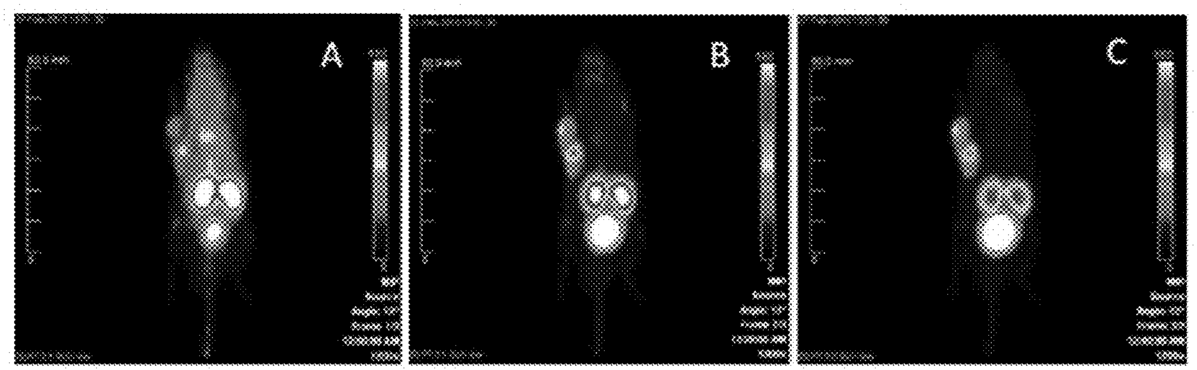
FIG. 10 depicts the whole-body coronal slices (0.8 mm) from µPET imaging 0-20 min p.i. (left, A), 20-40 min p.i. (middle, B), and 40-60 min p.i. (right, C) of I-23.

For μPET imaging, the labelling reaction mixture was diluted in injection buffer (0.25 M Na-Acetate 0.05% Tween-20 pH 7) by a factor of 6 to obtain 150 pmoles in 100 μL injection buffer. The anaesthetized mouse (2% sevoflurane, Abbott) was injected with 100 μL of $^{68}$Ga-labelled I-23 (~25 MBq) and placed in a small animal PET scanner (Inveon PET, Siemens). The imaging was performed 60 min post-injection and included a 15 min transmission scan before injection and a 60 min emission scan post-injection. Scans from μPET imaging were reconstructed iteratively using the space alternating generalized expectation maximization method (SAGE, 16 subsets, 4 iterations) applying median root prior correction and were converted to standardized uptake value (SUV) images. Quantitation was accomplished using an ROI (region of interest) technique and expressed as SUVmean. Results from this study are shown in FIG. 10.

The μPET images revealed MMP-14-selective tumor uptake in the xenograft model and rapid clearance from non-target crucial organs resulting in high imaging contrasts as early as 20 min post injection. The compound represents a highly promising radiopharmaceutical candidate for future clinical PET imaging.

Example 16. PET Imaging Studies of I-24

Figure 11:
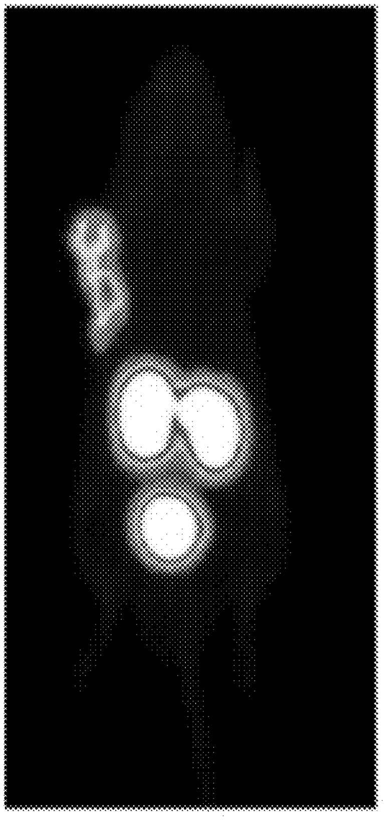
FIG. 11 depicts the whole-body coronal slices (0.8 mm) from µPET imaging 40-60 min p.i. of I-24.

The radiolabelling with Ga-68 was done as described before. The labelling reaction mixture was diluted in injection buffer (0.25 M Na-Acetate 0.05% Tween-20 pH 7) by a factor of 6 to obtain 150 pmoles in 100 μL injection buffer. The anaesthetized mouse (2% sevoflurane, Abbott) was injected with 100 μL of $^{68}$Ga-labelled I-24 (~19 MBq) and placed in a small animal PET scanner (Inveon PET, Siemens). The imaging was performed 60 min post-injection and included a 15 min transmission scan before injection and a 60 min emission scan post-injection. Scans from μPET imaging were reconstructed iteratively using the space alternating generalized expectation maximization method (SAGE, 16 subsets, 4 iterations) applying median root prior correction and were converted to standardized uptake value (SUV) images. Quantitation was accomplished using an ROI (region of interest) technique and expressed as SUVmean. Results from this study are shown in FIG. 11.

Example 17. PET Imaging of 17-69-07-N144 in Comparison to the Inactive Variant 17-69-07-N246

Figure 12:
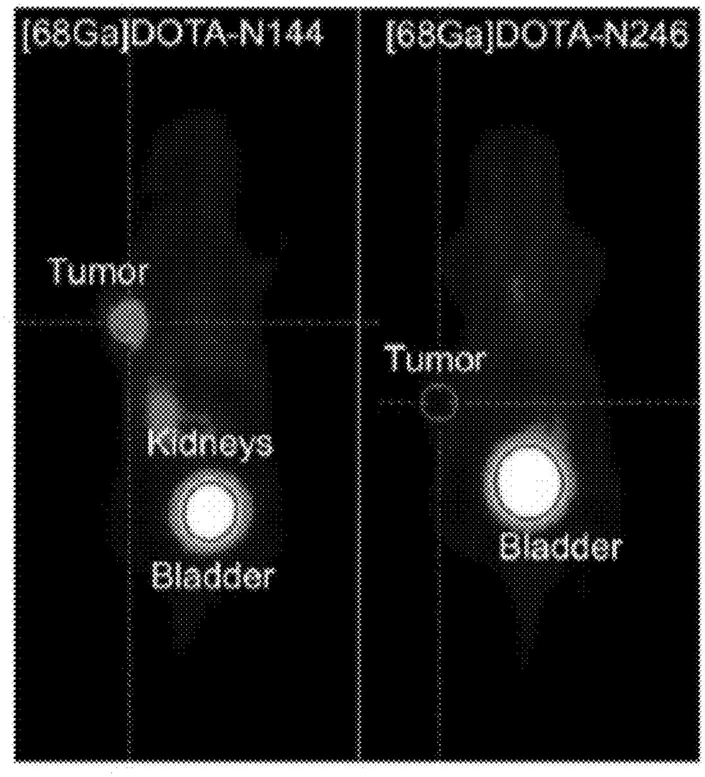
FIG. 12 depicts the µPET images 40-60 min p.i. of 17-69-07-N144 in comparison to the inactive 17-69-07-N246 confirmed a MMP-14-selective tumor uptake. A radiochelator DOTA was conjugated to the sequences to demonstrate in vivo imaging. 17-69-07-N144, which does not comprise chemical modification, shows a tumour specific signal at 2.46% ID/g at the 1 hour timepoint.

The radiolabelling with Ga-68 was done as described before. The labelling reaction mixture was diluted in injection buffer (0.25 M Na-Acetate 0.05% Tween-20 pH 7) by a factor of 6 to obtain 150 pmoles in 100 μL injection buffer. The anaesthetized mouse (2% sevoflurane, Abbott) was injected with 100 μL of $^{68}$Ga-labelled 17-69-07-N144 and 17-69-07-N246 and placed in a small animal PET scanner (Inveon PET, Siemens). The imaging was performed 60 min post-injection and included a 15 min transmission scan before injection and a 60 min emission scan post-injection. Scans from μPET imaging were reconstructed iteratively using the space alternating generalized expectation maximization method (SAGE, 16 subsets, 4 iterations) applying median root prior correction and were converted to standardized uptake value (SUV) images. Quantitation was accomplished using an ROI (region of interest) technique and expressed as SUVmean. Results from this study are shown in FIG. 12.

Figure 13:
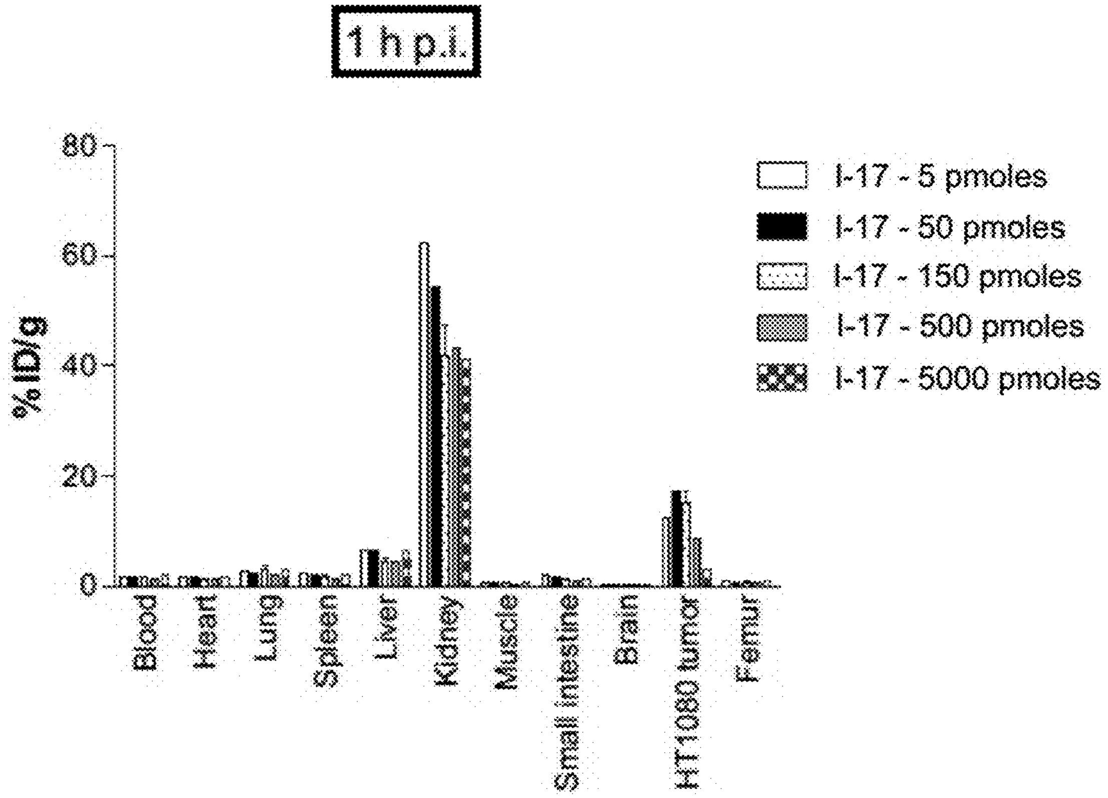
FIG. 13 depicts the organ distribution of Lu-177 labelled I-17 at different doses.
Figure 14:
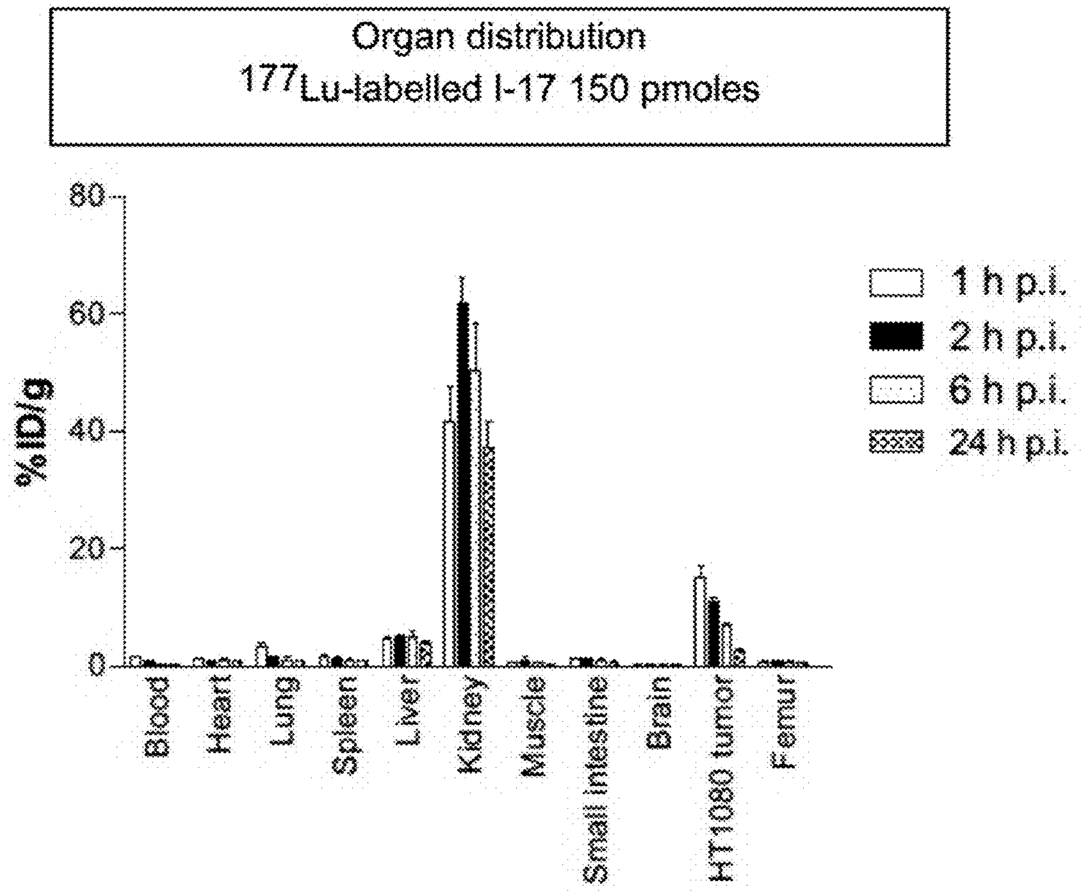
FIG. 14 depicts the organ distribution of Lu-177 labelled I-17 at different time points.

Example 18. Determining Binding to EphA2 and Pharmacokinetics of Bicyclic Peptide-DOTA Conjugates in Xenograft Models: I-17 Organ Distribution and Dose Study Using varying quantities of I-17 and a constant quantity of $^{177}$Lu (approx. 50 kBq/mouse), a variety of doses were assessed in biodistribution studies using HT1080 xenograft mice. Biodistribution was performed at 1 h post injection. The results of this study are shown in FIGS. 13 and 14.

A dose of 50 to 150 pmol was found to be optimal. The tumor uptake was slightly blocked at a dose of 500 pmoles and nearly completely blocked using 5 nmoles of I-17.

Example 19. Organ Distribution of Different EphA2 Variants (Stabilized and Higher Affinity)

I-13 to I-15 represent higher affinity and higher stability DOTA-labelled Bicycles targeting EphA2. I-17 represents a stabilized candidate-like molecule for EphA2. I-18 contains an additional stabilization in Loop 1, at the price of slightly lower affinity. I-28 is an inactive variant of I-17.

Figure 15:
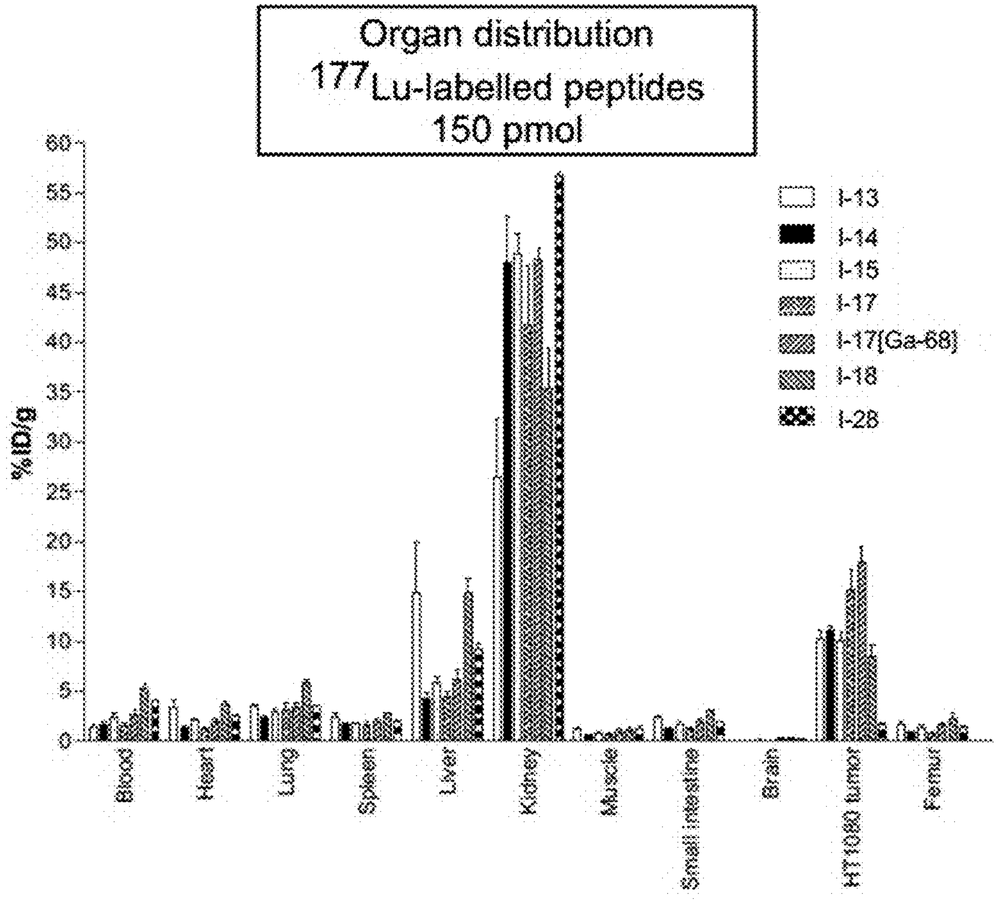
FIG. 15 depicts the organ distribution of Ga-68/Lu-177 labelled peptides I-13, I-14, I-15, I-17, I-18 and I-28 at a dose of 150 pmol 1 h p.i.
Figure 16:
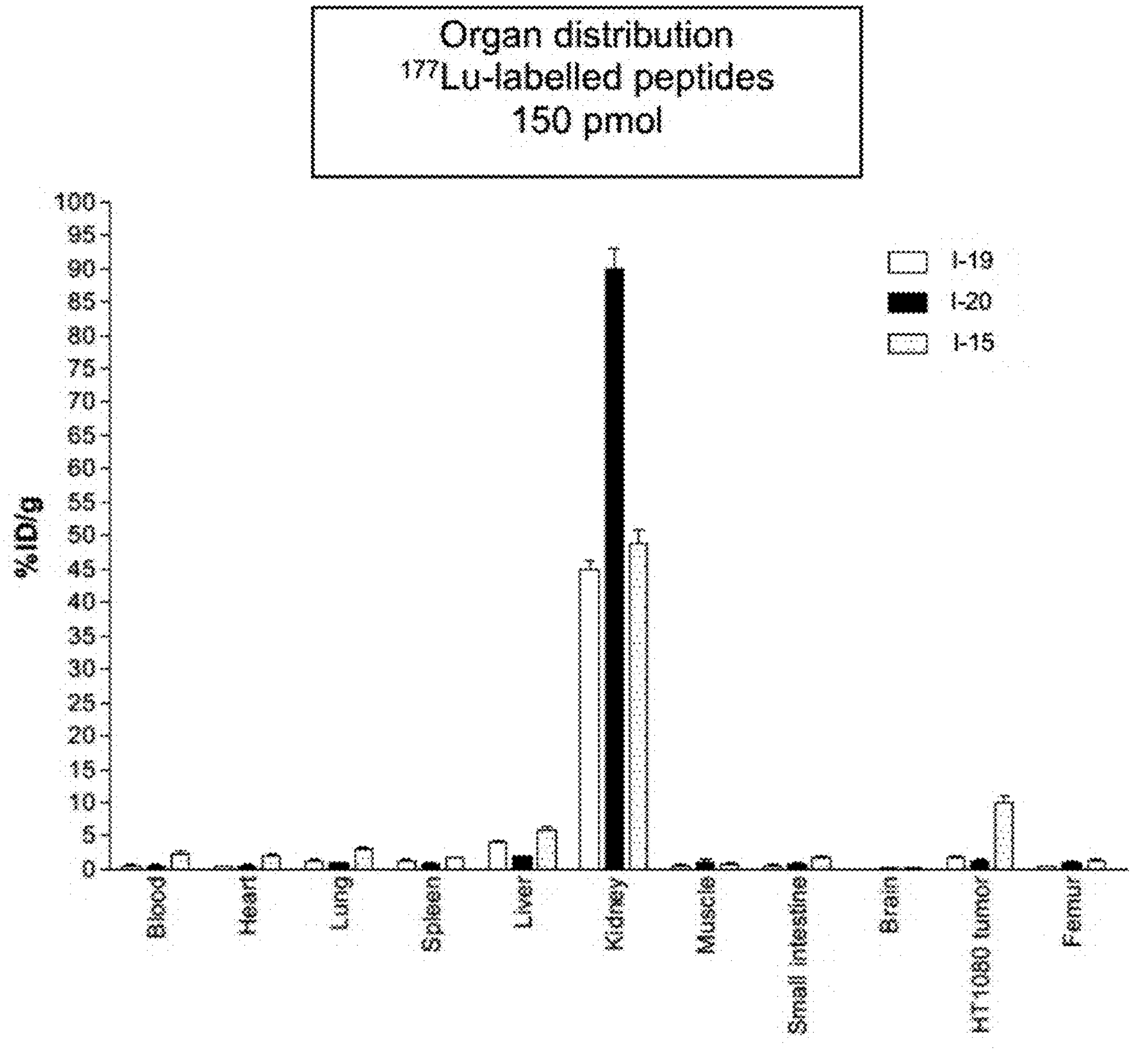
FIG. 16 depicts the organ distribution of Lu-177 labelled peptides at a dose of 150 pmol 1 h p.i. I-19 is not stabilized, I-20 is partially stabilized and I-15 is fully stabilized.
Figure 17:
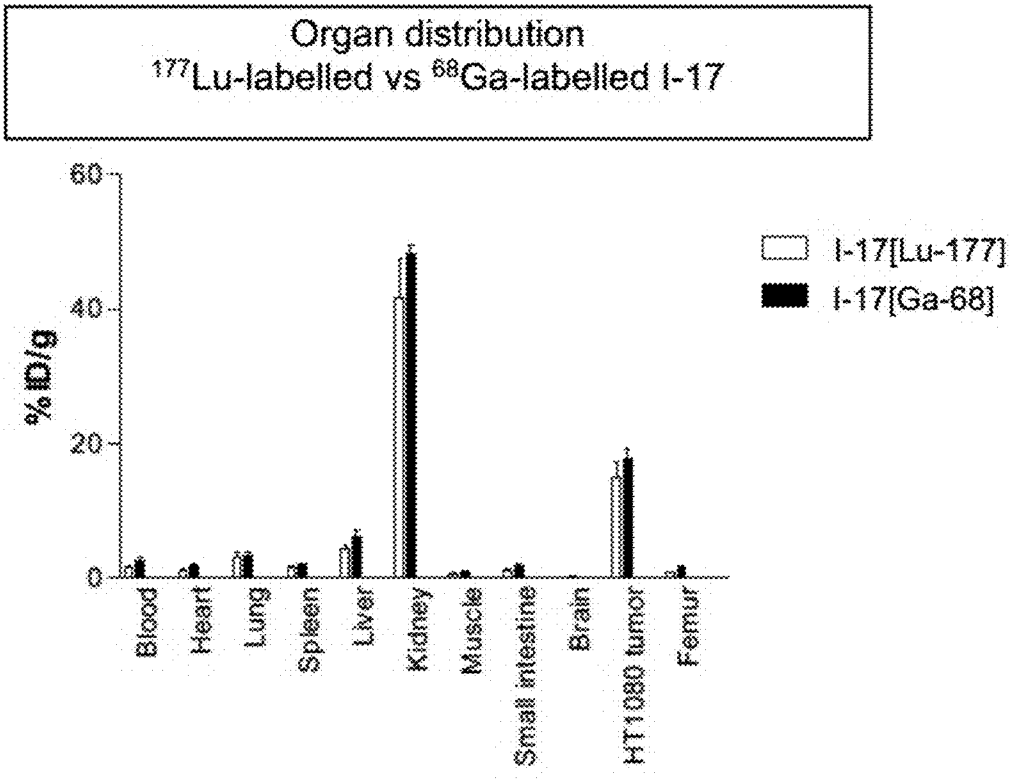
FIG. 17 depicts the organ distribution of Ga-68/Lu-177 labelled I-17 at a dose of 150 pmol 1 h p.i.

The results of this study are shown in FIGS. 15-17.

Example 20. μPET Imaging of I-13 and I-15

The radiolabelling with Ga-68 was done as described before. The labelling reaction mixture was diluted in injection buffer (0.25 M Na-Acetate 0.05% Tween-20 pH 7) by a factor of 6 to obtain 150 pmoles in 100 μL injection buffer. The anaesthetized mouse (2% sevoflurane, Abbott) was injected with 100 μL of $^{68}$Ga-labelled I-13 and I-15 and placed in a small animal PET scanner (Inveon PET, Siemens). The imaging was performed 60 min post-injection and included a 15 min transmission scan before injection and a 60 min emission scan post-injection. Scans from μPET imaging were reconstructed iteratively using the space alternating generalized expectation maximization method (SAGE, 16 subsets, 4 iterations) applying median root prior correction and were converted to standardized uptake value (SUV) images. Quantitation was accomplished using an ROI (region of interest) technique and expressed as SUVmean.

Figure 18:
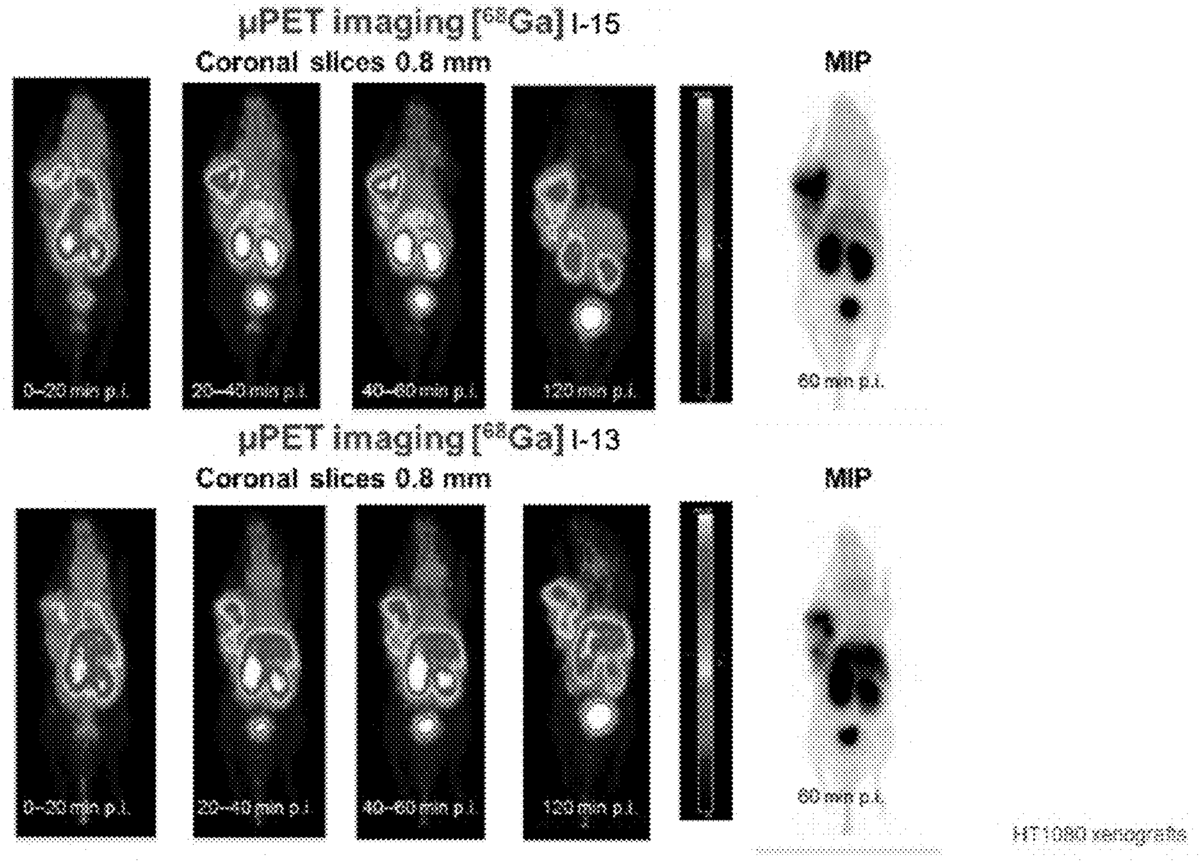
FIG. 18 depicts the whole-body coronal slices (0.8 mm) and maximum intensity projections (MIP) from µPET imaging for I-13 and I-15.

The results of this study are shown in FIG. 18.

The high liver uptake of I-13 which has been shown already in the organ distribution (FIG. 15) could be confirmed in the PET imaging as well. I-15 presented with a clearly reduced liver uptake. The tumor signal was extremely high for both compounds.

Example 21. Specific Cell Uptake and Internalization of I-19

To determine the specific cell uptake and internalization of I-19, $10^5$ cells were seeded in poly-L-lysine coated 24-well cell culture plates 24 h before incubation. After washing, the cells were incubated with 30 nM of the radiolabeled compound for 45 min at 37° C. and at 4° C., respectively. Specific cellular uptake was determined by competitive blocking with 100 μM of the respective cold compound (non-DOTA). Cellular uptake was terminated by washing 4 times with 1 mL of ice-cold PBS. Cells were subsequently incubated twice with 0.5 mL glycine-HCl in PBS (50 mM, pH=2.8) for 5 min to remove the surface-bound fraction. The cells were washed with 1 mL of ice-cold PBS and lysed using 0.3 N NaOH (0.5 mL). The surface-bound and the internalized fractions were measured in a gamma counter. The cell uptake was calculated as percent of the initially added radioactivity bound to $10^6$ cells [% ID/$10^6$ cells]. Specific cell surface binding was observed; no internalization was observed.

Figure 19:
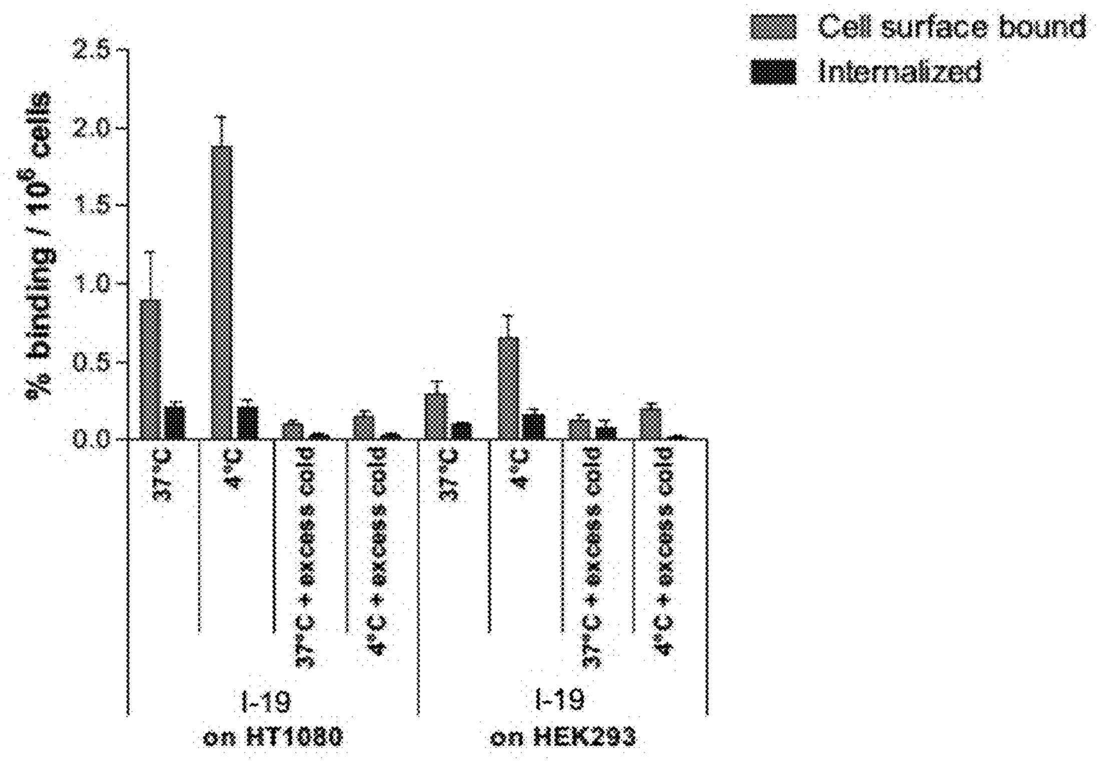
FIG. 19 depicts the cell surface binding and internalization of the $^{177}$Lu labeled compound I-19 at 37° C. and 4° C. on HT1080 and HEK293.

These results are shown in FIG. 19.

Example 22. Determining Binding to CD38 and Pharmacokinetics of Bicyclic Peptide-DOTA Conjugates in Xenograft Models: Internalization Experiments with Monomeric Bicycle I-21

The compound I-21 was labeled with Ga-68 and used with a concentration of 30 nM in the assays. The exposure time was 45 minutes at 37° C. Blocking was done by using the same compound but non-labeled (concentration was 110 μM).

Figure 20:
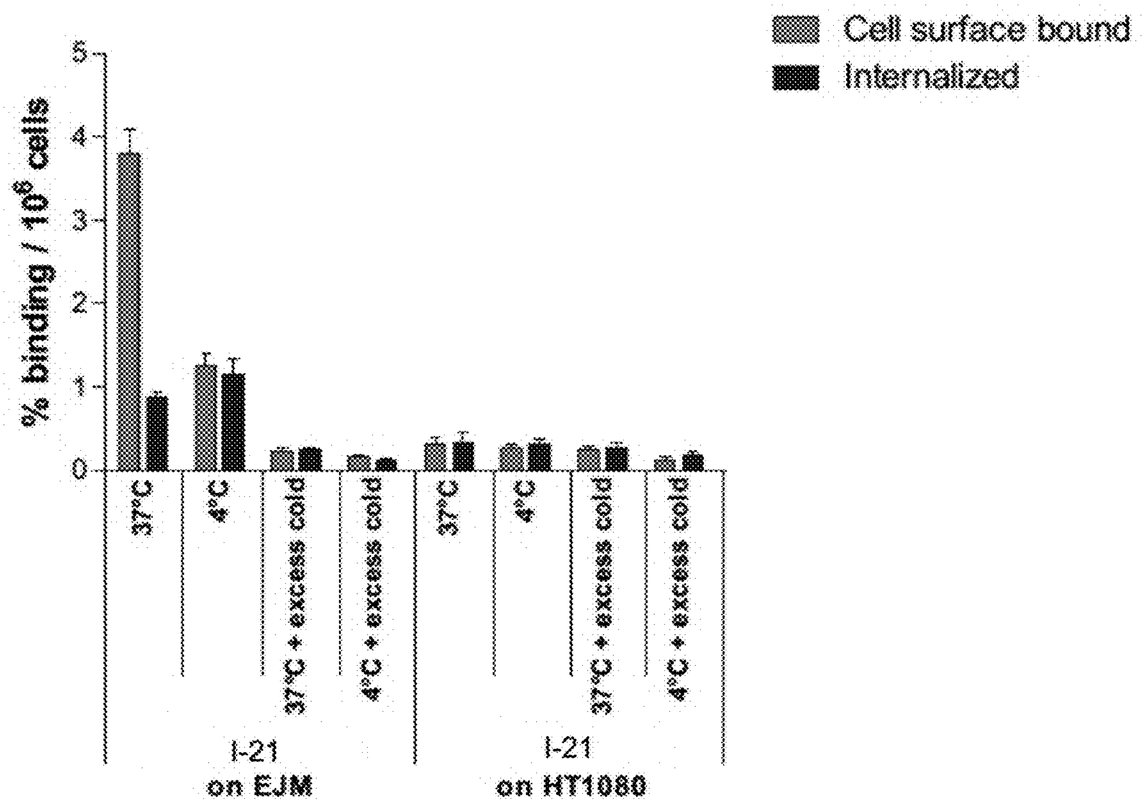
FIG. 20 depicts the cell surface binding and internalization of the $^{177}$Lu labeled compound I-21 at 37° C. and 4° C. on EJM and HT1080.
Figure 21:
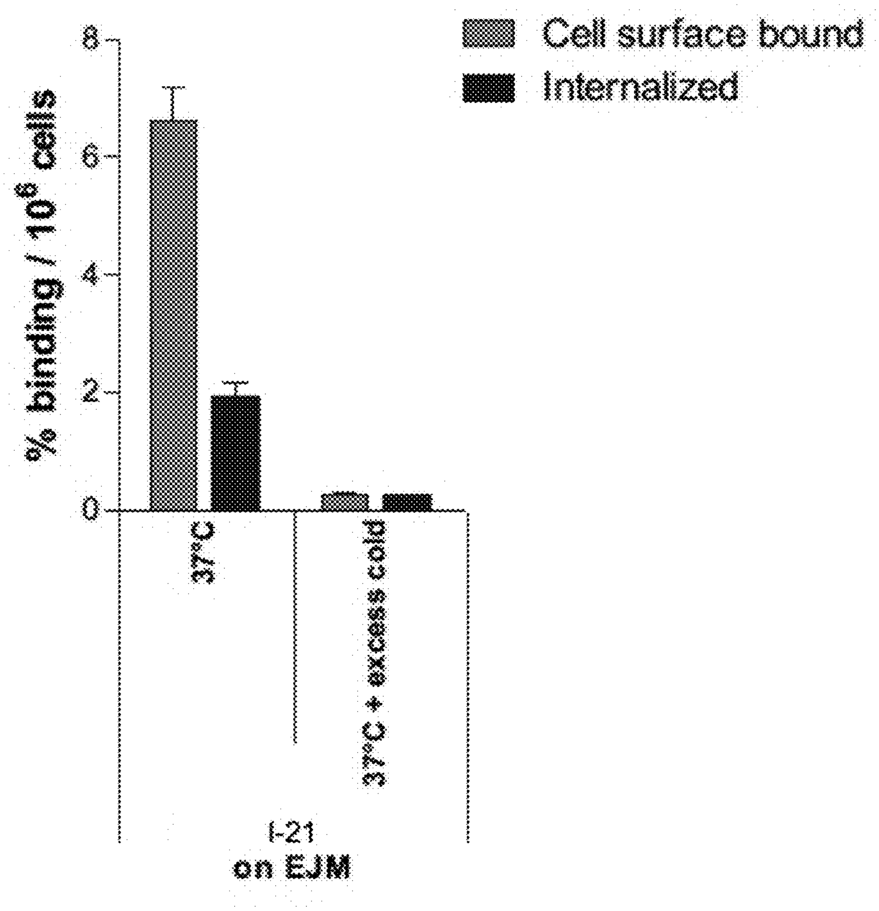
FIG. 21 depicts the cell surface binding and internalization of the $^{177}$Lu labeled compound I-21 at 37° C. and 4° C. on EJM.

These results are shown in FIGS. 20 and 21. While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

Figure 22:
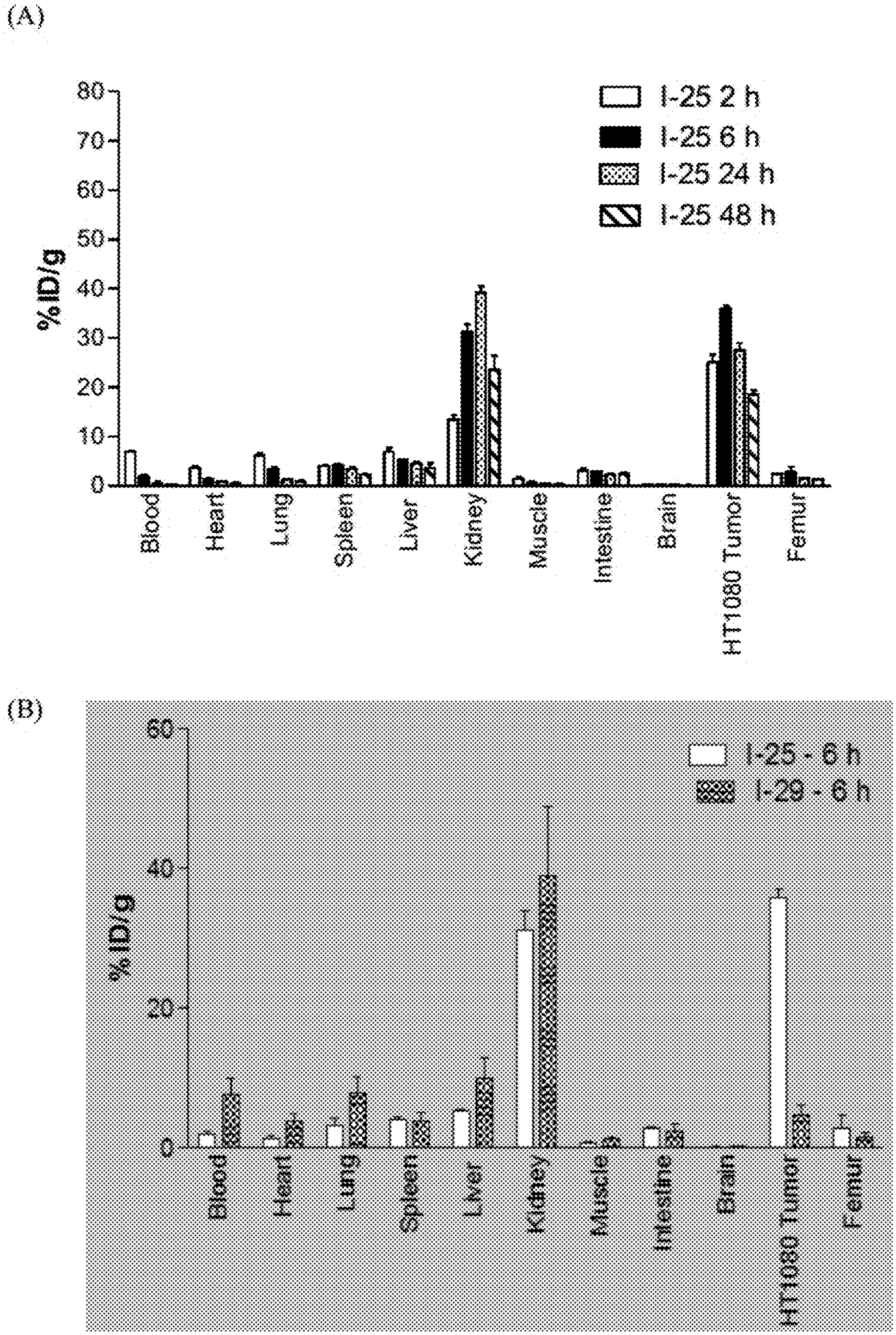
FIG. 22 depicts: (A) the organ distribution of Lu-177 labelled I-25 at different time points after a dose of 750 pmole/mouse; and (B) the organ distribution of Lu-177 labelled I-25 (active) and I-29 (inactive) at 750 pmole/mouse.

Example 23. 1-25 (a Palmitoylated, MT1-MMP Specific Bicyclic Peptide) Organ Distribution and Dose Study Applying the exemplary procedures as described in Example 10, a palmitoylated bicyclic peptide derivative I-25 was generated based on stabilised I-23, where its N-terminus was modified with an extended sarcosine oligomer spacer terminated with palmitoic acid, and where a lysine modified with DOTA was placed within the sarcosine spacer. An organ distribution study investigating additional time points (2, 6 and 24 h) with the optimal dose of 750 pmole/mouse (FIG. 22A) shows a high tumour accumulation of 25.03±1.61% ID/g as early as 2 h p.i. At 6 h p.i., the tumor uptake of $^{177}$Lu-labelled BCY-C5 reached a maximum of 35.88±1.11% ID/g whereas most of the activity in the background organs was cleared. At later time points, $^{177}$Lu-labelled BCY-C5 is further cleared from circulation and therefore presents extremely high tumor-to-organ ratios (tumour to blood signal ratio at 6 hrs is 19, and at 48 hrs is 97), making this molecule an attractive option for molecular diagnostic imaging.

A biodistribution study using $^{177}$Lu-labelled I-29 was performed, which is a non-MT1-MMP binding "mutant" of I-25 wherein D-Ala5 is replaced with L-Ala5, and Glu6 is replaced with L-Ala5. This mutant essentially alters/removes sidechains key to the interaction with MT1-MMP and serves as an inactive control peptide. The molecule is essentially the palmitoylated inactive version of I-27 described herein. This inactive, palmitoylated control peptide was assessed in the mouse xenograft tumour model and compared against the active I-25 comparator, at the 6 hour timepoint where tumour uptake is maximal (750 pmole per mouse). The tumour uptake measured for I-29 was 4.8%, which is ~8 fold lower than the active I-25 (FIG. 22B), indicating that significant, target-selective uptake is occurring in the palmitoylated I-25, and making I-25 a powerful imaging reagent for MT1-MMP expressing tumours in vivo.

We claim:

1. A method of diagnosing or imaging a disorder, disease, or condition in a patient comprising administering to said patient a compound of Formula I-a:

I-a

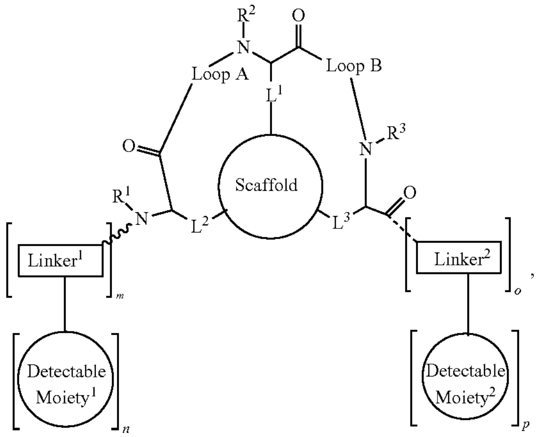

or a pharmaceutically acceptable salt thereof, or a pharmaceutical composition thereof, wherein:

Ring A is

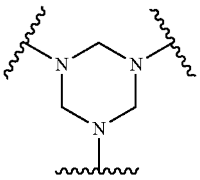

or

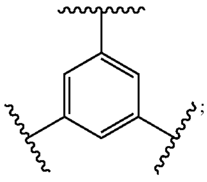

;

each of $L^1$, $L^2$, and $L^3$ is independently $—CH_2SCH_2CH_2C(O)—$ or $—CH_2SCH_2—$;

each of R is independently hydrogen or $C_{1-4}$ alkyl;

each of m, n, o, and p is independently 0 or 1, wherein at least one of n and p is 1;

each of q and r is independently 1, 2, 3, 4, 5, 6, 7, 8, or 9;

$R^1$ is R or —C(O)R;

each of $R^4$ and $R^6$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each of $R^{4'}$ and $R^{6'}$ is independently hydrogen or methyl;

each of $R^2$, $R^3$, $R^5$, and $R^7$ is independently hydrogen or $C_{1-4}$ aliphatic, or:

an $R^5$ group and its adjacent $R^4$ group are optionally taken together with their intervening atoms to form a 4-8 membered saturated or partially unsaturated monocyclic heterocyclic ring having 1-2 heteroatoms independently selected from nitrogen, oxygen, or sulfur; or an $R^7$ group and its adjacent $R^6$ group are optionally taken together with their intervening atoms to form a 4-8 membered saturated or partially unsaturated monocyclic heterocyclic ring having 1-2 heteroatoms independently selected from nitrogen, oxygen, or sulfur;

Loop A is a bivalent natural or unnatural amino acid residue or peptide attached to the amino acid residue linked to $L^2$ and the amino acid residue linked to $L^1$, wherein Loop A comprises:

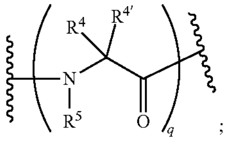

;

Loop B is a bivalent natural or unnatural amino acid residue or peptide attached to the amino acid residue linked to $L^1$ and the amino acid residue linked to $L^3$, wherein Loop B comprises:

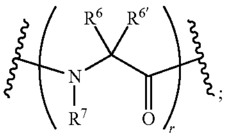

Linker[1] is hydrogen, —C(O)R,

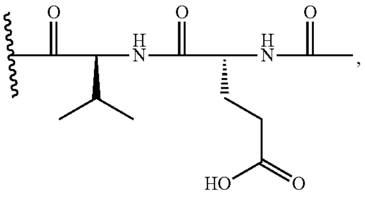 [SMILES: *C(=O)[C@H](NC(=O)[C@H](CCC(=O)O)NC(C)=O)C(C)C]

or a bivalent moiety that connects the N-terminus of the Bicycle with Detectable Moiety[1], wherein when n is 0, then Linker[1] is hydrogen, —C(O)R, or

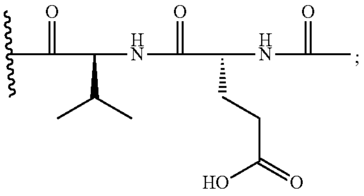 [SMILES: *C(=O)[C@H](NC(=O)[C@H](CCC(=O)O)NC(C)=O)C(C)C]

Linker[2] is —$NH_2$ or a bivalent moiety that connects the C-terminus of the Bicycle with Detectable Moiety[2], wherein when p is 0, then Linker[2] is —$NH_2$; and wherein each of Detectable Moiety[1] and Detectable Moiety[2] is selected from:

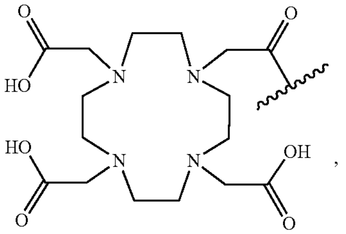

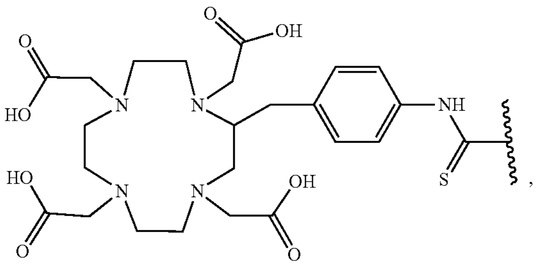

-continued

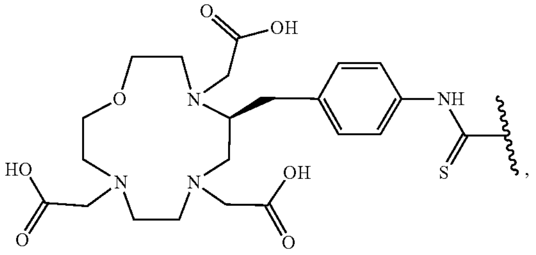

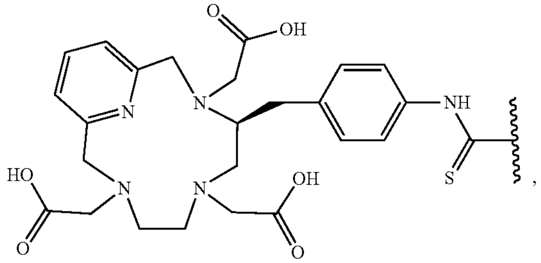

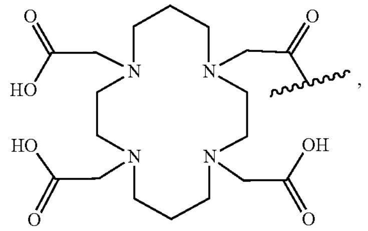

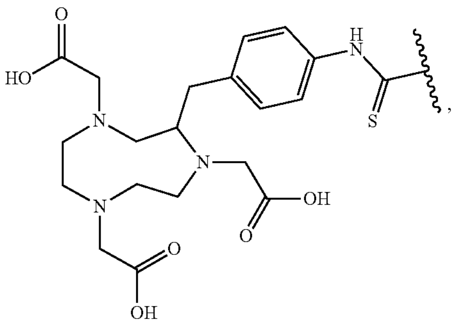

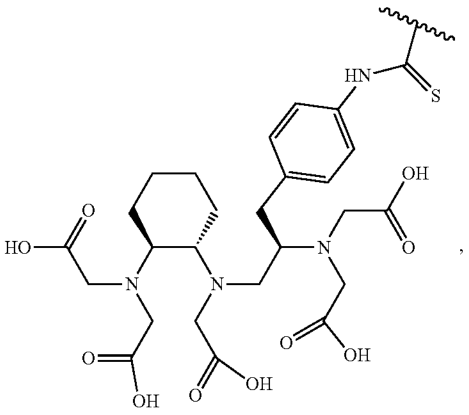

-continued
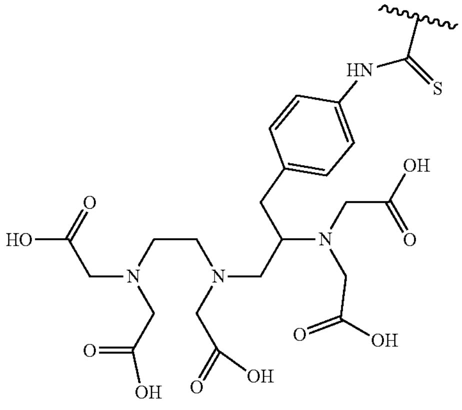
,
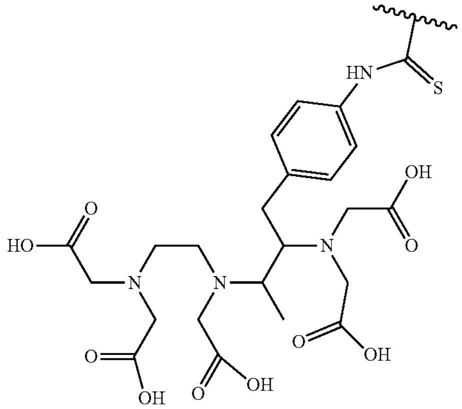
,
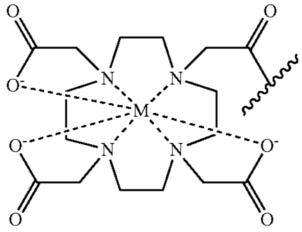
,
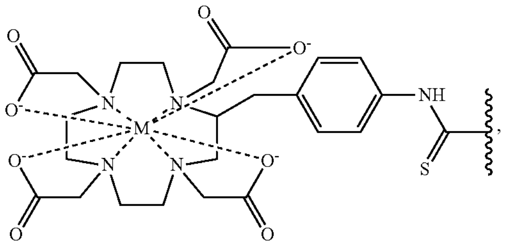
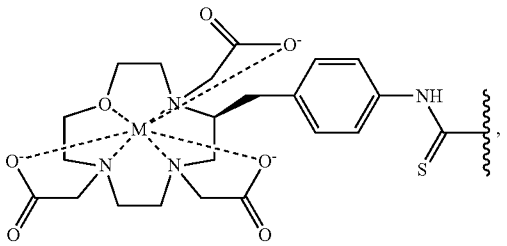
-continued
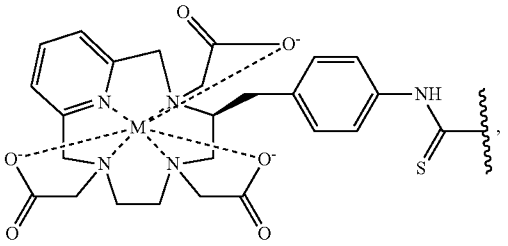
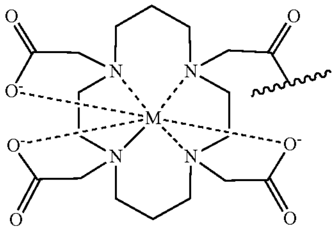
,
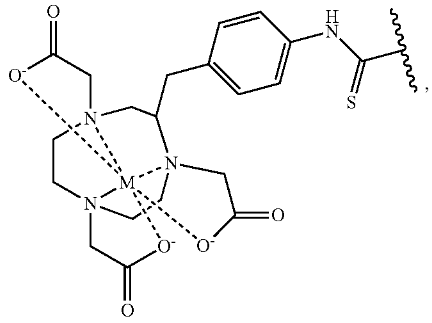
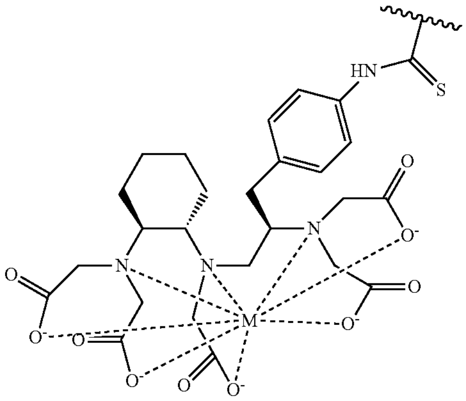
,
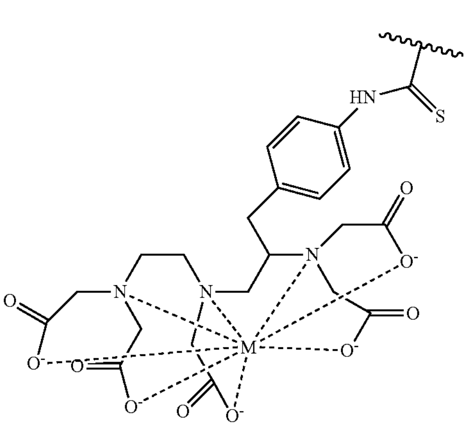

-continued

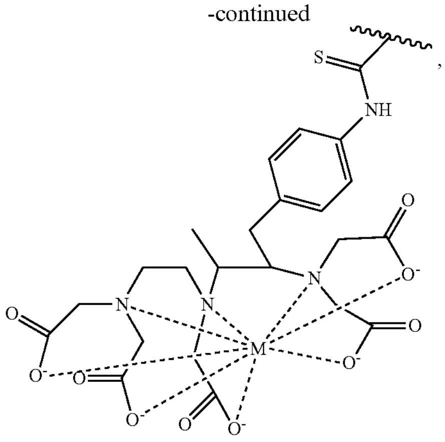

, and

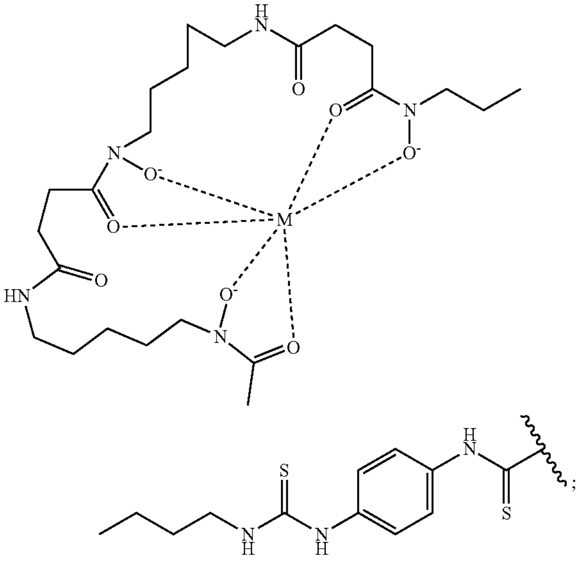

;

wherein M is a radiometal;

with the proviso that the compound is not a bicyclic peptide ligand comprising a polypeptide and a molecular scaffold, wherein the molecular scaffold is 1,3,5-tris(bromomethyl)benzene (TBMB) and forms covalent bonds with cysteine residues of the polypeptide, and wherein the polypeptide has an amino acid sequence selected from:

DOTA-GSar6-C-S-W-P-A-R-C-L-H-Q-D-L-C(SEQ ID NO: 74);

DOTA-A-C-Y-N-E-F-G-C-E-D-F-Y-D-I-C(SEQ ID NO: 75);

DOTA [Lu]-A-C-Y-N-E-F-G-C-E-D-F-Y-D-I-C(SEQ ID NO: 76);

DOTA-A-A-C-Y-N-E-F-G-C-E-D-F-Y-D-I-C(SEQ ID NO: 77), wherein all amino acids are D amino acids; and DOTA-A-A-C-(D-Ala)-N-E-(1Nal)-(D-Ala)-C-E-D-F-(4BrPhe)-D-(tBuGly)-C(SEQ ID NO: 78), wherein D-Ala is D-alanine; 1Nal is 1-naphthylalanine; 4BrPhe is 4-bromophenylalanine; and tBuGly is tert-butylglycine.

2. The method of claim 1, wherein the disorder, disease or condition is a cancer or proliferative disorder.

3. The method of claim 2, wherein the cancer or proliferative disorder is selected from tumors of epithelial origin (adenomas and carcinomas); hematological malignancies and premalignant hematological disorders and disorders of borderline malignancy; hematological malignancies and related conditions of myeloid lineage; tumors of mesenchymal origin; tumors of the central or peripheral nervous system; endocrine tumors; ocular and adnexal tumors; germ cell and trophoblastic tumors; pediatric and embryonal tumors; and syndromes which leave the patient susceptible to malignancy.

* * * * *